(12) United States Patent
Shutske et al.

(10) Patent No.: US 7,253,165 B2
(45) Date of Patent: Aug. 7, 2007

(54) BENZISOXAZOLYL-, PYRIDOISOXAZOLYL-AND BENZTHIENYL-PHENOXY DERIVATIVES USEFUL AS $D_4$ ANTAGONISTS

(75) Inventors: Gregory M. Shutske, Pittstown, NJ (US); James A. Hendrix, Hillsborough, NJ (US); John G. Jurcak, Bethlehem, PA (US); Brian S. Freed, Phillipsburg, NJ (US); Nicholas J. Hrib, Hillsborough, NJ (US); John D. Tomer, IV, Greenfield, IN (US); Reda G. Hanna, Allentown, PA (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 441 days.

(21) Appl. No.: 10/844,245

(22) Filed: May 12, 2004

(65) Prior Publication Data
US 2005/0107377 A1   May 19, 2005

Related U.S. Application Data

(63) Continuation of application No. 10/088,251, filed as application No. PCT/US00/24961 on Sep. 13, 2000, now abandoned.

(60) Provisional application No. 60/229,349, filed on Sep. 14, 1999.

(51) Int. Cl.
C07D 498/02 (2006.01)
A61K 31/5377 (2006.01)
A61K 31/496 (2006.01)

(52) U.S. Cl. .............. 514/232.5; 514/252.14; 514/256; 514/302; 514/307; 514/379; 514/443; 546/115; 546/139; 548/241; 549/49; 544/106; 544/242; 544/359

(58) Field of Classification Search ............. 514/232.5, 514/252.14, 256, 302, 307, 379, 443; 544/106, 544/242, 359; 546/115, 139; 548/241; 549/49
See application file for complete search history.

(56) References Cited

U.S. PATENT DOCUMENTS

| | | | |
|---|---|---|---|
| 4,075,227 A | 2/1978 | Jones et al. | |
| 4,085,114 A | 4/1978 | Adachi et al. | |
| 4,355,037 A | 10/1982 | Strupczewski et al. | |
| 4,408,053 A | 10/1983 | Strupczewski et al. | |
| 4,408,054 A | 10/1983 | Strupczewski et al. | |
| 4,427,691 A | 1/1984 | Shutske et al. | |
| 4,452,804 A | 6/1984 | Shutske et al. | |
| 4,469,869 A | 9/1984 | Strupczewski et al. | |
| 4,504,669 A | 3/1985 | Shutske et al. | |
| 4,528,376 A | 7/1985 | Strupczewski et al. | |
| 4,644,064 A | 2/1987 | Shutske et al. | |
| 4,728,651 A | 3/1988 | Ong et al. | |
| 4,769,472 A | 9/1988 | Ong et al. | |
| 5,114,936 A | 5/1992 | Wettlaufer et al. | |
| 5,143,923 A | 9/1992 | Hrib et al. | |
| 5,177,088 A | 1/1993 | Effland et al. | |
| 5,180,834 A | 1/1993 | Wettlaufer et al. | |
| 5,225,412 A | 7/1993 | Hrib et al. | |
| 5,225,414 A | 7/1993 | Henning et al. | |
| 5,254,595 A | 10/1993 | Guzzi et al. | |
| 5,256,672 A | 10/1993 | Wettlaufer et al. | |
| 5,321,037 A | 6/1994 | Nagano et al. | |
| 5,328,920 A | 7/1994 | Effland et al. | |
| 5,340,833 A | 8/1994 | Bridges et al. | |
| 5,576,319 A | 11/1996 | Baker et al. | |
| 5,593,994 A | 1/1997 | Batt et al. | |
| 5,696,113 A | 12/1997 | Palermo et al. | |
| 5,780,474 A | 7/1998 | Peglion et al. | |
| 5,843,940 A | 12/1998 | Cullinan et al. | |
| 5,852,022 A | 12/1998 | Palermo et al. | |
| 5,856,503 A | 1/1999 | Aebi et al. | |
| 5,932,586 A | 8/1999 | Batt et al. | |
| 5,965,554 A | 10/1999 | Palermo et al. | |
| 6,008,348 A | 12/1999 | Palermo et al. | |
| 6,022,880 A | 2/2000 | Effland et al. | |
| 6,103,724 A | 8/2000 | Laszlovszky et al. | |
| 6,121,293 A | 9/2000 | Cullinan et al. | |

FOREIGN PATENT DOCUMENTS

| | | |
|---|---|---|
| EP | 0058977 | 9/1982 |
| EP | 0221414 | 5/1987 |
| EP | 0729955 | 9/1996 |
| GB | 1269776 | 4/1972 |
| JP | 10095770 | 4/1998 |
| WO | WO 92/08718 | 5/1992 |
| WO | WO 97/23482 | 7/1997 |
| WO | WO 97/28115 | 8/1997 |
| WO | WO 97/40027 | 10/1997 |
| WO | WO 99/40067 | 8/1999 |
| WO | WO 01/19833 | 3/2001 |

OTHER PUBLICATIONS

Asghari, V., et. al., Dopamine D4 Receptor Repeat: Analysis of Different Native and Mutant Forms of the Human and Rat Genes, Molecular Pharmacology vol. 46, pp. 364-373 (1994).

(Continued)

Primary Examiner—Zinna N. Davis
(74) Attorney, Agent, or Firm—Barbara E. Kurys

(57) ABSTRACT

The compounds are of the class of benzisoxazolyl-, pyrido-isoxazolyl- and benzthienyl-phenoxy derivatives, useful as $D_4$ antagonists. Said compounds are useful for the treatment of medical conditions mediated by inhibition of $D_4$ receptor. These conditions comprise, for example, Attention Deficit Hyperactivity Disorder, Obsessive-Compulsive Disorder, Psychoses, Substance Abuse, Substance Dependence, Parkinson's Disease, Parkinsonism, Tardive Diskinesia, Gilles de la Tourette Syndrome, Conduct Disorder, and Oppositional Defiant Disorder. A further aspect of the invention is to provide a pharmaceutical composition, intermediates, and a method of making said class of compounds.

211 Claims, No Drawings

OTHER PUBLICATIONS

Bassitt, D.P., et. al., Clozapine Efficacy in Tardive Dyskinesia in Schizophrenic Patients, European Archives of Pyschiatry and Clinical Neuroscience vol. 248, pp. 209-211 (1998).

Benjamin, J., et. al., Population and Familial Association between the D4 Dopamine Receptor gene and Measures of Novelty Seeking, Nature Genetics vol. 12, pp. 81-84 (1996).

Bryce, M., et. al., Synthesis and Cyclic Voltammetric Behaviour of Some 3-Substituted Thiophenes and Pyrroles: Precursors for the Prepration of Conducting Polymers, Synthetic Metal, vol. 26, (1988) pp. 153-168.

Corbett, R., et. al., Iloperidone: Preclinical Profile and Early Clinical Evaluation, CNS Drug Review vol. 3, No. 2, pp. 120-147 (1997).

Crenshaw, R.R., et. al., Potential Antifertility Agents, 1. Substituted Diarl Derivatives of Benzo[b]thiophenes, Benzo[b]furans, 1H-2-Benzothiapyrans, and 2H-1-Benzothiapyrans1, Journal of Medicinal Chemistry, vol. 14, No. 12, (1971) pp. 1185-1190.

Cruz, C., et. al., Increased Prevalence of the Seven-Repeat Variant of the Dopamine D4 Receptor Gene in Patients with Obsessive-Compulsive Disorder with Tics, Neuroscience Letters vol. 231, pp. 1-4, (1997).

Ebstein, R.E., et. al., Dopamine D4 Receptor (D4DR) exon III Polymorphism Associated with the Human Personality Trait of Novelty Seeking, Nature Genetics vol. 12, (1996) pp. 78-80.

Elworthy, T. R., et. al., N-Arylpiperazinyl-N-Propylamino Derivatives of Heteroaryl Amides as Functional Uroselective a1-Adrenoceptor Antagonists, Indian Journal of Chemistry—part B Organic Including Medicinal vol. 40, pp. 2674-2687, (1997).

Erenberg, G., et. al. , Giles De La Tourette's Syndrome: Effects of Stimulant Drugs, Neurology vol. 35, No. 35, pp. 1346-1348, (1985).

Factor, S.A., et. al., The Emerging Role of Clozapine in the Treatment od Movement Disorders, Movement Disorders vol. 12, No. 4 (1997) pp. 483-496.

Feldpausch, D.L., et. al., The Role of Dopamine D4 Receptor in the Induction of Behavioral Sensitization to Amphetamine and Accompanying Biochemical and Molecular Adaptations, Journal of Pharmacology and Experimental Therapeutics vol. 266, pp. 497-508 (1998).

Friedman, J.H., et. al., Substituting Clozapine for Olanzapine in Psychiatrically Stable Parkinson's Disease Patients: Results of an Open Label for Pilot Study, Clinical Neuropharmacology, vol. 21, No. 5 pp. 285-288 (1998).

Grice, D.E., et. al., Linkage Disequillibrium between an Allele at the Dopamine D4 Receptor Locus and Tourette Syndrome, by the Transmission-Disequillibrium Test, American Journal of Human Genetics vol. 59, pp. 644-652 (1996).

Helsley, G.C., et. al., Piperidyalkylindoles. 1. Hypotensive Activity of 3-[2-(Phenoxypiperidyl)ethyl]indoles, Journal of Medicinal Chemistry, (1978), vol. 21, No. 3 pp. 309-312.

Lahoste, G., et. al., Dopamine D4 Receptor Gene Polymorphism is Associated with Attention Deficit Hyperactivity Disorder, Molecular Psychiatry vol. 1, pp. 121-124 (1996).

Lahti, R.A., et. al., Direct Determination of Dopamine D4 Receptors in Normal and Schizophrenic Postmortem Brain Tissue: A[3H]NGD-94-1 Study, Molecular Psychiatry vol. 3, pp. 528-533 (1998).

Magdo, I., et. al., 3D quantitative structure-activity relationship (CoMFA) study of heterocyclic arylpiperazine derivatives with 5-HT1A activity, Database Chemabs 'Online! Chemical Abstracts Service, Columbus, Ohio, US.

Ricketts, H., et al., Association of Long Variants of the Dopamine D4 Receptor Exon 3 Repeat Polymorphism with Parkinson's Disease, Clinical Genetics vol. 54, pp. 33-38 (1998).

Rubinstein, M., et. al., Mice Lacking Dopamine D4 Receptors are Supersitive to Ethanol, Cocaine, and Methamphetamine, Cell, vol. 90, pp. 991-1001 (1997).

Sall, D., et. al., Dibasic Benzo[b]thiophene Derivatives as a Novel Class of Active Site-Directed Thrombin Inhibitors. 1. Determination of the Serine Protease Selectivity, Structure—Activity Relationships, and Binding Orientation, Journal of Medicinal Chemistry vol. 40, No. 22, (1997) pp. 3489-3493.

Schoder, J., et. al. , D2 Dopamine Receptor Up-Regulation, Treatment Response, Neurological Soft Signs, and Extrapyramidal Side Effects in Schizophrenia: A Follow-Up Study with 123I-Iodobenzamide Single Photon Emission Compouted Tomography in the Drug Naive State and after Neuroleptic Treatment, Society of Biological Psychiatry vol. 43, pp. 660-665, (1998).

Seeman, P., et. al., Atypical Neuroleptics Have Low Affinity for Dopamine D2 Receptors or Are Selectivefor D4 Receptors, Neuropoychoppharmacology vol. 16, Iss. 2, pp. 92-135 (1997).

Seeman, P., et. al., Schizophrenia: Eleveation of dopamine D4-like sites, using [3H] Nemonapride and 125I Epidepride , European Journal of Pharmacology vol. 286 (1995) R3-R5.

Shields, P.G., et. al., Dopamine D4 Receptors and the Risk of Cigarette Smoke in African-Americans and Caucasions1, Cancer Epidermiology, Biomarkers & Prevention vol. 7, pp. 453-458 (1998).

Van Tol, H.M., et. al., Cloning of the gene for a human dopamine D4 receptor with high affinity for the antipsychotic clozapine, Letters to Nature, vol. 350, 1991, pp. 610-614.

Van Tol, H.M., et. al., The Dopamine D4 Receptor: A Novel Site for Antipsychotic Action , Clinical Neuropharmacology vol. 18, No. 1 pp. 5143-5153 (1995).

Vantol, H.M., et. al., Multiple Dopamine D4 Receptor Variants in the Human Population , Nature vol. 358—9 (1992)—pp. 149-152.

Zhu, J., et. al., Synthesis of 2-(4-Halogenobenzyl)-3-Arylbenzo[b]-Thiophenes and a 2-(4-Fluorobenzyl)-3-Arylbenzo[b]-Selenophene as Selective Ligands for Antiestrogen-Binding Sites.

Kongsamut, S., et. al., Iloperidone Binding to Human and Rat Dopamine and 5-HT Receptors, Database Chemabs online! Chemical Abstracts Service, Columbus, Ohio, US retrieved from STN Database Accession No. 126:70003 XP002154323 * Eur. J. Pharmacol. (1996) vol. 317, (2/3).

BENZISOXAZOLYL-, PYRIDOISOXAZOLYL-AND BENZTHIENYL-PHENOXY DERIVATIVES USEFUL AS $D_4$ ANTAGONISTS

FIELD OF THE INVENTION

The present invention comprises compounds of Formula I useful as therapeutic agents for conditions treated by antagonizing $D_4$ receptor stimulation, e.g., Attention Deficit Hyperactivity Disorder, Obsessive Compulsive Disorder and Psychoses. Intermediates, method of making the compounds and methods of using the compounds are also claimed.

BACKGROUND OF THE INVENTION

The relatively new science of molecular biology has allowed new insights into the mechanisms of CNS diseases via the isolation and cloning of receptor subtypes. Thus, while earlier functional studies had distinguished only two subtypes of dopamine receptor, to date five distinct subtypes have been identified. The dopamine $D_4$ receptor was first cloned in 1991 by Van Tol, Seeman, Civelli, et al. and shown to be localized in the limbic regions of the brain, areas associated with cognitive and emotional behaviors (Van Tol, H. H. M.; Bunzow, J. R.; Guan, H-C.; Sunahara, R. K.; P. Seeman, Niznik, H. B.; Civelli, O.; Cloning of the gene for a human dopamine $D_4$ receptor with high affinity for the antipsychotic clozapine. Nature 1991, 350, 610.)

The $D_4$ receptor was also localized to the frontal cortex implying a role in cognition and executive function. Furthermore, it has been reported that the selective $D_4$ antagonist NGD-94-1 caused improvement in performance retention in a passive avoidance test in rodents and improved performance in a spatial water maze task. (Tallman, J. NGD-94-1; A Specific Dopamine $D_4$ Antagonist. Catecholamines-Bridging Basic Science with Clinical Medicine. Goldstein, D. S.; Eisenhofer, G.; McCarty, R., Eds.; Academic Press: New York, 1997). The effects of this compound in these assays are consistent with the anatomical localization of the $D_4$ receptor in the cortex, hippocampus and thalamus.

Genetic linkage and association studies using polymorphism have been carried out to obtain insights into the possible roles for this receptor in disease. It has been reported that there is a positive association between the repeat polymorphism of seven repeat units and a number of clinical conditions which have a high degree of comorbidity such as Attention Deficit Hyperactivity Disorder and Obsessive Compulsive Disorder-tics (Cruz, C. et al., Increased prevalence of the seven-repeat variant of the dopamine $D_4$ receptor gene in patients with obsessive-compulsive disorder with tics. Neurosci. Lett. 1997, 231, 1. Van Tol, H. H. M. (1995) Clin Neuropharmacol. 18: S143-153).

One of the most remarkable polymorphisms in the human dopamine $D_4$ receptor is a variable number of 48 bp tandem repeats in the third cytoplasmic loop. Individuals with 2-10 tandem repeat units have been identified. Interestingly, this polymorphism appears to be primate-specific and has not been observed in rodents suggesting that these polymorphisms are evolutionarily recent events (Asghari, V. et al., Dopamine $D_4$ receptor repeat: analysis of different native and mutant forms of the human and rat genes (1994) Mol. Pharm. 46: 364-373).

The human $D_4$ receptor with seven repeat units has a number of unique characteristics which distinguish it from the other $D_4$ polymorphisms. This D4.7 variant has displayed a two- to threefold lower potency for the endogenous ligand dopamine than did the D4.2 variant ($EC_{50}$=40 nM vs. 15 nM) however, the functional implications of this lower affinity are not yet resolved.

Attention Deficit Hyperactivity Disorder (Hereinafter ADHD)

Attention deficit hyperactivity disorder (ADHD) is a disease which affects 3-5% of school age children. It is highly prevalent, making up to 50% of child psychiatry populations. The disease can also persist into adulthood, affecting 1-3% of adults. The diagnosis of ADHD revolve around three basic criteria: inattention, hyperactivity, and impulsivity. Approximately 50-70% of school-age children with the diagnosis of ADHD continue to manifest symptoms through middle adolescence, and almost one third will show some signs of the disorder in adulthood.

It has been shown that dopamine $D_4$ receptor gene polymorphism is associated with ADHD. Patients suffering from ADHD had a significant increase in the prevalence of 7-fold repeat form of the $D_4$ receptor, a variant which is unique for primates (LaHoste, G. J.; Swanson, J. M.; Wigal, S. B.; Glabe, C.; Wigal, T.; King, N.; Kennedy, J. L.; Dopamine $D_4$ receptor gene polymorphism is associated with attention deficit hyperactivity disorder. Mol. Psychiatry 1996, 1, 121). Interestingly, an excess of the D4.7 allele has also been associated with the personality trait of "novelty-seeking"; individuals scoring higher than average on this scale are characterized as impulsive, exploratory, fickle, excitable, quick-tempered and extravagant (Ebstein, R. P. et al.; Dopamine $D_4$ receptor ($D_4DR$) exon III polymorphism associated with the human personality trait of Novelty Seeking. Nature Genetics. 1996, 12, 78 and Benjamin, J. et al.; Population and familial association between the $D_4$ dopamine receptor gene and measures of Novelty Seeking. Nature Genetics. 1996, 12, 81).

This variant of the $D_4$ receptor may have a dysregulated response to dopamine, perhaps suggesting a gain of function for this receptor a) Van Tol, H. H. M.; Wu, C. M.; Guan, H-C.; Ohara, K.; Bunzow, J. R.; Civelli, O.; Kennedy, J.; Seeman, P.; Niznik, H. B.; Jovanovic, V.; Multiple dopamine $D_4$ receptor variants in the human population. Nature 1992, 352, 149. b) Van Tol, H. H. M.; Structural and Functional characteristics of the Dopamine $D_4$ Receptor. In Catecholamines Bridging Basic Science with Clinical Medicine. Goldstein, D. S.; Eisenhofer, G.; McCarty, R., Eds.; Academic Press: New York, 1997). Therefore, these data suggest that a $D_4$ antagonist may be efficacious in the treatment of ADHD without the side effect liability seen with current drug therapies.

Patients with ADHD also have markedly increased incidence of Conduct Disorder and Oppositional Defiant Disorder. Conduct Disorder is a disorder wherein the patient exhibits a repetitive and persistent pattern of behavior in which the basic rights of others or major age-appropriate societal norms or rules are violated. These behaviors fall into four main groupings: aggressive conduct that causes or threatens physical harm to other people or animals, nonagressive conduct that causes property loss or damage, deceitfulness or theft, and serious violations of rules. Oppositional Defiant Disorder is a disorder wherein the patient exhibits some of the patterns of behavior observed in Conduct Disorder (e.g., disobedience and opposition to authority figures), however it does not include the persistent pattern of the more serious forms of behavior in which either the basic rights of others or age-appropriate societal norms or rules are violated. Although children with ADHD often exhibit hyperactive and impulsive behavior that may be disruptive, this behavior does not by itself violate age-appropriate societal norms and therefore does not usually meet criteria for Conduct Disorder. No specific data regarding gene frequency is available for these conditions, which are relatively refractory to available pharmacotherapy. If abnormalities of the $D_4$ neurotransmission involved in the pathogenesis of ADHD, it would be likely that $D_4$ abnormalities would also play a role in these conditions.

Obsessive-Compulsive Disorder (Hereinafter OCD)

Obsessive-compulsive disorder is a neurosis characterized by the presence of recurrent ideas and fantasies (obsessions) and repetitive impulses or actions (compulsions) that patients recognize as morbid and toward which they feel a strong inner resistance. In the US it is estimated that approximately four million patients are afflicted with OCD; however, fewer than half are diagnosed and treated.

The same seven-repeat variant of the dopamine $D_4$ receptor gene has been found to show increased prevalence in patients suffering from obsessive-compulsive disorder with tics (Cruz, C. et al., Increased prevalence of the seven-repeat variant of the dopamine $D_4$ receptor gene in patients with obsessive-compulsive disorder with tics. Neurosci. Lett. 1997, 231, 1. Van Tol, H. H. M. (1995) Clin Neuropharmacol. 18: S143-153). It has also been reported that adolescents with OCD plus tics are more prone to show violent and aggressive obsessions than those without tics (Cruz, C. et al., Increased prevalence of the seven-repeat variant of the dopamine $D_4$ receptor gene in patients with obsessive-compulsive disorder with tics. Neurosci. Lett. 1997, 231, 1. Van Tol, H. H. M. (1995) Clin Neuropharmacol. 18: S143-153). As mentioned before, this $D_4$ variant has been shown to have a dysregulated response to dopamine. Thus OCD may also be a disorder associated with a gain of function at the $D_4$ receptor, which would respond to treatment with selective $D_4$ antagonists.

Schizophrenia

Schizophrenia is a severe mental illness affecting an estimated 1% of the world's population. The disease has an uncertain pathophysiology possibly leading to disruption of dopaminergic neural systems through poorly understood interactions of atomic, metabolic and genetic abnormalities. The schizophrenic patient suffers from psychotic symptoms broadly categorized as positive, negative or cognitive. The positive symptoms include delusions, hallucinations, irrational fears, and disorganization of thought. Negative or deficit symptoms include social withdrawal, impairment in role functioning, diminished or inappropriate affect, poverty of speech, marked lack of initiative or energy and the inability to experience pleasure. Cognitive symptoms comprise impairment of attention, verbal fluency, recall memory or executive function. Since the discovery of the clinical antipsychotic activity of chlorpromazine in the 1950s, the pharmacological antagonism of central dopamine receptors remains the only proven means for treating schizophrenia. This is evidenced by the number of agents with varied chemical structures that have been found to share the property of dopamine $D_2$ receptor antagonism and to have clinical benefit.

Recently using molecular biological techniques two families of dopamine receptors have been discovered namely the dopamine $D_1$ family ($D_1$ and $D_5$ receptor subtype) and the dopamine $D_2$ family ($D_2$, $D_3$, and $D_4$ receptor subtype). All clinically effective antipsychotic agents have been shown to bind to these receptor subtypes with varying affinities (Corbett, R. et al., 1997; Iloperidone: Preclinical Profile and early clinical evaluation. CNS Drugs Reviews 3(2): 120-147). A number of the recently introduced antipsychotic drugs with a profile for reduced extrapyramidal side effect liability have been shown to have greater affinity for the dopamine $D_4$ receptor subtype when compared to the dopamine $D_2$ receptor subtype. This greater affinity for the $D_4$ receptor compared to the $D_2$ receptor may contribute to these drugs having greater efficacy and less side effect liability than the traditional typical antipsychotic drugs (Seeman, P., Corbett, R. and Van Tol H. H. M. (1997) Atypical neuroleptics have low affinity for dopamine $D_2$ receptors or are selective for $D_4$ receptors. Neuropsychopharmacology 16 (2): 93-135.). Therefore, compounds with selective $D_4$ affinity may have efficacy against schizophrenia without causing the side effects associated with $D_2$ receptor blockade.

Substance Abuse/Substance Dependence

Repeated administration of psychostimulants such as d-amphetamine to rodents produces a progressive and long-lasting increase in behaviors such as locomotor activity, a phenomenon known as "behavioral sensitization" or "reverse tolerance". This enduring hypersensitivity to psychostimulants is also observed in humans and is thought to underlie drug addiction (Robinson, T. E. and Berridge, K. C. 1993 The neural basis of drug craving: an incentive sensitization theory of addiction Brain Research Reviews 18: 247-291). The mesolimbic dopamine system plays a critical role in the development of drug addiction. The development of behavioral sensitization to amphetamine is thought to reflect neuroadaptive biochemical and genomic responses triggered by the first exposure to the psychostimulant. Postsynaptic neuroplasticity results in alterations in dopamine receptor number and sensitivity. The function of the dopamine $D_2$ receptor family ($D_2$, $D_3$, and $D_4$ receptor subtypes) are all altered by the administration of amphetamine. The chronic administration of a selective dopamine $D_4$ receptor antagonist to rodents has been demonstrated to stop the development of behavioral sensitization to the administration of d-amphetamine indicating that selective dopamine $D_4$ antagonists may have efficacy for the treatment of drug abuse (Feldpausch D. L et al., 1998 The role of Dopamine $D_4$ receptor in the induction of behavioral sensitization to amphetamine and accompanying biochemical and molecular adaptations. Journal of Pharmacology and Experimental Therapeutics 266: 497-508).

A role for the $D_4$ receptor in substance abuse and substance dependence is supported by reports of an excess of long alleles (chiefly 7-repeat) of the $D_4$ exon 3 polymorphism in opiate and possibly alcohol abusers (Ebstein R P, Belmaker R H. 1997 Saga of an adventure gene: novelty seeking, substance abuse and the dopamine $D_4$ receptor ($D_4$DR) exon III repeat polymorphism. Mol Psychiatr 2:381-4; Kotler M, Cohen H, Segman R, et al. 1997 Excess dopamine $D_4$ receptor ($D_4$DR) exon III seven repeat allele in opioid-dependent subjects. Mol Psychiatr 2:251-4; Mel H, Horowitz R, Ohel N, et al. 1998 Additional evidence for an association between the dopamine $D_4$ receptor ($D_4$DR) exon III seven-repeat allele and substance abuse in opioid dependent subjects: Relationship of treatment retention to genotype and personality. Addiction Biology 3:473-81). Long alleles of the $D_4$ exon 3 polymorphism may also be associated with increased difficulty in quitting smoking, which may be related to nicotine addiction (Shields P G, Lerman C, Audrain J, et al. 1998 Dopamine $D_4$ receptors and the risk of cigarette smoking in African-Americans and Caucasians. Cancer Epidemiology, Biomarkers & Prevention 7:453-8).

Parkinson's Disease/Parkinsonism

Parkinson's disease is a progressive disorder of movement, characterized by tremor, rigidity, and bradykinesia. Other manifestations include depression, dementia (especially in advanced disease), and psychosis (especially as a complication of dopaminergic therapy). Parkinson's disease affects approximately 0.1% of the population, usually beginning after age 50. The major pathology is loss of dopaminergic neurons of the zona compacta in the substantia nigra. The major treatment is administration of dopamine precursors or agonists, but these are incompletely effective and are associated with side effects including dyskinesias, psychosis, and hypotension. Anticholinergic drugs are occasionally used, but are of limited efficacy and poorly tolerated.

Traditional antipsychotic drugs (neuroleptics) block the dopamine $D_2$ receptor and commonly produce symptoms of Parkinson's disease "Parkinsonism" in a dose-dependent manner corresponding to the potency of their $D_2$-blockade.

Dopamine synthesis in mouse dorsal striatum is increased in $D_4$ knockout mice (Rubinstein M, Phillips T J, Bunzow J R, et al. 1997 Mice lacking dopamine $D_4$ receptors are supersensitive to ethanol, cocaine, and methamphetamine. Cell 90:991-1001.). This suggests that a $D_4$ antagonist might have efficacy in treating Parkinson's disease, both in the treatment of the primary symptoms and in the treatment of both psychiatric and movement side-effects of standard dopaminergic therapies.

Several studies have suggested benefit of the atypical antipsychotic clozapine not only for treatment levodopa induced psychosis, but also for treatment of Parkinsonian symptoms themselves, especially tremor. These findings were reviewed by Factor and Friedman (Factor S A, Friedman J H. 1997 The emerging role of clozapine in the treatment of movement disorders. Movement Disorders 12:483-96). Clozapine, in addition to prominent $D_4$ blockade, has activity at multiple other receptors, notably serotonin 5-$HT_2$ and acetylcholine muscarinic. It is unlikely that anticholinergic effects account for clozapine's efficacy, as anticholinergic non-responders have responded dramatically to clozapine. While this may be due in part to 5-$HT_2$ antagonism; replacement of clozapine by olanzapine, a potent antagonist of 5-$HT_2$ (albeit with greater dopamine $D_2$ affinity than clozapine), was associated with increased Parkinsonian symptoms in a study of patients with Parkinson's disease (Friedman J H, Goldstein S, Jacques C. 1998 Substituting clozapine for olanzapine in psychiatrically stable parkinson's disease patients: Results of an open label pilot study. Clin Neuropharmacol 21:285-8). Dyskinesias and dystonia, associated with the use of levodopa, have also been reported to improve with clozapine (Factor S A, Friedman J H. 1997 The emerging role of clozapine in the treatment of movement disorders. Movement Disorders 12:483-96).

Further support for the potential role of the $D_4$ receptor in Parkinson's disease comes from a report of increased incidence of long ($\geq 6$ repeats) alleles of the $D_4$ exon 3 polymorphism in Parkinson's disease (Ricketts M H, Hamer R M, Manowitz P, et al. 1998 Association of long variants of the dopamine $D_4$ receptor exon 3 repeat polymorphism with Parkinsons-disease. Clinical Genetics 54:33-8).

Tardive Dyskinesia (Hereinafter TD)

Tardive dyskinesia is a movement disorder, consisting of involuntary choreiform, athetoid, or rhythmic movements of the tongue, jaw or extremities which develops as a result of (usually chronic) administration of neuroleptics and typically persists even after these drugs are discontinued. The overall prevalence of Neuroleptic-Induced Tardive Dyskinesia in patients who have received long-term neuroleptic treatment is estimated at 20-30% (American Psychiatric Association: Diagnostic and Statistical Manual of Mental Disorders, Fourth edition. Wash., D.C., American Psychiatric Association, 1994).

Increased concentrations of $D_4$ receptor have been reported in some post-mortem studies of schizophrenics (usually treated for extended periods with traditional neuroleptics) (Lahti R A, Roberts R C, Cochrane E V, et al. 1998 Direct determination of dopamine $D_4$ receptors in normal and schizophrenic postmortem brain tissue: A ($^3$H)NGD-94-1 study. Mol Psychiatr 3:528-33; Seeman P, Guan H C, Van Tol HH. 1995 Schizophrenia: elevation of dopamine $D_4$-like sites, using [$^3$H]nemonapride and [$^{125}$I]epidepride. Eur J Pharmacol 286:R3-5). An up-regulation of the $D_2$ receptor has been seen with chronic administration of the neuroleptic haloperidol in both animal and human studies (Schroder J, Silvestri S, Bubeck B, et al. 1998 $D_2$ dopamine receptor up-regulation, treatment response, neurological soft signs, and extrapyramidal side effects in schizophrenia: a follow-up study with $^{123}$I-iodobenzamide single photon emission computed tomography in the drug-naive state and after neuroleptic treatment. Biol Psychiatry 43:660-5). Use of these drugs might also be responsible for up-regulation of the $D_4$ receptor.

Improvement in TD has been seen with clozapine (Bassitt D P, Louza-Neto M R. 1998 Clozapine efficacy in tardive dyskinesia in schizophrenic patients. European Archives of Psychiatry & Clinical Neuroscience 248:209-11) a drug with prominent $D_4$ antagonism. While clozapine has other pharmacologic actions, notably 5$HT_2$ receptor blockade, an effect on T.D. has not to date been established for 5$HT_2$/$D_2$ receptor antagonists such as risperidone or olanzapine. The concern might be raised that chronic $D_4$ blockade might also cause tardive dyskinesia, however this complication has been exceedingly rare in patients treated with clozapine.

Gilles de la Tourette Syndrome (Hereinafter TS)

Gilles de la Tourette syndrome, a condition manifest by motor and vocal tics, with a prevalence of approximately 0.5% (most common in adolescents), is seen with increased frequency in patients with ADHD and/or OCD, and in family members of patients with those conditions. Use of stimulant drugs (which increase synaptic dopamine concentrations) in patients with ADHD has been associated with an increased incidence of tics and possibly TS (Erenberg G, Cruse R P, Rothner A D. 1985 Gille de la Tourette's syndrome: Effects of stimulant drugs. Neurology 35:1346-8). An increased incidence of the D4.7 allele has been reported in TS (Grice D E, Leckman J F, Pauls D L, et al. 1996 Linkage disequilibrium between an allele at the dopamine $D_4$ receptor locus and Tourette syndrome, by the transmission-disequilibrium test. American Journal of Human Genetics 59:644-52), and haloperidol (a $D_2$/$D_4$ dopamine antagonist) is effective at controlling tics.

SUMMARY OF THE INVENTION

According to one aspect of the present invention, there is provided a compound of formula I:

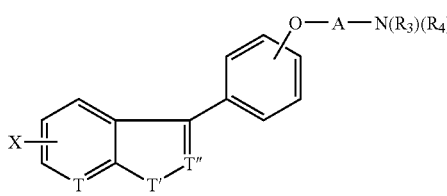

Formula I a pharmaceutically acceptable salt or stereoisomer thereof, wherein
  T, T' and T" are respectively
    C, O and N producing benzisoxazolyl,
    C, S and C producing benzthienyl, or
    N, O and N producing pyridoisoxazolyl;
  X is hydrogen or halo;
  A is —$CH_2CH_2$— or —$CH_2C(R_1)(R_2)CH_2$—, wherein
    $R_1$ is H, OH or $C_{1-6}$ alkoxy; and
    $R_2$ is H or $C_{1-6}$ alkyl;
  $R_3$ is $(CH_2)_n$ Q, $CH_2CH(OH)Q$ or $CH(CH_3)Q$, 1,2,3,4-tetrahydronaphthyl, indanyl optionally substituted with hydroxy, or adamantyl, wherein
    Q is thienyl, phenyl, furanyl, naphthyl, pyridyl, indolyl, indazolyl, cyclohexyl, 1,2-methylenedioxyphenyl, cyclohexenyl, 1H-pyrazolo[4.3-c]pyridyl, and
    Q is optionally substituted with one or two moieties independently selected from halo, $C_{1-6}$ alkyl, $C_{1-6}$ alkoxy, hydroxy, $S(O)_2NH_2$, trifluoromethyl, or cyano, and
    n is 0,1 or 2;
  $R_4$ is H or $C_{1-6}$ alkyl; or
  $R_3$ and $R_4$, together with the nitrogen atom to which $R_3$ and $R_4$ are attached, form 4,5,6,7-tetrahydrothieno [3,2,c] pyridinyl,1,4-dioxa-8-azo-spiro[4.5]decanyl, piperazinyl, morpholinyl, piperidinyl, pyrrolidinyl, azepanyl, azocanyl, 1,2,3,4-tetrahydroisoquinolinyl, 1,2,3,4-tetrahydro-1H-β-carbolinyl, or 8-aza-bicyclo[3.2.1.] octanyl, each of which may be mono- or independently di-substituted with halo, $C_{1-6}$ alkyl, $C_{1-6}$ alkoxy, $C_{1-6}$ alkoxymethyl, C(O)phenyl, OH, phenyl, CN, O-phenyl or $(CH_2)_mZ$,
    Z is benzisoxazolyl, indazolyl, benzisothiazolyl, benzthienyl, pyrimidinyl, pyridyl, 1,2-methylenedioxyphenyl, or phenyl, and
    Z, CH(OH)phenyl, phenyl or O-phenyl are optionally substituted with one or two moieties independently selected from halo, $C_{1-6}$ alkyl, $C_{1-6}$alkoxy, hydroxy, trifluoromethyl, $S(O)_2NH_2$ or cyano, and
    m is 0 or 1.

Another aspect of the invention is to provide a pharmaceutical composition comprising a compound of formula I in an amount effective to antagonize $D_4$ receptor stimulation and a pharmaceutically acceptable carrier.

In yet another of its aspects, the invention provides the use of compounds of Formulas I as $D_4$ receptor antagonists for the treatment of medical conditions mediated by inhibition of $D_4$ receptor. These conditions comprise, for example, Attention Deficit Hyperactivity Disorder, Obsessive-Compulsive Disorder, Psychoses, Substance Abuse, Substance Dependence, Parkinson's Disease, Parkinsonism, Tardive Diskinesia, Gilles de la Tourette Syndrome, Conduct Disorder, and Oppositional Defiant Disorder.

A further aspect of the invention is to provide intermediates and a method of making compounds of the formula I.

DETAILED DESCRIPTION OF THE PRESENT INVENTION

Terms used herein have the following meanings:

a) "Pharmaceutically acceptable salts" means either an acid addition salt or a basic addition salt which is compatible with the treatment of patients for the intended use.

"Pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid, and sulfonic acids such as methanesulfonic acid, naphthalene sulfonic acid, and 2-hydroxyethanesulfonic acid. Either the mono- or di-acid salts can be formed, and such salts can exist in either a hydrated solvated or substantially anhydrous form. In general, the acid addition salts of these compounds are more soluble in water and various hydrophilic organic solvents. Furthermore, in comparison to their free base forms, the acid addition salts generally demonstrate higher melting points.

"Pharmaceutically acceptable basic addition salts" means non-toxic organic or inorganic basic addition salts of the compounds of Formula (I) or any of its intermediates. Examples are alkali metal or alkaline-earth metal hydroxides such as sodium, potassium, calcium, magnesium or barium hydroxides; ammonia, and aliphatic, alicyclic, or aromatic organic amines such as methylamine, trimethylamine and picoline. The selection criteria for the appropriate salt will be known to one skilled in the art.

b) "Stereoisomers" is a general term for all isomers of the individual molecules that differ only in the orientation of their atoms in space. It includes mirror image isomers (enantiomers), geometric (cis/trans) isomers, and isomers of compounds with more than one chiral center that are not mirror images of one another (diastereoisomers).

c) "Alkyl" as used herein means a branched or straight chain alkyl (monovalent) or alkylene (divalent) hydrocarbon radical, as is appropriate to the formula, specified by the amount of carbons in the alkyl, e.g., $C_{1-6}$ alkyl means a one, two, three, four, five or six carbon branched or straight chain alkyl or alkylene, as the case may be, or any ranges thereof, for example, but not limited to $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$, $C_{5-6}$, etc.

d) "Patient" means a warm blooded animal, such as for example rat, mice, dogs, cats, guinea pigs, and primates such as humans.

e) "Treat" or "treating" means to alleviate symptoms, eliminate the causation of the symptoms either on a temporary or permanent basis, or to prevent or slow the appearance of symptoms of the named disorder or condition.

f) "Therapeutically effective amount" means a quantity of the compound which is effective in treating the named disorder or condition.

g) "Pharmaceutically acceptable carrier" is a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

h) "Psychoses" means conditions wherein the patient experiences a major mental disorder of organic and/or emotional origin characterized by derangement of the personality and loss of contact with reality, often with delusions, halucinations or illusions. Representative examples of psychotic illnesses include schizophrenia, schizophreniform disorder, schizoaffective disorder, delusional disorder, brief psychotic disorder, shared psychotic disorder, psychotic disorder not otherwise specified, and substance-induced psychotic disorder. See Diagnostic and Statistical Manual of Mental Disorders, 4th ed., American Psychiatric Association, incorporated herein by reference.

i) "Attention-Deficit/Hyperactivity Disorder" or "ADHD" means a condition wherein the patient exhibits a persistent pattern of inattention and/or hyperactivity-impulsivity that is more frequent and severe than is typically observed in individuals at a comparable level of development. It includes ADHD Combined Type, ADHD Predominantly Inattentive Type, and ADHD Predominantly hyperactive-Impulsive Type.

j) "Conduct Disorder" means a disorder wherein the patient exhibits a repetitive and persistent pattern of behavior in which the basic rights of others or major age-appropriate societal norms or rules are violated. These behaviors fall into four main groupings: aggressive conduct that causes or threatens physical harm to other people or animals, nonaggressive conduct that causes property loss or damage, deceitfulness or theft, and serious violations of rules.

k) "Oppositional Defiant Disorder" means a disorder wherein the patient exhibits some of the patterns of behavior observed in Conduct Disorder (e.g., disobedience and opposition to authority figures), however it does not include the persistent pattern of the more serious forms of behavior in which either the basic rights of others or age-appropriate societal norms or rules are violated.

l) "Obsessive-Compulsive Disorder" or "OCD" means a condition wherein the patient exhibits recurrent obsessions or compulsions that are severe enough to be time consuming (i.e., take more than an hour a day) or cause marked distress or significant impairment. Obsessions are persistent ideas, thoughts, impulses, or images that are experienced as intrusive and inappropriate and that cause marked anxiety or distress. Compulsions are repetitive behaviors (e.g, hand washing, ordering, checking) or mental acts (e.g., praying, counting, repeating words silently) the goal of which is to prevent or reduce anxiety or distress, not to provide pleasure or gratification.

m) "Substance Dependence" means a condition wherein the patient exhibits a maladaptive pattern of substance use, leading to clinically significant impairment or distress. There is a pattern of repeated self-administration that usually results in tolerance, withdrawal, and compulsive drug-taking.

n) "Substance Abuse" means a condition wherein the patient exhibits a maladaptive pattern of substance use manifested by recurrent and significant adverse consequences related to the repeated use of substances. There may be repeated failure to fulfill major role obligations, repeated use in situations in which it is physically hazardous, multiple legal problems, and recurrent social and interpersonal problems. Unlike the criteria for Substance Dependence, the criteria for Substance Abuse do not include tolerance, withdrawal, or a pattern of compulsive use and instead only include the harmful consequences of repeated use.

o) "Parkinson's Disease" means a slowly progressive neurological condition, characterized by tremor, rigidity, bradykinesia, and postural instability. Other manifestations include depression and dementia.

p) "Parkinsonism" means a condition where the patient exhibits parkinsonian signs or symptoms (i.e. tremor, muscular rigidity, or akinesia) that develop in association with the use of neuroleptic medication.

q) "Neuroleptic-Induced Tardive Dyskinesia" means a disorder characterized by involuntary movements of the tongue, jaw, trunk, or extremities which have developed in association with the use of neuroleptic medication. The involuntary movements may be choreiform, athetoid or rhythmic.

r) "Gilles de la Tourette Syndrome" means a condition manifested by motor and vocal tics. (A tic is a sudden, rapid, recurrent, nonrhythmic, stereotyped motor movement or vocalization.) The disturbance causes marked distress or significant impairment in social, occupational, or other important areas of functioning. The onset is before age eighteen years and the disturbance is not due to the physiological effects of a substance or general medical condition.

s) Unless otherwise specified, "halo" or "halogen" means Cl, Br, F and I.

t) "Aryl sulfonyl" means the radical:

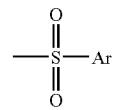

wherein Ar is phenyl optionally substituted one or more moieties from the group consisting of halogen, nitro, or $C_1$-$C_6$alkyl. "Brosyl" means the radical wherein Ar is p-bromobenzene. "Nosyl" means the radical wherein Ar is p-nitrobenzene. "Tosyl" means the radical wherein Ar is p-toluene.

"Alkyl sulfonyl" means the radical:

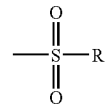

wherein R is $C_1$-$C_6$alkyl. "Mesyl" means the radical wherein R is $CH_3$.

u) "Sulfonic ester" means the radical:

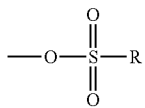

wherein R is $C_1$-$C_6$alkyl or phenyl optionally substituted with one or more moieties from the group consisting of halogen, nitro, or $C_1$-$C_6$alkyl. "Sulfonic esters" are, for example, brosylate, nosylate, tosylate, and mesylate.

v) "Parallel Synthesis" is a term used to describe the simultaneous synthesis of tens to millions of compounds in solution or on a solid phase. The key characteristic that distinguishes this approach from serial techniques is that it does not utilize mixtures.

As used herein, the terms used to describe specific chemical moieties are defined by the corresponding chemical drawings which are set forth on the following page:

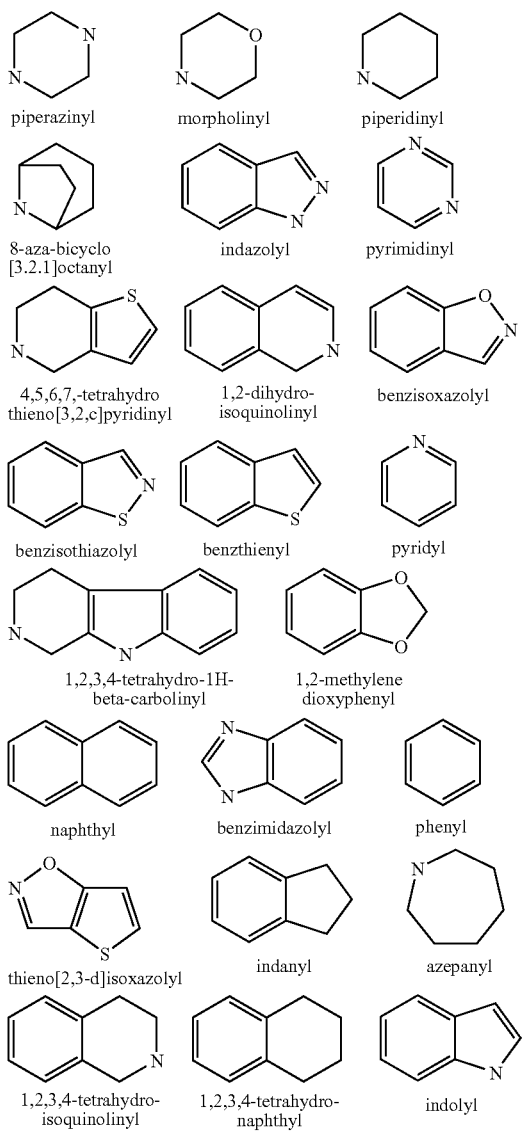

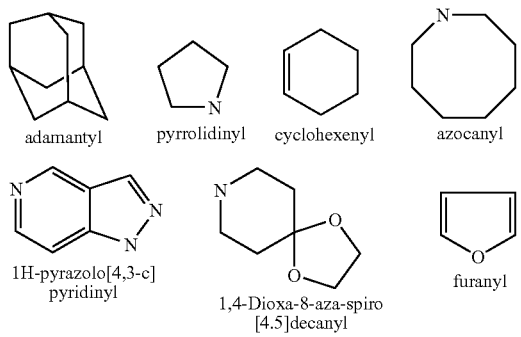

Specific embodiments of the invention are those compounds of Formula I set forth in Table 1.

An embodiment of the invention is the compound according to Formula 1 wherein T, T', and T" are respectively C, S, and C producing benzthienyl.

Another embodiment of the invention is the compound according to Formula 1 wherein T, T', and T" are respectively N, O, and N producing pyridoisoxazolyl.

Yet another embodiment of the invention is the compound according to Formula 1 wherein T, T', and T" are respectively C, O, and N producing benzisoxazolyl.

A preferred embodiment of the invention is the compound according to Formula 1 wherein T, T', and T" are respectively C, O, and N producing benzisoxazolyl; A is —$CH_2C$ $(R_1)(R_2)CH_2$; $R_1$ is H or OH; $R_2$ is H; $R_3$ is $(CH_2)_nQ$; n is 1 or 2; $R_4$ is H; Q is thienyl or phenyl; or $R_3$ and $R_4$, together with the nitrogen atom to which $R_3$ and $R_4$ are attached, form piperidinyl, azocanyl, morpholinyl, or pyrrolidinyl.

Most preferred embodiments of the invention are those compounds of Formula I set forth in Table 1 that exhibit enhanced $D_4$ potency.

Acid addition salts of the compound of Formula I are most suitably formed from pharmaceutically acceptable acids, and include for example those formed with inorganic acids, e.g. hydrochloric, sulphuric, or phosphoric acids, and organic acids, e.g. succinic, maleic, acetic or fumaric acid. Other non-pharmaceutically acceptable salts, e.g. oxalates, may be used for example in the isolation of compounds of Formula I for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base, e.g. sodium carbonate or potassium hydroxide, to liberate the free base which is then extracted into an appropriate solvent, such as ether. The free base is then separated from the aqueous portion, dried, and treated with the requisite acid to give the desired salt.

The compounds of the present invention can be prepared by processes analogous to those known in the art. Schemes I-IX illustrate methods for the synthesis of compounds of Formula I.

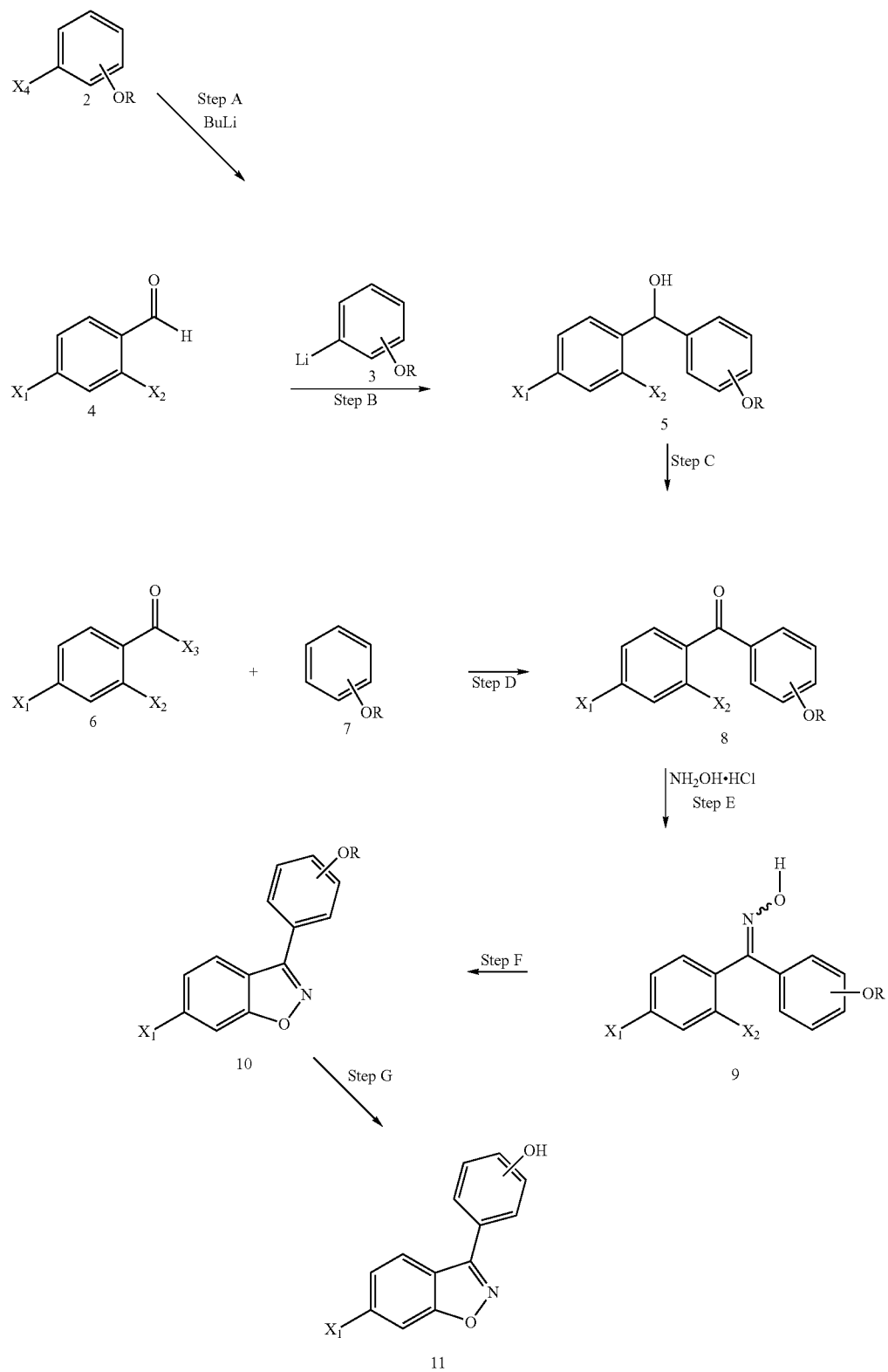
Scheme I
R = $C_1$-$C_6$ alkyl; $X_1$ = hydrogen or halo; $X_2$ = halo, preferably Cl; $X_3$ = Cl, Br, or I, preferably Cl;
$X_4$ = halo, preferably Br Scheme II
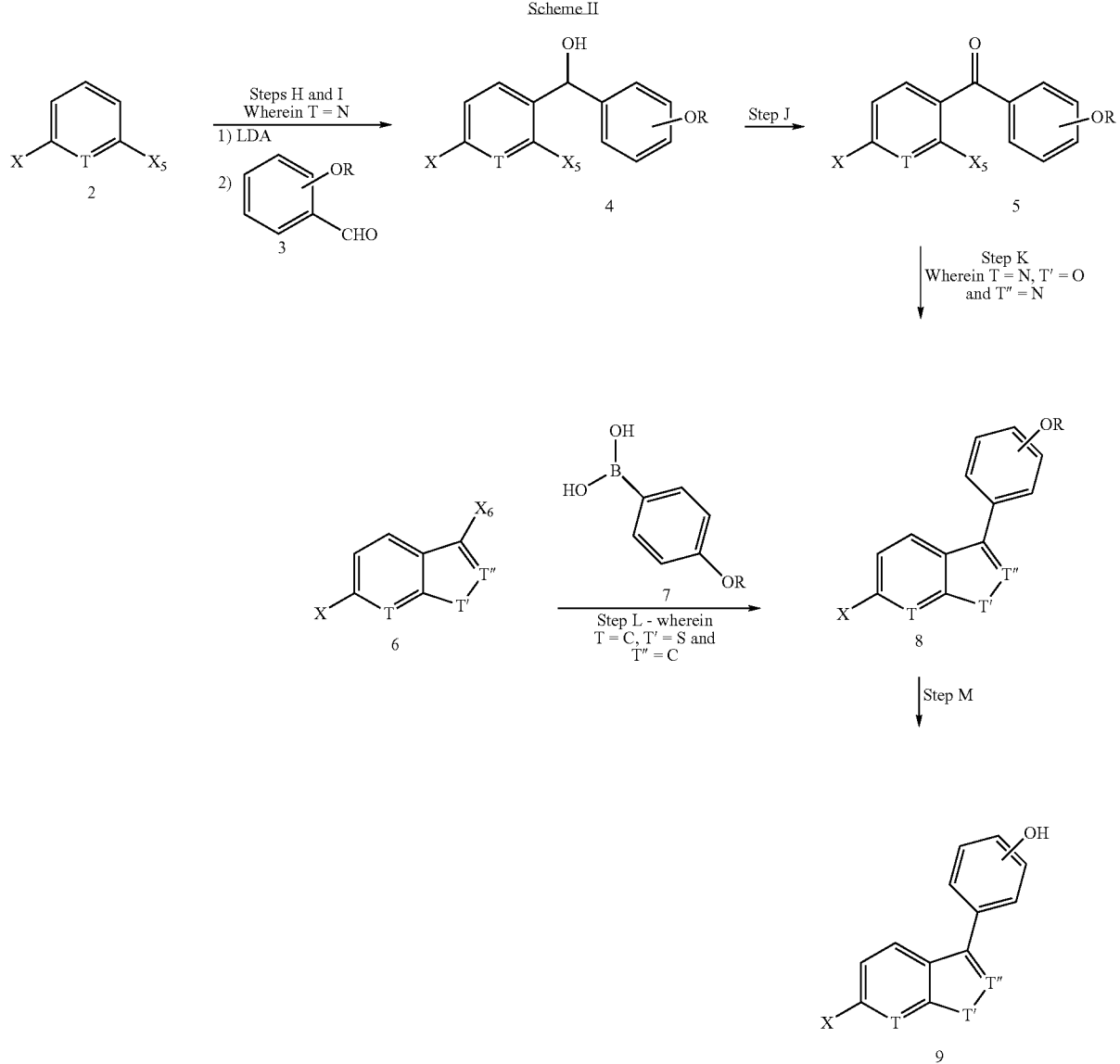
X is hydrogen or halo; $X_5$ = halo, preferably Cl; $X_6$ = halo, preferably Br;
R = $C_1$-$C_6$ alkyl; T, T', T" are respectively C, O, and N producing benzisoxazolyl, C, S, and C producing benzothienyl or N, O and N producing pyridoisoxazolyl
Scheme III
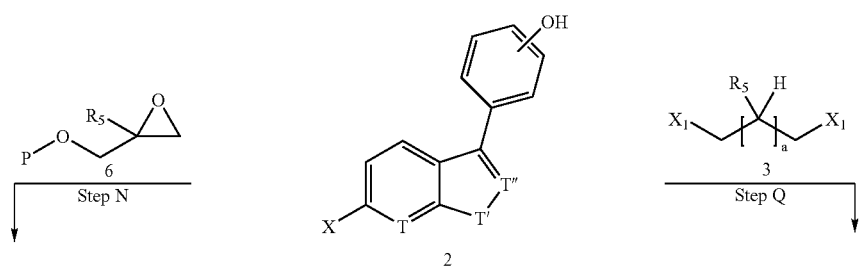

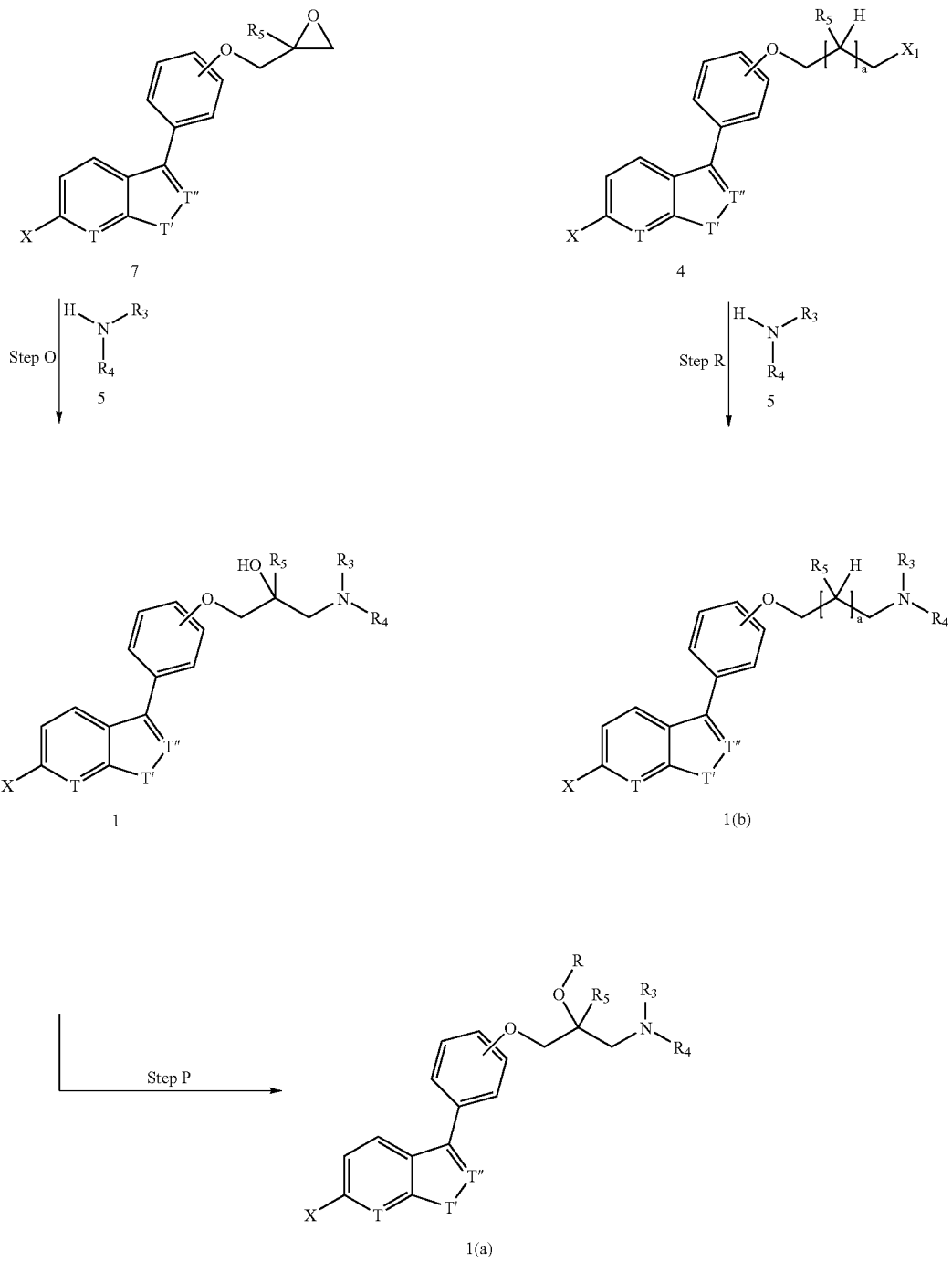

T, T′, T″ are respectively C, O and N producing benzisoxazolyl, C, S and C producing benzthienyl or N, O and N producing pyridoisoxazolyl; X = hydrogen or halo; $X_1$ is each independently Br, Cl. I, a sulfonic ester (such as tosylate, brosylate, nosylate, mesylate) or a nitrobenzoate ester, $R_5$ = hydrogen or $C_1$-$C_6$ alkyl; $R_3$ is $(CH_2)_yQ$, $CH_2CH(OH)Q$, $CH(CH_3)Q$, 1,2,3,4-tetrahydronaphthyl, indanyl optionally substituted with hydroxy, or adamantyl, where Q is thienyl, phenyl, furanyl, napthyl, pyridyl, indolyl, indazolyl, cyclohexyl, 1,2-methylenedioxyphenyl, cyclohexenyl, 1H-pyrazolo[4.3-c]pyridyl, and Q is optionally substituted with one or two moieties independently selected from halo, $C_1$-$C_6$ alkyl, $C_1$-$C_6$alkoxy, hydroxy, $S(O)_2NH_2$, trifluoromethyl, or cyano, and y is 0, 1 or 2; $R_4$ is H or $C_1$-$C_6$ alkyl; or $R_3$ and $R_4$, together with the nitrogen atom to which $R_3$ and $R_4$ are attached, form 4,5,6,7-tetrahydrothieno [3,2,c] pyridinyl, 1,4-dioxa-8-azo-spiro[4.5]decanyl, piperazinyl, morpholinyl, piperdinyl, pyrrolidinyl, azepanyl, azocanyl, 1,2,3,4-tetrahydroisoquinolinyl, 1,2,3,4-tetrahydro-1H-beta-carbolinyl, or 8-aza-bicylo[3.2.1]octanyl, each of which may be mono- or independently di-substituted with halo, $C_1$-$C_6$ alkyl, $C_1$-$C_6$ alkoxyl, $C_{1-6}$ alkoxymethyl, C(O)phenyl, OH, phenyl, CN, O-phenyl or $(CH_2)_mZ$, Z is benzisoxazolyl, indazolyl, benzisothiazolyl, benzthienyl, pyrimidinyl, pyridyl, 1,2-methylenedioxyphenyl, or phenyl, and Z, CH(OH)phenyl, phenyl or O-phenyl are optionally substituted with one or two moieties independently selected from halo, $C_1$-$C_6$ alkyl, $C_1$-$C_6$alkoxy, hyroxy, trifluoromethyl, $S(O)_2NH_2$ or cyano, m is 0 or 1; R is $C_1$-$C_6$ alkyl; a is 0 or 1; P is arylsulfonyl (such as tosyl), or alkylsulfonyl (such as mesyl), or nitrobenzoyl.

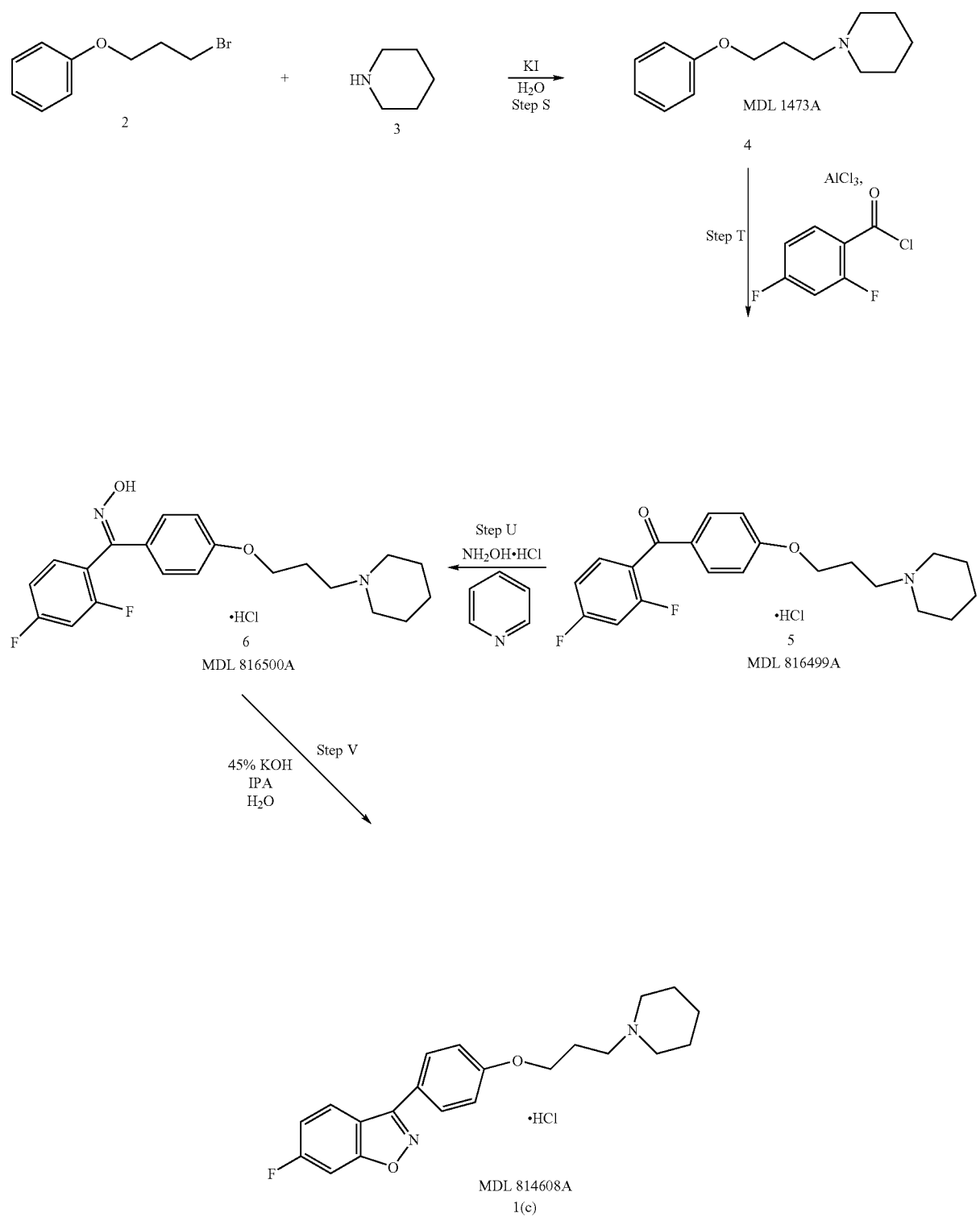

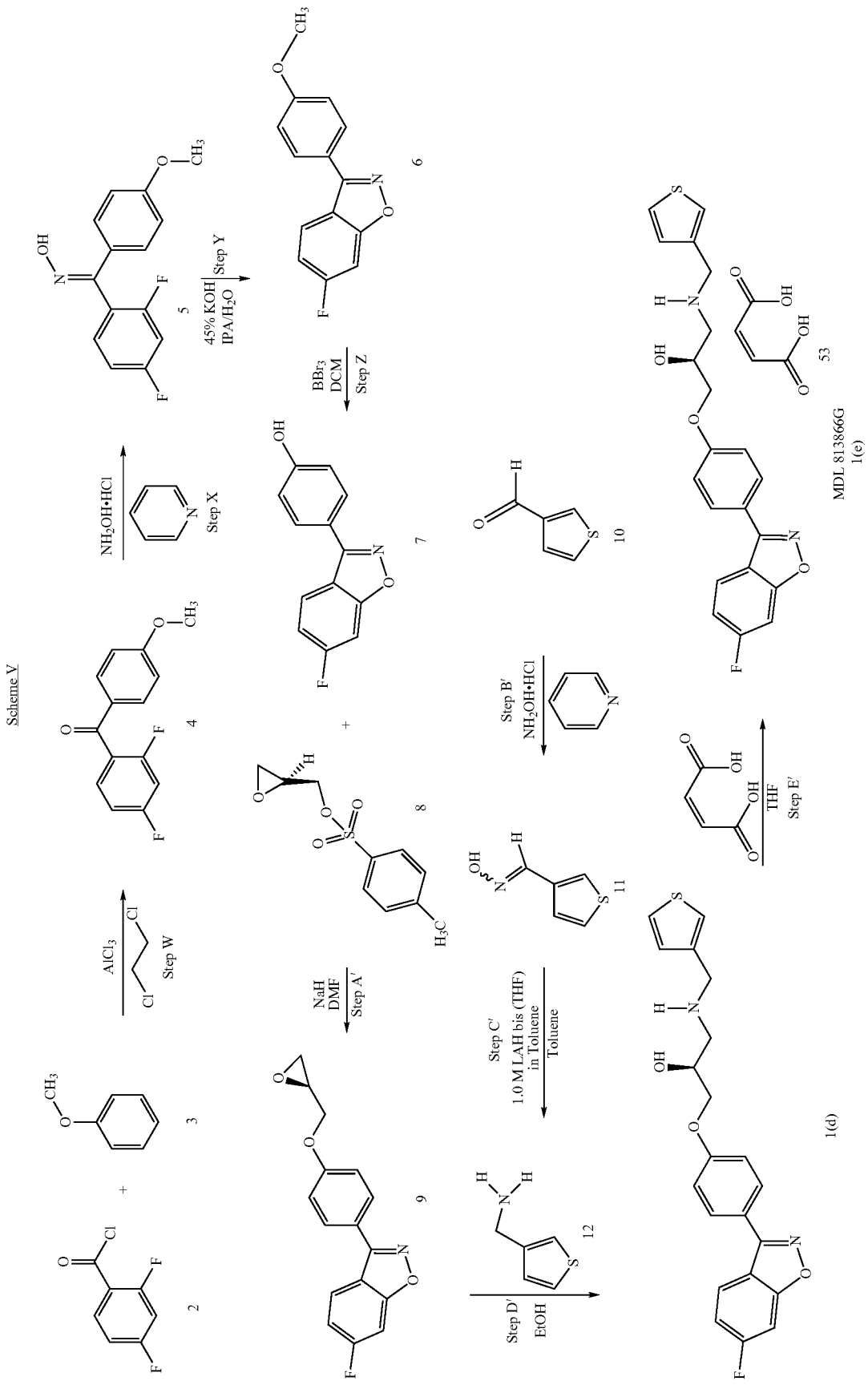
Scheme V

Scheme VI

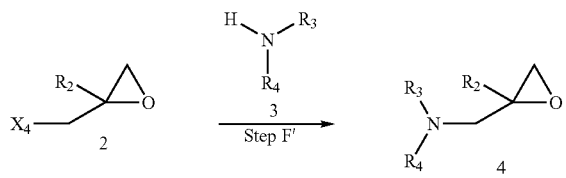

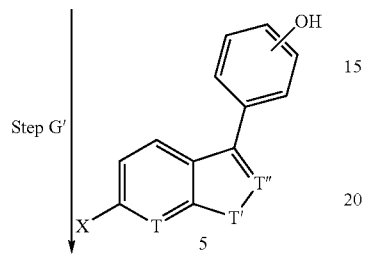

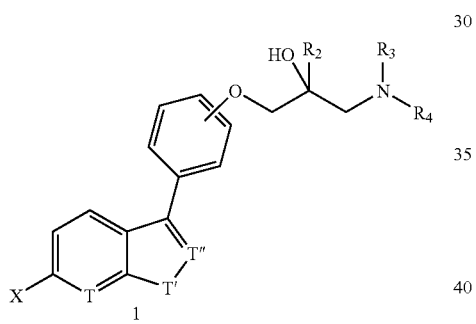

Scheme VII

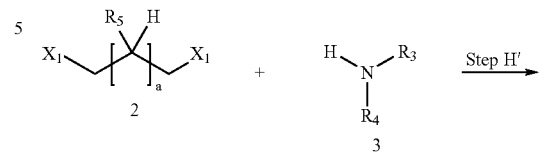

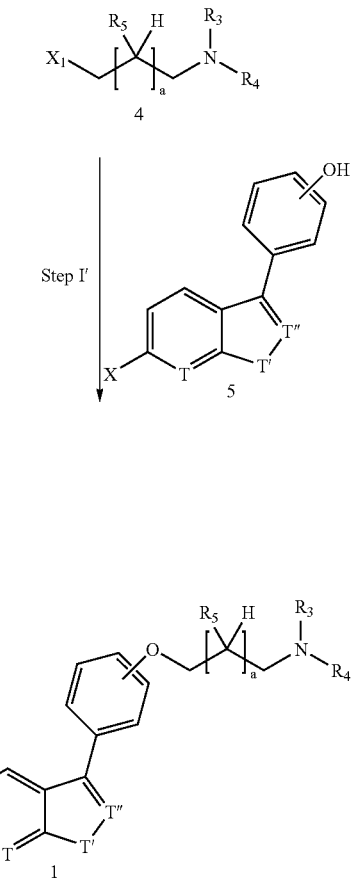

T, T', T" are respectively C, O and N producing benzisoxazolyl; C, S and C producing benzthienyl or N, O and N producing pyridoisoxazolyl; X = hydrogen or halo; $R_2$ = H or $C_{1-6}$ alkyl; $R_3$ is $(CH_2)_y$ Q, $CH_2CH(OH)Q$, $CH(CH_3)Q$, 1,2,3,4-tetrahydronapthyl, indanyl optionally substituted with hydroxy, or adamantyl, where Q is thienyl, phenyl, furanyl, napthyl, pyridyl, indolyl, indazolyl, cyclohexyl, 1,2-methylenedioxyphenyl, cyclohexenyl, 1H-pyrazolo[4.3-c]pyridyl, and Q is optionally substituted with one or two moieties independently selected from halo, $C_1$-$C_6$ alkyl, $C_1$-$C_6$alkoxyl, hydroxy, $S(O)_2NH_2$, trifluoromethyl, or cyano, and y is 0, 1 or 2; $R_4$ is H or $C_1$-$C_6$ alkyl; or $R_3$ and $R_4$, together with the nitrogen atom to which $R_3$ and $R_4$ are attached, form 4,5,6,7-tetrahydrothieno [3,2.c] pyridinyl, 1,4-dioxa-8-azo-spiro[4,5]decanyl, piperazinyl, morpholinyl, piperidinyl, pyrrolidinyl, azepanyl, azocanyl, 1,2,3,4-tetrahydroisoquinolinyl, 1,2,3,4-tetrahydro-1H-beta carbolinyl, or 8-aza-bicyclo[3.2.1]octanyl, each of which may be mono- or independently di-substituted with halo, $C_1$-$C_6$ alkyl, $C_1$-$C_6$ alkoxy, $C_{1-6}$ alkoxymethyl, C(O)phenyl, OH, phenyl, CN, O-phenyl or $(CH_2)_mZ$, Z is benzisoxazolyl, indazolyl, benzisothiazolyl, benthienyl, pyrimidinyl, pyridyl, 1,2-methylenedioxyphenyl, or phenyl, and Z, CH(OH)phenyl, phenyl or O-phenyl are optionally substituted with one or two moieties independently selected from halo, $C_1$-$C_6$ alkyl, $C_1$-$C_6$alkoxyl, hydroxy, trifluoromethyl, $S(O)_2NH_2$ or cyano; m is 0 or 1; $X_4$ is Br, Cl, I or a sulfonic ester (such as tosylate or nosylate).

T, T', T" are respectively C, O and N producing benzisoxazolyl; C, S and C producing benzthienyl or N, O and N producing pyridiosoxazolyl; X = hydrogen or halo; $X_1$ is each independently Br, Cl, I, an arylsulfonic ester (such as tosylate, brosylate and nosylsate), an alkylsulfonic ester (such as meyslate), or a nitrobenzoate ester; $R_3$ is $(CH_2)_yQ$, $CH_2CH(OH)Q$, $CH(CH_3)Q$, 1,2,3,4-tetrahydronapthyl, indanyl optionally substituted with hydroxy, or adamantyl, where Q is thienyl, phenyl, furanyl, napthyl, pyridyl, indolyl, indazolyl, cyclohexyl, 1,2-methylenedioxyphenyl, cyclohexenyl, 1H-pyrazolo[4,3-c]pyridyl, and Q is optionally substituted with one or two moieties independently selected from halo, $C_1$-$C_6$ alkyl, $C_1$-$C_6$alkoxy, hydroxy, $S(O)_2NH_2$, trifluoromethyl, or cyano, and y is 0, 1 or 2; $R_4$ is H or $C_1$-$C_6$ alkyl; or $R_3$ and $R_4$ together with the nitrogen atom to which $R_3$ and $R_4$ are attached, form 4,5,6,7-tetrahydrothieno-[3,2,c] pyridinyl, 1,4-dioxa-8-azo-spiro[4.5]decanyl, piperazinyl, morpholinyl, piperidinyl, pyrrolidinyl, azepanyl, azocanyl, 1,2,3,4-tetrahydroisoquinolinyl, 1,2,3,4-tetrahydro-1H-beta-carbolinyl, or 8-aza-bicyclo [3.2.1]octanyl, each of which may be mono- or independently di-substituted with halo, $C_1$-$C_6$ alkyl, $C_1$-$C_6$ alkoxyl, $C_{1-6}$ alkoxymethyl, C(O)phenyl, OH, phenyl, CN, O-phenyl or $(CH_2)_mZ$, Z is benzisoxazolyl, indazolyl, benzisothiazolyl, benzthienyl, pyrimidinyl, pyridyl, 1,2-methylenedioxyphenyl, or phenyl, and Z, CH(OH)phenyl, phenyl or O-phenyl are optionally substituted with one or two moieties independently selected from halo, $C_1$-$C_6$ alkyl, $C_1$-$C_6$alkoxyl, hydroxy, trifluoromethyl, $S(O)_2NH_2$ or cyano, m is 0 or 1; $R_5$ is H or $C_1$-$C_6$ alkyl; a is 0 or 1.

Scheme VIII

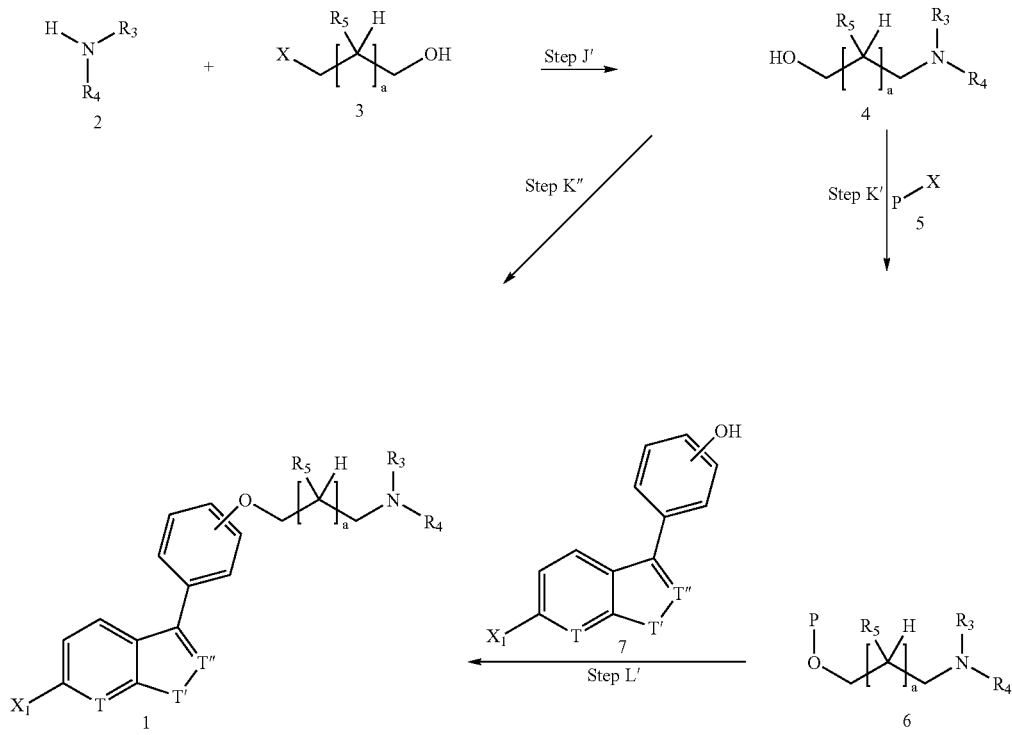

T, T', T'' are respectively C, O and N producing benzisoxazolyl, C, S and C producing benzthienyl or N, O and N producing pyridiosoxazolyl; P is arylsulfonyl (such as tosyl, brosyl and nosyl), alkylsulfonyl (such as mesyl) or nitrobenzoyl; X is Br, Cl, or I; $X_1$ is hydrogen or halo; $R_3$ is $(CH_2)_yQ$, $CH_2CH(OH)Q$, $CH(CH_3)Q$, 1,2,3,4-tetrahydronaphthyl, indanyl optionally substituted with hydroxy, or adamantyl, where Q is thienyl, phenyl, furanyl, naphthyl, pyridyl, indolyl, indazolyl, cyclohexyl, 1,2-methylenedioxyphenyl, cyclohexenyl, 1H-pyrazolo[4.3-c]pyridyl, and Q is optionally substituted with one or two moieties independently selected from halo, $C_1$-$C_6$ alkyl, $C_1$-$C_6$alkoxy, hydroxy. $S(O)_2NH_2$, trifluoromethyl, or cyano, and y is 0, 1 or 2; $R_4$ is H or $C_1$-$C_6$ alkyl; or $R_3$ and $R_4$, together with the nitrogen atom to which $R_3$ and $R_4$ are attached, form 4,5,6,7-tetrahydrothieno-[3,2,c]pyridinyl, 1,4-dioxa-8-azo-spiro[4.5]decanyl, piperazinyl, morpholinyl, piperidinyl, pyrrolidinyl, azepanyl, azocanyl, 1,2,3,4-tetrahydroisoquinolinyl, 1,2,3,4-tetrahydro-1H-beta-carbolinyl, or 8-aza-bicyclo[3.2.1]octanyl, each of which may be mono- or independently di-substituted with halo, $C_1$-$C_6$ alkyl, $C_1$-$C_6$ alkoxy, $C_{1-6}$ alkoxymethyl, C(O)phenyl, OH, phenyl, CN, O-phenyl or $(CH_2)_mZ$, Z is benzisoxazolyl, indazolyl, benzisothiazolyl, benzthienyl, pyrimidinyl pyridyl, 1,2-methylenedioxyphenyl, or phenyl, and Z, CH(OH)phenyl or O-phenyl are optionally substituted with one or two moieties independently selected from halo, $C_1$-$C_6$ alkyl, $C_1$-$C_6$alkoxy, hydroxy, trifluromethyl, $S(O)_2NH_2$ or cyano, m is 0 or 1; a is 0 or 1; and $R_5$ is H or $C_1$-$C_6$ alkyl.

Scheme IX

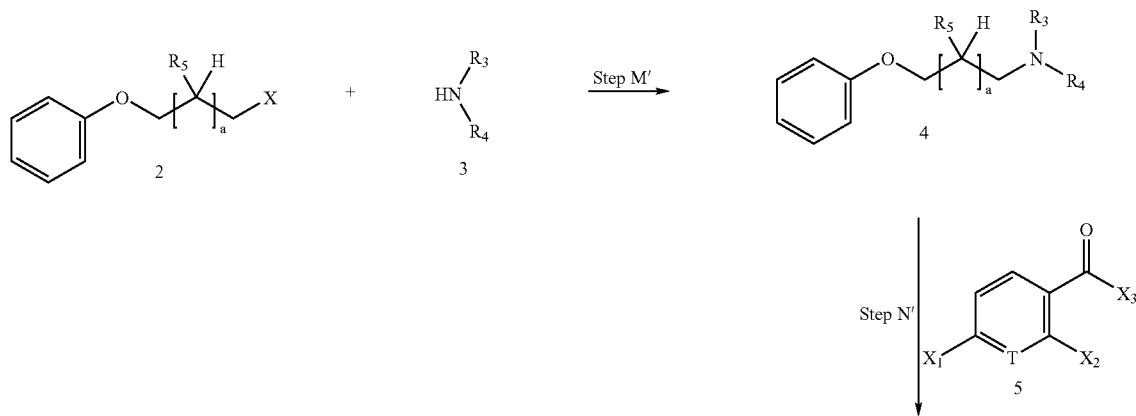

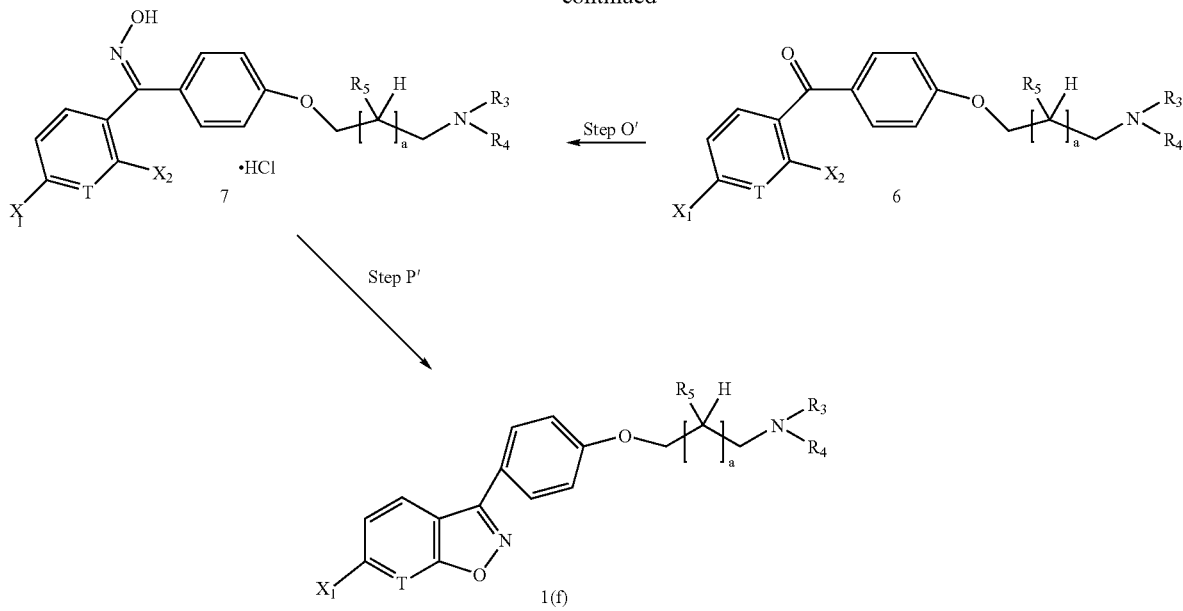

T = C or N; a = 0 or 1; X = Br, Cl or I, preferably Br; $X_1$ = hydrogen or halo; $X_2$ = halo; $X_3$ is Br, Cl, or I; $R_3$ is $(CH_2)_yQ$, $CH_2CH(OH)Q$, $CH(CH_3)Q$, 1,2,3,4-tetrahydronaphthyl, indanyl optionally substituted with hydroxy, or adamantyl, where Q is thienyl, phenyl, furanyl, naphthyl, pyridyl, indolyl, indazolyl, cyclohexyl, 1,2-methylenedioxy-phenyl, cyclohexenyl, 1H-pyrazolo[4.3-c]pyridyl, and Q is optionally substituted with one or two moieties independently selected from halo, $C_1$-$C_6$ alkyl, $C_1$-$C_6$ alkoxy, hydroxy, $S(O)_2NH_2$, trifluoromethyl, or cyano, and y is 0, 1 or 2; $R_4$ is H or $C_1$-$C_6$ alkyl; or $R_3$ and $R_4$, together with the nitrogen atom to which $R_3$ and $R_4$ are attached, form 4,5,6,7-tetrahydrothieno-[3,2,c] pyridinyl, 1,4-dioxa-8-azo-spiro[4.5]decanyl, piperazinyl, morpholinyl, piperidinyl, pyrrolidinyl, azepanyl, azocanyl, 1,2,3,4-tetrahydroisoquinolinyl, l,2,3,4-tetrahydro-1H-beta-carbolinyl, or 8-aza-bicyclo[3.2.1]octanyl, each of which may be mono- or independently di-substituted with halo, $C_1$-$C_6$ alkyl, $C_1$-$C_6$ alkoxy, $C_{1-6}$ alkoxyymethyl, C(O)phenyl, OH, phenyl, CN, O-phenyl or $(CH_2)_mZ$, Z is benzisoxazolyl, indazolyl, benzisothiazolyl, benzthienyl, pyrimidinyl, pyridyl, 1,2-methylenedioxyphenyl, or phenyl, and Z, CH(OH)phenyl, phenyl or O-phenyl are optionally substituted with one or two moieties independently selected from halo, $C_1$-$C_6$ alkyl, $C_1$-$C_6$alkoxy, hydroxy, trifluoromethyl, $S(OH)_2NH_2$ or cyano; and $R_5$ is H or $C_1$-$C_6$ alkyl.

In Scheme I, Steps A and B, n-butyl lithium is reacted with the appropriate alkoxy compound of structure 2 to give the corresponding lithiated compound of structure 3. The lithiated compound of structure 3 is then reacted with the appropriate aldehyde of structure 4 to give the corresponding substituted carbinol of structure 5 using techniques and procedures well known to one of ordinary skill in the art.

For example, n-butyl lithium can be reacted with the appropriate alkoxy compound of structure 2 in a suitable aprotic solvent, such as tetrahydrofuran. The reactants are typically stirred together at −78° C. for a period of time ranging from 10 minutes to 1 hour. The resulting lithiated compound of structure 6 is then reacted with the appropriate aldehyde of structure 4 and stirred together for a period of time ranging from 1 hour to 16 hours. The resulting substituted carbinol of structure 5 is recovered by a quench of the reaction mixture with cold water followed by extractive methods as are known in the art. The crude substituted carbinol of structure 5 may then be purified by chromatography or may be used in the next step without purification.

In Scheme I, Step C, the substituted carbinol of structure 5 is oxidized to give the corresponding substituted methanone of structure 8.

For example, manganese oxide can be reacted with the appropriate substituted carbinol of structure 5 in a suitable inert solvent, such as toluene. The reactants are typically stirred together at reflux temperatures for a period of time ranging from 2 hours to 16 hours. The resulting substituted methanone of structure 8 is recovered from the reaction mixture by filtration methods as are known in the art. The crude substituted methanone of structure 8 may then be purified by chromatography and trituration with a suitable inert solvent, such as pentane.

Alternatively, in Scheme I, Step D, the substituted benzoyl halide of structure 6 is reacted with an appropriate alkoxy benzene of structure 7 to give the corresponding substituted methanone of structure 8.

For example, the substituted benzoyl halide of structure 6 can be reacted with the appropriate alkoxy benzene of structure 7 and aluminum chloride in a suitable aprotic solvent, such as 1,2-dichloroethane. The reactants are typically stirred together at −3° C. for a period of time ranging from 1 to 16 hours. The resulting substituted methanone of structure 8 is recovered by extractive methods as are known in the art.

In Scheme I, Step E, the substituted methanone of structure 8 is reacted with hydroxylamine hydrochloride to give the corresponding methanone oxime of structure 9.

For example, the substituted methanone of structure 8 can be reacted with pyridine and hydroxylamine hydrochloride. The reactants are typically stirred together at 100° C. for a period of time ranging from 4 hours to 16 hours. The resulting oxime of structure 9 is recovered by extractive methods as are known in the art. The crude oxime of structure 9 may then be purified by recrystallization or may be used in the next step without purification.

In Scheme I, Step F, the oxime of structure 9 is reacted with an appropriate base to give the corresponding substituted phenyl benzisoxazole of structure 10.

For example, the methanone oxime of structure 9 can be reacted with the potassium tert-butoxide in an appropriate aprotic solvent, such as tetrahydrofuran. The reactants are typically stirred together at room temperature for a period of time ranging from 1.5 hours to 8 hours, followed by a reflux for a period of time ranging from 1.5 hours to 16 hours. The resulting substituted benzisoxazole of structure 10 is recovered from the reaction mixture by extractive methods as are known in the art. The crude substituted benzisoxazole of structure 10 may then be purified by chromatography and trituration with an appropriate solvent, such as pentane.

In Scheme I, Step G, the substituted benzisoxazole of structure 10 is reacted with boron tribromide to give the corresponding substituted benzisoxazole phenol of structure 11.

For example, the substituted benzisoxazole of structure 10 can be reacted with boron tribromide in a suitable inert solvent, such as dichloromethane. The reactants are typically stirred together at 0° C. for a period of time ranging from 3 hours to 16 hours. The resulting substituted benzisoxazole of structure 10 is recovered by a s quench of the reaction mixture with methanol followed by extractive methods as are known in the art and trituration.

In Scheme II, Steps H and I, an appropriate compound of the structure 2 is reacted with an appropriate aldehyde of the structure 3 to give the corresponding alcohol of the structure 4.

For example, the compound of structure 2 is reacted with lithium diisopropyl amide and an appropriate aldehyde of the structure 3. The reactants are typically stirred together for a period of time ranging from 45 minutes to 4 hours. The resulting alcohol of structure 4 is recovered from the reaction mixture by extractive methods as are known in the art. The crude alcohol of structure 4 may then be purified by chromatography.

In Scheme II, Step J, the alcohol of structure 4 is oxidized to give the corresponding substituted methanone of structure 5.

For example, the alcohol of structure 4 can be reacted with manganese oxide in a suitable inert solvent, such as toluene. The reactants are typically stirred together at reflux for a period of time ranging from 1 hour to 16 hours. The resulting substituted methanone of structure 5 is recovered from the reaction mixture by filtration methods as are known in the art.

In Scheme II, Step K, the substituted methanone of structure 5 is reacted with the potassium anion of acetone oxime to give the corresponding O-pyridyl oxime which is then cyclized in aqueous acid to give the compound of structure 8 (wherein T=N, T'=O and T"=N).

For example, the substituted methanone of structure 5 can be reacted with hydroxylamine hydrochloride to form the appropriate oxime, in a suitable aprotic solvent, such as dimethylformamide. The reactants are typically stirred together at room temperature for a period of time ranging from 4 to 16 hours. The resulting O-aryl oxime may then be cyclized in the presence of a suitable base, such as potassium t-butoxide, in a suitable solvent, such as dimethylformamide. The compound of structure 8 may be recovered from the reaction mixture by extractive methods as is known in the art. The crude cyclized compound of structure 8 may then be purified by chromatography.

Alternatively, in Step L, the appropriate thiophene of structure 6 is reacted with the appropriate phenyl boronic acid of structure 7 to give the corresponding compound of structure 8 (wherein T=C, T'=S and T"=C).

For example, the appropriate halothiophene of structure 6 can be coupled (Suzuki) with the appropriate boronic acid of structure 7, an appropriate base such as sodium bicarbonate and an appropriate transition metal catalyst, in a suitable aprotic solvent, such as toluene. The reactants are typically stirred together at a temperature ranging from 80° C. to reflux for a period of time ranging from 4.5 hours to 24 hours. The resulting compound of structure 8 is recovered by extractive methods as are known in the art. The crude compound of structure 8 may then be purified by chromatography. Alternatively, a Stille coupling may be employed to generate the compound of structure 8.

In Scheme II, Step M, the compound of structure 8 is reacted with boron tribromide to give the corresponding phenol of structure 9.

For example, the compound of structure 8 can be reacted with boron tribromide in a suitable inert solvent, such a 1,2-dichloroethane. The reactants are typically stirred together at a temperature ranging from 0° C. to 80° C. for a period of time ranging from 4 to 16 hours. The resulting phenol of structure 9 is recovered by a quench of the reaction mixture with sodium hydrogen carbonate, extractive methods as is known in the art and trituration.

In Scheme III, Step N, the phenol of structure 2 is reacted with an appropriate sulfonic ester or nitrobenzoate of the structure 6 to give the corresponding oxiranyl compound of structure 7.

For example, the phenol of structure 2 can be reacted with an appropriate sulfonic ester or nitrobenzoate of the structure 6, (such as (2R)-(−)-glycidyl-3-nitrobenzene sulfonate or (2R)-(−)-2-methylglycidyl 4-nitrobenzoate or (2S)-(+)-glycidyl tosylate) and sodium hydride, in a suitable aprotic solvent, such as dimethylformamide. The reactants are typically stirred together at room temperature for a period of time ranging from 16 hours to 2 days. The resulting oxiranyl compound of structure 7 is recovered by a quench of the reaction mixture with water, followed by extractive methods as are known in the art. The crude oxiranyl compound of structure 7 may then be purified by chromatography or recrystallization.

In Scheme III, Step O, the oxiranyl compound of structure 7 is reacted with the appropriate substituted amine of structure 5 to give the corresponding coupled compound of structure 1.

For example, the oxiranyl compound of structure 7 can be reacted with the appropriate substituted amine of structure 5 and an appropriate base, if needed, in a suitable aprotic solvent, such as acetonitrile. The reactants are typically stirred together at a temperature ranging from 50° C. to reflux for a period of time ranging from 3 hours to overnight. The resulting coupled compound of structure 1 is recovered by filtration or extractive methods as are known in the art. The crude coupled compound of structure 1 may then be purified by chromatography, recrystallization or salt formation.

Alternatively, in Scheme VI, Step G', the amino oxiranyl compound of structure 4 and the appropriate substituted thienyl or isoxazolyl phenol of structure 5 are reacted to give the corresponding coupled compound of structure 1.

For example, the amino oxiranyl compound of structure 4 can be reacted with the appropriate substituted thienyl or isoxazolyl phenol of structure 5 in the presence of aqueous sodium hydroxide, to form the appropriate coupled compound of structure 1. One skilled in the art would appreciate that when $R_4$=H, the nitrogen may require a protecting group. See *Protective Groups in Organic Synthesis*, $2^{nd}$ ed., Theodora W. Greene, et al. John Wiley and Sons, Inc., incorporated herein by reference, for appropriate protecting groups. The reactants are typically stirred together at room temperature for a period of 6 hours. The resulting coupled compound of structure 1 may be recovered from the reaction mixture by extractive methods as is known in the art. The crude coupled compound of structure 1 may then be purified by chromatography, recrystallization or salt formation.

In Scheme III, Step P, the coupled compound of structure 1 is alkylated with the appropriate alkylating agent to give the corresponding alkylated compound of structure 1(a).

For example, the coupled compound of structure 1 can be reacted, under nitrogen, with an appropriate base, such as potassium bis(trimethylsilyl)amide, in a suitable anhydrous, aprotic solvent, such as tetrahydrofuran. The reactants are typically stirred together at a temperature of about −20° C. for about 0.5 hours, treated with an appropriate alkylating agent, such as dimethyl sulfate and then stirred for an additional 1 hour at −20° C. The reaction is allowed to warm to room temperature and the alkylated compound of structure 1(a) is recovered by extractive methods as are known in the art. The crude alkylated compound of structure 1(a) may then be purified by chromatography, recrystallization or salt formation.

In Scheme III, Step Q, the phenol of structure 2 is reacted with the appropriate compound of the structure 3 to give the corresponding coupled compound of structure 4.

For example, the phenol of structure 2 can be reacted with the appropriate compound of the structure 3 and the appropriate base, in a suitable aprotic solvent, such as acetone. The reactants are typically stirred together at a temperature ranging from 25° C. to reflux for a period of time ranging from 6 hours to overnight. The resulting coupled compound of structure 4 is recovered by filtration or extractive methods as are known in the art. The crude coupled compound of structure 4 may then be purified by chromatography and recrystallization.

In Scheme III, Step R, the coupled compound of structure 4 is reacted with the appropriate amine of structure 5 to give the corresponding coupled compound of structure 1(b).

For example, the coupled compound of structure 4 can be reacted with the appropriate amine of structure 5 and the appropriate base, such as potassium carbonate, in a suitable aprotic solvent, such as acetonitrile. The reactants are typically stirred together at a temperature of about 75° C. for a period of time up to 24 hours. The resulting coupled compound of structure 1(b) is recovered by extractive methods as are known in the art. The crude, coupled compound 1(b) may be purified by chromatography, salt formation or recrystallization.

Scheme IV illustrates the synthesis of the compound labeled MDL 814608A.

Scheme V illustrates the synthesis of the compound MDL labeled 813866G.

Alternatively, in Scheme VII, Step H', the appropriate alkyl halide of structure 2 and the appropriate amine of structure 3 are reacted to form the halo alkyl amine of structure 4.

For example, the appropriate alkyl halide of structure 2 and the appropriate amine of structure 3 can be reacted in the presence of a suitable base, such as fused sodium acetate. The reactants are typically stirred and heated together at reflux, for several hours. The resulting halo alkyl amine of structure 4 may be recovered from the reaction mixture by extractive methods as is known in the art. The crude halo alkyl amine of structure 4 may then be purified by distillation and further extractive methods as is known in the art.

In Step I', the appropriate halo alkyl amine of structure 4 and the appropriate substituted thienyl or isoxazolyl phenol of structure 5 are reacted to give the corresponding amino alkoxy compound of structure 1.

For example, the appropriate substituted thienyl or isoxazolyl phenol of structure 5 can be reacted in the presence of sodium hydroxide in a suitable aprotic solvent, such as dichloromethane, to form the appropriate sodium salt of the substituted thienyl or isoxazolyl phenol of structure 5. The appropriate sodium salt of structure 5 is then combined with the appropriate halo alkyl amine of structure 4 in a suitable aprotic solvent, such as toluene. The reactants are typically stirred and heated together at reflux, for a period of time of about 24 hours. The reaction mixture may then be cooled and filtered to recover the amino alkoxy compound of structure 1. The crude amino alkoxy compound of structure 1 may then be purified by chromatography, recrystallization or salt formation.

As a second alternative, in Scheme VIII, Step J', the appropriate amine of structure 2 and the appropriate halo alcohol of structure 3 are reacted to give the corresponding hydroxy alkyl amine of structure 4.

For example, the appropriate amine of structure 2 can be reacted in the presence of water, with a suitable halo alcohol, such as 2-chloroethanol. The reactants are typically stirred and heated together for a period of time of ~5 hours. Typically, the mixture is cooled and then sodium hydroxide is added, followed by additional heat for ~30 minutes. The resulting hydroxy alkyl amine of structure 4 may be recovered from the reaction mixture by extractive methods as is known in the art. The water may be removed and the hydroxy alkyl amine of structure 4 may be purified by distillation or chromatography.

In Step K', the appropriate hydroxy alkyl amine of structure 4 and the appropriate sulfonate ester halide of structure 5 are reacted to give the corresponding sulfonate ester alkyl amine of structure 6. In the case where $R_4$=H, protection of the amine may be required, for example, with t-butoxycarbonyl. One skilled in the art would appreciate that such a protecting group as t-butoxycarbonyl can be removed by methods known to one skilled in the art, such as acid hydrolysis.

For example, the appropriately protected hydroxy alkyl amine of structure 4 and the appropriate sulfonate ester halide of structure 5 can be reacted in the presence of triethylamine in a suitable aprotic solvent, such as dichloromethane. The reactants are typically stirred together at room temperature. The resulting sulfonate ester alkyl amine of structure 6 may be recovered from the reaction mixture by extractive methods as is known in the art. The crude sulfonate ester alkyl amine of structure 6 may then be purified by chromatography.

As another alternative, when $R_5$ is hydrogen, in Scheme VIII, Step K", the appropriate hydroxy alkyl amine of structure 4 and the appropriate substituted thienyl or isoxazolyl phenol of structure 7 can be reacted to give the corresponding compound of structure 1.

For example, the appropriate substituted thienyl or isoxazolyl phenol of structure 7 in an appropriate solvent such as dichloromethane can be treated with triphenylphosphine, diethylazodicarboxylate and the appropriate hydroxy alkyl amine of structure 4 in an appropriate solvent such as dichloromethane at room temperature for a period of one to several hours. The resulting compound of structure 1 may be recovered from the reaction mixture by extractive methods as is known in the art. The crude compound of structure 1 may be purified by chromatography, salt formation or recrystallization. Other appropriate solvents for this reaction would be tetrahydrofuran, dioxane or diethyl ether, and other appropriate reagents would be tributylphosphine and diisopropylcarbodiimide or N,N,N',N'-tetramethyldicarboxamide. (References: O. Mitsunobu, Synthesis 1-28 (1981); T. A. Rano et al., Tetrahedron Lett. 36, 3789-3792 (1995).

In Step L', the appropriate sulfonate ester alkyl amine of structure 6 and the appropriate substituted thienyl or isoxazolyl phenol of structure 7 are reacted to give the corresponding compound of structure 1.

For example, the appropriate sulfonate ester alkyl amine of structure 6 and the appropriate substituted thienyl or isoxazolyl phenol of structure 7 can be reacted in the presence of potassium carbonate in a suitable aprotic solvent, such as acetonitrile. The reactants are typically stirred and heated together at 75° C. overnight. The resulting compound of structure 1 may be recovered from the reaction mixture by extractive methods as is known in the art. The crude compound of structure 1 may be purified by chromatography, salt formation or recrystallization.

In Scheme IX, Step M', the appropriate phenoxyalkyl halide of structure 2 is reacted with the appropriately substituted amine of structure 3 to give the corresponding phenoxyalkylamine of structure 4. Throughout Scheme IX, one skilled in the art would appreciate that certain moieties, if present, such as a secondary amino group, may require a protecting group.

For example, the appropriate phenoxyalkyl halide of structure 2 can be reacted with the appropriately substituted amine of structure 3 by mixing them in a suitable solvent, such as water, with an appropriate additive such as potassium iodide, if needed. The reactants are stirred together typically at a temperature ranging from 40° C. to reflux for a period of time ranging from 4 hours to overnight. The reaction mixture is then cooled and the resulting compound of structure 4 is recovered by extractive methods as are known in the art. The crude compound of structure 4 may be purified by distillation under vacuum or by chromatography.

In Step N', the phenoxyalkylamine of structure 4 is reacted with an aroyl halide of structure 5 to give the aryl-[(aminoalkoxy)-aryl]methanone of structure 6.

For example, the corresponding phenoxyalkylamine of structure 4 can be stirred in a suitable solvent such as dichloromethane under nitrogen and cooled to a temperature between −2 to 8° C. A suitable Lewis Acid catalyst can then be added while cooling is maintained. Suitable Lewis Acids may include aluminum chloride, zinc chloride or boron trifluoride etherate. Then the appropriate aroyl halide can be added while maintaining the temperature from −10 to 15° C. After that the reaction mixture can be allowed to warm up (20° C.) over a time period of 2-4 hours. The mixture can then be quenched into ice and neutralized with a suitable reagent such as, 50% sodium hydroxide. The crude product is isolated from the reaction mixture by separation of the organic layer, extraction of the aqueous layer with a suitable solvent, combining the organic layers and drying over a suitable agent such as $MgSO_4$. The solution containing the crude product of structure 6 is filtered and concentrated and the crude product is purified by methods known to one skilled in the art to give the aryl-[(aminoalkoxy)-aryl]methanone of structure 6.

In Step O' the aryl-[(aminoalkoxy)-aryl]methanone of structure 6 is reacted with hydroxylamine to give the corresponding aryl-[(aminoalkoxy)-aryl]methanone oxime hydrochloride of structure 7.

For example, the substituted methanone of structure 6 is mixed with hydroxylamine hydrochloride in a suitable solvent such as pyridine, under nitrogen. The mixture is heated to a temperature of approximately 80° C. for a period of from 2-6 hours. The mixture can then be cooled to room temperature and the volatiles can be removed and the crude mixture acidified with hydrochloric acid to give the crude hydrochloride salt of the oxime, of structure 7. This salt can then be purified by techniques which are known to one skilled in the art.

In Step P', the aryl-[(aminoalkoxy)-aryl]methanone oxime hydrochloride of structure 7 is cyclized to give the appropriate substituted benzisoxazole or pyridylisoxazole of compound 1(f).

For example, aryl-[(aminoalkoxy)-aryl]methanone oxime hydrochloride of structure 7 can be stirred in a suitable protic solvent such as isopropyl alcohol, methanol, ethanol or 2-methoxymethanol, any of which may be mixed with water. The mixture is treated with an appropriate base such as 45% potassium hydroxide solution or potassium carbonate with catalytic copper powder. Alternatively, the oxime of structure 7 can be stirred with an anhydrous solvent such as dimethylformamide or N-methylpyrrolidine under nitrogen. The mixture is treated with an appropriate base such as sodium hydride or potassium t-butoxide with catalytic copper powder. The reaction is held at a temperature from 40° C. to approximately 80° C., for a period of 4 hours to overnight. The mixture can be cooled and filtered, and the crude product isolated and purified by methods known to one skilled in the art, to give the appropriate substituted benzisoxazole or pyridylisoxazole of compound 1(f).

Starting materials for use in the general synthetic procedures outlined in Schemes I-IX are readily available to one of ordinary skill in the art, unless otherwise specified in the Examples section.

The $D_4$ binding profile of the present compounds indicates their utility as pharmaceuticals that may be useful as a neuroleptic for the treatment of various conditions in which $D_4$ receptor stimulation is implicated, such as for the treatment of anxiety and schizophrenia. Accordingly, in another of its aspects, the present invention provides pharmaceutical compositions useful to treat $D_4$-related medical conditions in which a compound of Formula I is present in an amount effective to antagonize $D_4$ receptor stimulation, together with a pharmaceutically acceptable carrier. In another of its aspects, the invention provides a method for treating medical conditions for which a $D_4$ antagonist is indicated, which comprises the step of administering to the patient an amount of a compound of Formula II effective to antagonize $D_4$ receptor stimulation, and a pharmaceutically acceptable carrier therefor.

For use in medicine, the compounds of the present invention can be administered in a standard pharmaceutical composition. The present invention therefore provides, in a further aspect, pharmaceutical compositions comprising a pharmaceutically acceptable carrier and a Formula I compound or a pharmaceutically acceptable salt, solvate, or hydrate thereof, in an amount effective to antagonize $D_4$ receptor stimulation.

In treating a patient afflicted with a condition described above, a compound of formula (I) can be administered in any form or mode which makes the compound bioavailable in therapeutically effective amounts, including orally, sublingually, buccally, subcutaneously, intramuscularly, intravenously, transdermally, intranasally, rectally, topically, and the like. One skilled in the art of preparing formulations can determine the proper form and mode of administration depending upon the particular characteristics of the compound selected for the condition or disease to be treated, the stage of the disease, the condition of the patient and other relevant circumstances. For example, see Remington's Pharmaceutical Sciences, 18th Edition, Mack Publishing Co. (1990), incorporated herein by reference.

The compounds of Formula I can be administered alone or in the form of a pharmaceutical composition in combination with pharmaceutically acceptable carriers, the proportion and nature of which are determined by the solubility and chemical properties of the compound selected, the chosen route of administration, standard pharmaceutical practice and other relevant criteria.

The compounds of the present invention may be administered orally, for example, in the form of tablets, troches, capsules, elixirs, suspensions, solutions, syrups, wafers, chewing gums and the like and may contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors.

The compounds of Formula (I) of this invention may also be administered topically, and when done so the carrier may suitably comprise a solution, ointment or gel base. The base, for example, may comprise one or more of petrolatum, lanolin, polyethylene glycols, bee wax, mineral oil, diluents such as water and alcohol, and emulsifiers and stabilizers.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials.

The dosage range at which the compounds of Formula I exhibit their ability to act therapeutically can vary depending upon the particular disease or condition being treated and its severity, the patient, the formulation, other underlying disease states that the patient is suffering from, and other medications that may be concurrently administered to the patient. Generally, the compounds of Formula I will exhibit their therapeutic activities at dosages of between about 0.001 mg/kg of patient body weight/day to about 100 mg/kg of patient body weight/day.

EXAMPLES

The following examples present typical syntheses as described in Schemes I-IX. These examples are understood to be illustrative only and are not intended to limit the scope of the present invention in any way. As used herein, the following terms have the indicated meanings: "g" refers to grams; "mmol" refers to millimoles; "mL" refers to milliliters; "C" refers to degrees Celsius; "TLC" refers to thin layer chromatography; "LC/MS" refers to liquid chromatography mass spectrometry; "APCI" refers to atmospheric pressure chemical ionization; "mp" refers to melting point; "ppm" refers to parts per million; "TMS" refers to tetramethylsilane; "GC/MS" refers to gas chromatography/mass spectroscopy; "Hz" refers to hertz; "MHz" refers to megahertz; "NMR" refers to nuclear magnetic resonance; "M/S" refers to mass spectra; "IR" refers to infrared spectra.

The following Table sets forth references to relevant starting materials for syntheses described herein. Where no synthesis for the starting material is indicated, the starting material is either known, available commercially, or can be prepared by conventional means. The U.S. Patents cited in the Table and elsewhere are herein incorporated by reference.

Starting Material by Reference

| Starting Material (SM) Number | Name of Compound | Structure | Reference |
|---|---|---|---|
| 1 | Thiophen-3-yl-methylamine hydrochloride | 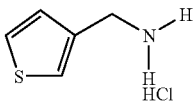 | M. R. Bryce, A. D. Chissel, N. R. M. Smith, D. Parker and P. Kathirgamanathan, Synthetic metals Vol. 26, pp. 153-168 (1988). |
| 2 | 4-(4-Fluoro-phenyl)-piperidine | 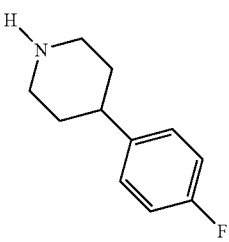 | Perregaard, J., Moltzen, E. K., Meier, E., Sanchez, C., J. Med. Chem. 1995, 38, 1998-2008. |

-continued

Starting Material by Reference

| Starting Material (SM) Number | Name of Compound | Structure | Reference |
|---|---|---|---|
| 3 | 3-Piperazin-1-yl-1H-indazole | 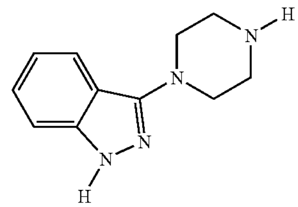 | U.S. Pat. No. 4,954,503. |
| 4 | 6-Fluoro-3-piperazin-1-yl-1H-indazole | 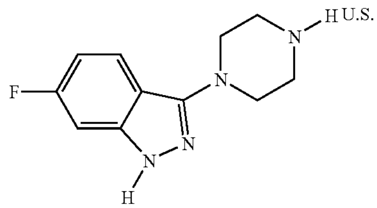 | U.S. Pat. No. 4,954,503. |
| 5 | 4-(4-Fluoro-phenoxy)-piperidine | 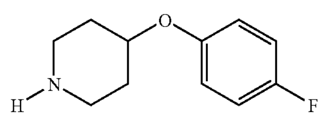 | U.S. Pat. No. 3,260,723. |
| 6 | {2-[3-(3-Bromo-phenyl)-pyrazolo[4,3-c]pyridin-1-yl]-ethyl}-methyl-amine | 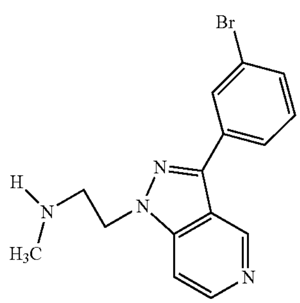 | U.S. Pat. No. 5,264,576 |
| 7 | 4-(3-Chloro-phenoxy)-piperidine | 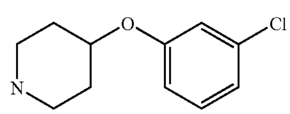 | Journal of Medicinal Chemistry, 1978, Vol. 21, No. 3, page 309. |
| 8 | 6-fluoro-3-piperidme-4-yl-benzo[d]isoxazole | 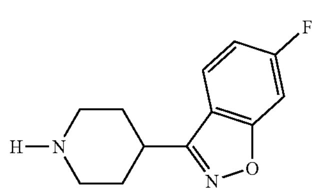 | U.S. Pat. No. 4,355,037 |
| 9 | Thiophen-3-yl-methylamine | 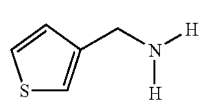 | Example 2A |
| 10 | (S)-oxiranylmethyl-thiophen-3-ylmethyl-amine | 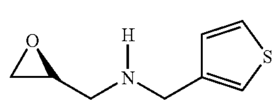 | U.S. Pat. No. 3,336,196 |

Example 1

MDL 814608A

Synthesis of 6-fluoro-3-[4-(3-piperidin-1-yl-propoxy)-phenyl]-benzo[d]isoxazole hydrochloride (Scheme IV, Compound 1c)

Scheme IV, Step S

Synthesis of 1-(3-phenoxy-propyl)-piperidine (Scheme IV, Compound 4)

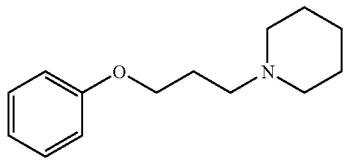

Mix 3-phenoxypropyl bromide (801.5 g, 3.73 mol), potassium iodide (61.8 g, 0.37 mol, 0.10 equivalents) and water (4.0 L) in a 12-L, 3-necked flask fitted with: a stirrer, thermometer in a side-arm adapter, connected to a Firestone® valve and an addition funnel fitted with a gas outlet adapter, connected to a bubbler. Add piperidine (634.6 g, 7.45 mol, 2.0 equivalents) over 1 hour, without cooling under nitrogen. The temperature at the end of the addition is 40° C. Heat the reaction mixture and maintain the temperature at 50° C. for 6 hours. Monitor the progress of the reaction by HPLC (Column=300×3.9 mm Phenomenex Bondclone 10 CN; mobile phase=65% acetonitrile:35% 0.1N ammonium formate buffer; flow=1.5 mL/minute; wavelength=215 nm; $R_T$: 3-phenoxypropyl bromide=2.3 minutes; 37=4.4 minutes). Typically, the conversion is 94%. Cool the reaction mixture to ambient temperature over a time period of 14 hours and extract with dichloromethane (2×4.0 L). Combine the organic extracts and dry over $MgSO_4$ (400 g). Filter off the drying agent and wash with dichloromethane (1.0 L). Concentrate the filtrate (35-40° C./50 torr) to give 800 g, 98% Yield) of 4, as an oil. HPLC analysis shows that 37 is 90% pure. Purify 4 (16.5 g portion) by distillation under vacuum and collect the title compound (10 g) as a colorless liquid at 99-105° C./0.3 mm: $^1$H NMR ($CDCl_3$, 200 MHz) δ 1.38-1.5 (m, 2H), 1.5-1.64 (m, 4H), 1.9-2.1 (m, 6H), 4.0 (t, 2H), 6.85-6.95 (m. 3H), 7.22-7.3 (t, 2H). Analysis calculated for $C_{14}H_{21}NO$: C, 76.67; H, 9.65; 6.39. Found: C, 76.55; H, 9.50; N, 6.22. [M+H]$^+$=220 m/e.

Scheme IV, Step T

Synthesis of (2,4-difluoro-phenyl)-[3-(3-piperidin-1-yl-propoxy)-phenyl]methanone hydrochloride (Scheme IV, Compound 5)

Mix 4 (0.777 kg, 3.54 mol) and dichloromethane (8.0 L) in a 22-L, 3-necked flask fitted with a stirrer and a thermometer, in a side-arm adapter, connected to a Firestone® valve. Stir the mixture and cool (−2° C.) under nitrogen. Add aluminum chloride (1.53 kg, 11.5 mol) via a "gooch" tube, over a time period of 1.5 hours. Maintain the reaction temperature (−2 to 8° C.) during addition and stir at −2 to 0° C. for 45 minutes. Add 2,4-difluorobenzoyl chloride (0.98 kg, 7.96 mol) over 1 hour, while maintaining the temperature (−2 to 10° C.). Allow the reaction mixture to warm up (20° C.) over a time period of 2 hours and monitor the progress of the reaction by HPLC (Column=300×3.9 mm Phenomenex Bondclone 10 CN; mobile phase=65% acetonitrile/ 35% 0.1N ammonium formate buffer; flow=1.5 mL/minute; wavelength=215 nm; $R_T$: 4=4.4 min; 5=3.6 min). Typically, conversion is 100%. Pour the reaction mixture into ice (17 kg) over a time period of 20 minutes and stir for 30 minutes. Add a 50% sodium hydroxide solution (3.0 L). All solids dissolve after adding 2.7 L. The pH of the mixture is 12.5. Stir the mixture for 15 minutes, separate the layers, extract the aqueous phase with dichloromethane (2 L), combine the organic layers and dry over 300 g of $MgSO_4$. Filter off the drying agent through celite and wash with dichloromethane (1.0 L). The filtration is slow. Concentrate the filtrate at 50° C./50 torr to give 1.676 kg of an oil. Add tert-butyl methyl ether (4.0 L) to the oil, heat (60° C.) for 15 minutes and filter through celite. Further dilute the filtrate with tert-butyl methyl ether (7.0 L) to eliminate cloudiness of the solution. Add hydrochloric acid in diethyl ether (3.5 L), which stains positive to congo red paper, over a period of time of 30 minutes, at 15-25 ° C. and stir for an additional 30 minutes. Filter off the precipitated solid, wash the filter cake with with tert-butyl methyl ether (8 L) and air dry to give 5 (1.129 kg, 81% Yield) as a solid. HPLC analysis shows 38 to be 98.3% pure. Heat a mixture of 5 (20 g) and isopropyl alcohol (120 mL) while maintaining the temperature (80° C.) for 10 minutes, and filter hot. Wash the insoluble solid (minor amount) with hot (60° C.) isopropyl alcohol (20 mL). Stir the filtrate and cool (20° C.) over the time period of 18 hours. Cool (5° C.) the mixture and maintain for 1 hour, filter off the solid, wash with cold (5° C.) isopropyl alcohol (20 mL) and dry at 80° C./50 torr for 72 hours to give the title compound (12.6 g, 63% Yield): mp 165.5-167.5° C.; $^1$H NMR (DMSO-$d_6$, 200 MHz) δ 1.25-1.5 (br S, 1H), 1.6-1.9 (m, 5H), 2.16-2.3 (m, 2H), 2.75-3 (br s, 2H), 3.1-3.2 (m, 2H), 3.35-3.55 (m, 2H), 4.12-4.26 (t, 2H), 7.05-7.12 (d, 2H), 7.25 (t, 1H), 7.45 (t, 1H), 7.62 (quar, 1H), 7.7-7.8 (d, 2H), 10.4-10.7 (br s, 1H). Analysis calculated for $C_{21}H_{23}NO_2F_2 \cdot HCl$: C, 63.71; H, 6.11; N, 3.54. Found: C, 63.62, H, 5.81; N, 3.38. [M+H]hu +=360 m/e.

Scheme IV, Step U

Synthesis of (2,4-difluoro-phenyl)-[3-(3-piperidin-1-yl-propoxy)-phenyl]-methanone oxime hydrochloride (Scheme IV, Compound 6)

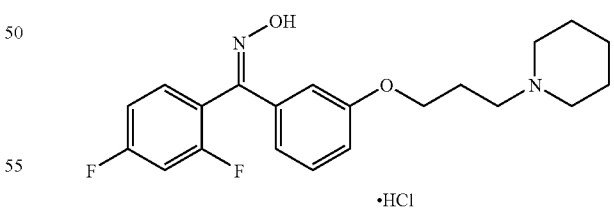

Mix 5 (1.108 kg, 2.8 mol), hydroxylamine hydrochloride (0.778 kg, 11.2 mol) and pyridine (5.54 L) in a 12-L, 3-necked flask fitted with a stirrer, thermometer in a side-arm adapter connected to a Firestone® valve and a reflux condenser fitted with a gas outlet adapter connected to a bubbler. Heat the mixture and maintain the temperature (80° C.) for 2 hours, under nitrogen. Monitor the progress of the reaction by HPLC (Column=300×3.9 mm Phenomenex Bondclone 10 CN; mobile phase=65% acetonitrile:35%

0.1N ammonium formate buffer; flow=1.5 mL/minute; wavelength=215 nm; $R_T$: 5=3.6 min; 6=3.0 min). Typically, the conversion is 100%. Cool the reaction mixture to ambient temperature and remove the solvent at 40-60° C./50 torr to give a solid. Add water (10 L) and 6N hydrochloric acid (0.75 L) to the solid residue over a time period of 30 minutes at 15-25° C. The pH of the mixture is 1.5. Stir the mixture for 30 minutes, filter off the solid and wash with water (8.0 L) and dry (60° C.) in a forced air oven to give 6 (0.967 kg, 84% Yield). HPLC analysis shows 6 to be 98.2% pure. Mix 6 (16.8 g), isopropyl alcohol (300 mL), water (34 mL) and maintain heat (80° C.) for 10 minutes under nitrogen. Allow the mixture to cool (20° C.) over a time period of 18 hours. Filter off the solid and wash with a mixture of isopropyl alcohol:water (90:10) and dry at 75° C./50 torr for 24 hours to give 6 (13.5 g, 80% Yield): mp 213.5-215° C.; $^1$H NMR (DMSO-$d_6$, 200MHz) δ 1.2-1.5 (br s, 1H), 1.55-1.9 (m, 5H), 2.1-2.3 (m, 2H), 2.7-2.95 (m, 2H), 3.0-3.2 (m, 2H), 3.3-3.5 (m, 2H), 4.1 (t, 2H), 6.9-7.0 (m, 2H), 7.1-7.5 (m, 5H), 10.4-10.7 (br s, 1H), 11.48 (s, 0.8H), 11.7 (s, 0.2H). Analysis calculated for $C_{21}H_{24}N_2O_2F_2 \cdot HCl$: C, 61.39; H, 6.13; N, 6.82. Found: C, 61.28; H, 5.94; N, 6.73. Purity by LC/MS (APCI)=100% area, $[M+H]^+$=375 m/e.

Scheme IV, Step V

Synthesis of 6-fluoro-3-[4-(3-piperidin-1-yl-propoxy)-phenyl]-benzo[d]isoxazole hydrochloride (Scheme IV, Compound 1c)

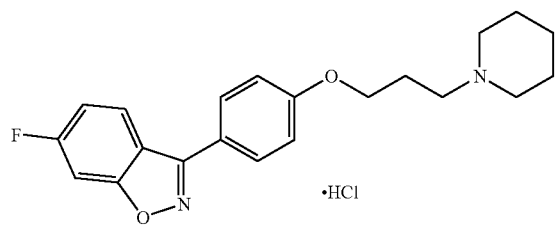

Mix 6 (0.950 kg, 2.31 mol), water (1.66 L) and isopropyl alcohol (3.9 L) in a 12-L, 3-necked flask fitted with a stirrer, thermometer in a side-arm adapter connected to a Firestone® valve and a reflux condenser fitted with a gas outlet adapter connected to a bubbler. Heat the mixture to 75° C. under nitrogen and add a 45% potassium hydroxide solution (6.93 mol), in one portion. A brief exotherm to 80° C. is observed. Monitor the progress of the reaction by HPLC (Column=300×3.9 mm Phenomenex Bondclone 10 CN; mobile phase=65% acetonitrile:35% 0.1N ammonium formate buffer; flow=1.5 mL/minute; wavelength=215 nm; $R_T$: 1(c)=3.8 min; 6=3.0 min). After 2 hours, add additional 45% potassium hydroxide solution (0.144 kg, 1.15 mol), HPLC conversion=78%. Typically, within 5 hours, the conversion is 78%. Note: HPLC shows 78% conversion @ 215 nm. Cool the mixture to room temperature over a time period of 17 hours, and filter to clarify the solution. Cool (10° C.) the filtrate and a solid precipitate forms. Add 6N hydrochloric acid (1.5 L) over a time period of 45 minutes (pH=1.5) and at 10-15° C. Stir the mixture for 1.5 hours at 5-10° C. Filter (slow process) off the solid, wash with water (6 L) and dry (50° C.) in a forced air oven to give 1(c) (0.70 kg, 78% yield). Combine 1(c) (0.70 kg) and a mixture of isopropyl alcohol:water (90:10) (10 L) and heat (82° C.) for 15 minutes and cool to room temperature over 18 hours. Cool (0° C.) the mixture for 1.5 hours, filter off the solid, wash with a mixture of isopropyl alcohol:water (90:10) (0.7 L) and dry (50° C.) in a forced air oven to give 1(c) (0.583 kg, 65% Yield). Combine 1(c) (0.582 kg) and a mixture of isopropyl alcohol:water (90:10) (9.25 L), heat (82° C.) for 15 minutes and cool to room temperature over a time period of 12 hours. Filter off the solid, wash with a mixture of isopropyl alcohol:water (90:10) (1.0L) and dry at 75° C./50 torr to give 1(c) (0.496 kg, 55.0% Yield). Combine 1(c) (0.480 kg), dichloromethane (4.0 L) and water (2.0 L) in a 12-L, 3-necked flask fitted with a stirrer, thermometer in a side-arm adapter connected to a Firestone® valve, and an addition funnel. Add a 50% sodium hydroxide solution (0.125 L) over 20 minutes and stir for 15 minutes. Separate the organic phase and dry over 0.2 kg of $MgSO_4$. Filter off the drying agent and wash with dichloromethane (0.5 L). Concentrate the filtrate at 40° C./50 torr to give 1(c) (0.415 kg) as the free base. Mix the free base of 1(c) (0.415 kg) with ethyl acetate (0.415 L) and heat (76° C.) for 5 minutes. Add heptane (4.15 L), temperature=60° C. Heat the mixture to 76° C. and add additional heptane (2.07 L). Stir and cool the mixture to room temperature (22° C.) over a time period of 18 hours. Cool the mixture back down to 0° C. for 1 hour, filter off the solid, wash with heptane (1.0 L) and air dry to give 1(c) (0.340 kg). Heat (35° C.) a mixture of 1(c) (0.340 kg) in isopropyl alcohol (1.7 L) to obtain a homogeneous solution. Add water (0.680 L) to the mixture, cool (28-32° C.) in an ice bath and add 6N hydrochloric acid (0.25 L) over 10 minutes. Stir the mixture at 10-28° C. for 2 hours, filter off the solid, wash with a mixture of isopropyl alcohol (90:10) (1.0 L), air dry for 32 hours and then dry at 100° C./50 torr to give the title compound (0.360 kg, 40% yield): mp 208-209.5° C.; $^1$H NMR (DMSO-$d_6$, 200 MHz) δ 1.2-1.95 (br m, 6H), 2.2-2.35 (m, 2H), 2.7-3.6 (br m, 6H), 4.2 (t, 2H), 7.18 (d, 2H), 7.4 (t, 2H), 7.8 (d, 1H), 7.95 (d, 2H), 8.18 (m, 2H), 10.2-11.2 (br s, 1H). Analysis calculated for $C_{21}H_{23}N_2O_2F \cdot HCl$: C, 64.53; H, 6.19; N, 7.17. Found: C, 64.29; H, 6.22; N, 7.16. Purity by LC/MS (APCI)=100% area, $[M+H]^+$=355 m/e.

Example 2

MDL 813866

Synthesis of (S)-1-[4-(6-fluoro-benzo[d]isoxazol-3-yl)-phenoxy]-3-[(thiophen-3-ylmethyl)-amino]-propan-2-ol maleate (Scheme III, Compound 1 and Scheme V, Compound 1e)

Scheme I, Step D and Scheme V, Step W

Synthesis of (2,4-difluoro-phenyl)-(4-methoxy-phenyl)-methanone (Scheme I, Compound and Scheme V, Compound 4)

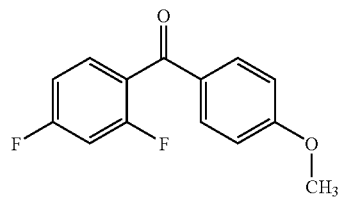

Combine 2,4-difluorobenzoyl chloride (227.8 g, 1.29 mol), anisole (154.2 mL, 1.42 mol) and 1,2-dichloroethane (2.28 L) and cool (−3° C.) under a nitrogen atomsphere.

Add aluminum chloride (209.8 g, 1.57 mol) over 45 minutes. The solution color turns from clear to yellow. Pour the reaction mixture over a mixture of ice (1700 g) and concentrated HCl (640 mL) over 2 minutes. The color of the mixture turns from yellow to clear. Separate layers and wash organic layer with 10% potassium carbonate (1600 mL), water (1600 mL), dry (MgSO$_4$), filter and concentrate to give a solid. Stir the solid in heptane (960 mL) and filter to give the title compound as a white solid (258.1 g, 81% Yield): $^1$H NMR (CDCl$_3$, 200 MHz) δ 3.9 (s, 3H), 6.95 (m, 4H), 7.55 (quar, 1H), 7.8 (d, 2H). Purity by LC/MS (APCI)=100% area, [M+H]$^+$=248 m/e.

Scheme I, Step E and Scheme V, Step X

Synthesis of (2,4-difluoro-phenyl)-(4-methoxy-phenyl)-methanone oxime (Scheme I, Compound 9 and Scheme V, Compound 5)

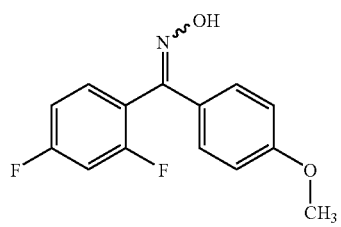

Mix (2,4-difluoro-phenyl)-(4-methoxy-phenyl)-methanone (257 g, 1.04 mol), hydroxylamine hydrochloride (143.9 g, 2.07 mol) and pyridine (1.29 L, 15.89 mol), under a nitrogen atmosphere and heat (100° C.). Cool reaction mixture to room temperature and concentrate to an oily residue. Partition residue between ethyl acetate (2700 mL) and water (1600 mL). Wash organic layer with 1 N HCl solution (2×800 mL), water (2×1 L), saturated sodium chloride (1 L), dry (MgSO$_4$) and concentrate to give the title compound as an oil. (270.84 g, 99% Yield): $^1$H NMR (CDCl$_3$, 200 MHz) δ 3.8-3.82 (2 s, 3H), 6.8-7.0 (m, 3H), 7.2 (m, 1H), 7.4 (d, 2H), 7.5 (d, 1H), 8.4-8.6 (br s, 1H). Purity by LC/MS (APCI)=100% area, [M+H]$^+$=264 m/e.

Scheme I, Step F and Scheme V, Step Y

Synthesis of 6-fluoro-3-(4-methoxy-phenyl)-benzo[d]isoxazole (Scheme I, Compound 10 and Scheme V, Compound 6)

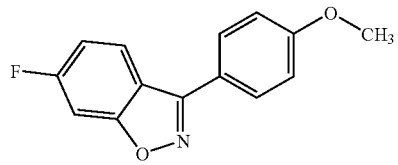

Combine (2,4-difluoro-phenyl)-(4-methoxy-phenyl)-methanone oxime (277.5 g, 1.05 mol), water (200 mL) and isopropyl alcohol (1140 mL) and heat (~75-80° C.) under a nitrogen atmosphere. Add 45% potassium hydroxide (591.5 g), in one portion, followed by water (75 mL). Immediate exotherm to 82° C. Continue heating for 5.3 hours. Cool reaction mixture to room temperature overnight. Cool reaction mixture in an ice bath, filter and wash (2×250 mL) filter cake with a cold mixture of isopropyl alcohol and water (20:80). Let filter cake dry to the air to give the title compound (182.7 g, 73% Yield): $^1$H NMR (CDCl$_3$, 200 MHz) δ 3.9 (s, 3H), 7.1 (m, 3H), 7.3 (m, 1H), 7.85 (m, 3H). Purity by LC/MS (APCI)=100% area, [M+H]$^+$=244 m/e.

Scheme I, Step G and Scheme V, Step Z

Synthesis of 4-(6-fluoro-benzo[d]isoxazol-3-yl)-phenol (Scheme I, Compound 11 and Scheme V, Compound 7)

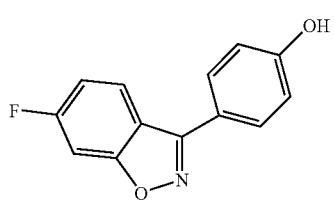

Add a 1.0 M solution of boron tribromide (2.31 L, 2.31 mol) in dichloromethane (1.87 L) to a cold (0° C.) solution of 6-fluoro-3-(4-methoxy-phenyl)-benzo[d]isoxazole (187.2 g, 0.77 mol) in dichloromethane, over ~2 hours. Warm to room temperature overnight. Cool reaction mixture to ~3° C. and add methanol (4 L) over a period of time of 1 hour, keeping the temperature of the reaction mixture at 3-10° C. Gas evolution occurs. Concentrate (40-50° C., 50 torr) reaction mixture to give a gray solid. Heat to dissolve the gray solid in isopropyl alcohol (550 mL) at reflux. Cool (room temperature), followed by 0-5° C. for 1 hour. Filter off the solid and wash filter cake with cold (0° C.) isopropyl alcohol (265 mL) and dry to air. Subsequently dry the solid in the oven (60° C., 50 torr) overnight to give the title compound (147.2 g, 83% Yield): $^1$H NMR (DMSO-d$_6$, 200 MHz) δ 7.0 (d, 2H), 7.4 (t, 1H), 7.8 (d, 1H), 7.84 (d, 2H), 8.18 (m, 1H). Purity by LC/MS (APCI)=100% area, [M+H]$^+$= 230 m/e.

Scheme III, Step N and Scheme V, Step A'

Synthesis of (S)-6-fluoro-3-(4-oxiranylmethoxy-phenyl)-benzo[d]isoxazole (Scheme III, Compound 7 and Scheme V, Compound 9)

MDL 813236, MDL 813236-001

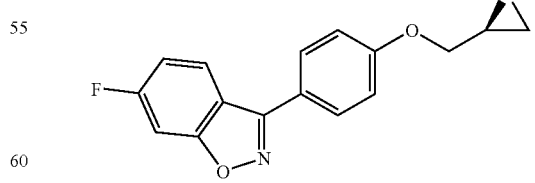

To a cold (−5° C.) solution of sodium hydride (32.1 g, 0.80 mol, 60% dispersion in mineral oil) in dimethylformamide (1000 mL) and under a nitrogen atmosphere, add dropwise a solution of 3-(6-fluoro-benzo[d]isoxazol-3-yl)-phenol (147.2 g, 0.64 mol) in dimethylformamide (500 mL)

over 38 minutes. Add, dropwise, (2S)-(+)-glycidyl tosylate (161.2 g, 0.71 mol) dissolved in dimethylformamide (650 mL), over 5 minutes. Temperature of reaction mixture maintained at 5-7° C. Let reaction mixture warm to room temperature and stir overnight. Add additional sodium hydride (6.42 g, 0.16 mol, 60% dispersion in mineral oil) to the reaction mixture and stir for 2.7 hours. Pour reaction mixture into cold ice water (15 kg) to form a white precipitate and stir for ~1 hour. Filter and wash the filter cake with water (5×750 mL) to obtain a solid. Dry solid to the air and in a forced air oven (70° C.) overnight to give the title compound (168.5 g, 92% Yield): $^1$H NMR (DMSO-$d_6$, 200 MHz) δ 2.9 (m, 1H), 3.4 (m, 2H), 3.95 (m, 1H), 4.5 (dd, 1H), 7.2 (d, 2H), 7.4 (t, 1H), 7.8 (d, 1H), 8.0 (d, 2H), 8.2 (m, 1H). Purity by LC/MS (APCl)=100% area, [M+H]$^+$=286 m/e.

Scheme III, Step O and Scheme V, Step D'

Synthesis of (S)-1-[4-(6-fluoro-benzo[d]isoxazol-3-yl)-phenoxy]-3-[(thiophen-3-ylmethyl)-amino]-propan-2-ol (Scheme III, Compound 1 and Scheme V, Compound 1d)

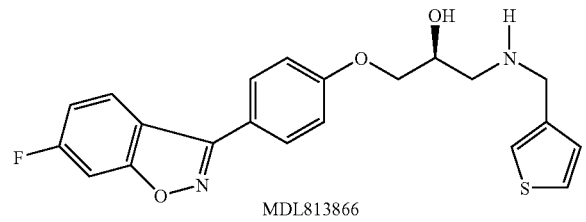

MDL813866

Combine (S)-6-fluoro-3-(4-oxiranylmethoxy-phenyl)-benzo[d]isoxazole (122.80 g, 0.43 mol), thiophen-3-yl-methylamine [see Example 2A for the synthesis] (73 g, 0.64 mol), ethanol (1 L) and heat (reflux) for ~2 hours. Cool to room temperature overnight and cool to 0° C. with an ice bath. Filter reaction mixture, wash with cold (0° C.) ethanol. Air dry the compound and subsequently place in a vacuum oven (75° C./50 torr) overnight to give the title compound (121.0 g, 76.5% yield): $^1$H NMR (DMSO-$d_6$, 200 MHz) δ 2.7 (m, 3H), 3.8 (m, 2H), 3.9-4.2 (m, 3H), 5.1 (m, 1H), 7.02-7.5 (m, 6H), 7.8 (m, 3H), 8.2 (dd, 1H).

Alternatively, the procedure can be performed as follows:

MDL 813866A

Combine (S)-6-fluoro-3-(4-oxiranylmethoxy-phenyl)-benzo[d]isoxazole (500 mg, 1.75 mmol), thiophen-3-yl-methylamine (793 mg, 7.0 mmol), ethanol (5.0 mL) and heat (~80° C.) for 6.5 hours. Reaction mixture is a homogeneous solution after 20 minutes. Thin layer chromatography (4% ethyl acetate in dichloromethane) shows that the isoxazole is consumed. Stir the reaction mixture for 3 days at room temperature. Dilute reaction mixture with chloroform (30 mL) and concentrate (in vacuo). Purify the compound by column chromatography (silica) to obtain a white solid that is dried (0.5 mm Hg). Dissolve the free base in 10% methanol in chloroform (30 mL) and add ethereal HCl to a pH~2-3. Concentrate the reaction mixture (in vacuo) and recrystallize (methanol) the salt and dry (60° C., 0.5 mm Hg) to give the title compound as an off-white solid (334 mg, 44% Yield). mp=246-248° C. Microanalysis (C, H, N) is consistent with the final, desired compound. [α]$^{22}_D$=−7.81, c (MeOH)=0.64.

As a second alternative, the procedure can be performed as follows:

(Scheme VI, Compound 1)

Combine the 4-(6-fluoro-benzo[d]isoxazol-3-yl)-phenol (5 g, 0.0218 mol), (S)-oxiranylmethyl-thiophen-3-ylmethyl-amine (3.69 g, 0.0218 mol) (Table No. 1, SM 10), water (20 mL), and concentrated sodium hydroxide (0.2 mL) and stir at room temperature for 6 hours. Separate out the solid and let stand overnight. Decant the supernatant solution and add water (10 mL) to the residue and then dissolve in acetone (20 mL). From solution, the compound crystallizes. To purify, the compound may be recrystallized from an appropriate solvent.

Scheme III, Step O and Scheme V, Step E'

Synthesis of (S)-1-[4-(6-fluoro-benzo[d]isoxazol-3-yl)-phenoxy]-3-[(thiophen-3-ylmethyl)-amino]-propan-2-ol maleate (Scheme III, Compound 1 and Scheme V, Compound 1e)

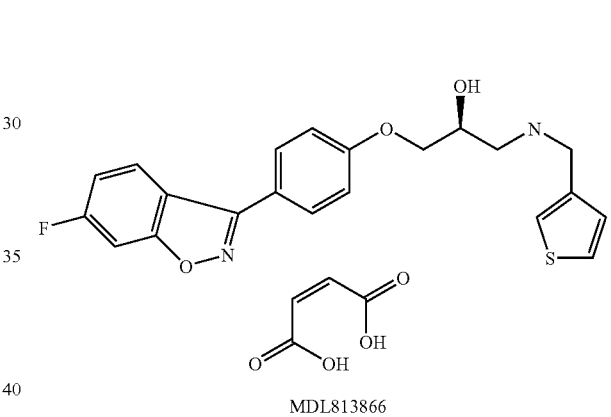

MDL813866

Dissolve 1(d) (100 g) in tetrahydrofuran (750 mL), under nitrogen, at a temperature of ~60° C. When the pot temperature is 54° C., add a solution of maleic acid (30.6 g, 0.26 mol) in tetrahydrofuran (120 mL) over 10 minutes. Stir and cool to room temperature. Cool (~−5° C.) in an ice bath, filter, and wash with cold (−5° C.) tetrahydrofuran (2×100 mL). Air dry the compound, re-dissolve in tetrahydrofuran (500 mL), heat to reflux, filter the mixture through celite and wash with tetrahydrofuran (~50 mL). Heat to re-dissolve the compound and allow to cool to room temperature. Precipitate forms at a temperature of ~50° C. Stir overnight, cool (−5° C.) in an ice bath, filter off the precipitate and wash with cold (−5° C.) tetrahydrofuran (2×40 mL). Dry the compound to the air, followed by the vacuum oven (60° C.), overnight, to give the title compound (74 g, 57% Yield) as the maleate salt: mp=152.5-154° C.; $^1$H NMR (DMSO-$d_6$, 200 MHz) δ 3.0 (m, 2H), 3.2 (m, 2H), 4.1 (d, 1H), 4.2 (br s, 2H), 5.9 (br s, 1H), 6.2 (s, 2H), 7.2 (d, 1H), 7.26 (d, 1H), 7.4 (t, 1H), 7.6-7.75 (m, 1H), 7.82 (d, 1H), 8.0 (d, 1H), 8.18 (m, 1H), 8.8-9.0 (br s, 1H). Analysis calculated for $C_{21}H_{19}N_2O_3FS \cdot C_4H_4O_4$: C, 58.36; H, 4.51: N, 5.44. Found: C, 58.37; H, 4.56; N, 5.25. [α]$_D^{25}$=−7.201 (c=9.981 mg/mL, methanol). Purity by LC/MS (APCl)=100% area, [M+H]$^+$= 399 m/e.

Example 2A

Synthesis of thiophen-3-yl-methylamine (Scheme V, Compound 12)

Scheme V, Step B'

Synthesis of thiophene-3-carbaldehyde oxime (Scheme V, Compound 11)

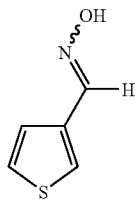

Dissolve hydroxylamine hydrochloride (725 g, 10.43 mol) in pyridine (3 L), which causes an exotherm (23-30° C.). Cool (25° C.) the reaction mixture, under nitrogen and add 3-thiophenecarboxaldehyde (585 g, 5.2 mol) over ~1 hour while maintaining the temperature from 22-27° C. Concentrate (60° C./50 torr) the reaction mixture to an oily residue and partition between ethyl acetate (2 L) and water (1 L). Extract the organic layer with 1 N HCl (2×600 mL), followed by water (3×500 mL). Dry (MgSO$_4$), filter, wash the solid with ethyl acetate (500 mL) and concentrate (60° C./60 torr) to give the title compound as a semi-solid residue (575 g, 99% Yield: $^1$H NMR (CDCl$_3$, 200 MHz) δ 7.3-7.55 (m, 3H), 8.2 (s, 1H), 8.7-9.2 (br s, 1H).

Scheme V, Step C'

Synthesis of thiophen-3-yl-methylamine (Scheme V, Compound 12)

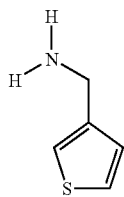

Add a solution of thiophene-3-carbaldehyde oxime (97.2 g, 0.9 mol) in tetrahydrofuran (500 mL) to cold (18° C.) lithium aluminum hydride bis tetrahydrofuran complex (1.0 M solution in tetrahydrofuran, 1.75 L), in a dropwise fashion, over ~0.5 hours. Alternatively, toluene may be used as the solvent. Gas evolution is observed and the addition temperature is maintained at 18-25° C. Let reaction mixture stir overnight. Cool reaction mixture and carefully quench with water (252 mL), over ~40 minutes. Add additional tetrahydrofuran (300 mL) to thin out the reaction mixture upon quenching and stir at room temperature for 3 hours. Add sodium sulfate (250 g), filter through celite, and concentrate (50-60° C./30 torr) reaction mixture to give the title compound as an oil (81.5 g, 82% Yield: $^1$H NMR (CDCl$_3$, 200 MHz) δ 1.5-1.8 (br s, 2H), 3.9 (s, 2H), 7.04 (d, 1H), 7.1 (d, 1H), 7.3 (m, 1H).

Example 3

Synthesis of 3-(6-fluoro-benzo[d]isoxazol-3-yl)-phenol (Scheme I, Compound 11)

Scheme I, Steps A and B

Synthesis of (2,4-difluoro-phenyl)-(3-methoxy-phenyl)-methanol (Scheme I, Compound 5)

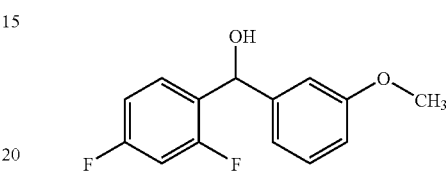

Add n-butyl lithium solution (2.5 M, 140 mL, 350 mmol) to 3-bromoanisole (44.6 mL, 352.2 mmol) in cold (−78° C.) tetrahydrofuran (anhydrous, 500 mL), dropwise. Let stir for 10 minutes and add 2,4 difluorobenzaldehyde (50 g, 351 mmol), dropwise, and stir for an additional 1 hour. After 1 hour the reaction is complete. Quench the reaction mixture with cold water, extract with ethyl acetate, dry (MgSO$_4$), and concentrate to give the crude, title compound (Compound 7) (90.21 g, >100% Yield). Use compound in a crude form or purify by column chromatography (20% ethyl acetate in heptane). NMR agrees with the final, desired compound.

Scheme I, Step C

Synthesis of (2,4-difluoro-phenyl)-(3-methoxy-phenyl)-methanone (Scheme I, Compound 8)

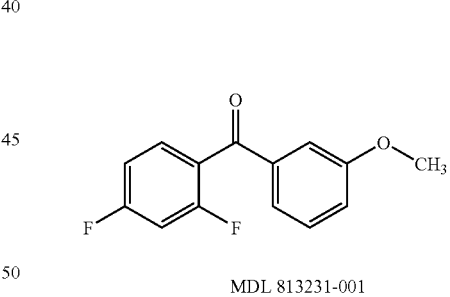

Combine (2,4-difluoro-phenyl)-(3-methoxy-phenyl)-methanol (Compound 7) (89.2 g, 357 mmol), manganese oxide (96 g, 1.1 mol), and toluene (500 mL) and heat to reflux, under a nitrogen atmosphere for 2 hours. TLC (30% ethyl acetate in heptane) shows that the reaction is complete. Filter reaction mixture through celite® and concentrate. Purify by column chromatography using a graded solvent mixture of 10% dichloromethane in heptane to 50% dichloromethane in heptane to give an oil. Cool overnight to solidify, and triturate with pentane to give the title compound as a white solid (51.7 g, 58% Yield). NMR is consistent with the final, desired compound. mp=50° C.-52° C.

Scheme I, Step E

Synthesis of (2,4-difluoro-phenyl)-(3-methoxy-phenyl)-methanone oxime (Scheme I, Compound 9)

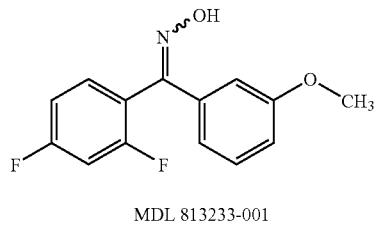

MDL 813233-001

Combine (2,4-difluoro-phenyl)-(3-methoxy-phenyl)-methanone (51.2 g, 0.206 mol) and pyridine (293.4 g, 300 mL). Add hydroxylamine hydrochloride (21.7 g, 0.312 mol) and heat to 100° C., under a nitrogen atmosphere, for 4 hours. TLC (20% ethyl acetate in heptane) shows that the reaction is complete. Concentrate the reaction mixture and dry (vacuum at 50° C.). Distribute the material between ethyl acetate and water. Wash the organic layer with 10% HCl, saturated sodium chloride, dry (MgSO$_4$) and concentrated to obtain the title compound as a white solid (53.66 g, 99% Yield). Use compound in a crude form or recrystallize from heptane and dry (P$_2$O$_5$). NMR and MS are consistent with the final, desired compound, which is a mixture of the Z-isomer (81%) and the E-isomer (19%). mp=122° C.-127° C.

Scheme I, Step F

Synthesis of 6-fluoro-3-(3-methoxy-phenyl)-benzo[d]isoxazole (Scheme I, Compound 10)

MDL 813235-001

Cool (2,4-difluoro-phenyl)-(3-methoxy-phenyl)-methanone oxime (52.66 g, 217 mmol) in tetrahydrofuran (500 mL) to 0° C. Add 1.0 M solution of potassium tert-butoxide in tetrahydrofuran (260 mL, 0.26 mol) and stir at room temperature for 1.5 hours. Reflux reaction mixture for an additional 1.5 hours. Cool to room temperature overnight. Dilute reaction mixture with ethyl acetate and water and separate. Dry the organic layer and concentrate to give the title compound as an oil. Purify by column chromatography (dichloromethane) and triturate with pentane to give the title compound as a white solid (30.2 g, 62% Yield). NMR and M/S are consistent with the final, desired compound. mp=68-69° C.

Scheme I, Step G

Synthesis of 3-(6-fluoro-benzo[d]isoxazol-3-yl)-phenol (Scheme I, Compound 11)

MDL 813422-001

Combine 6-fluoro-3-(3-methoxy-phenyl)-benzo[d]isoxazole (30 g, 0.123 mol) and dichloromethane (anhydrous, 360 mL) under nitrogen atmosphere and cool (0° C.). Slowly add 1.0 M solution of boron tribromide in dichloromethane (370 mL, 0.370 mol) over 1 hour and stir at 0° C. for 3 hours. TLC indicates that all starting material is consumed. Quench the reaction mixture with 150 mL methanol, concentrate and azeotrope off the boron tribromide two more times with methanol. Dissolve the material in ethyl acetate, wash with K$_2$CO$_3$, saturated sodium chloride, dry (MgSO$_4$) and concentrate. Triturate in heptane:dichloromethane (9:1), filter and wash with heptane and dry in the oven to give the title compound (26.93 g, 95% Yield). NMR and microanalysis (C, H, N) are consistent with the final, desired compound. mp=144-145° C.

Example 4

Synthesis of oxiranylmethoxy intermediates

Scheme III, Step N

Synthesis of (S)-6-fluoro-3-(3-oxiranylmethoxy-phenyl)-benzo[d]isoxazole (Scheme III, Compound 7)

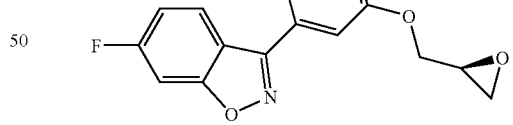

MDL 813423-001

To a cold (0° C.) solution of sodium hydride (1.83 g, 45.79 mmol) in dimethylformamide (120 mL) and under a nitrogen atmosphere, add a solution of 3-(6-fluoro-benzo[d]isoxazol-3-yl)-phenol (10 g, 43.63 mmol) in dimethylformamide (50 mL) and stir for 1 hour. Add, dropwise, (2S)-(+)-glycidyl tosylate (10.47 g, 45.87 mmol) dissolved in dimethylformamide (40 mL), over a period of time of 0.5 hours. Let reaction mixture warm to room temperature and stir for 2 days. Quench with water, concentrate and add ethyl acetate/water. Wash with water, saturated sodium chloride and dry (MgSO$_4$) to give the crude compound. Purify by column (silica) chromatography eluting with a graded solvent mixtures of toluene to 1% ether in toluene to give the title compound as a white solid (10.07 g, 81% Yield). NMR and microanalysis (C, H, N) are consistent with the final, desired compound. Chiral HPLC, 18.14 minutes [Chiralcel OD (250×4.6 mm), 98:2 heptane/ethanol @ 0.8 mL/min, UV @ 285 nm, 18.14] shows the title compound as 88.3% e.e. mp=83-84° C.

Scheme III, Step N

Synthesis of (R)-6-fluoro-3-(3-oxiranylmethoxyphenyl)-benzo[d]isoxazole (Scheme III, Compound 7)

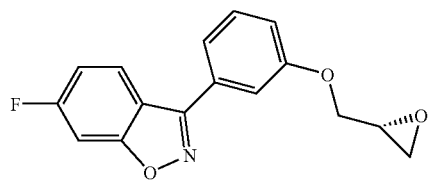

MDL 813424

The title compound is prepared from a mixture of sodium hydride in dimethylformamide, 3-(6-fluoro-benzo[d]isoxazol-3-yl)-phenol in dimethylformamide and (2R)-(−)-glycidyl tosylate in dimethylformamide essentially as described above except that the reaction mixture is diluted with water, extracted with ethyl acetate, washed with water (twice), dried (MgSO$_4$), concentrated and purified by column (silica) chromatography eluting with a graded solvent mixtures of toluene to 1% ether in toluene to give the title compound as a white solid (9.29 g, 75% Yield). NMR and microanalysis (C, H, N) are consistent with the final, desired compound. Chiral HPLC, 16.92 minutes, [Chiralcel OD (250×4.6 mm), 98:2 heptane/ethanol @ 0.8 mL/min, UV @ 285 nm, 18.14] shows the title compound as 95.5% e.e. mp=84-85° C.

Scheme III, Step N

Synthesis of (R)-6-fluoro-3-(4-oxiranylmethoxyphenyl)-benzo[d]isoxazole (Scheme III, Compound 7)

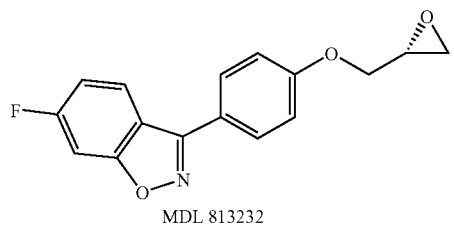

MDL 813232

To a cold (0° C.) solution of sodium hydride (1.80 g, 45.0 mmol) in dimethylformamide (anhydrous, 40 mL) and under a nitrogen atmosphere, add dropwise a solution of 3-(6-fluoro-benzo[d]isoxazol-3-yl)-phenol (10 g, 43.63 mmol) in dimethylformamide (anhydrous, 50 mL). Precipitate forms. Cool (0° C.) reaction mixture for 20 minutes and the material solidifies. Add dimethylformamide (anhydrous, 120 mL) and (2R)-(−)-glycidyl tosylate (10.47 g, 45.87 mmol) dissolved in dimethylformamide (40 mL), dropwise, over a period of time of 0.5 hours, while cooling with an ice bath. After this addition, the reaction mixture becomes homogeneous. Warm reaction mixture to room temperature and stir overnight. Pour reaction mixture into cold water (600 mL), stir for 1 hour under an ice bath, filter and wash the filter cake with water to obtain an off-white solid. Add dichloromethane (200 mL) to the off-white solid, wash with saturated sodium chloride and dry (MgSO$_4$). Directly purify by column (silica) chromatography (dichloromethane) and triturate with pentane to give the title compound as an off-white solid (9.70 g, 78% Yield). MS shows [M+H]$^+$= 286. NMR and microanalysis (C, H, N) are consistent with the final, desired compound. mp=132-133° C.

Example 5

Synthesis of 3-[4-(3-bromo-propoxy)-phenyl]-6-fluoro-benzo[d]isoxazole (Scheme III, Compound 4)

Scheme III, Step Q

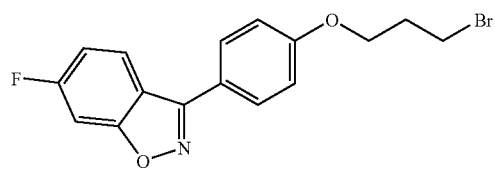

Stir a solution of 4-(6-fluoro-benzo[d]isoxazol-3-yl)-phenol (2.00 g, 8.726 mmol) in acetone (150 mL) and add cesium carbonate (7.12 g, 21.82 mmol) and 3-dibromopropane (4.43 mL, 43.63 mmol). Heat the reaction mixture at reflux overnight, in the dark. Filter the resulting suspension and thoroughly wash the cesium salts with acetone. Evaporate the filtrate and recrystallize the residue from ether to give the title compound as a pure white crystalline solid (0.814 g). Evaporate and purify the mother liquor by column (silica) chromatography (10% ethyl acetate in heptane) to obtain the title compound as a white solid (1.67 g). Combine the two white solids (Yield=81%). mp=182-186° C.

Scheme III, Step Q

Synthesis of 3-[4-(2-bromo-ethoxy)-phenyl]-6-fluoro-benzo[d]isoxazole (Scheme III, Compound 4)

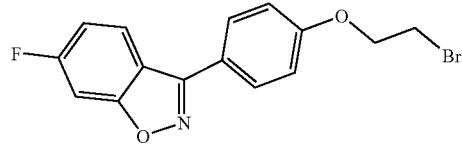

Combine 4-(6-fluoro-benzo[d]isoxazol-3-yl)-phenol (2.00 g, 8.726 mmol) and potassium carbonate (1.81 g, 13.088 mmol) in 1,2-dibromoethane (9.70 mL) and heat at reflux for 6 hours. Cool reaction mixture to room temperature and dilute with ethyl acetate (150 mL) and wash with water (50 mL), 10% HCl (50 mL), water (50 mL), saturated sodium chloride (50 mL), dry (MgSO$_4$), filter and evaporate.

Purify the residue by column chromatography (5% ethyl acetate in heptane) to obtain the title compound as a white solid (1.21 g, 41% Yield).

Example 6

Synthesis of 4-benzo[b]thiophen-3-yl-phenol (Scheme II, Compound 9)

Scheme II, Step L

Synthesis of 3-(4-methoxy-phenyl)-benzo[b]thiophene (Scheme II, Compound 8)

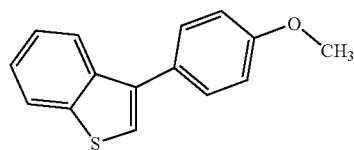

Mix 3-bromobenzo[b]thiophene (5.83 g, 27.4 mmol), tetrakis(triphenylphosphine)palladium (O) (1.00 g, 0.865 mmol) and toluene (60 mL) and purge with nitrogen. Rapidly, add a 2 M aqueous solution of sodium carbonate (27 mL) and purge with nitrogen. Add a solution of 4-methoxyphenylboronic acid (4.57 g, 30.1 mmol) in methanol (13 mL), purge with nitrogen and heat at a gentle reflux for 4.5 hours. Let cool and stir at room temperature, overnight. TLC (30% diclorometane in heptane) shows that all starting material is consumed. Dilute reaction mixture with ethyl acetate (100 mL). Wash with 2 M sodium carbonate (75 mL), water (75 mL), saturated sodium chloride (75 mL), dry (MgSO$_4$) and concentrate (in vacuo) to give a residue. Purify the residue by column (silica) chromatography (20% dichloromethane in heptane) to give a mixture as a residue. Dissolve the residue in 30% ether in heptane, filter, evaporate and dry (0.5 mm Hg, room temperature) to give the title compound as a clear oil (5.47 g, 83% Yield).

Scheme II, Step M

Synthesis of 4-benzo[b]thiophen-3-yl-phenol (Scheme II, Compound 9)

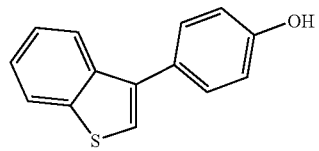

Cool a solution of 3-(4-methoxy-phenyl)-benzo[b]thiophene (5.00 g, 20.8 mmol) and dichloromethane (anhydrous, 120 mL). Add 1.0 M solution of boron tribromide in dichloromethane (60.0 mL, 60.0 mmol) over a time period of 15 minutes. Stir reaction mixture at 0° C. for 2 hours and let warm and stir at room temperature overnight. TLC (40% dichloromethane in heptane) shows that the starting material is consumed. Transfer reaction mixture to a mixture of ice:water (200 g:200 mL) via a cannula and let stir for 0.5 hours. Separate the layers and extract the aqueous layer with dichloromethane (250 mL). Combine organic layers, wash with water (2×200 mL), dry (MgSO$_4$), and concentrate (in vacuo) to obtain a brown, viscid residue. Purify residue by column (silica) chromatography (dichloromethane) to obtain a clear oil, which solidifies. Dry (room temperature, 0.8 mm Hg) for 3 hours to give the title compound (4.35 g, 92% Yield).

Example 7

Synthesis of 2-(4-benzo[b]thiophen-3-yl-phenoxymethyl)-oxirane (Scheme III, Compound 7)

Scheme III, Step N

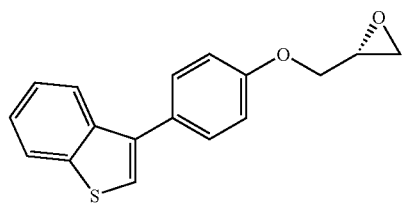

Cool a mixture of sodium hydride (585 mg, 60% dispersion in mineral oil, 14.6 mmol) in dimethylformamide (20 mL, anhydrous), with an ice bath, under a nitrogen atmosphere. Add a solution of 4-benzo[b]thiophen-3-yl-phenol (3.0 g, 13.3 mmol) in dimethylformamide (20 mL) over a period of 5 minutes. Reaction mixture has noticeable gas evolution and is a yellow mixture. Stir at room temperature for 0.5 hours and cool via an ice bath to give a yellow solution. Rapidly, add a solution of (2R)-(−)-glycidyl 3-nitrobenzenesulfonate (3.78 g, 14.6 mmol) in dimethylformamide (20 mL) and stir at 0° C. for 35 minutes. The reaction mixture is a red-orange color. Stir reaction mixture at room temperature overnight. Pour the reaction mixture into cold (0° C.) water (300 mL) and extract with ethyl acetate (3×100 mL). Combine the organic layers, wash with water (100 mL), saturated sodium chloride (100 mL), dry (MgSO$_4$) and concentrate (in vacuo) to give a brown oil. The brown oil is purified by column chromatography (dichloromethane) to give a light green/clear, viscous oil. The oil is dried (0.5 mm Hg) at room temperature for 3 hours to give the title compound as a solid (3.19 g, 85% Yield).

Example 8

Synthesis of 3-isoxazolo[5,4-b]pyridin-3-yl-phenol (Scheme II, Compound 9)

Scheme II, Steps H and I

Synthesis of (2-chloro-pyridin-3-yl)-(3-methoxy-phenyl)-methanol (Scheme II, Compound 4)

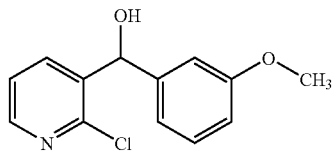

Combine 2.5 M n-butyl lithium in hexane (40 mL), diisopropyl amine (14 mL, 0.10 mol) and cold (−68° C.) tetrahydrofuran (250 mL) and stir for 20 minutes, to generate lithium diisopropylamide. Add 2-chloro-pyridine (9.5 mL, 0.10 mol) dissolved in tetrahydrofuran (10 mL) and stir for 45 minutes. Add m-anisaldehyde (13.6 g, 0.10 mol) in 10 mL tetrahydrofuran, stir for 45 minutes and let warm to room temperature over the weekend. Pour reaction mixture into water, add saturated ammonium chloride (50 mL), separate and dry. Extract with ether (twice), wash combined aqueous layers with saturated sodium chloride, dry, evaporate and purify by flash (silica) chromatography using a graded solvent mixture of dichloromethane to 10% ethyl acetate in dichloromethane to give the title compound as an oil (12.74 g, 51% Yield). NMR agrees with the final, desired compound.

Scheme II, Step J

Synthesis of (2-chloro-pyridin-3-yl)-(3-methoxy-phenyl)-methanone (Scheme II, Compound 5)

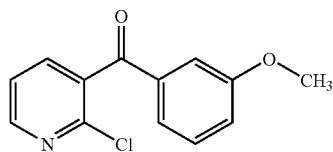

Combine (2-chloro-pyridin-3-yl)-(3-methoxy-phenyl)-methanol (9.40 g, 37.6 mmol), manganese (IV) oxide (30.0 g, 0.345 mol) and toluene (500 mL) and heat to reflux for one hour. Filter reaction mixture through celite, wash with toluene:dichloromethane mixture and evaporate to give the title compound (1.63 g, 66% Yield).

Scheme II, Step K

Synthesis of 3-(3-methoxy-phenyl)-isoxazolo[5,4-b]pyridine (Scheme II, Compound 8)

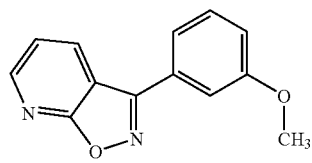

Combine acetone oxime (3.1 g, 42.4 mmol) in dimethylformamide (15 mL) and add potassium t-butoxide (4.76 g, 42.4 mmol) and stir for 1 hour. Add (2-chloro-pyridin-3-yl)-(3-methoxy-phenyl)-methanone (8.40 g, 34 mmol) dissolved in dimethylformamide (10 mL) and stir at room temperature, overnight. Separate the product between water and ether and evaporate. Purify by column (silica) chromatography (10% ethyl acetate/dichloromethane) and then reflux in a mixture of 1:1 ethanol:5% aqueous hydrochloric acid. Work-up with 5% aqueous sodium hydroxide and ether and purify by flash chromatography (5% ethyl acetate in dichloromethane) to give the title compound (5.21 g, 68% Yield).

Scheme II, Step M

Synthesis of 3-isoxazolo[5,4-b]pyridin-3-yl-phenol (Scheme II, Compound 9)

MDL 813545

Combine 3-(3-methoxy-phenyl)-isoxazolo[5,4-b]pyridine (4.97 g, 21.97 mmol) and 1,2-dichloroethane (anhydrous, 50 mL), under a nitrogen atmosphere and cool (~5° C.). Add a solution of boron tribromide (19.26 g, 77.89 mmol) in 1,2-dichloroethane (20 mL), dropwise and stir at 50° C. overnight. Cool (0° C.) the reaction mixture and quench with a solution of sodium hydrogen carbonate, dropwise. Pour the reaction mixture over a solution of dilute sodium hydrogen carbonate (~300 mL) and stir for 1 hour. Filter and collect the solid. Extract the filtrate with chloroform, dry ($Na_2SO_4$), filter, evaporate, and combine with previously collected solid. Triturate with ether, filter and dry under vacuum to give the title compound as a white solid (4.2 g, 90% Yield). Microanalysis (C, H, N) is consistent with the final, desired compound. mp=175-178° C.

Example 9

Synthesis of (R)-3-(3-oxiranylmethoxy-phenyl)-isoxazolo[5,4-b]pyridine (Scheme III, Compound 7)

Scheme III, Step N

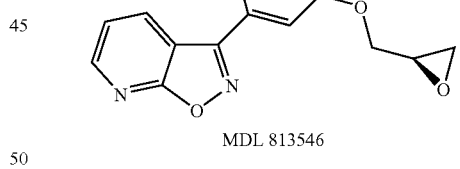

MDL 813546

Combine 3-isoxazolo[5,4-b]pyridin-3-yl-phenol (5.15 g, 24.27 mmol) and dimethylformamide (anhydrous, 50 mL), add sodium hydride (60% in oil, 1.16 g, 29.12 mmol) and stir for 20 minutes. Add (2R)-(+)-glycidyl tosylate (5.54 g, 24.27 mmol), portionwise, and stir overnight at room temperature. Pour reaction mixture over water (400 mL), extract with ethyl acetate, dry ($Na_2SO_4$), filter and evaporate. Purify by column (silica) chromatography using a graded solvent mixture of 0.5% methanol in dichloromethane to 2% methanol in dichloromethane and recrystallize from ethyl acetate to give the title compound as off-white crystals (4.4 g, 68% Yield). Chiral HPLC (Chiralcel OD column, heptane:ethanol (80:20), UV @ 254 nm, flow=0.75 mL/minute) shows a retention time of 21.46 minutes, 98.56 purity (approximately 97.9% ee). Elemental analysis (C, H, N) is consistent with the final, desired compound. mp=91-93° C.

Example 10

Synthesis of 6-fluoro-3-[4-(3-piperidin-1-yl-propoxy)-phenyl]-benzo[d]isoxazole (Scheme III, Compound 1b)

Scheme III, Step R

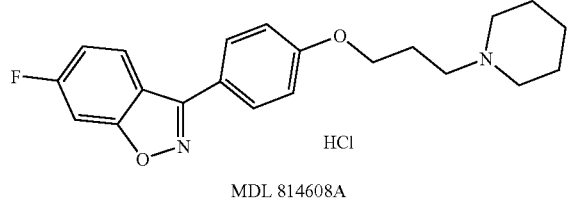

MDL 814608A

Combine 3-[4-(3-bromo-propoxy)-phenyl]-6-fluoro-benzo[d]isoxazole (0.727 g, 2.08 mmol), piperidine (0.707 g, 8.30 mmol), potassium carbonate (0.575 g, 4.16 mmol) and acetonitrile (7.0 mL) and heat (75° C.) overnight. Cool (45° C.) reaction, filter through a Waters Sep-Pak 1 g Silica cartridge (ethyl acetate) and concentrate (in vacuo). Purify the crude product by column (silica) chromatography with a graded solvent mixture of 5% methanol in dichloromethane to 10% methanol in dichloromethane. Concentrate to give a colorless oil and dry under vacuum (0.6 mm Hg, room temperature) for 3 hours to obtain a waxy, off-white solid. Acidify the free base with ethereal HCl, recrystallize (ethanol:ethyl acetate) and dry (in vacuo, 0.6 mm Hg, 60° C.) for 3 hours to give the title compound as the salt (0.336 g, 41% Yield). Microanalysis (C, H, N) is consistent with the final, desired compound. mp=202-205° C.

Example 10A

Alternative Preparation of 6-fluoro-3[4-(3-piperidin-1-yl)-propoxy)-phenyl]-benzo[d]isoxazole (Scheme VII, Compound 1)

STEP H':

Preparation of 1-(3-bromo-propyl)-piperidine (Scheme VII, Compound 4)

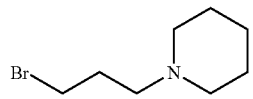

Combine piperidine (5.0 g, 58.7 mmol), fused sodium acetate (4.82 g, 58.7 mmol) and 1,3-dibromopropane (11.85 g, 58.7 mmol) and reflux for several hours. Pour the mixture into water and add sodium carbonate to create a basic pH. Remove the unreacted 1,3-dibromopropane by distillation. Extract the left-over residue with ether and evaporate to obtain the final, desired compound.

STEP I':

Preparation of 6-fluoro-3[4-(3-piperidin-1-yl)-propoxy)-phenyl]-benzo[d]isoxazole (Scheme VII, Compound 1)

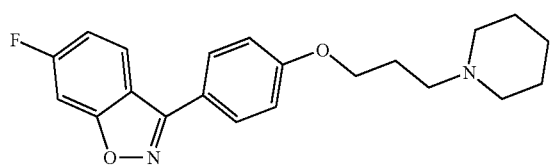

Stir a solution of 4-(6-fluoro-benzo[d]isoxazol-3-yl)-phenol (2.00 g, 8.726 mmol) in dimethylformamide (150 mL) and add cesium carbonate (7.12 g, 21.82 mmol) and 1-(3-bromo-propyl)-piperidine (3.6 g, 17.45 mmol). Heat the reaction mixture at 110° C. overnight. Cool to room temperature and quench in water. Extract the aqueous phase with ethyl acetate. Combine the organic extracts, wash with water and then with brine, then dry over magnesium sulfate. Filter the solids, evaporate the filtrate and purify the residue by column (silica) chromatography with a graded solvent mixture of 5% methanol in dichloromethane to 10% methanol in dichloromethane to obtain the title compound as a waxy solid.

Example 10(B)

Alternative Preparation of 6-fluoro-3[4-(3-piperidin-1-yl)-propoxy)-phenyl]-benzo[d]isoxazole (Scheme VIII, Compound 1)

STEP J':

Preparation of 3-piperidin-1-yl-propan-1-ol (Scheme VIII, Compound 4)

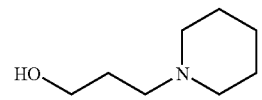

Combine piperidine (18.01 g, 0.212 mol), 3-chloro-1-propanol (10 g, 0.106 mol) and water (3.2 g, 0.18 mol) and heat on a steam-bath for ~5 hours. Add sodium hydroxide (6.35 g, 0.16 mol) to the cooled solution and heat the resulting mixture on a steam-bath for ~30 minutes. Add water, separate the organic layer, and extract the aqueous layer with dichloromethane, twice. Combine the organic layers and wash with water, dry with sodium sulfate and evaporate the solvent to give the final, desired compound. The final compound may be purified by chromatography.

STEP K':

Preparation of toluene-4-sulfonic acid 3-piperidin-1-yl-propyl ester (Scheme VIII, Compound 6)

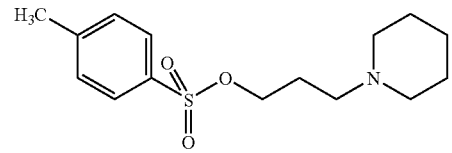

Add p-toluenesulfonyl-chloride (1.33 g, 6.98 mmol), portionwise, to a mixture of 3-piperidin-1-yl-propan-1-ol (1 g, 6.98 mmol), triethylamine (1.41 g, 13.9 mmol) and dichloromethane (6 mL). Stir the resulting suspension vigorously overnight at room temperature. Add water, separate the organic layer, and extract the aqueous layer with dichloromethane, twice. Combine the organic layers and wash with water, dry with sodium sulfate and evaporate the solvent to give the final, desired compound. The final compound may be purified by chromatography.

STEP L':

Preparation of 6-fluoro-3-[4-(3-piperidin-1-yl)-propoxy)-phenyl]-benzo[d]isoxazole (Scheme VIII, Compound 1)

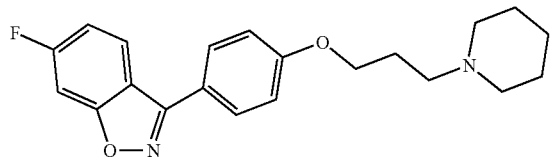

The title compound is prepared from a mixture of toluene-4-sulfonic acid 3-piperidin-1-yl-propyl ester and 4-(6-fluoro-benzo-[d]isoxazol-3-yl)-phenol essentially as described in Example 10 A, Scheme VII, Step I'.

Example 11

Preparation of benzyl-{3-[4-(6-fluoro-benzo[d]isoxazol-3-yl)-phenoxy]-propyl}-amine hydrochloride (Scheme III, Compound 1b)

Scheme III, Step R

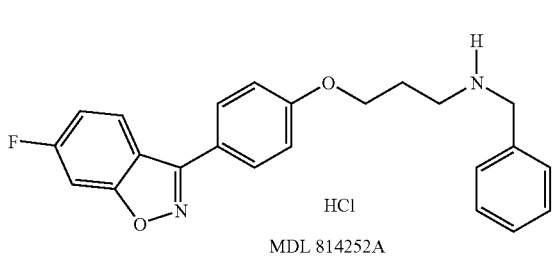

MDL 814252A

The title compound is prepared from a mixture of 3-[4-(3-bromo-propoxy)-phenyl]-6-fluoro-benzo[d]isoxazole, benzylamine, potassium carbonate and acetonitrile essentially as described above in Example 10 except that the compound is recrystallized from methanol. Microanalysis (C, H, N) is consistent with the final, desired compound. mp>265° C.

Example 12

Synthesis of {3-[4-(6-fluoro-benzo[d]isoxazol-3-yl)-phenoxy]-propyl}-thiophen-3-ylmethyl-amine hydrochloride (Scheme III, Compound 1b)

Scheme III, Step R

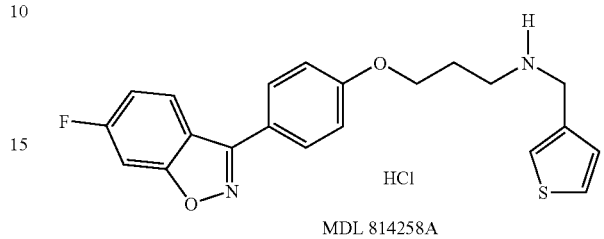

MDL 814258A

The title compound is prepared from a mixture of 3-[4-(3-bromo-propoxy)-phenyl]-6-fluoro-benzo[d]isoxazole, thiophen-3-yl-methylamine (Table No. 1, SM 9), potassium carbonate and acetonitrile essentially as described above in Example 10 except that the compound is recrystallized from methanol. Microanalysis (C, H, N) is consistent with the final, desired compound. mp=262-265° C.

Examples 13-19

Examples 13-19 are prepared using techniques of parallel synthesis. Experimental conditions are described in detail for Example 13, with any variations in procedures being noted for Examples 14-19.

Example 13

Synthesis of benzyl-{3-[4-(6-fluoro-benzo[d]isoxazol-3-yl)-phenoxy]-propyl}-amine (Scheme III, Compound 1b)

Scheme III, Step R

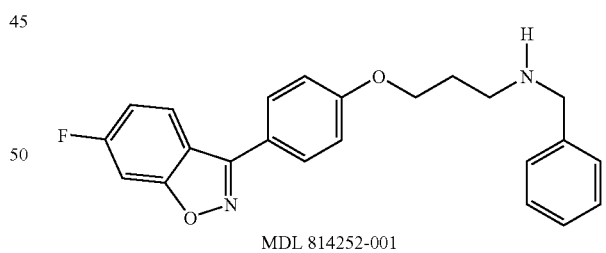

MDL 814252-001

Mix 3-[4-(3-bromo-propoxy)-phenyl]-6-fluoro-benzo[d] isoxazole (150 mg, 0.43 mmol), benzylamine (92.2 mg, 0.861 mmol), potassium carbonate(130.6 mg, 0.95 mmol, 2.2 equivalents), potassium iodide (7.2 mg, 0.043 mmol) and 4%-5% aqueous acetonitrile (4-6 mL). Under a nitrogen atmosphere, heat (70°-75° C.) overnight. Dilute reaction mixture with ethyl acetate, filter to remove the solids and concentrate (in vacuo). Purify the crude reaction mixture by column (silica) chromatography using a Waters Sep-Pak 10 g cartridge eluted with ethyl acetate to give the title compound as a solid (89.23 mg, 55.1% Yield). Purity by LC/MS=95%, $[M+H]^+=377$.

Example 13A

Synthesis of 6-fluoro-3-[4-(2-pyrrolidin-1-yl-ethoxy)-phenyl]-benzo[d]isoxazole (Scheme III, Compound 1b)

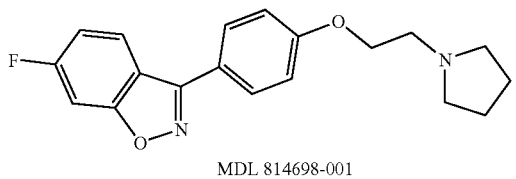

MDL 814698-001

The title compound is prepared from a mixture of 3[4-(2-bromo-ethoxy)-phenyl]-6-fluoro-benzo[d]isoxazole, pyrrolidine, potassium carbonate, potassium iodide and 5% aqueous acetonitrile at 75° C. essentially as described above in Example 13, except that the column is eluted with 10% methanol in ethyl acetate. Purity by LC/MS=99%, $[M+H]^+$=327.

Example 13B

Synthesis of 6-fluoro-3-{4-[3-(4-methyl-piperidin-1-yl)-propoxy]-phenyl}-benzo[d]isoxazole (Scheme III, Compound 1b)

Scheme III, Step R

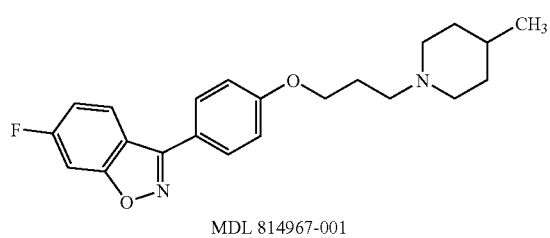

MDL 814967-001

The title compound is prepared from a mixture of 3-[4-(3-bromo-propoxy)-phenyl]-6-fluoro-benzo[d], 4-methylpiperidine, potassium carbonate, potassium iodide and 5% aqueous acetonitrile, at 75° C., essentially as described above in Example 13, except that the column is eluted with 10% methanol in ethyl acetate or ethyl acetate. Purity by LC/MS=100%, $[M+H]^+$=369.

Example 14

Synthesis of {3-[4-(6-fluoro-benzo[d]isoxazol-3-yl)-phenoxy]-propyl}-indan-2-yl-amine hydrochloride (Scheme III, Compound 1b)

Scheme III, Step R

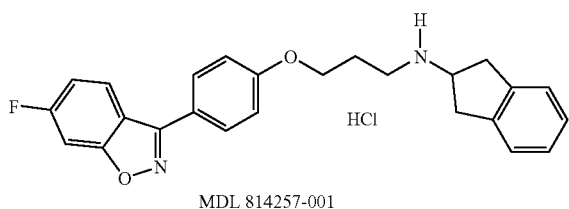

MDL 814257-001

The title compound is prepared from a mixture of 3-[4-(3-bromo-propoxy)-phenyl]-6-fluoro-benzo[d]isoxazole, 2-aminoindan hydrochloride, potassium carbonate, potassium iodide and 4% aqueous acetonitrile essentially as described above in Example 13 except that 3.2 equivalents of potassium carbonate is used. Purity by LC/MS=93%, $[M+H]^+$=403.

Example 15

Synthesis of {3-[4-(6-fluoro-benzo[d]isoxazol-3-yl)-phenoxy]-propyl}-(2-fluoro-benzyl)-amine (Scheme III, Compound 1b)

Scheme III, Step R

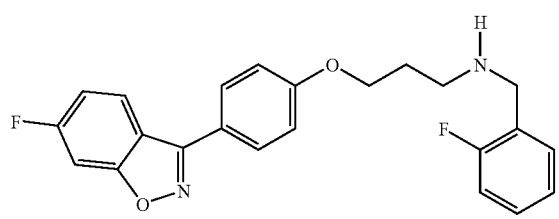

MDL 814253-001

The title compound is prepared from a mixture of 3-[4-(3-bromo-propoxy)-phenyl]-6-fluoro-benzo[d]isoxazole, 2-fluorobenzylamine, potassium carbonate, potassium iodide and 4% aqueous acetonitrile essentially as described above in Example 13. Purity by LC/MS=94%, $[M+H]^+$=395.

Example 16

Synthesis of (2-chloro-benzyl)-{3-[4-(6-fluoro-benzo[d]isoxazol-3-yl)-phenoxy]-propyl}-amine (Scheme III, Compound 1b)

Scheme III, Step R

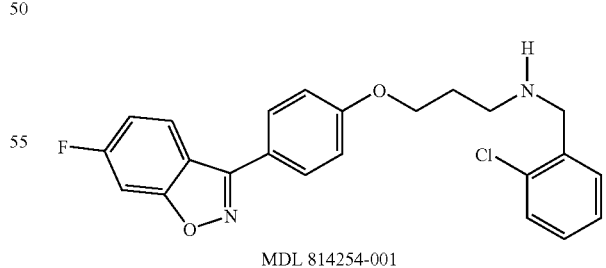

MDL 814254-001

The title compound is prepared from a mixture of 3-[4-(3-bromo-propoxy)-phenyl]-6-fluoro-benzo[d]isoxazole, 2-chlorobenzylamine, potassium carbonate, potassium iodide and 4% aqueous acetonitrile essentially as described above in Example 13. Purity by LC/MS=95%, $[M+H]^+$=411.

Example 17

Synthesis of (3,4-difluoro-benzyl)-{3-[4-(6-fluoro-benzo[d]isoxazol-3-yl)-phenoxy]-propyl}-amine (Scheme III, Compound 1b)

Scheme III, Step R

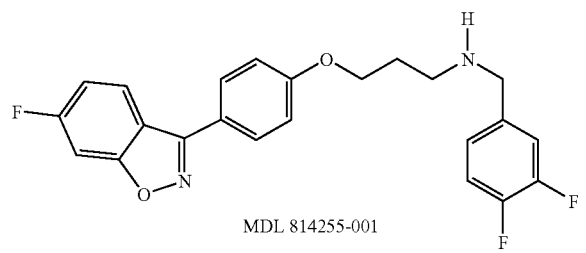

MDL 814255-001

The title compound is prepared from a mixture of 3-[4-(3-bromo-propoxy)-phenyl]-6-fluoro-benzo[d]isoxazole, 3,4-difluorobenzylamine, potassium carbonate, potassium iodide and 4% aqueous acetonitrile essentially as described above in Example 13. Purity by LC/MS=96%, [M+H]$^+$=413.

Example 18

Synthesis of (3,4-dichloro-benzyl)-{3-[4-(6-fluoro-benzo[d]isoxazol-3-yl)-phenoxy]-propyl}-amine (Scheme III, Compound 1b)

Scheme III, Step R

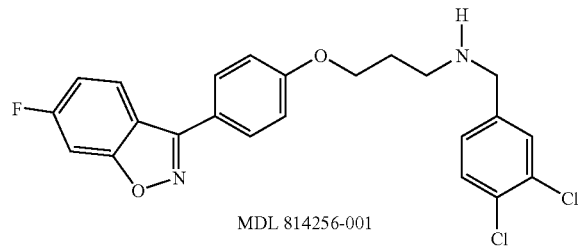

MDL 814256-001

The title compound is prepared from a mixture of 3-[4-(3-bromo-propoxy)-phenyl]-6-fluoro-benzo[d]isoxazole, 3,4-dichlorobenzylamine, potassium carbonate, potassium iodide and 4% aqueous acetonitrile essentially as described above in Example 13. Purity by LC/MS=95%, [M+H]$^+$=445.

Example 19

Synthesis of {3-[4-(6-fluoro-benzo[d]isoxazol-3-yl)-phenoxy]-propyl}-thiophen-3-ylmethyl-amine (Scheme III, Compound 1b)

Scheme III, Step R

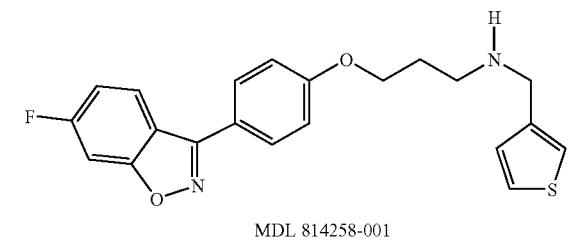

MDL 814258-001

The title compound is prepared from a mixture of 3-[4-(3-bromo-propoxy)-phenyl]-6-fluoro-benzo[d]isoxazole, thiophen-3-yl-methylamine hydrochloride (Table No. 1, SM 1), potassium carbonate, potassium iodide and 4% aqueous acetonitrile essentially as described above in Example 13 except that 3.2 equivalents of potassium carbonate is used. Purity by LC/MS=95%, [M+H]$^+$=383.

Example 20

Synthesis of 6-fluoro-3-(4-{2-[4-(4-fluoro-phenyl)-piperidin-1-yl]-ethoxy}-phenyl)-benzo[d]isoxazole hydrochloride (Scheme III, Compound 1b)

Scheme III, Step R

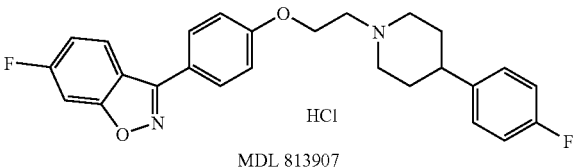

MDL 813907

Add 4-(4-fluoro-phenyl)-piperidine (133 mg, 0.744 mol) (See Table No.1, SM 2) to a suspension of 3-[4-(2-bromo-ethoxy)-phenyl]-6-fluoro-benzo[d]isoxazole (250 mg, 0.744 mol) in a mixture of water:acetonitrile (0.1 mL:2.5 mL). Then add potassium carbonate (164 mg, 1.63 mmol) and potassium iodide (12 mg, 1.07 mmol) and heat at reflux for 8 hours. Stir at room temperature for 72 hours, filter the suspension and wash the solid thoroughly with dichloromethane. Dilute the resulting solution with dichloromethane (5 mL) and wash with water (5 mL), 10% HCl (5 mL), water (5 mL), saturated sodium chloride (5 mL), dry (MgSO$_4$), filter and evaporate to give a white solid. Dissolve the solid in a minimum amount of chloroform and add 1.0 M HCl in ether and stir under a nitrogen atmosphere for 1 hour. Collect the solid by vacuum filtration, wash thoroughly with ether and dry to give the title compound (168 mg, 48% Yield). Microanalysis (C, H, N) is consistent with the final, desired compound. mp-235-239° C.

Example 20A

Synthesis of 6-fluoro-3-[4-(2-piperidin-1-yl-ethoxy)-phenyl]-benzo[d]isoxazole (Scheme III, Compound 1b)

Scheme III, Step R

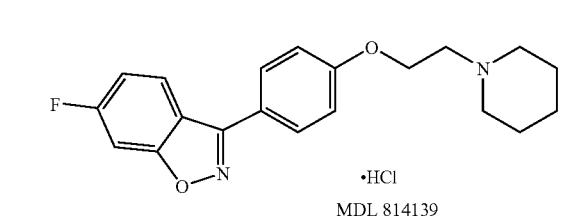

MDL 814139

Combine 3-[4-(2-bromo-ethoxy)-phenyl]-6-fluoro-benzo[d]isoxazole (550 mg, 1.63 mmol), potassium carbonate (500 mg, 3.62 mmol), piperidine-$d_{11}$ (630 mg, 6.55 mmol) and 5% aqueous acetonitrile. Under a nitrogen atmosphere, heat to reflux overnight. Cool to room temperature and pour the reaction mixture into water resulting in white solid precipitation. Collect the solid and dry in vacuo. Dissolve the solid in ethyl acetate and filter to remove the insoluble materials and concentrate in vacuo. Take the solid up in diethyl ether, filter and precipitate the hydrochloride salt out of solution by addition of hydrogen chloride in diethyl ether. Collect the desired salt and dry in vacuo to give the title compound as a solid (410 mg, 67% Yield).

Alternatively, the procedure can be performed as follows:

MDL 814139

Combine 4-(6-fluoro-benzo[d]isoxazol-3-yl)-phenol (500 mg, 2.18 mmol), and dichloromethane (8.65 mL) and add triphenylphosphine (587 mg, 2.18 mmol), diethylazodicarboxylate (0.35 mL, 2.18 mmol) and 1-piperidineethanol (0.29 mL, 2.18 mmol) to result in a yellow solution. Stir at room temperature for 3.5 hours, then dilute with ether (22 mL), wash with 5% aqueous sodium hydroxide (3×5 mL), brine (5 mL) and dry (MgSO$_4$). Purify the residue via flash column chromatography (ethyl acetate) to give the free base as a pink solid. Take up the pink solid in dry ether (10 mL) and add 1.0 M hydrogen chloride in ether (5 mL). Stir the suspension at room temperature for 1 hour and collect the white solid by suction filtration, wash with ether and dry to give the title compound as a pink solid (216 mg, 26% Yield). mp=218-223° C.

Example 20B
Synthesis of 2-{2-[4-(6-fluoro-benzo[d]isoxazol-3-yl)-phenoxy]-ethyl}-1,2,3,4tetrahydro-isoquinoline (Scheme III, Compound 1b)

Scheme III, Step R

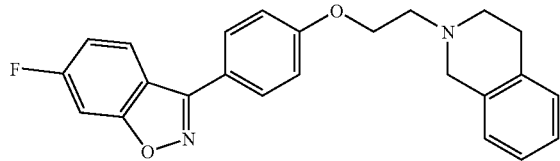

MDL 814110

Combine 3-[4-(2-bromo-ethoxy)-phenyl]-6-fluoro-benzo[d]isoxazole (200 mg, 0.595 mmol), 1,2,3,4-tetrahydroisoquinoline (0.08 mL, 0.595 mmol), potassium carbonate (181 mg, 1.31 mmol), potassium iodide (10 mg, 0.06 mmol) and 4% aqueous acetonitrile. Stir at 70° C. for 18 hours and cool to room temperature. Filter the reaction mixture and wash the solids with dichloromethane. Evaporate the filtrate to give the title compound as a brown solid (130 mg, 56% Yield). Purity by LC/MS=68%, [M+H]$^+$=389.

Example 20C
Synthesis of benzyl-{2-[4-(6-fluoro-benzo[d]isoxazol-3-yl)-phenoxy]-ethyl}-amine (Scheme III, Compound 1b)

Scheme III, Step R

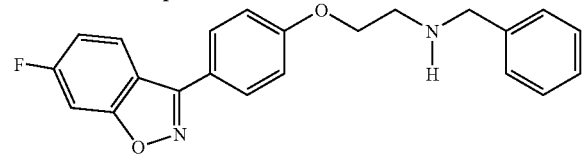

MDL 814112

The title compound is prepared from a mixture of 3-[4-(2-bromo-ethoxy)-phenyl]-6-fluoro-benzo[d]isoxazole, benzylamine, potassium carbonate, potassium iodide and 4% aqueous acetonitrile essentially as described above in Example 20B, except that the reaction mixtures were poured directly onto a column and eluted with a step gradient consisting of dichloromethane and 5% methanol in dichloromethane. Purity by LC/MS=77%, [M+H]$^+$=363.

Examples 21-55

Examples 21-55 are prepared using techniques of parallel synthesis. Experimental conditions are described in detail for Example 21, with any variations in procedures being noted for Examples 22-55.

Example 21

Synthesis of (S)-1-(4-benzyl-piperidin-1-yl)-3-[4-(6-fluoro-benzo[d]isoxazol-3-yl)-phenoxy]-propan-2-ol (Scheme III, Compound 1)

Scheme III, Step O

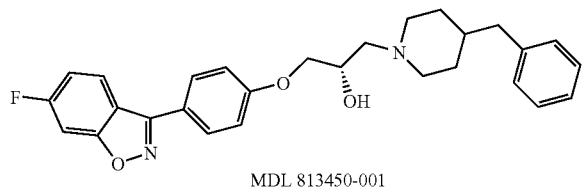

MDL 813450-001

Combine (S)-6-fluoro-3-(4-oxiranylmethoxy-phenyl)-benzo[d]isoxazole (150 mg, 0.526 mmol) dissolved in dimethylformamide (~2 mL) and add 0.13 M solution of 4-benzylpiperidine in ethanol (~4 mL) and heat for 10 hours at 85° C. Concentrate and purify the reaction mixture by flash (silica) chromatography on a Water's Sep-Pak 5 g silica cartridge using a graded solvent mixture of dichloromethane to 10% methanol in dichloromethane to give the title compound (169.9 mg, 70% Yield). Purity by LC/MS=99%, [M+H]$^+$=461.

Example 22

Synthesis of (R)-1-diethylamino-3-[4-(6-fluoro-benzo[d]isoxazol-3-yl)-phenoxy]-propan-2-ol (Scheme III, Compound 1)

Scheme III Step O

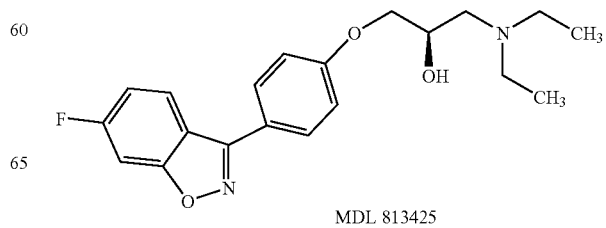

MDL 813425

The title compound is prepared from a mixture of (R)-6-fluoro-3-(4-oxiranylmethoxy-phenyl)-benzo[d]isoxazole in dimethylformamide and diethylamine in ethanol essentially as described above in Example 21. Purity by LC/MS=100%, [M+H]$^+$=359.

Example 23

Synthesis of (R)-1-(4-benzyl-piperidin-1-yl)-3-[4-(6-fluoro-benzo[d]isoxazol-3-yl)-phenoxy]-propan-2-ol (Scheme III, Compound 1)

Scheme III, Step O

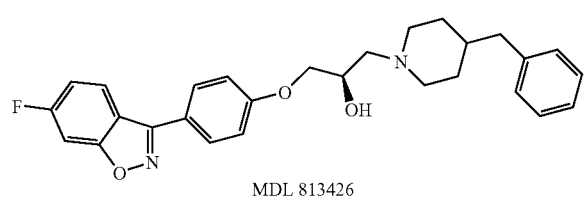

MDL 813426

The title compound is prepared from a mixture of (R)-6-fluoro-3-(4-oxiranylmethoxy-phenyl)-benzo[d]isoxazole in dimethylformamide and 4-benzylpiperidine in ethanol essentially as described above in Example 21. Purity by LC/MS=99%, [M+H]$^+$=461.

Example 24

Synthesis of (R)-1-[4-(6-fluoro-benzo[d]isoxazol-3-yl)-phenoxy]-3-morpholin-4-yl-propan-2-ol (Scheme III, Compound 1)

Scheme III, Step O

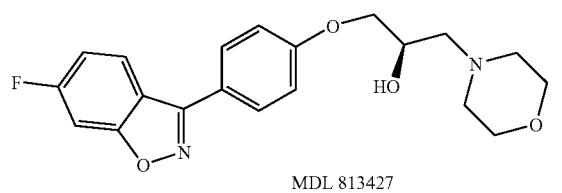

MDL 813427

The title compound is prepared from a mixture of (R)-6-fluoro-3-(4-oxiranylmethoxy-phenyl)-benzo[d]isoxazole in dimethylformamide and morpholine in ethanol essentially as described above in Example 21. Purity by LC/MS=100%, [M+H]$^+$=373.

Example 25

Synthesis of (R)-1-[4-(6-fluoro-benzo[d]isoxazol-3-yl)-phenoxy]-3-(4-methyl-piperazin-1-yl)-propan-2-ol (Scheme III, Compound 1)

Scheme III, Step O

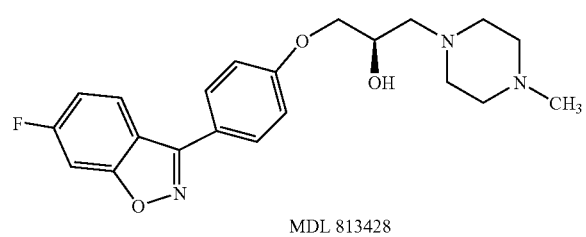

MDL 813428

The title compound is prepared from a mixture of (R)-6-fluoro-3-(4-oxiranylmethoxy-phenyl)-benzo[d]isoxazole in dimethylformamide and 1-methylpiperazine in ethanol essentially as described above in Example 21. Purity by LC/MS=90%, [M+H]$^+$=386. Remaining 10% identified as N(CH$_3$)$_2$ adduct.

Example 26

Synthesis of (R)-1-[4-(6-fluoro-benzo[d]isoxazol-3-yl)-phenoxy]-3-(4-phenyl-piperazin-1-yl)-propan-2-ol (Scheme III, Compound 1)

Scheme III, Step O

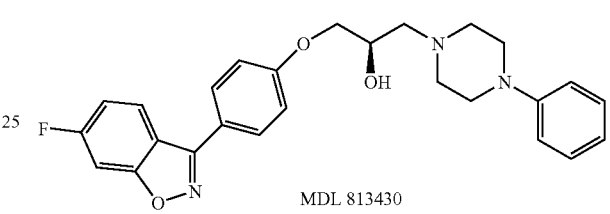

MDL 813430

The title compound is prepared from a mixture of (R)-6-fluoro-3-(4-oxiranylmethoxy-phenyl)-benzo[d]isoxazole in dimethylformamide and 1-phenylpiperazine in ethanol essentially as described above in Example 21. Purity by LC/MS=99%, [M+H]$^+$=448.

Example 27

Synthesis of (R)-1-[4-(6-fluoro-benzo[d]isoxazol-3-yl)-phenoxy]-3-(methyl-phenethyl-amino)-propan-2-ol (Scheme III, Compound 1)

Scheme III, Step O

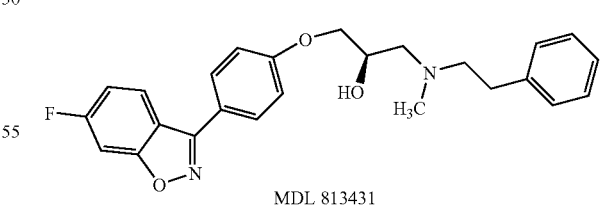

MDL 813431

The title compound is prepared from a mixture of (R)-6-fluoro-3-(4-oxiranylmethoxy-phenyl)-benzo[d]isoxazole in dimethylformamide and N-methylphenethylamine in ethanol essentially as described above in Example 21. Purity by LC/MS=100%, [M+H]$^+$=421.

Example 28

Synthesis of (R)-1-(3,4-dihydro-1H-isoquinolin-2-yl)-3-[4-(6-fluoro-benzo[d]isoxazol-3-yl)-phenoxy]-propan-2-ol (Scheme III, Compound 1)

Scheme III, Step O

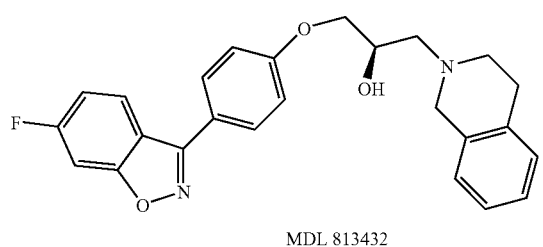

MDL 813432

The title compound is prepared from a mixture of (R)-6-fluoro-3-(4-oxiranylmethoxy-phenyl)-benzo[d]isoxazole in dimethylformamide and 1,2,3,4-tetrahydroisoquinoline in ethanol essentially as described above in Example 21. Purity by LC/MS=99%, [M+H]$^+$=419.

Example 29

Synthesis of (R)-1-[4-(6-fluoro-benzo[d]isoxazol-3-yl)-phenoxy]-3-(4-pyridin-2-yl-piperazin-1-yl)-propan-2-ol (Scheme III, Compound 1)

Scheme III, Step O

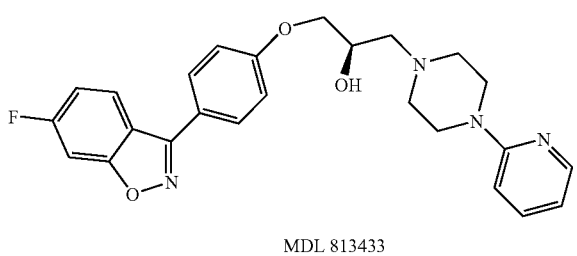

MDL 813433

The title compound is prepared from a mixture of (R)-6-fluoro-3-(4-oxiranylmethoxy-phenyl)-benzo[d]isoxazole in dimethylformamide and 1-pyridin-2-yl-piperazine in ethanol essentially as described above in Example 21. Purity by LC/MS=100%, [M+H]$^+$=449.

Example 30

Synthesis of (R)-1-(cyclohexyl-methyl-amino)-3-[4-(6-fluoro-benzo[d]isoxazol-3-yl)-phenoxy]-propan-2-ol (Scheme III, Compound 1)

Scheme III, Step O

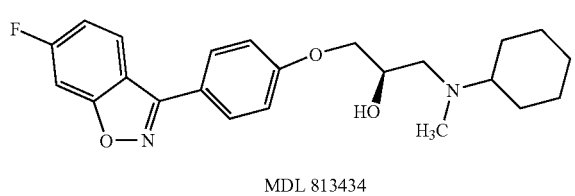

MDL 813434

The title compound is prepared from a mixture of (R)-6-fluoro-3-(4-oxiranylmethoxy-phenyl)-benzo[d]isoxazole in dimethylformamide and N-methylcyclohexylamine in ethanol essentially as described above in Example 21. Purity by LC/MS=100%, [M+H]$^+$=399.

Example 31

Synthesis of (R)-(R)-1-[4-(6-fluoro-benzo[d]isoxazol-3-yl)-phenoxyl]-3-(2-methoxymethyl-pyrrolidin-1-yl)-propan-2-ol (Scheme III, Compound 1)

Scheme III, Step O

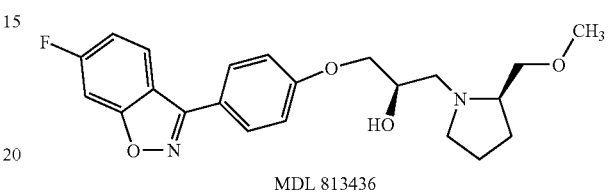

MDL 813436

The title compound is prepared from a mixture of (R)-6-fluoro-3-(4-oxiranylmethoxy-phenyl)-benzo[d]isoxazole in dimethylformamide and (S)-(+)-2-(methoxymethyl)pyrrolidine in ethanol essentially as described above in Example 21. Purity by LC/MS=100%, [M+H]$^+$=401.

Example 32

Synthesis of (R)-1-[4-(6-fluoro-benzo[d]isoxazol-3-yl)-phenoxy]-3-piperidin-1-yl-propan-2-ol (Scheme III, Compound 1)

Scheme III, Step O

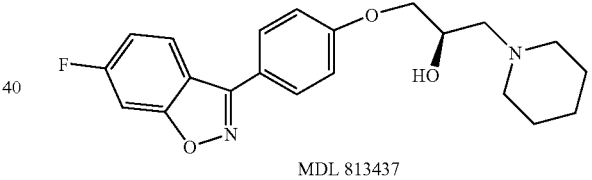

MDL 813437

The title compound is prepared from a mixture of (R)-6-fluoro-3-(4-oxiranylmethoxy-phenyl)-benzo[d]isoxazole in dimethylformamide and piperidine in ethanol essentially as described above in Example 21. Purity by LC/MS=100%, [M+H]$^+$=371.

Example 33

Synthesis of (R)-1-[4-(6-fluoro-benzo[d] isoxazol-3-yl)-phenoxy]-3-[4-(1-H-indazol-3-yl-piperazin-1-yl]-propan-2-ol (Scheme III, Compound 1)

Scheme III, Step O

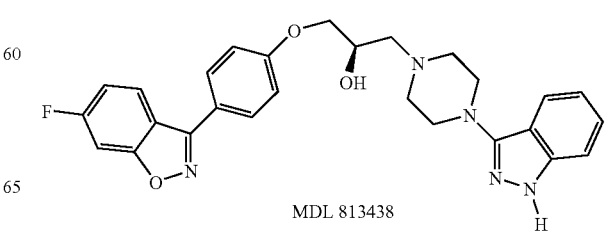

MDL 813438

The title compound is prepared from a mixture of (R)-6-fluoro-3-(4-oxiranylmethoxy-phenyl)-benzo[d]isoxazole in dimethylformamide and 3-piperazin-1-yl-1H-indazole (Table No. 1, SM 3) in ethanol essentially as described above in Example 21. Purity by LC/MS=100%, [M+H]⁺= 488.

Example 34

Synthesis of (R)-1-[4-(6-fluoro-benzo[d]isoxazol-3-yl)-phenoxy]-3-[4-(6-fluoro-benzo[d]isoxazol-3-yl)-piperidin-1-yl]-propan-2-ol (Scheme III, Compound 1)

Scheme III, Step O

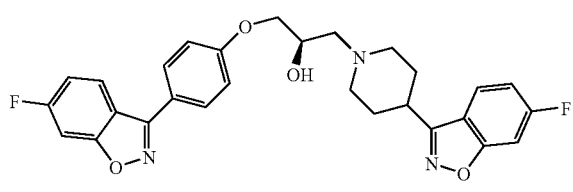

MDL 813439

The title compound is prepared from a mixture of (R)-6-fluoro-3-(4-oxiranylmethoxy-phenyl)-benzo[d]isoxazole in dimethylformamide and 6-fluoro-3-piperidine-4-yl-benzo[d]isoxazole (Table No.1, SM 8) in ethanol essentially as described above in Example 21. Purity by LC/MS=100%, [M+H]⁺=506.

Example 35

Synthesis of (R)-1-[4-(6-fluoro-benzo[d]isoxazol-3-yl)-phenoxy]-3-(4-phenyl-piperidin-1-yl)-propan-2-ol (Scheme III, Compound 1)

Scheme III, Step O

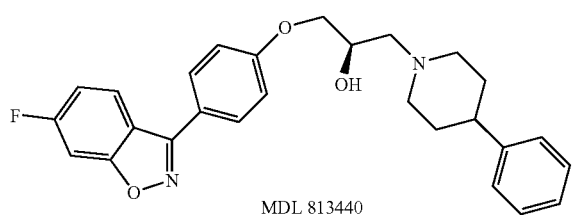

MDL 813440

The title compound is prepared from a mixture of (R)-6-fluoro-3-(4-oxiranylmethoxy-phenyl)-benzo[d]isoxazole in dimethylformamide and 4-phenylpiperidine in ethanol essentially as described above in Example 21. Purity by LC/MS=100%, [M+H]⁺=447.

Example 36

Synthesis of (R)-1-[4-(6-fluoro-benzo[d]isoxazol-3-yl)-phenoxy]-3-[4-(4-fluoro-phenoxy)-piperidin-1-yl]-propan-2-ol (Scheme III, Compound 1)

Scheme III, Step O

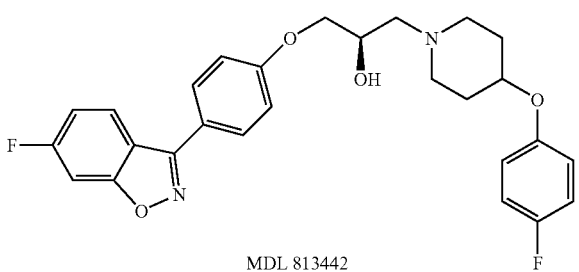

MDL 813442

The title compound is prepared from a mixture of (R)-6-fluoro-3-(4-oxiranylmethoxy-phenyl)-benzo[d]isoxazole in dimethylformamide and 4-(4-fluoro-phenoxy)-piperidine (Table No.1, SM 5) in ethanol essentially as described above in Example 21. Purity by LC/MS=86%, [M+H]⁺=481 and 8%, [M+H]⁺=573.

Example 37

Synthesis of (R)-1-[4-(6-fluoro-benzo[d]isoxazol-3-yl)-phenoxy]-3-(1,2,3,4-tetrahydro-β-carbolin-2-yl)-propan-2-ol (Scheme III, Compound 1)

Scheme III, Step O

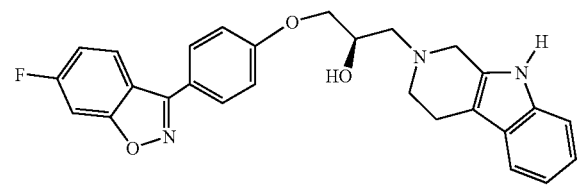

MDL 813443

The title compound is prepared from a mixture of (R)-6-fluoro-3-(4-oxiranylmethoxy-phenyl)-benzo[d]isoxazole in dimethylformamide and noreleagnine in ethanol essentially as described above in Example 21. Purity by LC/MS=99%, [M+H]⁺=458.

Example 38

Synthesis of (R)-1-{3-[4-(6-fluoro-benzo[d]isoxazol-3-yl)-phenoxy]-2-hydroxy-propyl}-4-phenyl-piperidin-4-ol (Scheme III, Compound 1)

Scheme III, Step O

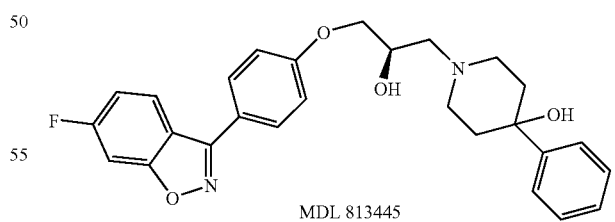

MDL 813445

The title compound is prepared from a mixture of (R)-6-fluoro-3-(4-oxiranylmethoxy-phenyl)-benzo[d]isoxazole in dimethylformamide and 4-hydroxy-4-phenylpiperidine in ethanol essentially as described above in Example 21. Purity by LC/MS=100%, [M+H]⁺=463.

Example 39

Synthesis of (R)-1-[4-(6-fluoro-benzo[d]isoxazol-3-yl)-phenoxy]-3-[4-(6-fluoro-1H-indazol-3-yl)-piperazin-1-yl]-propan-2-ol (Scheme III, Compound 1)

Scheme III, Step O

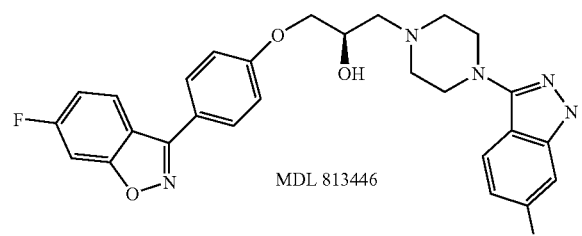

MDL 813446

The title compound is prepared from a mixture of (R)-6-fluoro-3-(4-oxiranylmethoxy-phenyl)-benzo[d]isoxazole in dimethylformamide and 6-fluoro-3-piperazin-1-yl-1H-indazole (Table No.1, SM 4) in ethanol essentially as described above in Example 21. Purity by LC/MS=100%, $[M+H]^+=$ 506.

Example 40

Synthesis of (R)-2-(4-{3-[4-(6-fluoro-benzo[d]isoxazol-3-yl)-phenoxy]-2-hydroxy-propyl}-piperazin-1-yl)-benzonitrile (Scheme III, Compound 1)

Scheme III, Step O

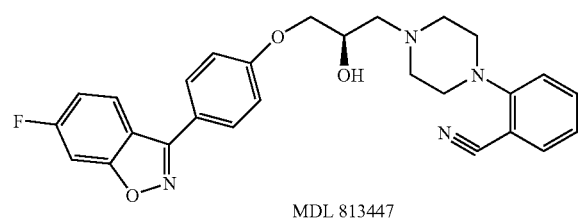

MDL 813447

The title compound is prepared from a mixture of (R)-6-fluoro-3-(4-oxiranylmethoxy-phenyl)-benzo[d]isoxazole in dimethylformamide and 1-(2-cyanophenyl)piperazine in ethanol essentially as described above in Example 21. Purity by LC/MS=100%, $[M+H]^+=473$.

Example 41

Synthesis of (R)-1-({2-[3-(3-bromo-phenyl)-pyrazolo[4,3-c]pyridin-1-yl]-ethyl}-methyl-amino)-3-[4-(6-fluoro-benzo[d]isoxazol-3-yl)-phenoxy]-propan-2-ol (Scheme III, Compound 1)

Scheme III, Step O

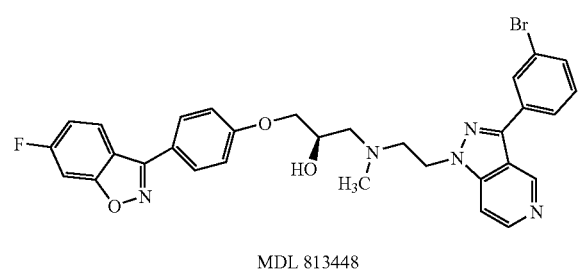

MDL 813448

The title compound is prepared from a mixture of (R)-6-fluoro-3-(4-oxiranylmethoxy-phenyl)-benzo[d]isoxazole in dimethylformamide and {2-[3-(3-bromo-phenyl)-pyrazolo[4,3-c]pyridin-1-yl]-ethyl}-methyl-amine (Table No. 1, SM 6) in ethanol essentially as described above in Example 21. Purity by LC/MS=100%, $[M+H]^+=616$.

Example 42

Synthesis of (S)-1-[4-(6-fluoro-benzo[d]isoxazol-3-yl)-phenoxy]-3-morpholin-4-yl-propan-2-ol (Scheme III, Compound 1)

Scheme III, Step O

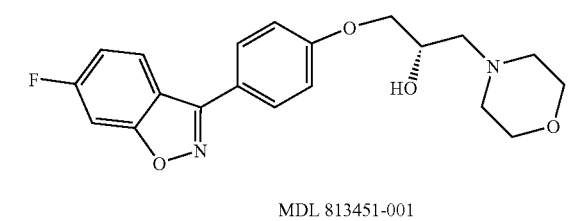

MDL 813451-001

The title compound is prepared from a mixture of (S)-6-fluoro-3-(4-oxiranylmethoxy-phenyl)-benzo[d]isoxazole in dimethylformamide and morpholine in ethanol essentially as described above in Example 21. Purity by LC/MS=100%, $[M+H]^+=373$.

Example 43

Synthesis of (S)-1-[4-(6-fluoro-benzo[d]isoxazol-3-yl)-phenoxy]-3-(4-phenyl-piperazin-1-yl)-propan-2-ol (Scheme III, Compound 1)

Scheme III, Step O

MDL 813454

The title compound is prepared from a mixture of (S)-6-fluoro-3-(4-oxiranylmethoxy-phenyl)-benzo[d]isoxazole in dimethylformamide and 1-phenylpiperazine in ethanol essentially as described above in Example 21. Purity by LC/MS=99%, $[M+H]^+=448$.

Example 44

Synthesis of (S)-1-[4-(6-fluoro-benzo[d]isoxazol-3-yl)-phenoxy]-3-(methyl-phenethyl-amino)-propan-2-ol (Scheme III, Compound 1)

Scheme III, Step O

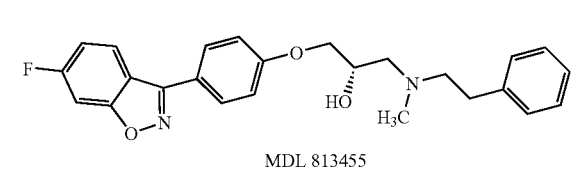

MDL 813455

The title compound is prepared from a mixture of (S)-6-fluoro-3-(4-oxiranylmethoxy-phenyl)-benzo[d]isoxazole in dimethylformamide and N-methylphenethylamine in ethanol essentially as described above in Example 21. Purity by LC/MS=100%, [M+H]⁺=421.

Example 45

Synthesis of (S)-1-(3,4-dihydro-1H-isoquinolin-2-yl)-3-[4-(6-fluoro-benzo[d]isoxazol-3-yl)-phenoxy]-propan-2-ol (Scheme III, Compound 1)

Scheme III, Step O

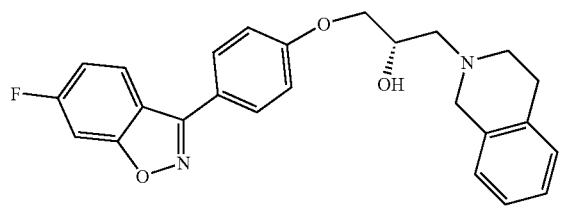

MDL 813456

The title compound is prepared from a mixture of (S)-6-fluoro-3-(4-oxiranylmethoxy-phenyl)-benzo[d]isoxazole in dimethylformamide and 1,2,3,4-tetrahydroisoquinoline in ethanol essentially as described above in Example 21. Purity by LC/MS=98%, [M+H]⁺=419.

Example 46

Synthesis of (S)-1-[4-(6-fluoro-benzo[d]isoxazol-3-yl)-phenoxy]-3-(4-pyridin-2-yl-piperazin-1-yl)-propan-2-ol (Scheme III, Compound 1)

Scheme III, Step O

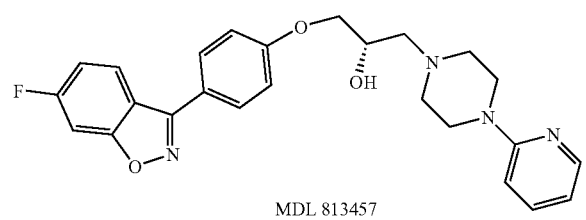

MDL 813457

The title compound is prepared from a mixture of (S)-6-fluoro-3-(4-oxiranylmethoxy-phenyl)-benzo[d]isoxazole in dimethylformamide and 1-pyridin-2-yl-piperazine in ethanol essentially as described above in Example 21. Purity by LC/MS=100%, [M+H]⁺=449.

Example 47

Synthesis of (S)-1-(cyclohexyl-methyl-amino)-3-[4-(6-fluoro-benzo[d]isoxazol-3-yl)-phenoxy]-propan-2-ol (Scheme III, Compound 1)

Scheme III, Step O

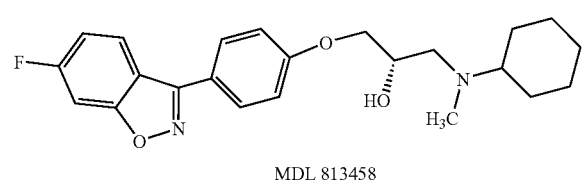

MDL 813458

The title compound is prepared from a mixture of (S)-6-fluoro-3-(4-oxiranylmethoxy-phenyl)-benzo[d]isoxazole in dimethylformamide and N-methylcyclohexylamine in ethanol essentially as described above in Example 21. Purity by LC/MS=100%, [M+H]⁺=399.

Example 48

Synthesis of (S)-1-[4-(6-fluoro-benzo[d]isoxazol-3-yl)-phenoxy]-3-piperidin-1-yl-propan-2-ol (Scheme III, Compound 1)

Scheme III Step O

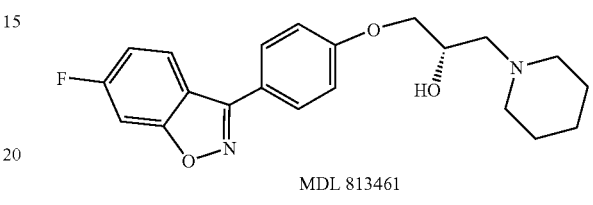

MDL 813461

The title compound is prepared from a mixture of (S)-6-fluoro-3-(4-oxiranylmethoxy-phenyl)-benzo[d]isoxazole in dimethylformamide and piperidine in ethanol essentially as described above in Example 21. Purity by LC/MS=100%, [M+H]⁺=371.

Example 49

Synthesis of (S)-1-[4-(6-fluoro-benzo[d]isoxazol-3-yl)-phenoxy]-3-[4-(1H-indazol-3-yl)-piperazin-1-yl]-propan-2-ol (Scheme III, Compound 1)

Scheme III, Step O

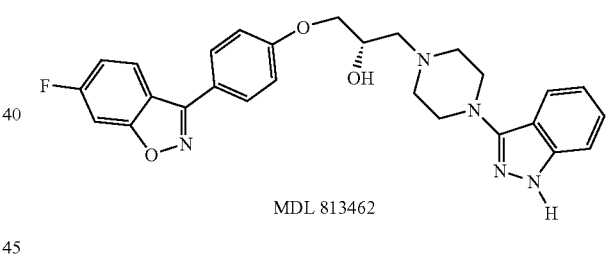

MDL 813462

The title compound is prepared from a mixture of (S)-6-fluoro-3-(4-oxiranylmethoxy-phenyl)-benzo[d]isoxazole in dimethylformamide and 3-piperazin-1-yl-1H-indazole (Table No.1, SM 3) in ethanol essentially as described above in Example 21. Purity by LC/MS=100%, [M+H]⁺=488.

Example 50

Synthesis of (S)-1-[4-(6-fluoro-benzo[d]isoxazol-3-yl)-phenoxy]-3-(4-phenyl-piperidin-1-yl)-propan-2-ol (Scheme III, Compound 1)

Scheme III, Step O

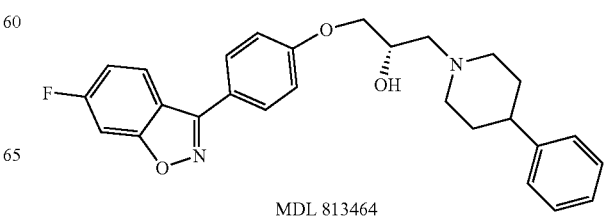

MDL 813464

The title compound is prepared from a mixture of (S)-6-fluoro-3-(4-oxiranylmethoxy-phenyl)-benzo[d]isoxazole in dimethylformamide and 4-phenylpiperidine in ethanol essentially as described above in Example 21. Purity by LC/MS=100%, [M+H]⁺=447.

Example 51

Synthesis of (S)-1-[4-(6-fluoro-benzo[d]isoxazol-3-yl)-phenoxy]-3-[4-(4-fluoro-phenoxy)-piperidin-1-yl]-propan-2-ol (Scheme III, Compound 1)

Scheme III, Step O

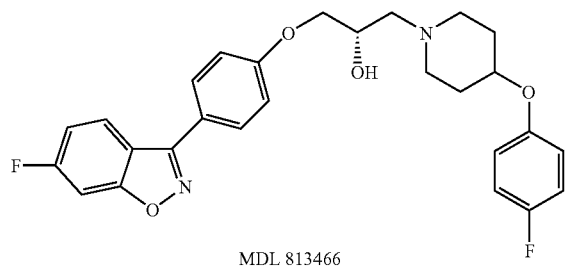

MDL 813466

The title compound is prepared from a mixture of (S)-6-fluoro-3-(4-oxiranylmethoxy-phenyl)-benzo[d]isoxazole in dimethylformamide and 4-(4-fluoro-phenoxy)-piperidine (Table No.1, SM 5) in ethanol essentially as described above in Example 21. Purity by LC/MS=88%, [M+H]⁺=481.

Example 52

Synthesis of (S)-1-[4-(6-fluoro-benzo[d]isoxazol-3-yl)-phenoxy]-3-(1,2,3,4-tetrahydro-β-carbolin-2-yl)-propan-2-ol (Scheme III, Compound 1)

Scheme III, Step O

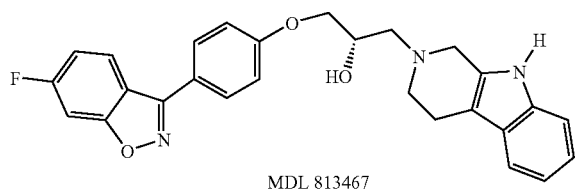

MDL 813467

The title compound is prepared from a mixture of (S)-6-fluoro-3-(4-oxiranylmethoxy-phenyl)-benzo[d]isoxazole in dimethylformamide and noreleagnine in ethanol essentially as described above in Example 21. Purity by LC/MS=99%, [M+H]⁺=458.

Example 53

Synthesis of (S)-1-{3-[4-(6-fluoro-benzo[d]isoxazol-3-yl)-phenoxy]-2-hydroxy-propyl}-4-phenyl-piperidin4-ol (Scheme III, Compound 1)

Scheme III, Step O

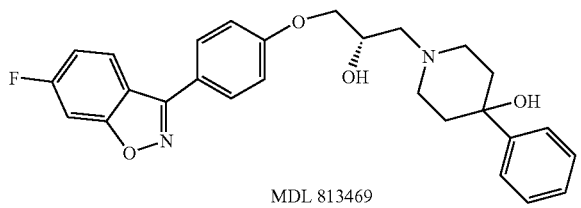

MDL 813469

The title compound is prepared from a mixture of (S)-6-fluoro-3-(4-oxiranylmethoxy-phenyl)-benzo[d]isoxazole in dimethylformamide and 4-hydroxy4-phenylpiperidine in ethanol essentially as described above in Example 21. Purity by LC/MS=100%, [M+H]⁺=463.

Example 54

Synthesis of (S)-1-[4-(6-fluoro-benzo[d]isoxazol-3-yl)-phenoxy]-3-[4-(6-fluoro-1H-indazol-3-yl)-piperazin-1-yl]-propan-2-ol (Scheme III, Compound 1)

Scheme III, Step O

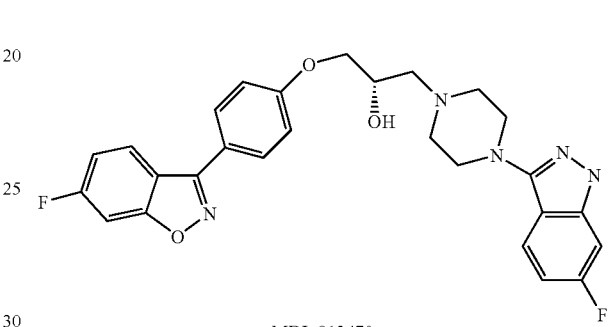

MDL 813470

The title compound is prepared from a mixture of (S)-6-fluoro-3-(4-oxiranylmethoxy-phenyl)-benzo[d]isoxazole in dimethylformamide and 6-fluoro-3-piperazin-1-yl-1H-indazole (Table No.1, SM 4) in ethanol essentially as described above in Example 21. Purity by LC/MS=100%, [M+H]⁺=506.

Example 55

Synthesis of (S)-2-(4-{3-[4-(6-fluoro-benzo[d]isoxazol-3-yl)-phenoxy]-2-hydroxy-propyl}-piperazin-1-yl)-benzonitrile (Scheme III, Compound 1)

Scheme III, Step O

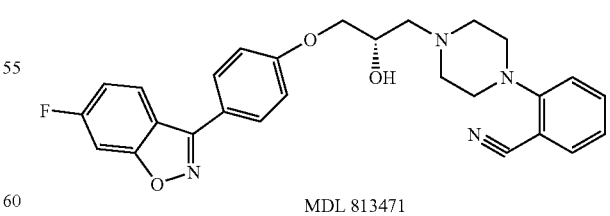

MDL 813471

The title compound is prepared from a mixture of (S)-6-fluoro-3-(4-oxiranylmethoxy-phenyl)-benzo[d]isoxazole in dimethylformamide and 1-(2-cyanophenyl)piperazine in ethanol essentially as described above in Example 21. Purity by LC/MS=100%, [M+H]⁺=473.

Example 56

Synthesis of (S)-1-[4-(6-fluoro-benzo[d]isoxazol-3-yl)-phenoxy]-3-[4-(4-fluoro-phenyl)-piperidin-1-yl]-propan-2-ol hydrochloride (Scheme III, Compound 1)

Scheme III, Step O

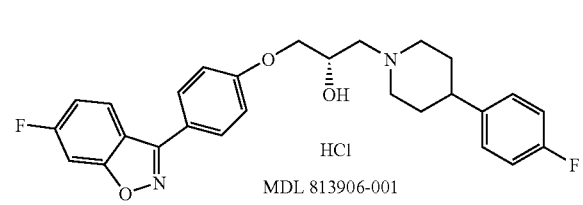

MDL 813906-001

Add (S)-6-fluoro-3-(4-oxiranylmethoxy-phenyl)-benzo[d]isoxazole (500 mg, 1.75 mmol) to a stirred solution of 4-(4-fluoro-phenyl)-piperidine (348 mg, 1.94 mmol) (See Table No.1, SM 2) in ethanol (absolute, 8.30 mL), heat at reflux for 3 hours and then cool to room temperature. Collect the resulting white precipitate by suction filtration, wash with ethanol and ether and dry to give the desired product as a pure white solid. Dissolve the solid in dichloromethane (10 mL) and add 1 M HCl in ether (6 mL) to form a suspension. Stir suspension at room temperature for 1 hour, collect the white solid by suction filtration and wash with ether and dry to give the title compound as a pure white solid (731 mg, 83% Yield). Microanalysis (C, H, N) is consistent with the final, desired compound. mp=250-253° C.

Examples 57-69

Examples 57-69 are prepared using techniques of parallel synthesis. Experimental conditions are described in detail for Example 57, with any variations in procedures being noted for Examples 58-69.

Example 57

Synthesis of (R)-1-[3-(6-fluoro-benzo[d]isoxazol-3-yl)-phenoxy]-3-[(thiophen-3-ylmethyl)-amino]-propan-2-ol (Scheme III, Compound 1)

Scheme III, Step O

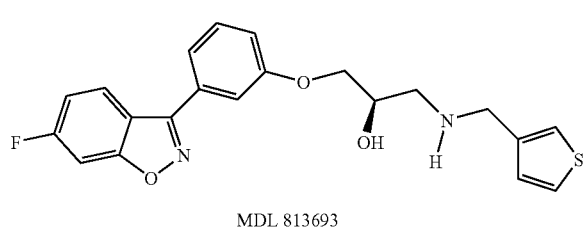

MDL 813693

To a solution of (R)-6-fluoro-3-(3-oxiranylmethoxy-phenyl)-benzo[d]isoxazole (150 mg, 526 mmol) in dichloroethane (2 mL) add thiophen-3-yl-methylamine (119 mg, 1.05 mmol) (Table No.1, SM 9) and ethanol (2 mL) and heat at 85° C. for 10 hours. Cool reaction mixture at −25° C. and concentrate. Purify the compound on a Waters Sep-Pak silica cartridge using solvent mixtures anywhere from 1% to 10% methanol in dichloromethane to give the title compound (113.0 mg, 68% Yield). Purity by LC/MS=~100%, [M+H]+=399.

Example 58

Synthesis of (R)-1-[3-(6-fluoro-benzo[d]isoxazol-3-yl)-phenoxy]-3-(indan-1-ylamino)-propan-2-ol (Scheme III, Compound 1)

Scheme III, Step O

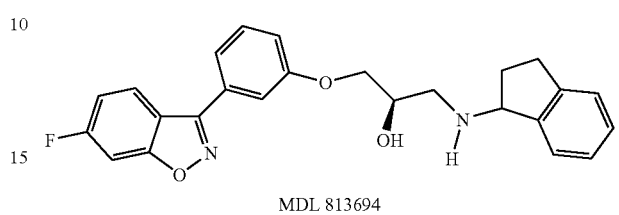

MDL 813694

The title compound is prepared from a mixture of (R)-6-fluoro-3-(3-oxiranylmethoxy-phenyl)-benzo[d]isoxazole in dichloroethane, 1-aminoindan and ethanol, essentially as described above in Example 57. Purity by LC/MS=91%, [M+H]+=419.

Example 59

Synthesis of (R)-1-[3-(6-fluoro-benzo[d]isoxazol-3-yl)-phenoxy]-3-[(thiophen-2-ylmethyl)-amino]-propan-2-ol (Scheme III, Compound 1)

Scheme III, Step O

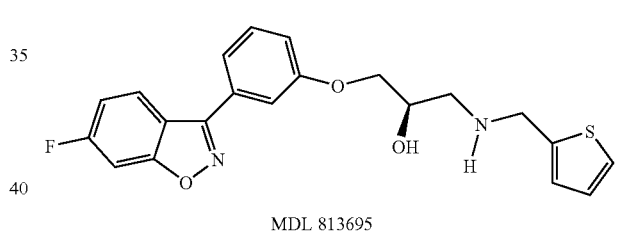

MDL 813695

The title compound is prepared from a mixture of (R)-6-fluoro-3-(3-oxiranylmethoxy-phenyl)-benzo[d]isoxazole in dichloroethane, 2-thiophenemethylamine and ethanol, essentially as described above in Example 57. Purity by LC/MS=100%, [M+H]+=399.

Example 59A

Synthesis of (S)-1-[3-(6-fluoro-benzo[d]isoxazol-3-yl)-phenoxy]-3-[(thiophen-2-ylmethyl)-amino]-propan-2-ol (Scheme III, Compound 1)

Scheme III, Step O

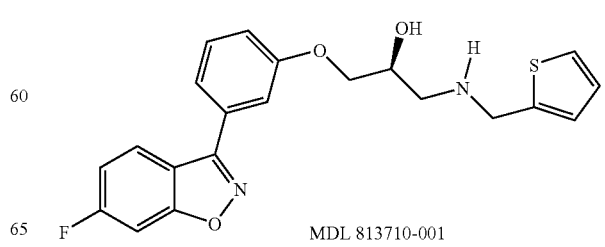

MDL 813710-001

The title compound is prepared from a mixture of (S)-6-fluoro-3-(3-oxiranylmethoxy-phenyl)-benzo[d]isoxazole in dichloroethane, 2-thiophenemethylamine and ethanol, essentially as described above in Example 57. Purity by LC/MS=96%, [M+H]$^+$=399.

Example 60

Synthesis of of (R)-1-benzylamino-3-[3-(6-fluoro-benzo[d]isoxazol-3-yl)-phenoxy]-propan-2-ol
(Scheme III, Compound 1)

Scheme III, Step O

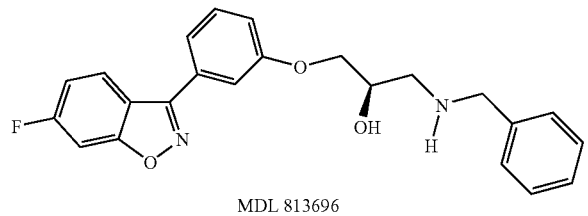

MDL 813696

The title compound is prepared from a mixture of (R)-6-fluoro-3-(3-oxiranylmethoxy-phenyl)-benzo[d]isoxazole in dichloroethane, benzylamine and ethanol, essentially as described above in Example 57. Purity by LC/MS=88%, [M+H]$^+$=393.

Example 61

Synthesis of (R)-1-[3-(6-fluoro-benzo[d]isoxazol-3-yl)-phenoxy]-3-(3-fluoro-benzylamino)-propan-2-ol
(Scheme III, Compound 1)

Scheme III, Step O

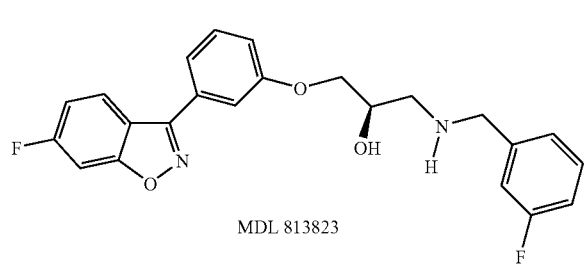

MDL 813823

The title compound is prepared from a mixture of (R)-6-fluoro-3-(3-oxiranylmethoxy-phenyl)-benzo[d]isoxazole in dichloroethane, 3-fluorobenzylamine, and ethanol, essentially as described above in Example 57. Purity by LC/MS=96%, [M+H]$^+$=411.

Example 62

Synthesis of (R)-1-[3-(6-fuoro-benzo[d]isoxazol-3-yl)-phenoxy]-3-(4-fluoro-benzylamino)-propan-2-ol
(Scheme III, Compound 1)

Scheme III, Step O

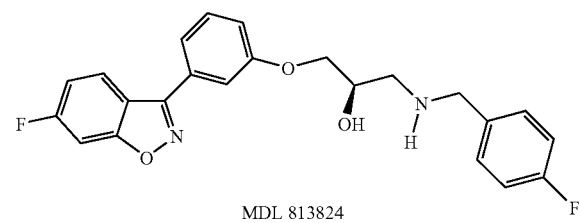

MDL 813824

The title compound is prepared from a mixture of (R)-6-fluoro-3-(3-oxiranylmethoxy-phenyl)-benzo[d]isoxazole in dichloroethane, 4-fluorobenzylamine and ethanol, essentially as described above in Example 57. Purity by LC/MS=93%, [M+H]$^+$=411.

Example 63

Synthesis of (R)-1-(4-chloro-benzylamino)-3-[3-(6-fluoro-benzo[d]isoxazol-3-yl)-phenoxy]-propan-2-ol
(Scheme III, Compound 1)

Scheme III, Step O

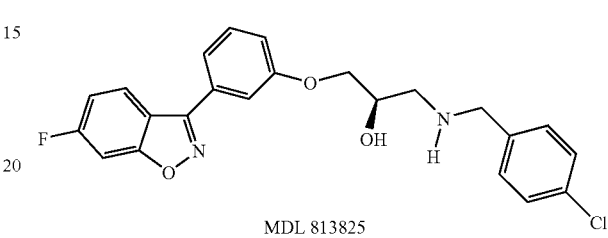

MDL 813825

The title compound is prepared from a mixture of (R)-6-fluoro-3-(3-oxiranylmethoxy-phenyl)-benzo[d]isoxazole in dichloroethane, 4-chlorobenzylamine, and ethanol, essentially as described above in Example 57. Purity by LC/MS=95%, [M+H]$^+$=427.

Example 64

Synthesis of (R)-1-[3-(6-fluoro-benzo[d]isoxazol-3-yl)-phenoxy]-3-(4-methyl-benzylamino)-propan-2-ol
(Scheme III, Compound 1)

Scheme III, Step O

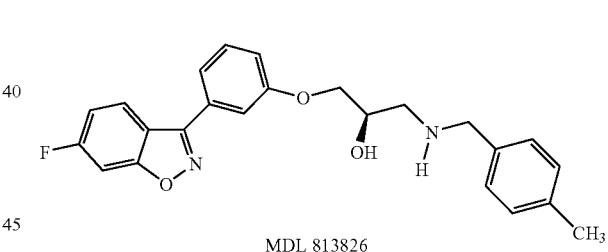

MDL 813826

The title compound is prepared from a mixture of (R)-6-fluoro-3-(3-oxiranylmethoxy-phenyl)-benzo[d]isoxazole in dichloroethane, 4-methylbenzylamine, and ethanol, essentially as described above in Example 57. Purity by LC/MS=89%, [M+H]$^+$=407.

Example 65

Synthesis of (R)-1-[3-(6-fluoro-benzo[d]isoxazol-3-yl)-phenoxy]-3-phenethylamino-propan-2-ol
(Scheme III, Compound 1)

Scheme III, Step O

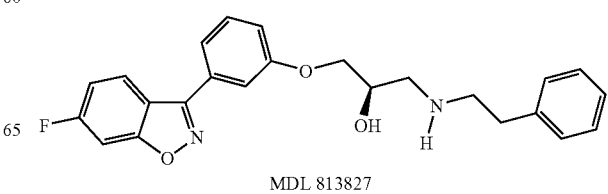

MDL 813827

The title compound is prepared from a mixture of (R)-6-fluoro-3-(3-oxiranylmethoxy-phenyl)-benzo[d]isoxazole in dichloroethane, phenethylamine, and ethanol, essentially as described above in Example 57. Purity by LC/MS=~88%, [M+H]⁺=407.

Example 66

Synthesis of (R)-1-(2-cyclohex-1-enyl-ethylamino)-3-[3-(6-fluoro-benzo[d]isoxazol-3-yl)-phenoxy]-propan-2-ol (Scheme III, Compound 1)

Scheme III, Step O

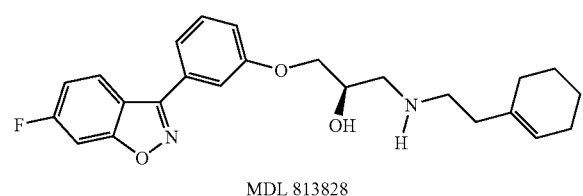

MDL 813828

The title compound is prepared from a mixture of (R)-6-fluoro-3-(3-oxiranylmethoxy-phenyl)-benzo[d]isoxazole in dichloroethane, 2-(1-cyclohexenyl)ethylamine, and ethanol, essentially as described above in Example 57. Purity by LC/MS-80%, [M+H]⁺=411.

Example 67

Synthesis of (R)-1-{3-[3-(6-fluoro-benzo[d]isoxazol-3-yl)-phenoxy]-2-hydroxy-propylamino}-indan-2-ol (Scheme III, Compound 1)

Scheme III, Step O

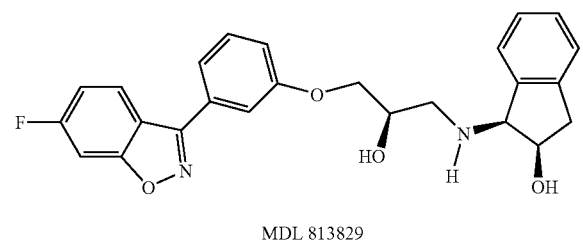

MDL 813829

The title compound is prepared from a mixture of (R)-6-fluoro-3-(3-oxiranylmethoxy-phenyl)-benzo[d]isoxazole in dichloroethane, (1S, 2R)-(–)-cis-1-amino-2-indanol, and ethanol, essentially as described above in Example 57. Purity by LC/MS=100%, [M+H]⁺=435.

Example 68

Synthesis of (R)-1-[4-(3-chloro-phenoxy)-piperidin-1-yl]-3-[3-(6-fluoro-benzo[d]isoxazol-3-yl)-phenoxy]-propan-2-ol (Scheme III, Compound 1)

Table No.1, SM 7:

Synthesis of 4-(3-Chloro-phenoxy)-piperidine

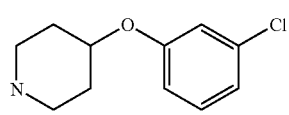

Compound prepared according to *Journal of Medicinal Chemistry*, 1978, Vol. 21, No. 3, page 309-312.

Scheme III, Step O

Synthesis of (R)-1-[4-(3-chloro-phenoxy)-piperidin-1-yl]-3-[3-(6-fluor-benzo[d]isoxazol-3-yl)-phenoxyl-propan-2-ol (Scheme III, Compound 1)

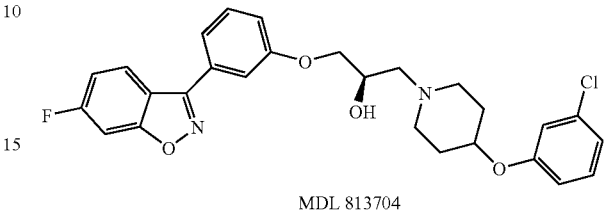

MDL 813704

The title compound is prepared from a mixture of (R)-6-fluoro-3-(3-oxiranylmethoxy-phenyl)-benzo[d]isoxazole in dichloroethane, and 4-(3-chloro-phenoxy)-piperidine (Table No.1, SM 7), essentially as described above in Example 57. Purity by LC/MS=100%, [M+H]⁺=497.

Example 69

Synthesis of (R)-1-[3-(6-fluoro-benzo[d]isoxazol-3-yl)-phenoxy]-3-(4-pyrimidin-2-yl-piperazin-1-yl)-propan-2-ol (Scheme III, Compound 1)

Scheme III, Step O

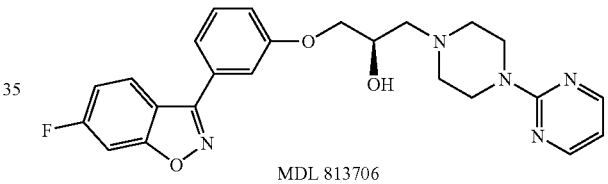

MDL 813706

The title compound is prepared from a mixture of (R)-6-fluoro-3-(3-oxiranylmethoxy-phenyl)-benzo[d]isoxazole in dichloroethane and and 2-piperazin-1-yl-pyrimidine, essentially as described above in Example 57. Purity by LC/MS=100%, [M+H]⁺=450.

Examples 70-93

Examples 70-93 are prepared using techniques of parallel synthesis. Experimental conditions are described in detail for Example 70, with any variations in procedures being noted for Examples 71-93.

Example 70

Synthesis of (R)-1-[3-(6-fluoro-benzo[d]isoxazol-3-yl)-phenoxy]-3-(1,2,3,4-tetrahydro-naphthalen-1-ylamino)-propan-2-ol (Scheme III, Compound 1)

Scheme III, Step O

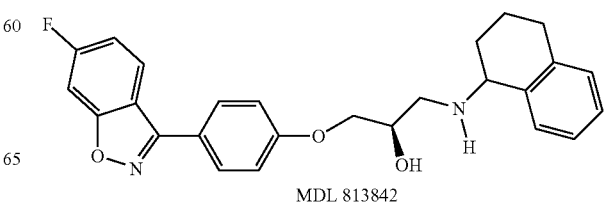

MDL 813842

The title compound is prepared from a mixture of (R)-6-fluoro-3-(4-oxiranylmethoxy-phenyl)-benzo[d]isoxazole in dimethylformamide and 1,2,3,4-tetrahydro-1-naphthylamine in ethanol, essentially as described above in Example 21, except that: when the reaction is complete, the solids are filtered off and washed with ethanol and the compound is purified on a Waters Sep-Pak silica cartridge using solvent mixtures anywhere from 1% to 10% methanol in dichloromethane to give the title compound. Purity by LC/MS=100%, [M+H]$^+$=433.

Example 71
Synthesis of (R)-1-[4-(6-fluoro-benzo[d]isoxazol-3-yl)-phenoxy]-3-[(thiophen-3-ylmethyl)-amino]-propan-2-ol (Scheme III, Compound 1)

Scheme III, Step O

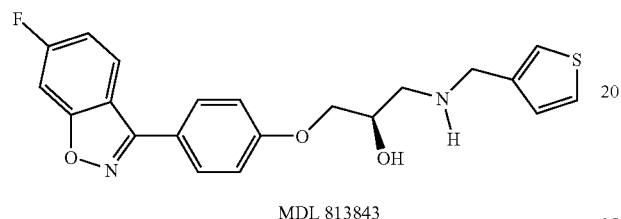

MDL 813843

The title compound is prepared from a mixture of (R)-6-fluoro-3-(4-oxiranylmethoxy-phenyl)-benzo[d]isoxazole in dimethylformamide and thiophen-3-yl-methylamine hydrochloride (Table No. 1, SM) in ethanol essentially as described above in Example 70. Purity by LC/MS=99%, [M+H]$^+$=399.

Example 72
Synthesis of (R)-1-[4-(6-fluoro-benzo[d]isoxazol-3-yl)-phenoxy]-3-(indan-1-ylamino)-propan-2-ol (Scheme III, Compound 1)

Scheme III, Step O

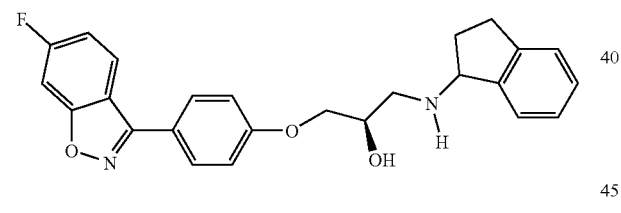

MDL 813844

The title compound is prepared from a mixture of (R)-6-fluoro-3-(4-oxiranylmethoxy-phenyl)-benzo[d]isoxazole in dimethylformamide and 1-aminoindan in ethanol, essentially as described above in Example 70. Purity by LC/MS=94%, [M+H]$^+$=419.

Example 73
Synthesis of (R)-1-[4-(6-fluoro-benzo[d]isoxazol-3-yl)-phenoxy]-3-[(thiophen-2-ylmethyl)-amino]-propan-2-ol (Scheme III, Compound 1)

Scheme III, Step O

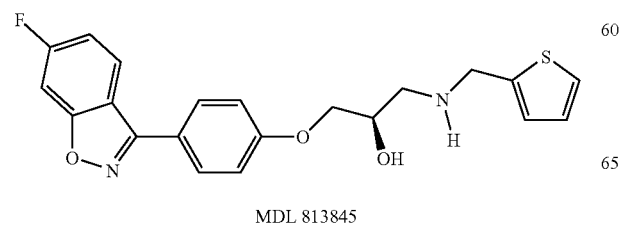

MDL 813845

The title compound is prepared from a mixture of (R)-6-fluoro-3-(4-oxiranylmethoxy-phenyl)-benzo[d]isoxazole in dimethylformamide and 2-thiophenemethylamine in ethanol, essentially as described above in Example 70. Purity by LC/MS=100%, [M+H]$^+$=399.

Example 74
Synthesis of (R)-1-(1-benzyl-piperidin4-ylamino)-3-[4-(6-fluoro-benzo[d]isoxazol-3-yl)-phenoxy]-propan-2-ol (Scheme III, Compound 1)

Scheme III, Step O

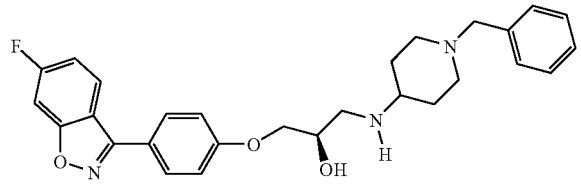

MDL 813846

The title compound is prepared from a mixture of (R)-6-fluoro-3-(4-oxiranylmethoxy-phenyl)-benzo[d]isoxazole in dimethylformamide and 4-amino-1-benzylpiperidine in ethanol, essentially as described above in Example 70. Purity by LC/MS=100%, [M+H]$^+$=476.

Example 75
Synthesis of (R)-1-benzylamino-3-[4-(6-fluoro-benzo[d]isoxazol-3-yl)-phenoxy]-propan-2-ol (Scheme III, Compound 1)

Scheme III, Step O

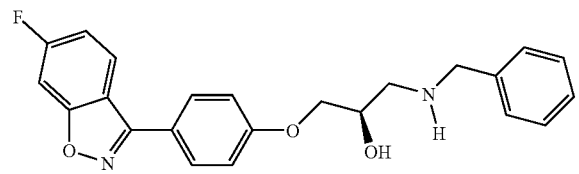

MDL 813847, MDL 814300

The title compound is prepared from a mixture of (R)-6-fluoro-3-(4-oxiranylmethoxy-phenyl)-benzo[disoxazole in dimethylformamide and benzylamine in ethanol, essentially as described above in Example 70. Purity by LC/MS=100%, [M+H]$^+$=393.

Example 76

Synthesis of (R)-1-[4-(6-fluoro-benzo[d]isoxazol-3-yl)-phenoxy]-3-(2-fluoro-benzylamino)-propan-2-ol (Scheme III, Compound 1)

Scheme III, Step O

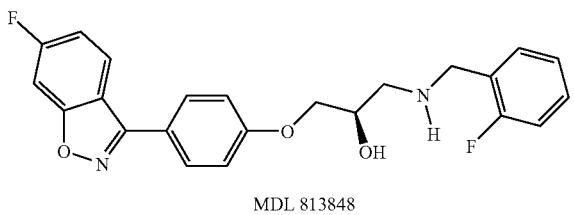

MDL 813848

The title compound is prepared from a mixture of (R)-6-fluoro-3-(4-oxiranylmethoxy-phenyl)-benzo[d]isoxazole in dimethylformamide and 2-fluorobenzylamine in ethanol, essentially as described above in Example 70. Purity by LC/MS=100%, [M+H]$^+$=411.

Example 77

Synthesis of (R)-1-(2-chloro-benzylamino)-3-[4-(6-fluoro-benzo[d]isoxazol-3-yl)-phenoxy]-propan-2-ol (Scheme III, Compound 1)

Scheme III, Step O

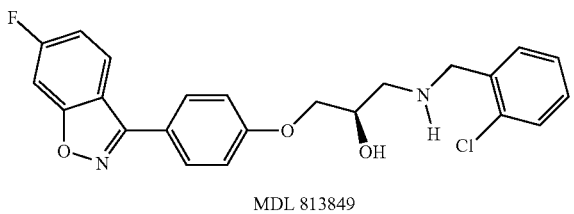

MDL 813849

The title compound is prepared from a mixture of (R)-6-fluoro-3-(4-oxiranylmethoxy-phenyl)-benzo[d]isoxazole in dimethylformamide and 2-chlorobenzylamine in ethanol, essentially as described above in Example 70. Purity by LC/MS=98%, [M+H]$^+$=427.

Example 78

Synthesis of (R)-1-[4-(6-fluoro-benzo[d]isoxazol-3-yl)-phenoxy]-3-(2-methoxy-benzylamino)-propan-2-ol (Scheme III, Compound 1)

Scheme III, Step O

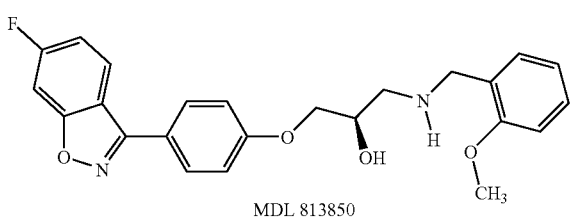

MDL 813850

The title compound is prepared from a mixture of (R)-6-fluoro-3-(4-oxiranylmethoxy-phenyl)-benzo[d]isoxazole in dimethylformamide and 2-methoxybenzylamine in ethanol, essentially as described above in Example 70. Purity by LC/MS=100%, [M+H]$^+$=423.

Example 79

Synthesis of (R)-1-[4-(6-fluoro-benzo[d]isoxazol-3-yl)-phenoxy]-3-(3-fluoro-benzylamino)-propan-2-ol (Scheme III, Compound 1)

Scheme III, Step O

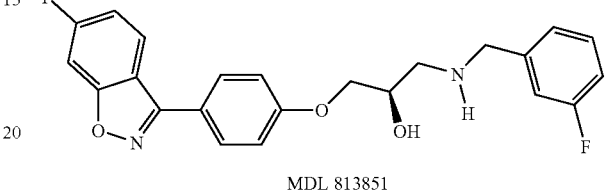

MDL 813851

The title compound is prepared from a mixture of (R)-6-fluoro-3-(4-oxiranylmethoxy-phenyl)-benzo[d]isoxazole in dimethylformamide and 3-fluorobenzylamine in ethanol, essentially as described above in Example 70. Purity by LC/MS=100%, [M+H]$^+$=411.

Example 80

Synthesis of (R)-1-[4-(6-fluoro-benzo[d]isoxazol-3-yl)-phenoxy]-3-(3-methoxy-benzylamino)-propan-2-ol (Scheme III, Compound 1)

Scheme III, Step O

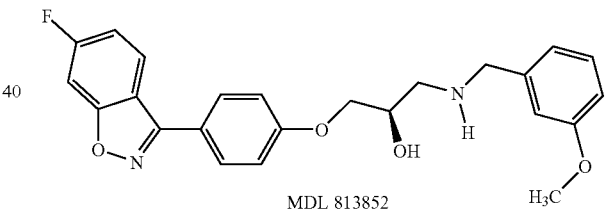

MDL 813852

The title compound is prepared from a mixture of (R)-6-fluoro-3-(4-oxiranylmethoxy-phenyl)-benzo[d]isoxazole in dimethylformamide and 3-methoxybenzylamine in ethanol, essentially as described above in Example 70. Purity by LC/MS=100%, [M+H]$^+$=423.

Example 81

Synthesis of (R)-1-[4-(6-fluoro-benzo[d]isoxazol-3-yl)-phenoxy]-3-(4-fluoro-benzylamino)-propan-2-ol (Scheme III, Compound 1)

Scheme III, Step O

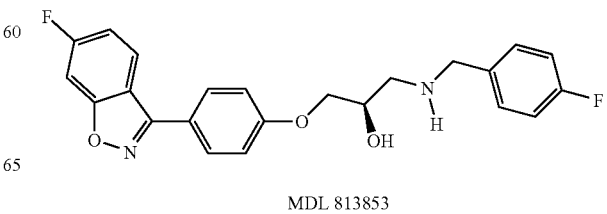

MDL 813853

The title compound is prepared from a mixture of (R)-6-fluoro-3-(4-oxiranylmethoxy-phenyl)-benzo[d]isoxazole in dimethylformamide and 4-fluorobenzylamine in ethanol, essentially as described above in Example 70. Purity by LC/MS=100%, [M+H]$^+$=411.

Example 82

Synthesis of (R)-1-(4-chloro-benzylamino)-3-[4-(6-fluoro-benzo[d]isoxazol-3-yl)-phenoxy]-propan-2-ol (Scheme III, Compound 1)

Scheme III, Step O

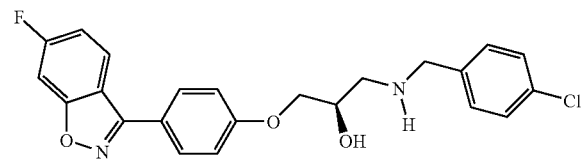

MDL 813854

The title compound is prepared from a mixture of (R)-6-fluoro-3-(4-oxiranylmethoxy-phenyl)-benzo[d]isoxazole in dimethylformamide and 4-chlorobenzylamine in ethanol, essentially as described above in Example 70. Purity by LC/MS=<100%, [M+H]$^+$=427.

Example 83

Synthesis of (R)-1-[4-(6-fluoro-benzo[d]isoxazol-3-yl)-phenoxy]-3-(4-methoxy-benzylamino)-propan-2-ol (Scheme III, Compound 1)

Scheme III, Step O

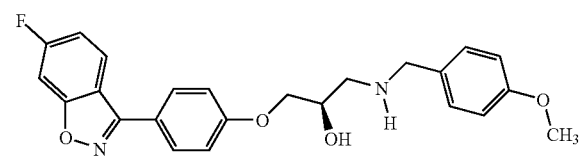

MDL 813855

The title compound is prepared from a mixture of (R)-6-fluoro-3-(4-oxiranylmethoxy-phenyl)-benzo[d]isoxazole in dimethylformamide and 4-methoxybenzylamine in ethanol, essentially as described above in Example 70. Purity by LC/MS=100%, [M+H]$^+$=423.

Example 84

Synthesis of (R)-1-[4-(6-fluoro-benzo[d]isoxazol-3-yl)-phenoxy]-3-(4-methyl-benzylamino)-propan-2-ol (Scheme III, Compound 1)

Scheme III, Step O

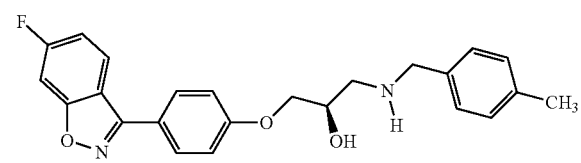

MDL 813856

The title compound is prepared from a mixture of (R)-6-fluoro-3-(4-oxiranylmethoxy-phenyl)-benzo[d]isoxazole in dimethylformamide and 4-methylbenzylamine in ethanol, essentially as described above in Example 70. Purity by LC/MS=100%, [M+H]$^+$=407.

Example 85

Synthesis of (R)-1-[4-(6-fluoro-benzo[d]isoxazol-3-yl)-phenoxy]-3-(2-hydroxy-2-phenyl-ethylamino)-propan-2-ol (Scheme III, Compound 1)

Scheme III, Step O

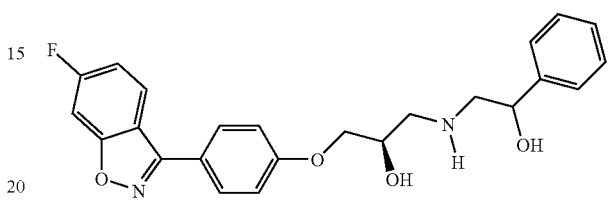

MDL 813857

The title compound is prepared from a mixture of (R)-6-fluoro-3-(4-oxiranylmethoxy-phenyl)-benzo[d]isoxazole in dimethylformamide and 2-amino-1-phenylethanol in ethanol, essentially as described above in Example 70. Purity by LC/MS=100%, [M+H]$^+$=423.

Example 86

Synthesis of (R)-1-[4-(6-fluoro-benzo[d]isoxazol-3-yl)-phenoxy]-3-phenethylamino-propan-2-ol (Scheme III, Compound 1)

Scheme III, Step O

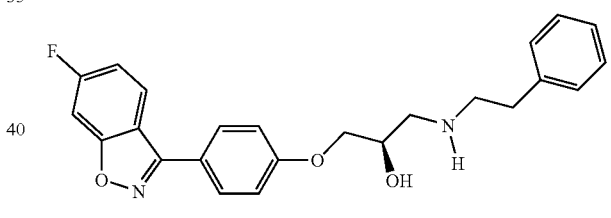

MDL 813858

The title compound is prepared from a mixture of (R)-6-fluoro-3-(4-oxiranylmethoxy-phenyl)-benzo[d]isoxazole in dimethylformamide and phenethylamine in ethanol, essentially as described above in Example 70. Purity by LC/MS=100%, [M+H]$^+$=407.

Example 87

Synthesis of (R)-1-(2-cyclohex-1-enyl-ethylamino)-3-[4-(6-fluoro-benzo[d]isoxazol-3-yl)-phenoxy]-propan-2-ol (Scheme III, Compound 1)

Scheme III, Step O

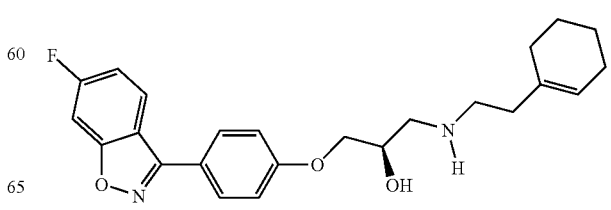

MDL 813859

The title compound is prepared from a mixture of (R)-6-fluoro-3-(4-oxiranylmethoxy-phenyl)-benzo[d]isoxazole in dimethylformamide and 2-(1-cyclohexenyl)ethylamine in ethanol, essentially as described above in Example 70. Purity by LC/MS=100%, [M+H]⁺=411.

Example 88
Synthesis of (R)-1-{3-[4-(6-fluoro-benzo[d]isoxazol-3-yl)-phenoxy]-2-hydroxy-propylamino}-indan-2-ol (Scheme III, Compound 1)

Scheme III, Step O

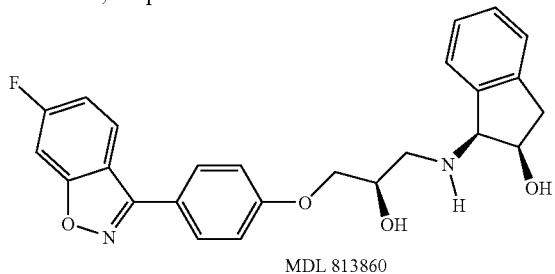

MDL 813860

The title compound is prepared from a mixture of (R)-6-fluoro-3-(4-oxiranylmethoxy-phenyl)-benzo[d]isoxazole in dimethylformamide and (1S, 2R)-(−)-cis-1-amino-2-indanol in ethanol, essentially as described above in Example 70. Purity by LC/MS=100%, [M+H]⁺=435.

Example 89
Synthesis of (R)-1-[4-(6-fluoro-benzo[d]isoxazol-3-yl)-phenoxy]-3-(indan-2-ylamino)-propan-2-ol (Scheme III, Compound 1)

Scheme III, Step O

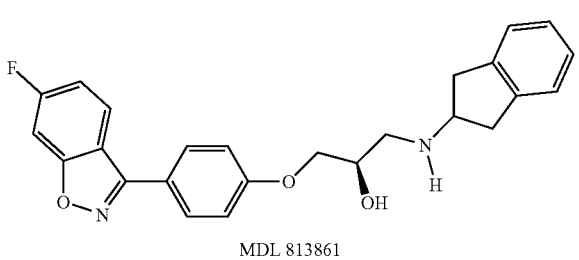

MDL 813861

The title compound is prepared from a mixture of (R)-6-fluoro-3-(4-oxiranylmethoxy-phenyl)-benzo[d]isoxazole in dimethylformamide and 2-aminoindan in ethanol, essentially as described above in Example 70. Purity by LC/MS=100%, [M+H]⁺=419.

Example 90
Synthesis of (R)-1-[4-(3-chloro-phenoxy)-piperidin-1-yl]-3-[4-(6-fluoro-benzo[d]isoxazol-3-yl)-phenoxy]-propan-2-ol (Scheme III, Compound 1)

Scheme III, Step O

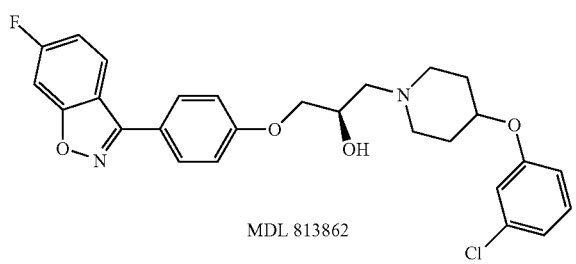

MDL 813862

The title compound is prepared from a mixture of (R)-6-fluoro-3-(4-oxiranylmethoxy-phenyl)-benzo[d]isoxazole in dimethylformamide and 4-(3-chlorophenoxy)-piperidine (Table No.1, SM 7) in ethanol, essentially as described above in Example 70. Purity by LC/MS=100%, [M+H]⁺=497.

Example 91
Synthesis of (R)-4-(4-chloro-phenyl)-1-{3-[4-(6-fluoro-benzo[d]isoxazol-3-yl)-phenoxy]-2-hydroxy-propyl}-piperidin-4-ol (Scheme III, Compound 1)

Scheme III, Step O

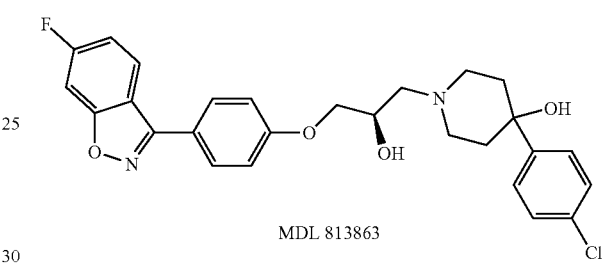

MDL 813863

The title compound is prepared from a mixture of (R)-6-fluoro-3-(4-oxiranylmethoxy-phenyl)-benzo[d]isoxazole in dimethylformamide and 4-(4-chlorophenyl)-4-hydroxypiperidine in ethanol, essentially as described above in Example 70. Purity by LC/MS=100%, [M+H]⁺=497.

Example 92
Synthesis of (R)-1-[4-(6-fluoro-benzo[d]isoxazol-3-yl)-phenoxy]-3-(4-pyrimidin-2-yl-piperazin-1-yl)-propan-2-ol (Scheme III, Compound 1)

Scheme III, Step O

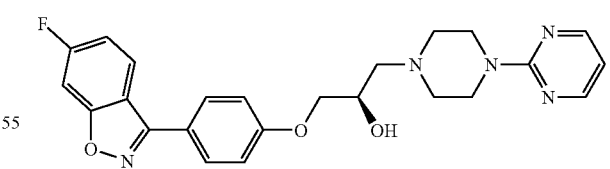

MDL 813889

The title compound is prepared from a mixture of (R)-6-fluoro-3-(4-oxiranylmethoxy-phenyl)-benzo[d]isoxazole in dimethylformamide and 2-piperazin-1-yl-pyrimidine in ethanol, essentially as described above in Example 70. Purity by LC/MS=-100%, [M+H]⁺=450.

Example 93

Synthesis of (R)-1-{3-[4-(6-fluoro-benzo[d]isoxazol-3-yl)-phenoxy]-2-hydroxy-propyl}-4-phenyl-piperidine-4-carbonitrile (Scheme III, Compound 1)

Scheme III, Step O

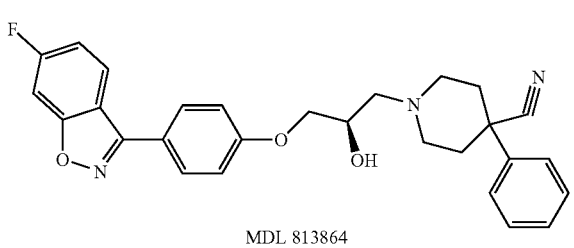

MDL 813864

The title compound is prepared from a mixture of (R)-6-fluoro-3-(4-oxiranylmethoxy-phenyl)-benzo[d]isoxazole in dimethylformamide and 4-cyano-4-phenylpiperidine in ethanol, essentially as described above in Example 70. Purity by LC/MS=<100%, [M+H]$^+$=472.

Examples 94-101

Examples 94-101 are prepared using techniques of parallel synthesis. Experimental conditions are described in detail for Example 94, with any variations in procedures being noted for Examples 95-101.

Example 94

Synthesis of (R)-1-(4-benzo[b]thiophen-3-yl-phenoxy)-3-(4-pyrimidin-2-yl-piperazin-1-yl)-propan-2-ol (Scheme III, Compound 1)

Scheme III, Step O

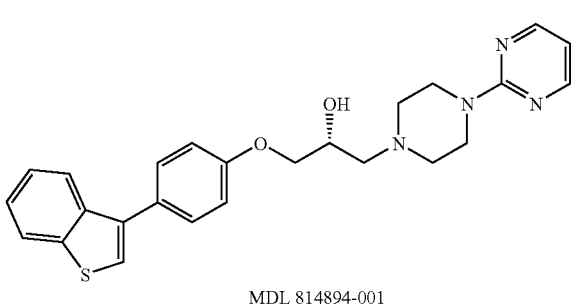

MDL 814894-001

Combine 2-(4-benzo[b]thiophen-3-yl-phenoxymethyl)-oxirane (200 mg, 0.708 mmol), 2-piperazin-1-yl-pyrimidine (465 mg, 2.83 mmol) and ethanol (4 mL). Apply heat (75° C.) to the homogeneous reaction mixtures and stir for 6 hours. Concentrate (in vacuo) and purify by column chromatography using a Waters Sep-Pak silica gel cartridge (10 g) and elution with graded solvent mixtures from 50% ethyl acetate in heptane to 100% ethyl acetate. Concentrate the appropriate fractions, dissolve in dichloromethane and re-evaporate under a stream of nitrogen. Dry the sample using medium heat and reduced pressure to give the title compound as a clear oil (0.285 mg, 90% Yield). Purity by LC/MS=99%, [M+H]$^+$=447.

Example 95

Synthesis of (R)-1-(4-benzo[b]thiophen-3-yl-phenoxy)-3-(2-chloro-benzylamino)-propan-2-ol (Scheme III, Compound 1)

Scheme III, Step O

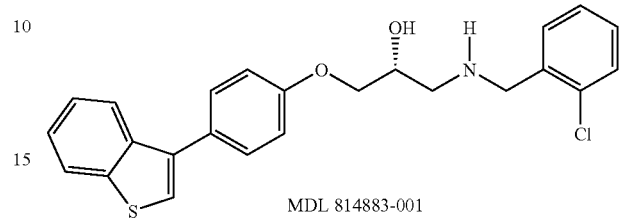

MDL 814883-001

The title compound is prepared from a mixture of 2-(4-benzo[b]thiophen-3-yl-phenoxymethyl)-oxirane, 2-chlorobenzylamine and ethanol essentially as described above in Example 94. Purity by LC/MS=99%, [M+H]$^+$=424.

Example 95A

Synthesis of 1-(4-benzo[b]thiophen-3-yl-phenoxy)-3-benzylamino-propan-2-ol (Scheme III, Compound 1)

Scheme III, Step O

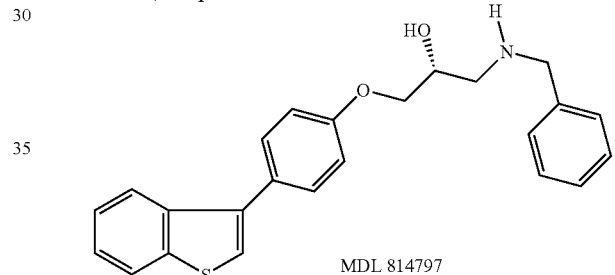

MDL 814797

The title compound is prepared from a mixture of 2-(4-benzo[b]thiophen-3-yl-phenoxymethyl)-oxirane, benzylamine and ethanol essentially as described above in Example 94 except that the reaction mixture is heated for 15.5 hours and the column chromatography is performed with a graded solvent mixture from 5% methanol in ethyl acetate to 10% methanol in ethyl acetate. Purity by LC/MS=100%, [M+H]$^+$=390.

Example 96

Synthesis of (R)-1-(4-benzo[b]thiophen-3-yl-phenoxy)-3-(4-fluoro-benzylamino)-propan-2-ol (Scheme III, Compound 1)

Scheme III, Step O

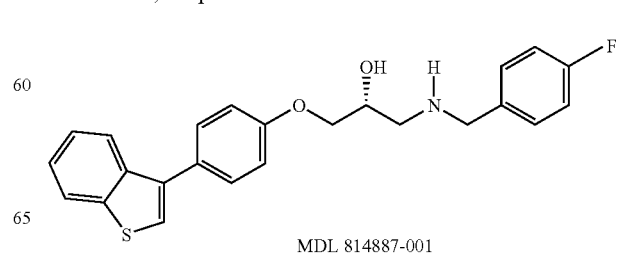

MDL 814887-001

The title compound is prepared from a mixture of 2-(4-benzo[b]thiophen-3-yl-phenoxymethyl)-oxirane, 4-fluorobenzylamine and ethanol essentially as described above in Example 94 except that the column chromatography is performed with a graded solvent mixture from 100% ethyl acetate to 10% methanol in ethyl acetate. Purity by LC/MS=100%, [M+H]$^+$=408.

Example 97

Synthesis of (R)-1-(4-benzo[b]thiophen-3-yl-phenoxy)-3-(2,6-difluoro-benzylamino)-propan-2-ol (Scheme III, Compound 1)

Scheme III, Step O

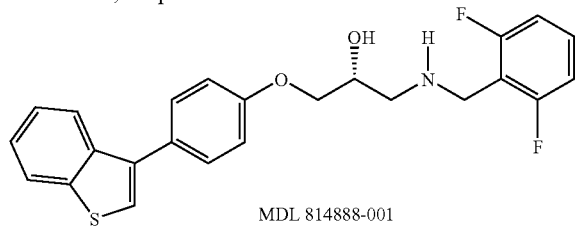

MDL 814888-001

The title compound is prepared from a mixture of 2-(4-benzo[b]thiophen-3-yl-phenoxymethyl)-oxirane, 2,6-difluorobenzylamine and ethanol essentially as described above in Example 94. Purity by LC/MS=99%, [M+H]$^+$=426.

Example 98

Synthesis of (R)-1-(4-benzo[b]thiophen-3-yl-phenoxy)-3-[(thiophen-2-ylmethyl)-amino]-propan-2-ol (Scheme III, Compound 1)

Scheme III, Step O

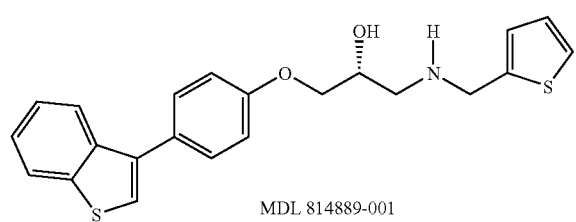

MDL 814889-001

The title compound is prepared from a mixture of 2-(4-benzo[b]thiophen-3-yl-phenoxymethyl)-oxirane, 2-thiophenemethylamine and ethanol essentially as described above in Example 94. Purity by LC/MS=99%, [M+H]$^+$=396.

Example 99

Synthesis of (R)-1-(4-benzo[b]thiophen-3-yl-phenoxy)-3-[(thiophen-3-ylmethyl)-amino]-propan-2-ol (Scheme III, Compound 1)

Scheme III, Step O

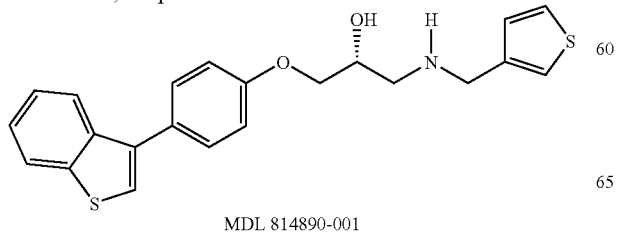

MDL 814890-001

The title compound is prepared from a mixture of 2-(4-benzo[b]thiophen-3-yl-phenoxymethyl)-oxirane, thiophen-3-yl-methylamine (Table No.1, SM 9) and ethanol essentially as described above in Example 96. Purity by LC/MS=99%, [M+H]$^+$=396.

Example 100

Synthesis of (R)-1-(4-benzo[b]thiophen-3-yl-phenoxy)-3-(indan-1-ylamino)-propan-2-ol (Scheme III, Compound 1)

Scheme III, Step O

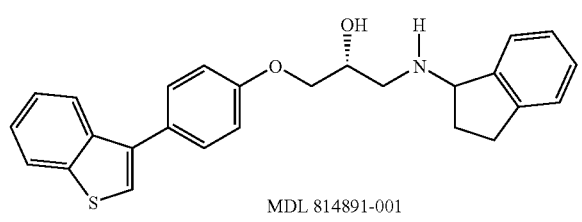

MDL 814891-001

The title compound is prepared from a mixture of 2-(4-benzo[b]thiophen-3-yl-phenoxymethyl)-oxirane, 1-aminoindane and ethanol essentially as described above in Example 96. Purity by LC/MS=100%, [M+H]$^+$=416.

Example 101

Synthesis of (R)-1-(4-benzo[b]thiophen-3-yl-phenoxy)-3-(3,4-dihydro-1H-isoquinolin-2-yl)-propan-2-ol (Scheme III, Compound 1)

Scheme III, Step O

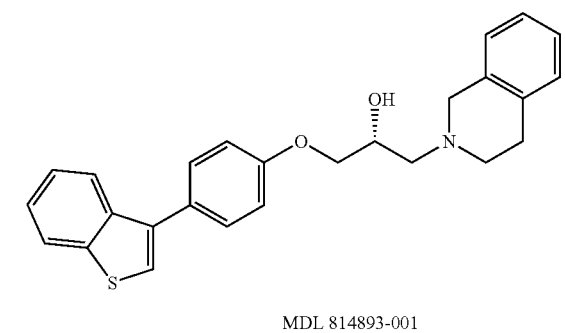

MDL 814893-001

The title compound is prepared from a mixture of 2-(4-benzo[b]thiophen-3-yl-phenoxymethyl)-oxirane, 1,2,3,4-tetrahydroisoquinoline and ethanol essentially as described above in Example 94. Purity by LC/MS=100%, [M+H]$^+$=416.

Examples 102-109

Examples 102-109 are prepared using techniques of parallel synthesis. Experimental conditions are described in detail for Example 102, with any variations in procedures being noted for Examples 103-109.

Example 102

Synthesis of (R)-1-[4-(3-chloro-phenoxy)-piperidin-1-yl]-3-(3-isoxazolo[5,4-b]pyridin-3-yl-phenoxy)-propan-2-ol (Scheme III, Compound 1)

Scheme III, Step O

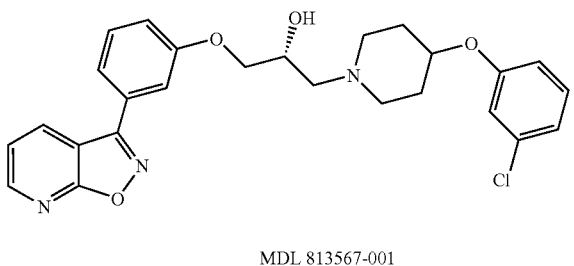

MDL 813567-001

Dilute a 0.370 M solution (in dimethylformamide) of (R)-3-(3-oxiranylmethoxy-phenyl)-isoxazolo[5,4-b]pyridine (140 mg, 0.522 mmol) with ethanol (3.0 mL) and add solution of 4-(3-chlorophenoxy)-piperidine (121.5 mg, 0.574 mmol, 1.1 equivalents) (Table No.1, SM 7) dissolved in ethanol (0.200 M solution). Under a vented argon atmosphere, reflux the reaction mixture overnight. Concentrate the reaction mixture and purify with a Waters Sep-Pak 5 g silica gel cartridge and elute with a graded solvent mixture from 1% methanol in dichloromethane to 5% methanol in dichloromethane to give the title compound (124.6 mg, 50% Yield). Purity by LC/MS=100%, [M+H]$^+$=480

Example 103

Synthesis of (R)-1-(benzyl-methyl-amino)-3-(3-isoxazolo[5,4-b]pyridin-3-yl-phenoxy)-propan-2-ol (Scheme III, Compound 1)

Scheme III, Step O

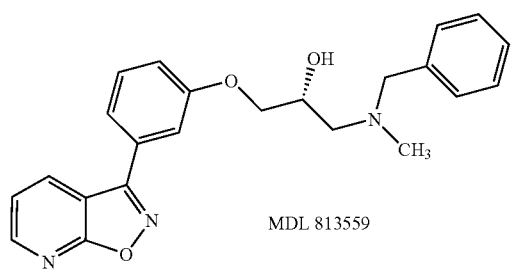

MDL 813559

The title compound is prepared from a mixture of (R)-3-(3-oxiranylmethoxy-phenyl)-isoxazolo[5,4-b]pyridine in dimethylformamide and ethanol and N-methylbenzylamine in ethanol essentially as described above in Example 102. Purity by LC/MS=100%, [M+H]$^+$=390.

Example 104

Synthesis of (R)-1-(3,4-dihydro-1H-isoquinolin-2-yl)-3-(3-isoxazolo[5,4-b]pyridin-3-yl-phenoxy)-propan-2-ol (Scheme III, Compound 1)

Scheme III, Step O

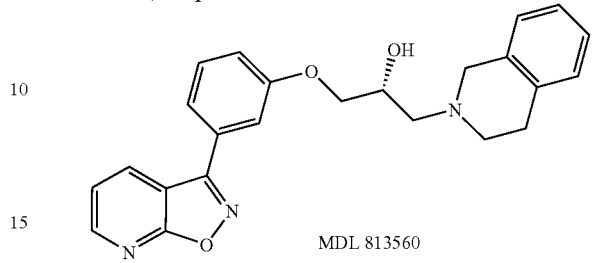

MDL 813560

The title compound is prepared from a mixture of (R)-3-(3-oxiranylmethoxy-phenyl)-isoxazolo[5,4-b]pyridine in dimethylformamide and ethanol and 1,2,3,4-tetrahydroisoquinoline in ethanol essentially as described above in Example 102. Purity by LC/MS=100%, [M+H]$^+$=402.

Example 105

Synthesis of (R)-1-(6,7-dihydro-4H-thieno[3,2-c]pyridin-5-yl)-3-(3-isoxazolo[5,4-b]pyridin-3-yl-phenoxy)-propan-2-ol (Scheme III, Compound 1)

Scheme III, Step O

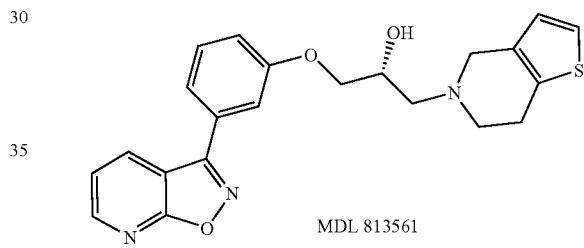

MDL 813561

The title compound is prepared from a mixture of (R)-3-(3-oxiranylmethoxy-phenyl)-isoxazolo[5,4-b]pyridine in dimethylformamide and ethanol and 4,5,6,7-tetrahydrothieno[3,2-c]pyridine in ethanol essentially as described above in Example 102. Purity by LC/MS=100%, [M+H]$^+$=408.

Example 106

Synthesis of (R)-1-(3-isoxazolo[5,4-b]pyridin-3-yl-phenoxy)-3-(4-pyrimidin-2-yl-piperazin-1-yl)-propan-2-ol (Scheme III, Compound 1)

Scheme III, Step O

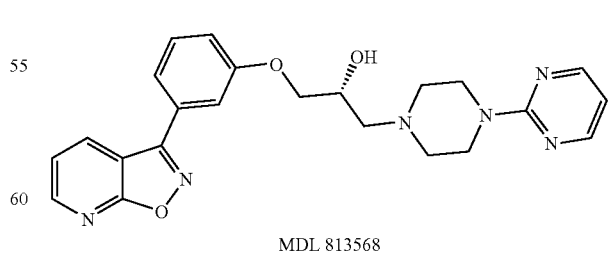

MDL 813568

The title compound is prepared from a mixture of (R)-3-(3-oxiranylmethoxy-phenyl)-isoxazolo[5,4-b]pyridine in dimethylformamide and ethanol and 2-piperazin-1-yl-pyrimidine in ethanol essentially as described above in Example 102. Purity by LC/MS=100%, [M+H]$^+$=433.

Example 107
Synthesis of (R)-2-{4-[2-hydroxy-3-(3-isoxazolo[5,4-b]pyridin-3-yl-phenoxy)-propyl]-piperazin-1-yl}-benzonitrile (Scheme III, Compound 1)

Scheme III, Step O

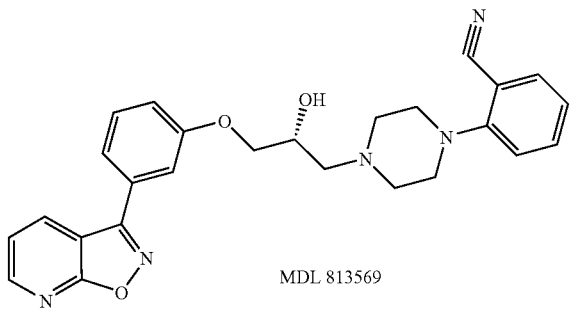

MDL 813569

The title compound is prepared from a mixture of (R)-3-(3-oxiranylmethoxy-phenyl)-isoxazolo[5,4-b]pyridine in dimethylformamide and ethanol and 1-(2-cyanophenyl)piperazine in ethanol essentially as described above in Example 102. Purity by LC/MS=100%, [M+H]⁺=456.

Example 108
Synthesis of (R)-1-[4-(6-fluoro-benzo[d]isoxazol-3-yl)-piperidin-1-yl]-3-(3-isoxazolo[5,4-b]pyridin-3-yl-phenoxy)-propan-2-ol (Scheme III, Compound 1)

Scheme III, Step O

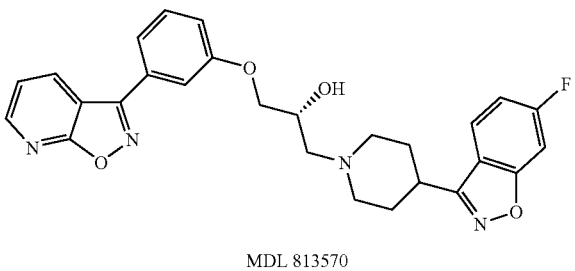

MDL 813570

The title compound is prepared from a mixture of (R)-3-(3-oxiranylmethoxy-phenyl)-isoxazolo[5,4-b]pyridine in dimethylformamide and ethanol and 6-fluoro-3-piperidine-4-yl-benzo[d]isoxazole (Table No. 1, SM 8) in ethanol essentially as described above in Example 102. Purity by LC/MS=100%, [M+H]⁺=489.

Example 109
Synthesis of (R)-1-[4-(6-fluoro-1H-indazol-3-yl)-piperazin-1-yl]-3-(3-isoxazolo[5,4-b]pyridin-3-yl-phenoxy)-propan-2-ol (Scheme III, Compound 1)

Scheme III, Step O

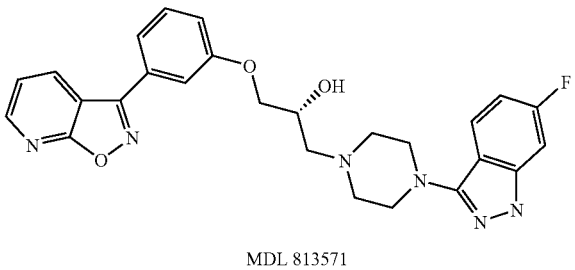

MDL 813571

The title compound is prepared from a mixture of (R)-3-(3-oxiranylmethoxy-phenyl)-isoxazolo[5,4-b]pyridine in dimethylformamide and ethanol and 6-fluoro-3-piperazin-1-yl-1H-indazole (Table No.1, SM 4) in ethanol essentially as described above in Example 102. Purity by LC/MS=100%, [M+H]⁺=489.

Example 110
Synthesis of 1-benzylamino-3-[4-(6-fluoro-benzo[d]isoxazol-3-yl)-phenoxy]-propan-2-ol (Scheme III, Compound 1)

Scheme III, Step O

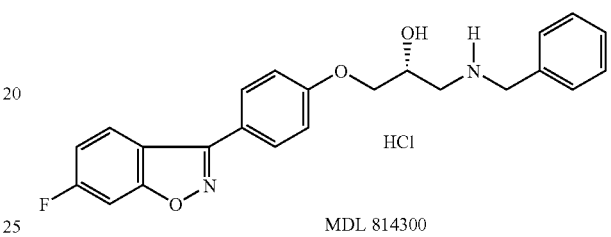

MDL 814300

Combine (R)-6-fluoro-3-(4-oxiranylmethoxy-phenyl)-benzo[d]isoxazole (29) (500 mg, 1.75 mmol), benzylamine (755 mg, 7.05 mmol), ethanol (5.0 ml) and heat (~80° C.) for 18.5 hours. At room temperature the reaction solidified. Dissolve reaction mixture with chloroform and concentrate (in vacuo). Purify the compound by column chromatography (silica) eluting with 10% ethanol in chloroform to obtain a white solid. Dissolve the free base in hot methanol and add ethereal HCl to a pH ~2-3. Concentrate the reaction mixture (in vacuo) and recrystallize (methanol) the salt and dry (60° C., 1.0 mm Hg) to give the title compound as white solid (233 mg, 46% Yield). mp=251-253° C. Microanalysis (C, H, N) is consistent with the final, desired compound. $[\alpha]^{22}_D$=+9.17, c (MeOH)=0.60.

Example 111
Synthesis of (R)-1-(adamantan-1-ylamino)-3-[4-(6-fluoro-benzo[d]isoxazol-3-yl)-phenoxy]-propan-2-ol (Scheme III, Compound 1)

Scheme III, Step O

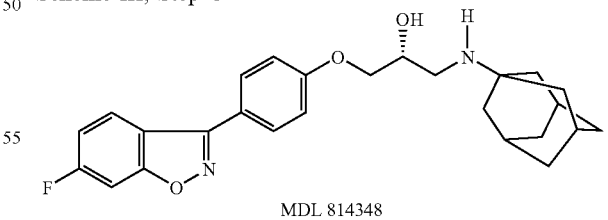

MDL 814348

Combine (R)-6-fluoro-3-(4-oxiranylmethoxy-phenyl)-benzo[d]isoxazole (29) (250 mg, 0.86 mmol), 1-adamantanamine (530 mg, 3.50 mmol), ethanol (4.0 ml) and heat (~80° C.) for 16 hours. Cool reaction to room temperature and concentrate (in vacuo). Purify the compound by column chromatography (silica) eluting with 28% aqueous ammonia/ethanol/chloroform (1:19:180) to obtain a white solid. Dry (50° C. at 0.5 mm Hg) to give 332 mg (86% yield) of the title compound. Purity by LC/MS=92%, [M+H]⁺=437.

Example 112
Synthesis of (R)-1-(3,4-dichloro-benzylamino)-3-[4-(6-fluoro-benzo[d]isoxazol-3-yl)-phenoxy]-propan-2-ol (Scheme III, Compound 1)

Scheme III, Step O

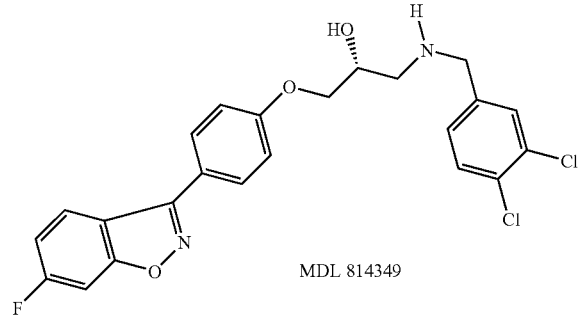

MDL 814349

Combine (R)-6-fluoro-3-(4-oxiranylmethoxy-phenyl)-benzo[d]isoxazole (29) (250 mg, 0.86 mmol), 3,4-dichlorobenzylamine (617 mg, 3.50 mmol), ethanol (4.0 ml) and heat (~80° C.) for 16 hours. Cool reaction at 0° C. for 1 h. Collect the solid product and wash with cold ethanol several times. Dry the solid at (50° C./0.5 mm Hg) overnight to give 313 mg (77% yield) of the title compound. Purity by LC/MS=96%, [M+H]$^+$=461.

Example 113
Synthesis of (R)-1-(2,4-difluoro-benzylamino)-3-[4-(6-fluoro-benzo[d]isoxazol-3-yl)-phenoxy]-propan-2-ol (Scheme III, Compound 1)

Scheme III, Step O

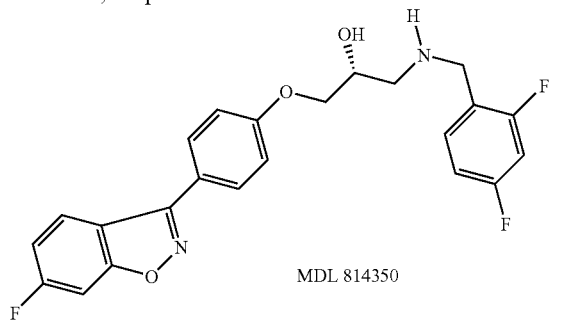

MDL 814350

The title compound is prepared from (R)-6-fluoro-3-(4-oxiranylmethoxy-phenyl)-benzo[d]isoxazole, 2,4-difluorobenzylamine, and ethanol essentially as described above in Example 112. Purity by LC/MS=96%, [M+H]$^+$=429.

Example 114
Synthesis of (R)-1-(2,6-difluoro-benzylamino)-3-[4-(6-fluoro-benzo[d]isoxazol-3-yl)-phenoxy]-propan-2-ol (Scheme III, Compound 1)

Scheme III, Step O

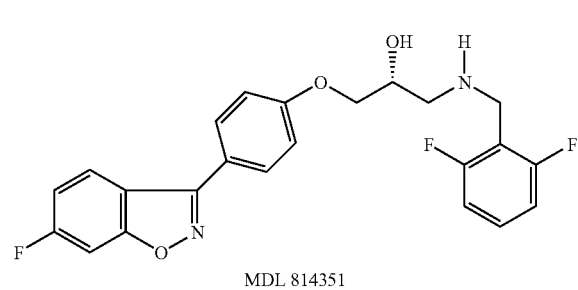

MDL 814351

The title compound is prepared from (R)-6-fluoro-3-(4-oxiranylmethoxy-phenyl)-benzo[d]isoxazole, 2,6-difluorobenzylamine, and ethanol essentially as described above in Example 112. Purity by LC/MS=96%, [M+H]$^+$=429.

Example 115
Synthesis of (R)-1-(3,4-difluoro-benzylamino)-3-[4-(6-fluoro-benzo[d]isoxazol-3-yl)-phenoxy]-propan-2-ol (Scheme III, Compound 1)

Scheme III, Step O

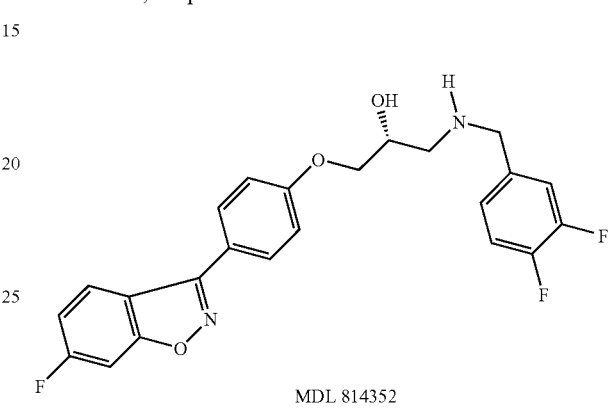

MDL 814352

The title compound is prepared from (R)-6-fluoro-3-(4-oxiranylmethoxy-phenyl)-benzo[d]isoxazole, 3,4-difluorobenzylamine, and ethanol essentially as described above in Example 112. Purity by LC/MS=97%, [M+H]$^+$=429.

Example 116
Synthesis of (R)-1-[4-(6-fluoro-benzo[d]isoxazol-3-yl)-phenoxy]-3-(2-trifluoromethyl-benzylamino)-propan-2-ol (Scheme III, Compound 1)

Scheme III, Step O

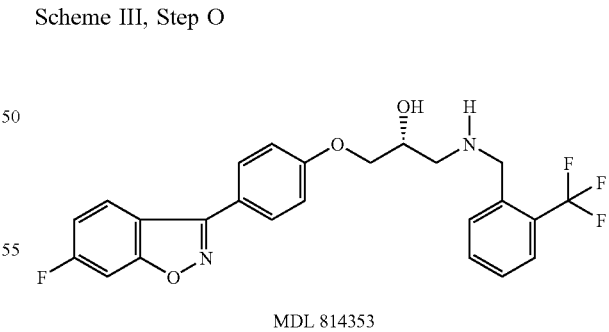

MDL 814353

The title compound is prepared from (R)-6-fluoro-3-(4-oxiranylmethoxy-phenyl)-benzo[d]isoxazole, 2-(trifluoromethyl)benzylamine, and ethanol essentially as described above in Example 112. Purity by LC/MS=96%, [M+H]$^+$=461.

Example 117
Synthesis of (R)-1-[4-(6-fluoro-benzo[d]isoxazol-3-yl)-phenoxy]-3-(4-trifluoromethyl-benzylamino)-propan-2-ol (Scheme III, Compound 1)

Scheme III, Step O

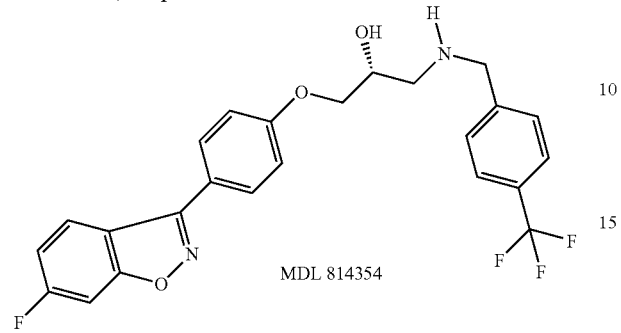

MDL 814354

The title compound is prepared from (R)-6-fluoro-3-(4-oxiranylmethoxy-phenyl)-benzo[d]isoxazole, 4-(trifluoromethyl)benzylamine, and ethanol essentially as described above in Example 112. Purity by LC/MS=95%, [M+H]$^+$=461.

Example 118
Synthesis of [3-(4-benzo[b]thiophen-3-yl-phenoxy)-propyl]-(2-chloro-benzyl)-amine (Scheme III, Compound 1b)

Scheme III, Step R:

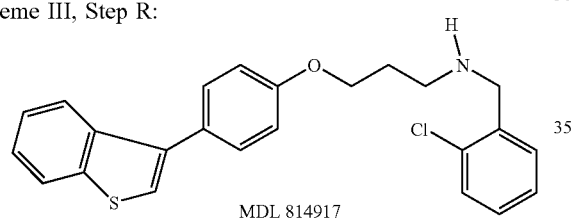

MDL 814917

Combine 3-[4-(3-bromo-propoxy)-phenyl]-benzo[b]thiophene (0.200 g, 0.576 mmol), 2-chlorobenzylamine (0.326 g, 2.30 mmol), potassium carbonate (0.200 g, 1.45 mmol) and acetonitrile (4.0 ml) and heat (75° C.) overnight. Cool reaction to room temperature, filter through a Waters Sep-Pak 1 g Silica cartridge (ethyl acetate) and concentrate (in vacuo). Purify the crude product by column (silica) chromatography with a graded solvent mixture of 40% ethyl acetate in dichloromethane to 100% ethyl acetate. Concentrate the appropriate fractions, dissolve in dichloromethane and re-evaporate under a stream of nitrogen. Dry sample under vacuum (0.5 mm Hg, 50° C.) overnight to obtain the title compound as a light amber oil (0.184 g, 78% Yield). Purity by LC/MS=98%, [M+H]$^+$=408.

Example 119
Synthesis of [3-(4-benzo[b]thiophen-3-yl-phenoxy)-propyl]-(2-fluoro-benzyl)-amine (Scheme III, Compound 1b)

Scheme III, Step R:

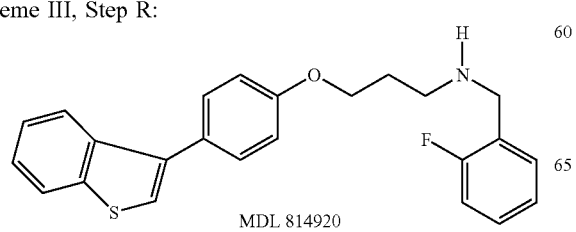

MDL 814920

The title compound is prepared from 3-[4-(3-bromo-propoxy)-phenyl]-benzo[b]thiophene, 2-fluorobenzylamine, potassium carbonate and acetonitrile essentially as described above in Example 118. Purity by LC/MS=100%, [M+H]$^+$=392.

Example 120
Synthesis of [3-(4-benzo[b]thiophen-3-yl-phenoxy)-propyl]-(2,6-difluoro-benzyl)-amine (Scheme III, Compound 1b)

Scheme III, Step R:

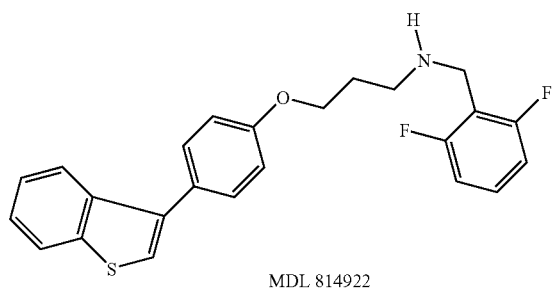

MDL 814922

The title compound is prepared from 3-[4-(3-bromo-propoxy)-phenyl]-benzo[b]thiophene, 2,4-difluorobenzylamine, potassium carbonate and acetonitrile essentially as described above in Example 118. Purity by LC/MS=98%, [M+H]$^+$=410.

Example 121
Synthesis of [3-(4-benzo[b]thiophen-3-yl-phenoxy)-propyl]-thiophen-2-ylmethyl-amine (Scheme III, Compound 1b)

Scheme III, Step R:

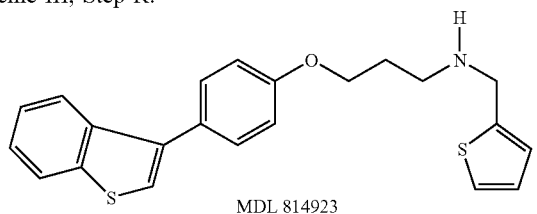

MDL 814923

The title compound is prepared from 3-[4-(3-bromo-propoxy)-phenyl]-benzo[b]thiophene, 2-thiophenemethylamine, potassium carbonate and acetonitrile essentially as described above in Example 118. Purity by LC/MS=97%, [M+H]$^+$=380.

Example 122
Synthesis of [3-(4-benzo[b]thiophen-3-yl-phenoxy)-propyl]-thiophen-3-ylmethyl-amine (Scheme III, Compound 1b)

Scheme III, Step R:

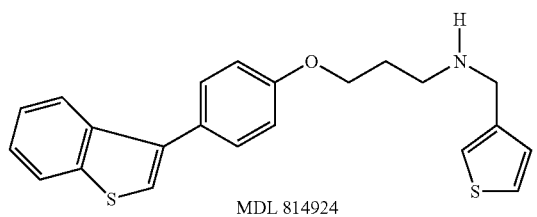

MDL 814924

The title compound is prepared from 3-[4-(3-bromo-propoxy)-phenyl]-benzo[b]thiophene, C-thiophene-3-yl-methylamine (Table No. 1, SM 9), potassium carbonate and acetonitrile essentially as described above in Example 118 except that the column chromatography is performed with a graded solvent mixture from 100% ethyl acetate to 10% methanol in ethyl acetate. Purity by LC/MS=99%, [M+H]⁺=380.

Example 123
Synthesis of [3-(4-benzo[b]thiophen-3-yl-phenoxy)-propyl]-indan-1-yl-amine (Scheme III, Compound 1b)

Scheme III, Step R:

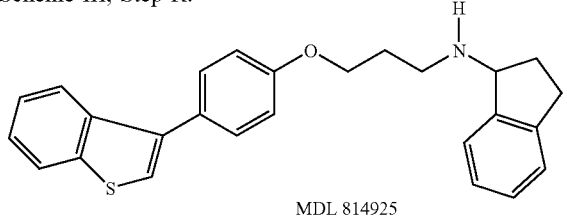

MDL 814925

The title compound is prepared from 3-[4-(3-bromo-propoxy)-phenyl]-benzo[b]thiophene, 1-aminoindan potassium carbonate and acetonitrile essentially as described above in Example 118 except that the column chromatography is performed with a graded solvent mixture from 100% ethyl acetate to 10% methanol in ethyl acetate. Purity by LC/MS=100%, [M+H]⁺=400.

Example 124
Synthesis of 2-[3-(4-benzo[b]thiophen-3-yl-phenoxy)-propyl]-1,2,3,4-tetrahydro-isoquinoline (Scheme III, Compound 1b)

Scheme III, Step R:

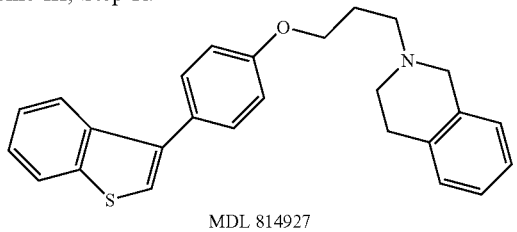

MDL 814927

The title compound is prepared from 3-[4-(3-bromo-propoxy)-phenyl]-benzo[b]thiophene, 1,2,3,4-tetrahydroisoquinoline, potassium carbonate and acetonitrile essentially as described above in Example 118. Purity by LC/MS=94%, [M+H]⁺=400.

Example 125
Synthesis of 2-{4-[3-(4-benzo[b]thiophen-3-yl-phenoxy)-propyl]-piperazin-1-yl}-pyrimidine (Scheme III, Compound 1b)

Scheme III, Step R:

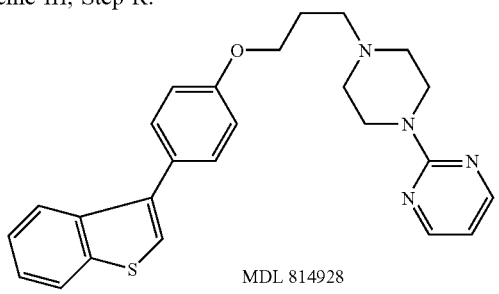

MDL 814928

The title compound is prepared from 3-[4-(3-bromo-propoxy)-phenyl]-benzo[b]thiophene, 1-(2-pyrimidyl)piperazine, potassium carbonate and acetonitrile essentially as described above in Example 118. Purity by LC/MS=99%, [M+H]⁺=431.

Example 126
Synthesis of 1-[3-(4-benzo[b]thiophen-3-yl-phenoxy)-propyl]-piperidine (Scheme III, Compound 1b)

Scheme III, Step R:

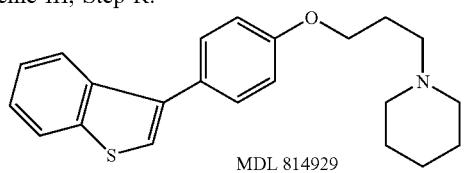

MDL 814929

The title compound is prepared from 3-[4-(3-bromo-propoxy)-phenyl]-benzo[b]thiophene, piperidine, potassium carbonate and acetonitrile essentially as described above in Example 118 except that the column chromatography is performed with a graded solvent mixture from 100% ethyl acetate to 10% methanol in ethyl acetate. Purity by LC/MS=99%, [M+H]⁺=352.

Example 127
Synthesis of 1-[3-(4-benzo[b]thiophen-3-yl-phenoxy)-propyl]-azepane (Scheme III, Compound 1b)

Scheme III, Step R:

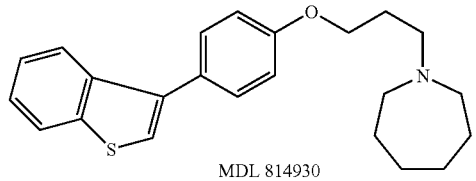

MDL 814930

The title compound is prepared from 3-[4-(3-bromo-propoxy)-phenyl]-benzo[b]thiophene, hexamethyleneimine, potassium carbonate and acetonitrile essentially as described above in Example 118 except that the column chromatography is performed with a graded solvent mixture from 100% ethyl acetate to 10% methanol in ethyl acetate. Purity by LC/MS=100%, [M+H]⁺=366.

Example 128
Synthesis of [3-(4-benzo[b]thiophen-3-yl-phenoxy)-propyl]-benzyl-amine (Scheme III, Compound 1b)

Scheme III, Step R:

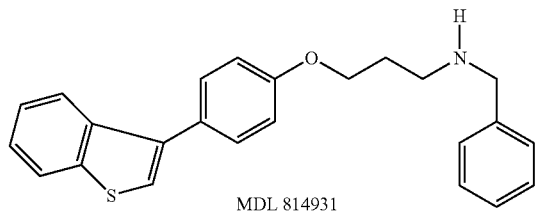

MDL 814931

The title compound is prepared from 3-[4-(3-bromo-propoxy)-phenyl]-benzo[b]thiophene, benzylamine, potassium carbonate and acetonitrile essentially as described above in Example 118 except that the column chromatography is performed with a graded solvent mixture from 100% ethyl acetate to 10% methanol in ethyl acetate. Purity by LC/MS=98%, [M+H]+=374.

Example 129

Synthesis of (R)-1-benzylamino-3-(3-isoxazolo[5,4-b]pyridin-3-yl-phenoxy)-propan-2-ol (Scheme III, Compound 1b)

Scheme III, Step R

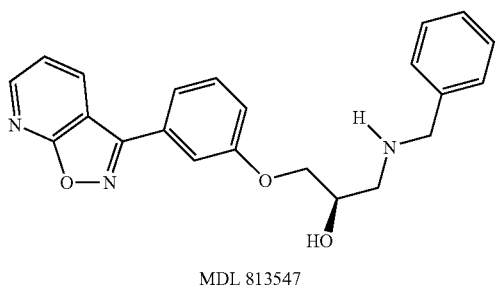

MDL 813547

The title compound is prepared from a mixture of (R)-3-(3-oxiranylmethoxy-phenyl)-isoxazolo[5,4-b]pyridine in dimethylformamide and ethanol and benzylamine in ethanol essentially as described above in Example 102, except that 1.5 equivalents of benzylamine is used.

Receptor Binding Assay $D_4$ receptor-binding affinities of the compounds were evaluated according to their ability to reduce binding of $^3$H-spiperone as compared to the reference compound clozapine. The potency of the test compound to reduce $^3$H-spiperone binding directly correlated to its binding affinity for the receptor.

$D_4$ Receptor Preparation

HEK 298 (human embryonic kidney) cells stably transfected with human $D_4$ receptor (D4.2 sub-type) were grown in NUNC cell factories for 5 days (75% confluency) without a media change and removed with versene (approximately 19 mg of cells per cell factory tray). The cells were then centrifuged in a Sorval centrifuge for 10 min, 5000 rpm (GS3 rotor) and the pellets quickly frozen in liquid nitrogen and stored at –80° C. until used in binding assay. When used in the assay, cells were thawed on ice for 20 min and then 10 mL of incubation buffer (50 mM Tris, 1 mM EDTA, 4 mM $MgCl_2$, 5 mM KCl, 1.5 mM $CaCl_2$, 120 mM NaCl, pH 7.4) was added. The cells were then vortexed to resuspend pellet and homogenized with a Kinematica, CH-6010 Kriens-LU, homogenizer for 15 seconds at setting 7. Concentration of receptor protein was determined using the Pierce BCA assay.

Total Spiperone Binding Assay

The incubation was started by the addition of 100 μl (50 μg protein) membrane homogenate to a solution of 300 μl incubation buffer and 100 μl (0.25 nM final conc.) $^3$H-spiperone (90 Ci/mmol, Amersham, diluted in borosilicate glass vial) in 96-well polypropylene plates (1 ML per well). The plates were vortexed and incubated at room temperature for 90 minutes. The binding reaction was stopped by filtering using a Packard Harvester. The samples were filtered under vacuum over glass fibre filter plates (Whatman GF/B) pre-soaked for 2 hours in 0.3% polyethylenimine (PEI) in 50 mM Tris buffer (pH 7.4). The filters were then washed 6 times with 7 mL ice cold 50 mM Tris buffer (pH 7.4). The filter plates were dried overnight and 35 μl of Microscint-O (Packard) was added. The plates were sealed and counted in the Packard Top Count (3 minutes per well).

Non-Specific Binding Assay for $D_4$

The incubation was started by the addition of 100 μl (50 μg protein) membrane homogenate to a solution of 200 μl incubation buffer, 100 μl $^3$H-spiperone (90 Ci/mmol, Amersham, diluted in borosilicate glass vial to 0.25 nM final conc.) and 100 μl (30 μM final conc.) of fresh dopamine (Research Biochemicals Inc., light protected and dissolved in incubation buffer) in 96-well polypropylene plates (1 mL per well). The plates were vortexed and incubated at room temperature for 90 minutes at which time the binding reaction was stopped by filtering. The filters were washed and counted using the same procedure as in the total binding assay described above to give the non-specific binding value (NSB).

Displacement Binding Assay

The incubation was started by the addition, in 96-well polypropylene plates (1 mL per well), of 100 μl (50 μg protein) membrane homogenate to a solution of 200 μl incubation buffer, 100 μl (0.25 nM final-conc.) $^3$H-spiperone (90 Ci/mmol, Amersham, diluted in borosilicate glass vial) and 100 μl of test compound that was prepared from 1 mM stock dissolved in DMSO and stored at –20° C. in polypropylene cryogenic storage vials until dilution in incubation buffer in 96-well polypropylene plates. The plates were vortexed and incubated at room temperature for 90 minutes at which time the binding reaction was stopped by filtering. The filters were washed and counted using the same procedure as in the total binding assay described above to give the displacement binding value ($B_D$).

Calculations

The test compounds were initially assayed at 1 and 0.1 μM and then at a range of concentrations chosen such that the middle dose would cause about 50% inhibition of $^3$H-spiperone binding. Specific binding in the absence of test compound ($B_0$) was the difference of total binding ($B_T$) minus non-specific binding (NSB) and similarly specific binding (in the presence of test compound) (B) was the difference of displacement binding ($B_D$) minus non-specific binding (NSB). $IC_{50}$ was determined from an inhibition response curve, logit-log plot of %B/$B_0$ vs concentration of test compound.

Ki was calculated by the Cheng and Prustoff transformation:

$$Ki=IC_{50}/(1+[L]/K_D)$$

where [L] is the concentration of $^3$H-spiperone used in the assay and $K_D$ is the dissociation constant of $^3$H-spiperone determined independently under the same binding conditions.

MK-801 Stereotypy in Mice

Mk-801 dose-dependently induces characteristic stereotypy marked by locomotion and falling behavior. This MK-801 induced behavior can be antagonized by novel neuroleptic agents. This assay can also assess time course effects following drug administration.

CD-1 or C57 male mice are individually placed in activity boxes (8 mice/drug) and allowed to acclimate for 60 minutes. The mice are then administered test compounds either i.p., s.c., or p.o., at 15, 30, or 60 minutes prior to MK-801 (0.2 mg/kg) administration. Mice are observed for the presence of locomotion and falling behaviors 15 minutes following MK-801. For the duration of action studies the test compounds are administered i.p., s.c., or p.o., at 30, 60, 120, 180, and 240 minutes prior to MK-801 administration. $ED_{50}$ values and 95% confidence limits are calculated by Litchfield and Wilcoxon method.

The following table contains information about the preparation of compounds within the scope of the present invention. The Example Number (column 3) refers to an exact or analogous procedure that may be used to prepare the Compound Number (column 1).

Benzisoxazolyl-, Pyridoisoxazolyl- and Benzthienyl-Phenoxy Derivatives Useful as $D_4$ Antagonists

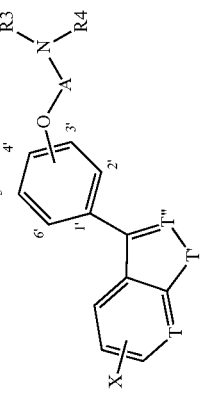

Wherein T, T' and T" are respectively C, O, N producing benzisoxazolyl and X = 6-Fluoro

| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 1 | 813425 | 22 | OH R-Configuration | OH R-Configuration | 4' | | 60 | | | |
| 2 | 813426 | 23 | OH R-Configuration | benzyl piperidine | 4' | | 51 | | | |
| 3 | 813427 | 24 | OH R-Configuration | morpholine | 4' | 0.088 | | | | |

-continued

Benzisoxazolyl-, Pyridoisoxazolyl- and Benzthienyl-Phenoxy Derivatives Useful as D₄ Antagonists

| Cmpd. No. | MDL No. | Example No. | A | N(R₃)(R₄) | Number of position of oxygen substitution | D₄ RBA K$_i$ (μM) | D₄ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 4 | 813428 | 25 | OH, R-Configuration | N-piperazine-N-CH₃ | 4' | | 52 | | | |
| 5 | 813430 | 26 | OH, R-Configuration | N-piperazine-N-phenyl | 4' | 0.017 | | IP | 50 | |
| 6 | 813431 | 27 | OH, R-Configuration | N(CH₃)-CH₂CH₂-phenyl | 4' | 0.0420 | | | | |
| 7 | 813432 | 28 | OH, R-Configuration | tetrahydroisoquinoline | 4' | 0.01 | | PO | 25 | |

Benzisoxazolyl-, Pyridoisoxazolyl- and Benzthienyl-Phenoxy Derivatives Useful as $D_4$ Antagonists

| Cmpd. No. | MDL No. | Example No. | A | N(R)$_3$(R)$_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 8 | 813433 | 29 | OH, R-Configuration | 4-(pyridin-2-yl)piperazin-1-yl | 4' | 0.009 | | PO | 37.5 | |
| 9 | 813434 | 30 | OH, R-Configuration | N-cyclohexyl-N-methylamino | 4' | 0.062 | | | | |
| 10 | 813436 | 31 | OH, R-Configuration | 2-(methoxymethyl)pyrrolidin-1-yl | 4' | | 55 | | | |

-continued

Benzisoxazolyl-, Pyridoisoxazolyl- and Benzthienyl-Phenoxy Derivatives Useful as D₄ Antagonists

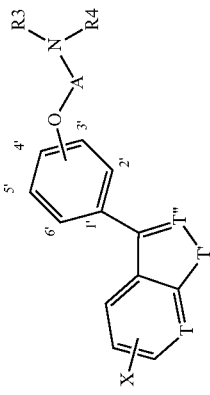

| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 11 | 813437 | 32 | OH, R-Configuration | piperidine | 4' | 0.032 | | | | |
| 12 | 813438 | 33 | OH, R-Configuration | indazole-piperazine | 4' | | 49 | | | |
| 13 | 813439 | 34 | OH, R-Configuration | 6-fluoro-benzisoxazole-piperidine | 4' | | 62 | | | |

-continued

Benzisoxazolyl-, Pyridoisoxazolyl- and Benzthienyl-Phenoxy Derivatives Useful as $D_4$ Antagonists

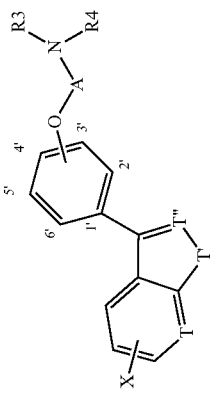

| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 14 | 813440 | 35 | OH R-Configuration | 4-phenylpiperidine | 4' | 0.013 | | PO | 87.5 | 18.6 |
| 15 | 813442 | 36 | OH R-Configuration | 4-(4-fluorophenoxy)piperidine | 4' | | 76 | | | |

-continued

Benzisoxazolyl-, Pyridoisoxazolyl- and Benzthienyl-Phenoxy Derivatives Useful as D₄ Antagonists

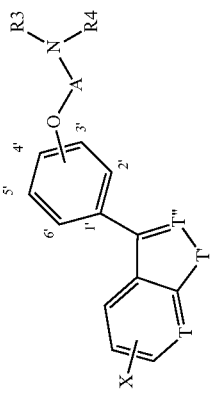

| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 16 | 813443 | 37 | OH R-Configuration | tetrahydro-β-carboline | 4' | | 44 | | | |
| 17 | 813445 | 38 | OH R-Configuration | 4-hydroxy-4-phenylpiperidine | 4' | 0.08 | | | | |
| 18 | 813446 | 39 | OH R-Configuration | 6-fluoro-3-(piperazinyl)-1H-indazole | 4' | | 60 | | | |

Benzisoxazolyl-, Pyridoisoxazolyl- and Benzthienyl-Phenoxy Derivatives Useful as $D_4$ Antagonists

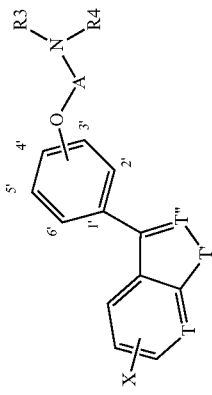

| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 19 | 813447 | 40 | R-Configuration (OH) | 2-cyanophenyl-methylpiperazine | 4' | 0.035 | | | | |
| 20 | 813448 | 41 | R-Configuration (OH) | 3-bromophenyl pyrazolopyridine with N-CH3 ethyl | 4' | | 93 | | | |
| 21 | 813450 | 21 | S-Configuration (OH) | 4-benzylpiperidine | 4' | | 56 | | | |

Benzisoxazolyl-, Pyridoisoxazolyl- and Benzthienyl-Phenoxy Derivatives Useful as D₄ Antagonists -continued

| Cmpd. No. | MDL No. | Example No. | A | N(R)₃(R)₄ | Number of position of oxygen substitution | D₄ RBA K_i (μM) | D₄ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 22 | 813451 | 42 | OH, S-Configuration | morpholine | 4' | | 64 | | | |
| 23 | 813454 | 43 | OH, S-Configuration | 4-phenylpiperazine | 4' | 0.067 | | | | |
| 24 | 813455 | 44 | OH, S-Configuration | N-methyl-N-(2-phenylethyl)amino | 4' | 0.109 | | | | |

-continued

Benzisoxazolyl-, Pyridoisoxazolyl- and Benzthienyl-Phenoxy Derivatives Useful as $D_4$ Antagonists

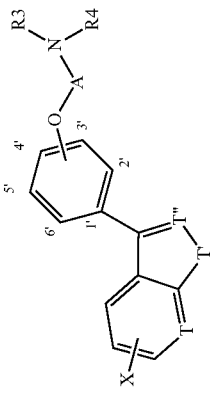

| Cmpd. No. | MDL No. | Example No. | A | $N(R_3)(R_4)$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 25 | 813456 | 45 | S-Configuration, OH | tetrahydroisoquinoline | 4' | 0.006 | | PO | 62.5 | |
| 26 | 813457 | 46 | S-Configuration, OH | 4-(2-pyridyl)piperazine | 4' | 0.03 | | | | |
| 27 | 813458 | 47 | S-Configuration, OH | N-methyl-N-cyclohexyl | 4' | | 66 | | | |
| 28 | 813461 | 48 | S-Configuration, OH | piperidine | 4' | 0.105 | | | | |

-continued

Benzisoxazolyl-, Pyridoisoxazolyl- and Benzthienyl-Phenoxy Derivatives Useful as D₄ Antagonists

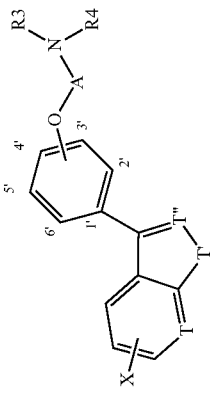

| Cmpd. No. | MDL No. | Example No. | A | N(R)₃(R)₄ | Number of position of oxygen substitution | D₄ RBA K_i (μM) | D₄ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 29 | 813462 | 49 | S-Configuration, OH | piperazinyl-indazole | 4' | | 41 | | | |
| 30 | 813464 | 50 | S-Configuration, OH | 4-phenylpiperidinyl | 4' | 0.057 | | | | |
| 31 | 813466 | 51 | S-Configuration, OH | 4-(4-fluorophenoxy)piperidinyl | 4' | | 66 | | | |

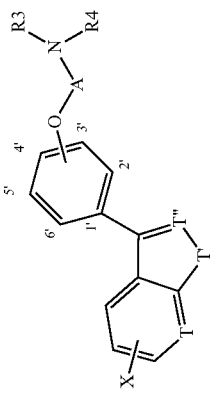

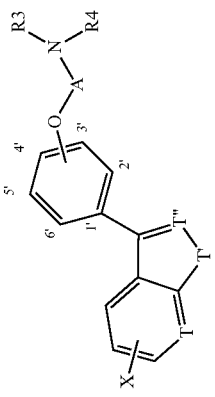

-continued

Benzisoxazolyl-, Pyridoisoxazolyl- and Benzthienyl-Phenoxy Derivatives Useful as $D_4$ Antagonists

| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 35 | 813471 | 55 | S-Configuration | piperazine-benzonitrile | 4' | | | | | |
| 36 | 813691 | 35 | R-Configuration | 4-phenylpiperidine | 4' | 0.018 | 67 | PO | 62.5 | |
| 37 | 813693 | 57 | R-Configuration | thiophenylmethylamine | 3' | | 78 | | | |

Benzisoxazolyl-, Pyridoisoxazolyl- and Benzthienyl-Phenoxy Derivatives Useful as D₄ Antagonists

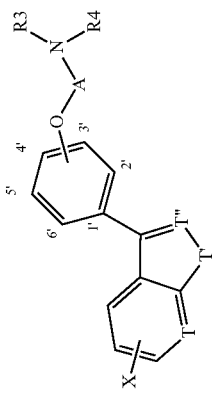

| Cmpd. No. | MDL No. | Example No. | A | N(R)₃(R)₄ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 38 | 813694 | 58 | OH R-Configuration | indanyl-NH- | 3' | | 54 | | | |
| 39 | 813695 | 59 | OH R-Configuration | thiophene-CH₂-NH- | 3' | | 68 | | | |
| 40 | 813696 | 60 | OH R-Configuration | benzyl-NH- | 3' | | 63 | | | |

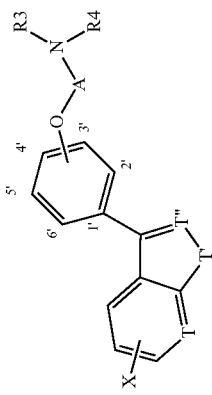

-continued

Benzisoxazolyl-, Pyridoisoxazolyl- and Benzthienyl-Phenoxy Derivatives Useful as $D_4$ Antagonists

| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 41 | 813704 | 68 | R-Configuration | piperidine-O-3-chlorophenyl | 3' | | 62 | | | |
| 42 | 813706 | 69 | R-Configuration | piperazine-pyrimidine | 3' | | 64 | | | |
| 43 | 813710 | 59A | S-Configuration | CH2-NH-thienyl | 3' | | 43 | | | |

-continued

Benzisoxazolyl-, Pyridoisoxazolyl- and Benzthienyl-Phenoxy Derivatives Useful as D₄ Antagonists

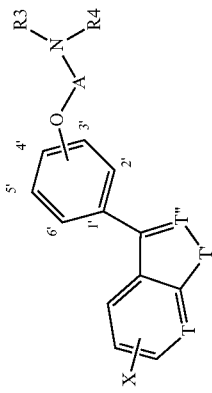

| Cmpd. No. | MDL No. | Example No. | A | N(R)₃(R)₄ | Number of position of oxygen substitution | D₄ RBA $K_i$ (μM) | D₄ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 44 | 813711 | 59A | S-Configuration | benzylamine | 3' | | 46 | | | |
| 45 | 813721 | 59A | S-Configuration | 2-pyrimidinyl piperazine | 3' | | 48 | | | |
| 46 | 813751 | 45 | S-Configuration | tetrahydroisoquinoline | 4' | 0.013* | | PO | 62.5 | 18.6 |

-continued

Benzisoxazolyl-, Pyridoisoxazolyl- and Benzthienyl-Phenoxy Derivatives Useful as $D_4$ Antagonists

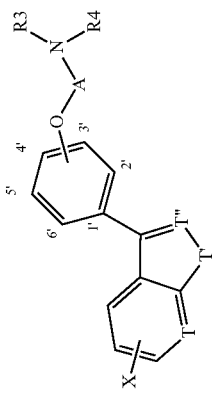

| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 47 | 813823 | 61 | OH, R-Configuration | 3-F benzyl NH | 3' | | 68 | | | |
| 48 | 813824 | 62 | OH, R-Configuration | 4-F benzyl NH | 3' | | 73 | | | |
| 49 | 813825 | 63 | OH, R-Configuration | 4-Cl benzyl NH | 3' | | 41 | | | |
| 50 | 813826 | 64 | OH, R-Configuration | 4-CH₃ benzyl NH | 3' | | 49 | | | |

-continued

Benzisoxazolyl-, Pyridoisoxazolyl- and Benzthienyl-Phenoxy Derivatives Useful as $D_4$ Antagonists

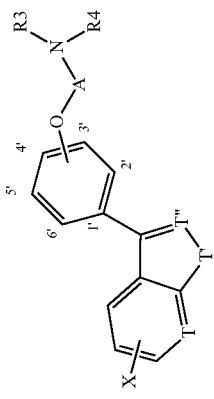

| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 51 | 813827 | 65 | OH R-Configuration | (phenethylamine) | 3' | | 44 | | | |
| 52 | 813828 | 66 | OH R-Configuration | (cyclohexenylethylamine) | 3' | | 51 | | | |
| 53 | 813829 | 67 | OH R-Configuration | (aminoindanol) | 3' | | 78 | | | |

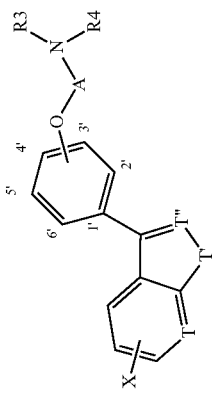

Benzisoxazolyl-, Pyridoisoxazolyl- and Benzthienyl-Phenoxy Derivatives Useful as $D_4$ Antagonists

| Cmpd. No. | MDL No. | Example No. | A | $N(R_3)(R_4)$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 54 | 813832 | 59A | S-Configuration, OH | 3-F-benzyl-NH- | 3' | | 49 | | | |
| 55 | 813833 | 59A | S-Configuration, OH | 4-F-benzyl-NH- | 3' | | 56 | | | |
| 56 | 813834 | 59A | S-Configuration, OH | 4-Cl-benzyl-NH- | 3' | | 41 | | | |
| 57 | 813835 | 59A | S-Configuration, OH | 4-CH3-benzyl-NH- | 3' | | 42 | | | |

-continued

Benzisoxazolyl-, Pyridoisoxazolyl- and Benzthienyl-Phenoxy Derivatives Useful as D₄ Antagonists

| Cmpd. No. | MDL No. | Example No. | A | N(R₃)(R₄) | Number of position of oxygen substitution | D₄ RBA K$_i$ (μM) | D₄ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 58 | 813838 | 59A | S-Configuration | (2-hydroxyindanyl amine) | 3' | | 51 | | | |
| 59 | 813842 | 70 | R-Configuration | (tetrahydronaphthyl amine) | 4' | 0.021 | | | | |
| 60 | 813843 | 71 | R-Configuration | (thienylmethyl amine) | 4' | 0.0024 | | IP | 37.5 | |

Benzisoxazolyl-, Pyridoisoxazolyl- and Benzthienyl-Phenoxy Derivatives Useful as $D_4$ Antagonists

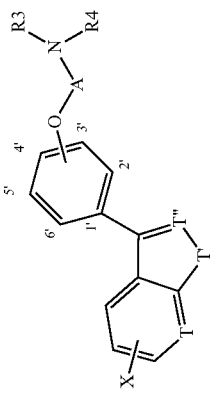

| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 61 | 813844 | 72 | R-Configuration | (indanyl-NH-) | 4' | 0.0075 | | PO | 25 | |
| 62 | 813845 | 73 | R-Configuration | (thienylmethyl-NH-) | 4' | 0.0053 | | PO | 25 | |
| 63 | 813846 | 74 | R-Configuration | (1-benzylpiperidin-4-yl-NH-) | 4' | | 57 | | | |
| 64 | 814300 | 75 | R-Configuration | (benzyl-NH-) | 4' | 0.0025* | | PO | 75 | |

-continued

Benzisoxazolyl-, Pyridoisoxazolyl- and Benzthienyl-Phenoxy Derivatives Useful as $D_4$ Antagonists

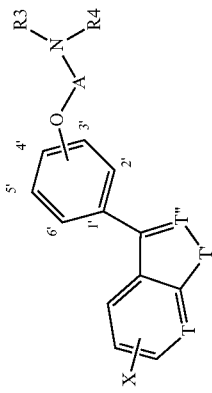

| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 65 | 813848 | 76 | OH R-Configuration | benzyl-2-F | 4' | 0.0025 | | PO | 75 | |
| 66 | 813849 | 77 | OH R-Configuration | benzyl-2-Cl | 4' | 0.0021 | | PO | 62.5 | |
| 67 | 813850 | 78 | OH R-Configuration | benzyl-2-OCH₃ | 4' | 0.025 | | | | |

-continued

Benzisoxazolyl-, Pyridoisoxazolyl- and Benzthienyl-Phenoxy Derivatives Useful as D₄ Antagonists

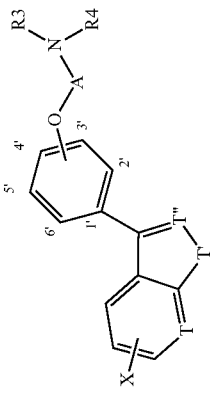

| Cmpd. No. | MDL No. | Example No. | A | N(R)₃(R)₄ | Number of position of oxygen substitution | D₄ RBA K$_i$ (μM) | D₄ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 68 | 813851 | 79 | OH, R-Configuration | NH-CH₂-C₆H₄-F (3-F) | 4' | 0.019 | | | | |
| 69 | 813852 | 80 | OH, R-Configuration | NH-CH₂-C₆H₄-OCH₃ (3-OMe) | 4' | 0.014 | | | | |
| 70 | 813853 | 81 | OH, R-Configuration | NH-CH₂-C₆H₄-F (4-F) | 4' | 0.01 | | PO | 50 | |

-continued

Benzisoxazolyl-, Pyridoisoxazolyl- and Benzthienyl-Phenoxy Derivatives Useful as $D_4$ Antagonists

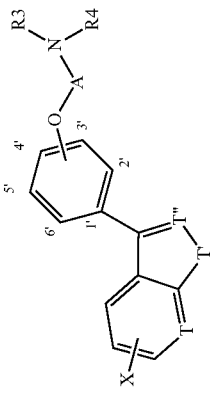

| Cmpd. No. | MDL No. | Example No. | A | $N(R_3)(R_4)$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 71 | 813854 | 82 | ⋯OH R-Configuration | 4-Cl-benzyl-NH- | 4' |  | 93 |  |  |  |
| 72 | 813855 | 83 | ⋯OH R-Configuration | 4-OCH3-benzyl-NH- | 4' | 0.03 |  |  |  |  |
| 73 | 813856 | 84 | ⋯OH R-Configuration | 4-CH3-benzyl-NH- | 4' | 0.013 |  |  |  |  |
| 74 | 813857 | 85 | ⋯OH R-Configuration | PhCH(OH)CH2-NH- | 4' |  | 91 |  |  |  |

Benzisoxazolyl-, Pyridoisoxazolyl- and Benzthienyl-Phenoxy Derivatives Useful as D₄ Antagonists

| Cmpd. No. | MDL No. | Example No. | A | N(R)₃(R)₄ | Number of position of oxygen substitution | D₄ RBA K$_i$ (μM) | D₄ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 75 | 813858 | 86 | OH, R-Configuration | phenethylamine | 4' | 0.027 | | | | |
| 76 | 813859 | 87 | OH, R-Configuration | cyclohexenyl-ethylamine | 4' | 0.011 | | | | |
| 77 | 813860 | 88 | OH, R-Configuration | 2-hydroxy-indanylamine | 4' | 0.015 | | | | |

Benzisoxazolyl-, Pyridoisoxazolyl- and Benzthienyl-Phenoxy Derivatives Useful as D$_4$ Antagonists

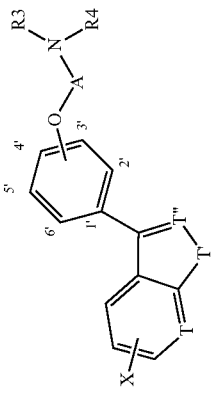

| Cmpd. No. | MDL No. | Example No. | A | N(R$_3$)(R$_4$) | Number of position of oxygen substitution | D$_4$ RBA K$_i$ (μM) | D$_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 78 | 813861 | 89 | OH, R-Configuration | indanyl-NH- | 4' | 0.0038 | | PO | 37.5 | |
| 79 | 813862 | 90 | OH, R-Configuration | 4-(3-chlorophenoxy)piperidinyl | 4' | | 81 | | | |
| 80 | 813863 | 91 | OH, R-Configuration | 4-(4-chlorophenyl)-4-hydroxypiperidinyl | 4' | | 76 | | | |

-continued

Benzisoxazolyl-, Pyridoisoxazolyl- and Benzthienyl-Phenoxy Derivatives Useful as $D_4$ Antagonists

| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 81 | 813864 | 93 | R-Configuration | 4-cyano-4-phenylpiperidine | 4' | 0.027 | | | | |
| 82 | 813865 | 21 | S-Configuration | tetrahydronaphthylamine | 4' | 0.034 | | | | |
| 83 | 813866 | 2 | S-Configuration | thiophen-3-ylmethylamine | 4' | 0.0034 | | PO | 87.5 | 3.6 |

-continued

Benzisoxazolyl-, Pyridoisoxazolyl- and Benzthienyl-Phenoxy Derivatives Useful as D$_4$ Antagonists

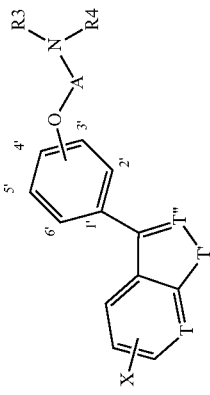

| Cmpd. No. | MDL No. | Example No. | A | N(R$_3$)(R)$_4$ | Number of position of oxygen substitution | D$_4$ RBA K$_i$ (μM) | D$_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 84 | 813867 | 21 | S-Configuration | (indanyl-CH$_2$-NH-) | 4' | 0.0079 | | PO | 25 | |
| 85 | 813868 | 21 | S-Configuration | (thienyl-CH$_2$-NH-) | 4' | 0.0022 | | PO | 37.5 | |
| 86 | 813869 | 21 | S-Configuration | (1-benzyl-piperidin-4-yl-NH-) | 4' | | 41 | | | |

-continued

Benzisoxazolyl-, Pyridoisoxazolyl- and Benzthienyl-Phenoxy Derivatives Useful as D₄ Antagonists

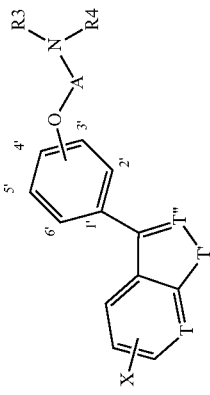

| Cmpd. No. | MDL No. | Example No. | A | N(R)₃(R)₄ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 87 | 813870 | 21 | S-Configuration | benzyl-NH- | 4' | 0.0068 | | PO | 12.5 | |
| 88 | 813871 | 21 | S-Configuration | 2-F-benzyl-NH- | 4' | 0.0025 | | IP | 50 | |
| 89 | 813872 | 21 | S-Configuration | 2-Cl-benzyl-NH- | 4' | 0.0013 | | PO | 25 | |

Benzisoxazolyl-, Pyridoisoxazolyl- and Benzthienyl-Phenoxy Derivatives Useful as D₄ Antagonists

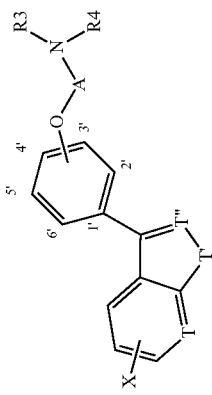

| Cmpd. No. | MDL No. | Example No. | A | $N(R_3)(R_4)$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 90 | 813873 | 21 | OH, S-Configuration | 2-methoxybenzyl-NH | 4' | 0.027 | | | | |
| 91 | 813874 | 21 | OH, S-Configuration | 3-fluorobenzyl-NH | 4' | 0.031 | | | | |
| 92 | 813875 | 21 | OH, S-Configuration | 3-methoxybenzyl-NH | 4' | 0.079 | | | | |

-continued

Benzisoxazolyl-, Pyridoisoxazolyl- and Benzthienyl-Phenoxy Derivatives Useful as $D_4$ Antagonists

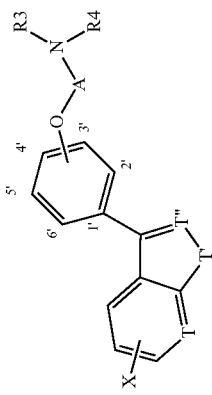

| Cmpd. No. | MDL No. | Example No. | A | N(R₃)(R₄) | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 93 | 813876 | 21 | S-Configuration (OH) | NH-CH₂-(4-F-phenyl) | 4' | | 86 | | | |
| 152 | 814702 | 13 | | dioxolane-piperidine | 4' | 0.0071 | | | | |
| 153 | 814967 | 13B | | 4-methylpiperidine | 4' | 0.0038 | | PO | 75 | |

-continued

Benzisoxazolyl-, Pyridoisoxazolyl- and Benzthienyl-Phenoxy Derivatives Useful as $D_4$ Antagonists

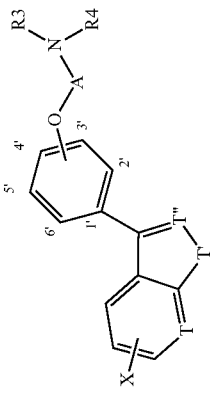

| Cmpd. No. | MDL No. | Example No. | A | N(R)₃(R)₄ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 154 | 814968 | 13B | (chain) | (piperidine-ethyl-CH₃) | 4' | 0.0112 | | PO | 25 | |
| 155 | 814969 | 13B | (chain) | (2,6-dimethylpiperidine) | 4' | | 46 | | | |
| 156 | 814970 | 13B | (chain) | (azepane) | 4' | 0.00388 | | PO | 50 | |

Benzisoxazolyl-, Pyridoisoxazolyl- and Benzthienyl-Phenoxy Derivatives Useful as $D_4$ Antagonists
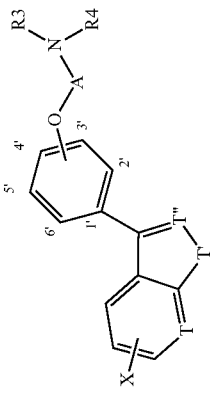
| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 157 | 814971 | 13B | 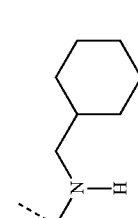 | 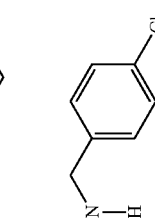 | 4' | 0.00835 | | PO | 50 | |
| 158 | 814972 | 13B |  | 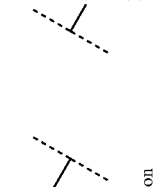 | 4' | 0.00842 | | PO | 37.5 | |
| 94 | 813877 | 21 | 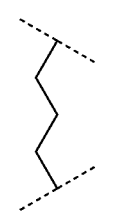 S-Configuration | 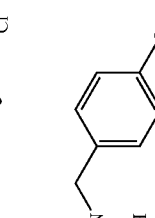 | 4' | 0.189 | | | | |
| 95 | 813878 | 21 |  S-Configuration | 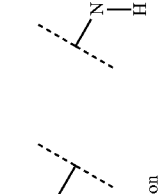 | 4' | 0.035 | | | | |

-continued

Benzisoxazolyl-, Pyridoisoxazolyl- and Benzthienyl-Phenoxy Derivatives Useful as $D_4$ Antagonists

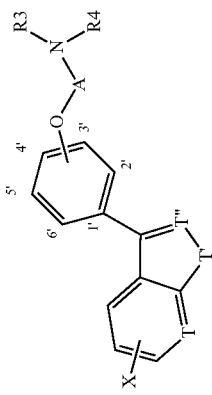

| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 96 | 813879 | 21 | OH S-Configuration | NH-CH2-C6H4-CH3 | 4' | 0.026 | | | | |
| 97 | 813880 | 21 | OH S-Configuration | NH-CH2-CH(OH)-Ph | 4' | | 85 | | | |
| 98 | 813881 | 21 | OH S-Configuration | NH-CH2-CH2-Ph | 4' | | 93 | | | |

-continued

Benzisoxazolyl-, Pyridoisoxazolyl- and Benzthienyl-Phenoxy Derivatives Useful as $D_4$ Antagonists

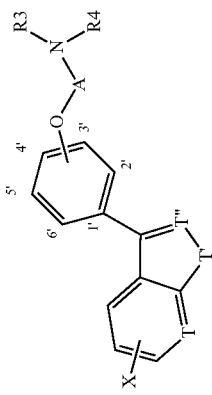

| Cmpd. No. | MDL No. | Example No. | A | $N(R_3)(R_4)$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 99 | 813882 | 21 | S-Configuration (OH) | cyclohexenyl-ethylamine | 4' | | 97 | | | |
| 100 | 813883 | 21 | S-Configuration (OH) | indanol-amine | 4' | | 89 | | | |
| 101 | 813884 | 21 | S-Configuration (OH) | 2-aminoindane | 4' | 0.012 | | | | |

Benzisoxazolyl-, Pyridoisoxazolyl- and Benzthienyl-Phenoxy Derivatives Useful as D$_4$ Antagonists
| Cmpd. No. | MDL No. | Example No. | A | N(R$_3$)(R$_4$) | Number of position of oxygen substitution | D$_4$ RBA K$_i$ (μM) | D$_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 102 | 813885 | 21 | 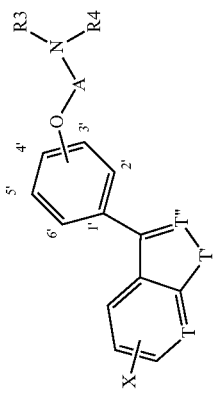 S-Configuration | 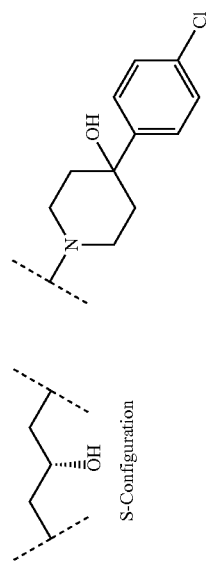 | 4' | | 59 | | | |
| 103 | 813886 | 21 | 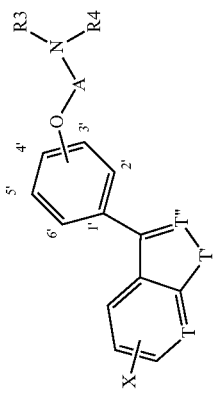 S-Configuration | 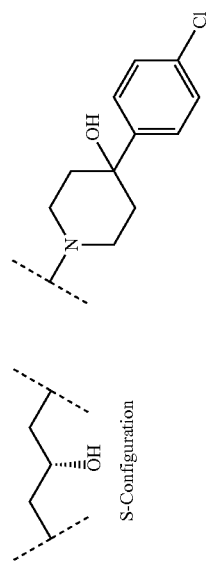 | 4' | | 55 | | | |

-continued

Benzisoxazolyl-, Pyridoisoxazolyl- and Benzthienyl-Phenoxy Derivatives Useful as D₄ Antagonists

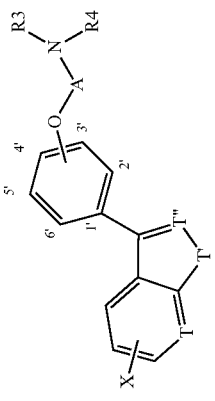

| Cmpd. No. | MDL No. | Example No. | A | N(R)₃(R)₄ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 104 | 813887 | 21 | OH S-Configuration | piperazine-pyrimidine | 4' | 0.017 | | | | |
| 105 | 813888 | 21 | OH S-Configuration | 4-cyano-4-phenylpiperidine | 4' | | 86 | | | |
| 106 | 813889 | 92 | OH R-Configuration | piperazine-pyrimidine | 4' | 0.0084 | | | | |

Benzisoxazolyl-, Pyridoisoxazolyl- and Benzthienyl-Phenoxy Derivatives Useful as D₄ Antagonists

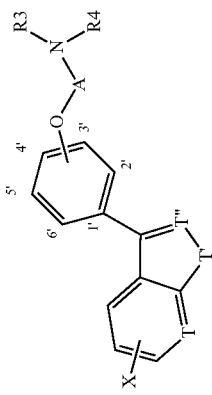

| Cmpd. No. | MDL No. | Example No. | A | N(R)₃(R)₄ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 107 | 813906 | 56 | S-Configuration (OH) | 4-fluorophenyl piperidine | 4' | | 93 | | | |
| 108 | 813907 | 20 | | 4-fluorophenyl piperidine | 4' | | 88 | | | |
| 109 | 813936 | 56 | R-Configuration (OH) | 4-fluorophenyl piperidine | 4' | 0.066 | | | | |

-continued

Benzisoxazolyl-, Pyridoisoxazolyl- and Benzthienyl-Phenoxy Derivatives Useful as D$_4$ Antagonists

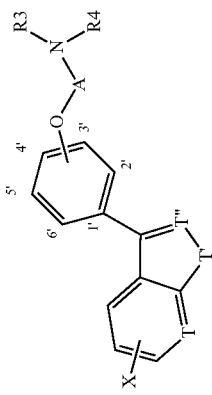

| Cmpd. No. | MDL No. | Example No. | A | N(R)$_3$(R)$_4$ | Number of position of oxygen substitution | D$_4$ RBA K$_i$ (μM) | D$_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 110 | 814056 | 57 | ⋯OH R-Configuration | 4-benzylpiperidinyl | 4' | | 48 | | | |
| 111 | 814063 | 57 | ⋯OH R-Configuration | 4-phenylpiperidinyl | 3' | | 62 | | | |
| 112 | 814065 | 57 | ⋯OH R-Configuration | N-benzyl-N-methyl | 3' | | 61 | | | |

-continued

Benzisoxazolyl-, Pyridoisoxazolyl- and Benzthienyl-Phenoxy Derivatives Useful as D₄ Antagonists

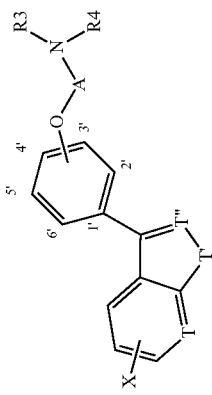

| Cmpd. No. | MDL No. | Example No. | A | N(R₃)(R₄) | Number of position of oxygen substitution | D₄ RBA K$_i$ (μM) | D₄ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 113 | 814071 | 57 | R-Configuration (CH with OH) | 4-methylpiperidinyl | 3' | | 67 | | | |
| 114 | 814088 | 59A | S-Configuration (CH with OH) | N-benzyl-N-methyl | 3' | | 44 | | | |
| 115 | 814110 | 20B | (CH₂)₃ | tetrahydroisoquinolinyl | 4' | 0.086 | | | | |

-continued
Benzisoxazolyl-, Pyridoisoxazolyl- and Benzthienyl-Phenoxy Derivatives Useful as D₄ Antagonists
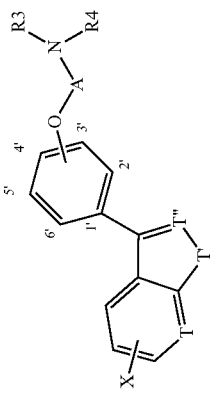
| Cmpd. No. | MDL No. | Example No. | A | N(R)₃(R)₄ | Number of position of oxygen substitution | D₄ RBA K_i (μM) | D₄ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 116 | 814111 | 20B | | 4-phenylpiperidinyl | 4' | 0.093 | | | | |
| 117 | 814112 | 20C | | benzylamino | 4' | 0.022 | | | | |
| 118 | 814113 | 20C | | 4-fluorobenzylamino | 4' | | 97 | | | |

-continued

Benzisoxazolyl-, Pyridoisoxazolyl- and Benzthienyl-Phenoxy Derivatives Useful as $D_4$ Antagonists

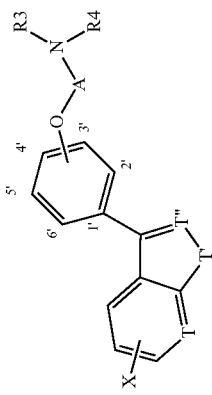

| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 119 | 814114 | 20C | | 3,4-dichlorobenzyl NH | 4' | | 83 | | | |
| 120 | 814139 | 20A | | piperidinyl | 4' | 0.0088 | | PO | | 7.67 |
| 121 | 814201 | 20 | | 4-(4-fluorophenyl)piperidinyl | 4' | | 91 | | | |

-continued

Benzisoxazolyl-, Pyridoisoxazolyl- and Benzthienyl-Phenoxy Derivatives Useful as D₄ Antagonists

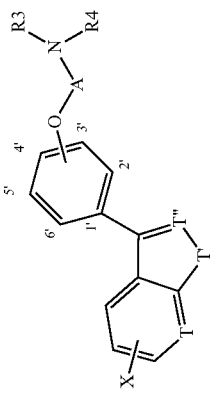

| Cmpd. No. | MDL No. | Example No. | A | $N(R_3)(R_4)$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 122 | 814252A | 11, 13 | ⁓ | benzyl-NH- | 4' | 0.00553* | | | | |
| 123 | 814252 | 11, 13 | ⁓ | benzyl-NH- | 4' | 0.014 | | PO | 75 | |
| 124 | 814253 | 15 | ⁓ | OH R-Configuration | 4' | 0.0068 | | PO | 25 | |
| 125 | 814254 | 16 | ⁓ | OH R-Configuration | 4' | 0.00254 | | PO | 50 | |

Benzisoxazolyl-, Pyridoisoxazolyl- and Benzthienyl-Phenoxy Derivatives Useful as D₄ Antagonists

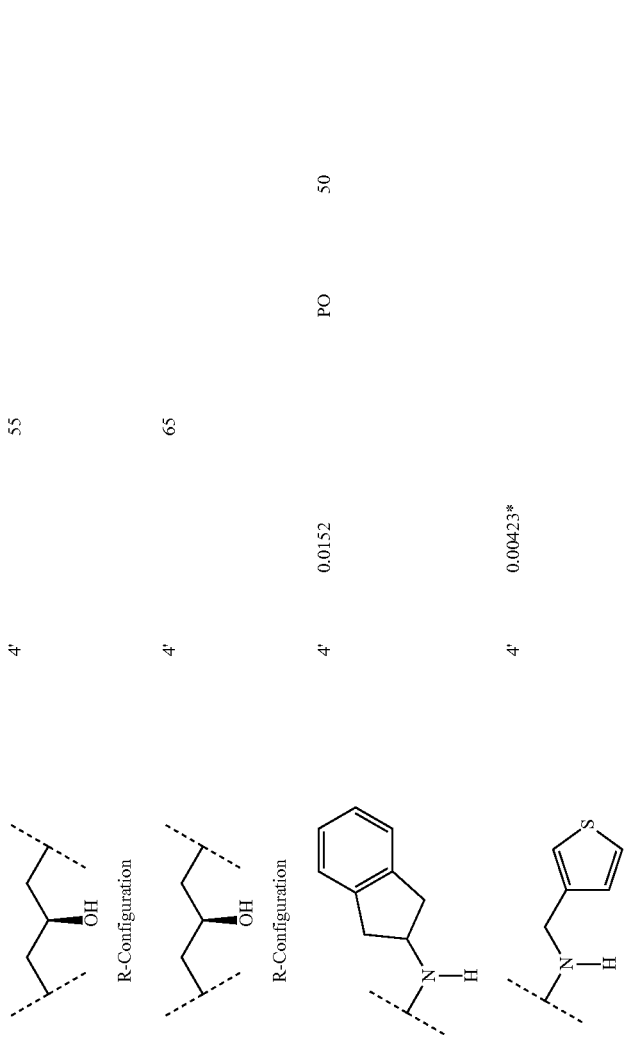

| Cmpd. No. | MDL No. | Example No. | A | N(R₃)(R₄) | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 126 | 814255 | 17 | ~~~ | 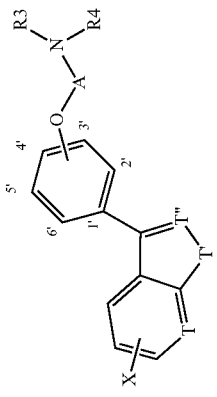 R-Configuration | 4' | | 55 | | | |
| 127 | 814256 | 18 | ~~~ | OH R-Configuration | 4' | | 65 | | | |
| 128 | 814257 | 14 | ~~~ | indanyl-NH | 4' | 0.0152 | | PO | 50 | |
| 129 | 814258A | 19 | ~~~ | thienylmethyl-NH | 4' | 0.00423* | | | | |

Benzisoxazolyl-, Pyridoisoxazolyl- and Benzthienyl-Phenoxy Derivatives Useful as D$_4$ Antagonists

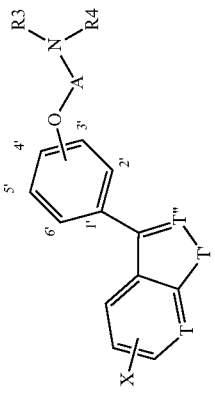

| Cmpd. No. | MDL No. | Example No. | A | N(R)$_3$(R)$_4$ | Number of position of oxygen substitution | D$_4$ RBA K$_i$ (µM) | D$_4$ RBA % Inhibition (@ 1 µM) | In Vivo Method | Antag. of MK 801 Stereotypy % Inhib. @ 20 mg/kg | In Vivo ED50 (mg/kg) |
|---|---|---|---|---|---|---|---|---|---|---|
| 130 | 814258 | 12 | | thiophene-CH$_2$-NH- | 4' | 0.0035 | | PO | 62.5 | |
| 131 | 814300 | 110 | OH R-Configuration | benzyl-NH- | 4' | 0.0077 | | | | |
| 132 | 814348 | 111 | OH R-Configuration | OH R-Configuration | 4' | | 97 | | | |
| 133 | 814349 | 112 | OH R-Configuration | OH R-Configuration | 4' | | 51 | | | |

-continued

Benzisoxazolyl-, Pyridoisoxazolyl- and Benzthienyl-Phenoxy Derivatives Useful as D₄ Antagonists

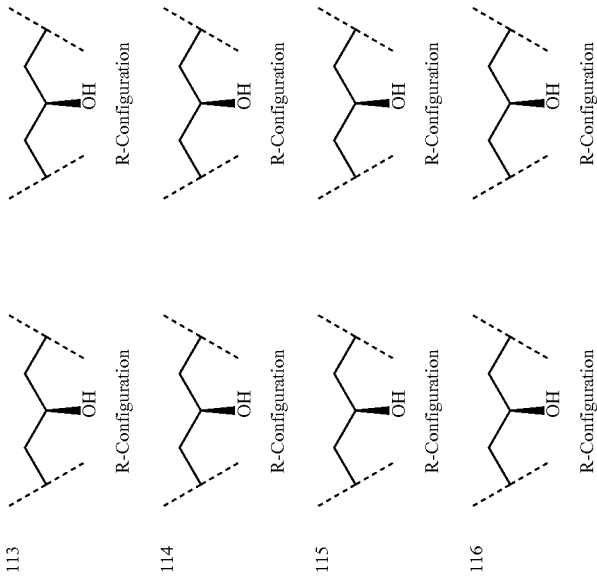

| Cmpd. No. | MDL No. | Example No. | A | $N(R_3)(R_4)$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 134 | 814350 | 113 | 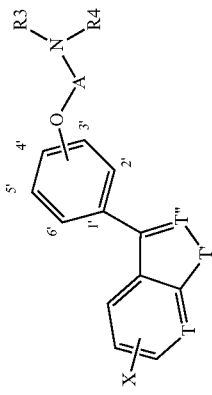 OH R-Configuration | OH R-Configuration | 4' | | 95 | | | |
| 135 | 814351 | 114 | OH R-Configuration | OH R-Configuration | 4' | 0.0068 | | PO | 75 | |
| 136 | 814352 | 115 | OH R-Configuration | OH R-Configuration | 4' | | 97 | | | |
| 137 | 814353 | 116 | OH R-Configuration | OH R-Configuration | 4' | | 85 | | | |

Benzisoxazolyl-, Pyridoisoxazolyl- and Benzthienyl-Phenoxy Derivatives Useful as $D_4$ Antagonists

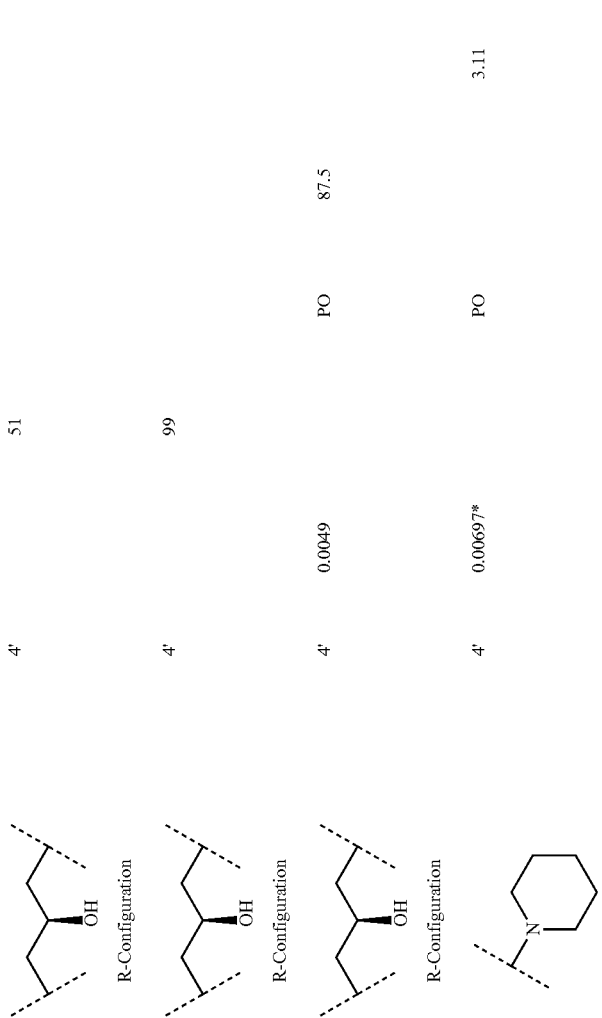

| Cmpd. No. | MDL No. | Example No. | A | N(R)₃(R)₄ | Number of position of oxygen substitution | $D_4$ RBA $K_i$ (µM) | $D_4$ RBA % Inhibition (@ 1 µM) | In Vivo Method | Antag. of MK 801 Stereotypy % Inhib. @ 20 mg/kg | In Vivo ED50 (mg/kg) |
|---|---|---|---|---|---|---|---|---|---|---|
| 138 | 814354 | 117 | OH R-Configuration | OH R-Configuration | 4' | | 51 | | | |
| 139 | 814606 | 13 | | OH R-Configuration | 4' | | 99 | | | |
| 140 | 814607 | 13 | | OH R-Configuration | 4' | 0.0049 | | PO | 87.5 | |
| 141 | 814608A | 1 | | piperidinyl | 4' | 0.00697* | | PO | | 3.11 |

-continued

Benzisoxazolyl-, Pyridoisoxazolyl- and Benzthienyl-Phenoxy Derivatives Useful as $D_4$ Antagonists

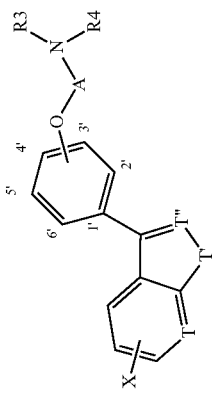

| Cmpd. No. | MDL No. | Example No. | A | $N(R_3)(R_4)$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 142 | 814608 | 1, 13 | | piperidine | 4' | 0.0098 | | | | |
| 143 | 814609 | 13 | | CH₂CH(OH)CH₂ R-Configuration | 4' | | 68 | | | |
| 144 | 814694 | 13 | | morpholine | 4' | | 88 | | | |
| 145 | 814695 | 13 | | 4-methylpiperidine | 4' | 0.015 | | | | |

-continued
Benzisoxazolyl-, Pyridoisoxazolyl- and Benzthienyl-Phenoxy Derivatives Useful as D4 Antagonists
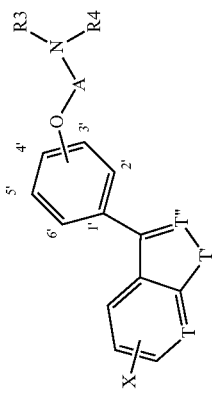
| Cmpd. No. | MDL No. | Example No. | A | N(R)3(R)4 | Number of position of oxygen substitution | D4 RBA Ki (µM) | D4 RBA % Inhibition (@ 1 µM) | In Vivo Method | Antag. of MK 801 Stereotypy % Inhib. @ 20 mg/kg | In Vivo ED50 (mg/kg) |
|---|---|---|---|---|---|---|---|---|---|---|
| 146 | 814696 | 13 | ⋮⋮ | piperidine-N with 4-ethyl-CH3 | 4' | 0.034 | | | | |
| 147 | 814697 | 13 | ⋮⋮ | 2,6-dimethylpiperidine | 4' | | 63 | | | |
| 148 | 814698 | 13A | ⋮⋮ | OH R-Configuration | 4' | | 92 | | | |

-continued

Benzisoxazolyl-, Pyridoisoxazolyl- and Benzthienyl-Phenoxy Derivatives Useful as $D_4$ Antagonists

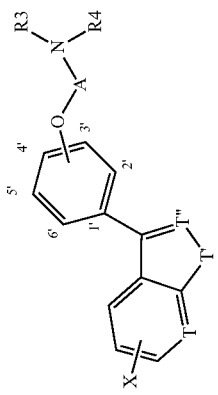

| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 149 | 814699 | 13 | (chain) | (azepanyl) | 4' | 0.023 | | | | |
| 150 | 814700 | 13 | (chain) | (azocanyl) | 4' | | 90 | | | |
| 151 | 814701 | 13 | (chain) | cyclohexylmethyl-NH | 4' | 0.0073 | | PO | 75 | |
| 159 | 814973 | 13B | (chain) | OH, R-Configuration | 4' | 0.00344 | | PO | 50 | |

-continued

Benzisoxazolyl-, Pyridoisoxazolyl- and Benzthienyl-Phenoxy Derivatives Useful as D₄ Antagonists

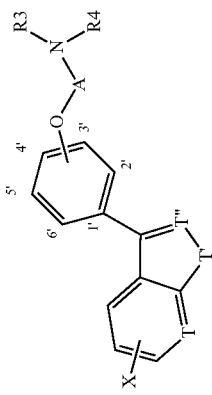

| Cmpd. No. | MDL No. | Example No. | A | $N(R_3)(R_4)$ | Number of position of oxygen substitution | $D_4$ RBA $K_i$ ($\mu$M) | $D_4$ RBA % Inhibition (@ 1 $\mu$M) | In Vivo Method | Antag. of MK 801 Stereotypy % Inhib. @ 20 mg/kg | In Vivo ED50 (mg/kg) |
|---|---|---|---|---|---|---|---|---|---|---|
| 160 | 814974 | 13B | ~~~ | N-phenylpiperazine | 4' | 0.0185 | | PO | 50 | |
| 161 | 814975 | 13B | ~~~ | OH R-Configuration | 4' | 0.04 | | | | |
| 162 | 814988 | 13B | ~~~ | OH R-Configuration | 4' | 0.011 | | PO | 12.5 | |
| 162A | 814976 | 13B | ~~~ | OH R-Configuration | 4' | | 86 | | | |

-continued

Benzisoxazolyl-, Pyridoisoxazolyl- and Benzthienyl-Phenoxy Derivatives Useful as $D_4$ Antagonists

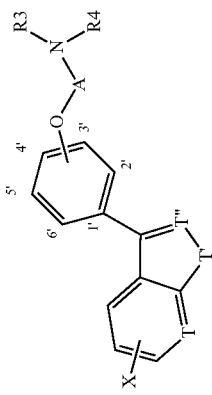

| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| | | | | Wherein T, T' and T" are respectively C, S, and C producing benzothienyl | | | | | | |
| 163 | 814797 | 95A | OH R-Configuration | 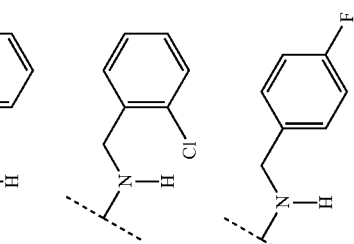 | 4' | | 69 | | | |
| 164 | 814883 | 95 | OH R-Configuration | 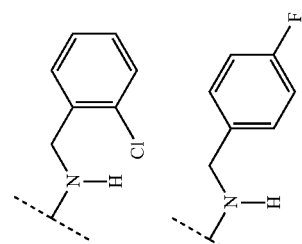 | 4' | | 85 | PO | 62.5 | |
| 165 | 814887 | 96 | OH R-Configuration | 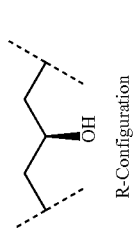 | 4' | | 53 | | | |
| 166 | 814888 | 97 | OH R-Configuration | 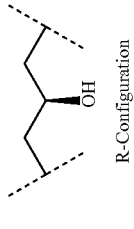 OH R-Configuration | 4' | | 71 | | | |

-continued

Benzisoxazolyl-, Pyridoisoxazolyl- and Benzthienyl-Phenoxy Derivatives Useful as D$_4$ Antagonists

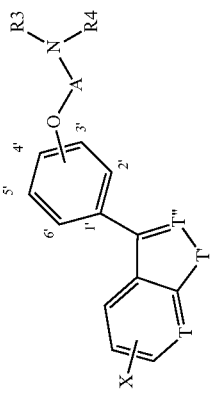

| Cmpd. No. | MDL No. | Example No. | A | N(R$_3$)(R$_4$) | Number of position of oxygen substitution | D$_4$ RBA K$_i$ (μM) | D$_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 167 | 801889 | 98 | OH R-Configuration | OH R-Configuration | 4' | | 81 | PO | 50 | |
| 168 | 814890 | 99 | OH R-Configuration | OH R-Configuration | 4' | | 72 | | | |
| 169 | 814891 | 100 | OH R-Configuration | OH R-Configuration | 4' | | 41 | | | |
| 170 | 814893 | 101 | OH R-Configuration | tetrahydroisoquinoline | 4' | | 64 | | | |

Benzisoxazolyl-, Pyridoisoxazolyl- and Benzthienyl-Phenoxy Derivatives Useful as $D_4$ Antagonists
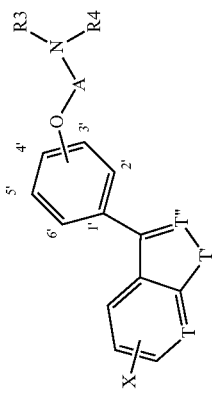
| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 171 | 814894 | 94 | ⋯OH R-Configuration | ⋯OH R-Configuration | 4' | | 52 | | | |
| 172 | 814917 | 118 | | ⌬Cl N—H | 4' | | 66 | | | |
| 173 | 814920 | 119 | | ⌬F N—H | 4' | | 61 | | | |
| 174 | 814922 | 120 | | ⋯OH R-Configuration | 4' | | 67 | | | |

-continued

Benzisoxazolyl-, Pyridoisoxazolyl- and Benzthienyl-Phenoxy Derivatives Useful as $D_4$ Antagonists

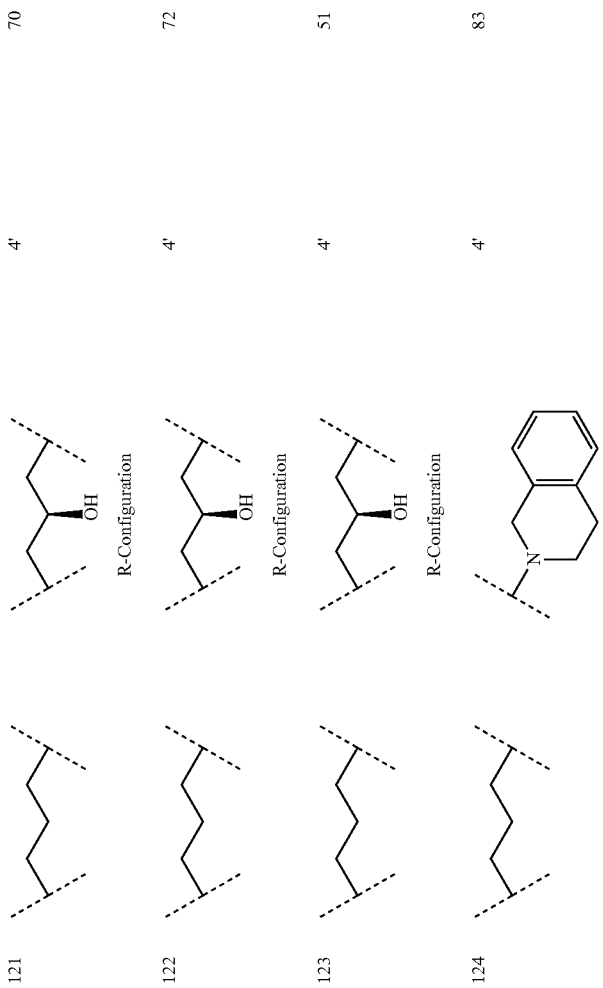

| Cmpd. No. | MDL No. | Example No. | A | $N(R_3)(R_4)$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 175 | 814923 | 121 | ～ | ～OH R-Configuration | 4' | | 70 | | | |
| 176 | 814924 | 122 | ～ | ～OH R-Configuration | 4' | | 72 | | | |
| 177 | 814925 | 123 | ～ | ～OH R-Configuration | 4' | | 51 | | | |
| 178 | 814927 | 124 | ～ | tetrahydroisoquinoline | 4' | | 83 | | | |

-continued

Benzisoxazolyl-, Pyridoisoxazolyl- and Benzthienyl-Phenoxy Derivatives Useful as $D_4$ Antagonists

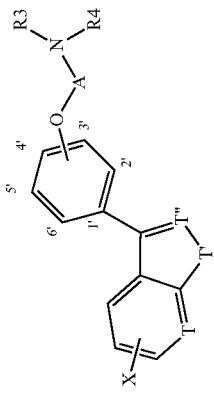

| Cmpd. No. | MDL No. | Example No. | A | $N(R_3)(R_4)$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 179 | 814928 | 125 | ⟋⟍⟋ | ⟋⟍⟋OH R-Configuration | 4' | | 62 | | | |
| 180 | 814929 | 126 | ⟋⟍⟋ | piperidine | 4' | | 68 | | | |
| 181 | 814930 | 127 | ⟋⟍⟋ | azepane | 4' | | 74 | | | |
| 182 | 814931 | 128 | ⟋⟍⟋ | benzylamine | 4' | | 51 | | | |

Wherein T, T' and T" are respectively N, O, and N producing pyridoisoxazolyl

-continued

Benzisoxazolyl-, Pyridoisoxazolyl- and Benzthienyl-Phenoxy Derivatives Useful as D₄ Antagonists

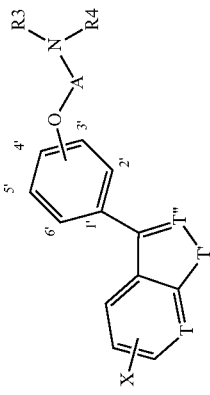

| Cmpd. No. | MDL No. | Example No. | A | $N(R)_3(R)_4$ | Number of position of oxygen substitution | $D_4$ RBA $K_i$ (µM) | $D_4$ RBA % Inhibition (@ 1 µM) | In Vivo Method | Antag. of MK 801 Stereotypy % Inhib. @ 20 mg/kg | In Vivo ED50 (mg/kg) |
|---|---|---|---|---|---|---|---|---|---|---|
| 184 | 813547 | 129 | OH R-Configuration | benzyl-NH- | 3' | | 43 | | | |
| 185 | 813548 | 129 | OH R-Configuration | 3-F-benzyl-NH- | 3' | | 41 | | | |
| 186 | 813549 | 129 | OH R-Configuration | 4-F-benzyl-NH- | 3' | | 50 | | | |
| 187 | 813551 | 129 | OH R-Configuration | 4-CH₃-benzyl-NH- | 3' | | 55 | | | |

Benzisoxazolyl-, Pyridoisoxazolyl- and Benzthienyl-Phenoxy Derivatives Useful as $D_4$ Antagonists

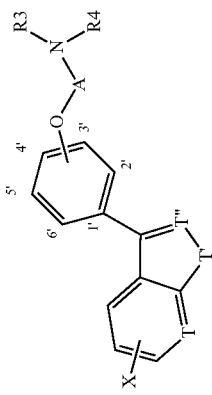

| Cmpd. No. | MDL No. | Example No. | A | N(R3)(R4) | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 188 | 813552 | 129 | ...OH R-Configuration | ...OH R-Configuration | 3' | | 45 | | | |
| 189 | 813559 | 103 | ...OH R-Configuration | N(CH3)-CH2-Ph | 3' | | 46 | | | |
| 190 | 813560 | 104 | ...OH R-Configuration | tetrahydroisoquinoline | 3' | | 47 | | | |
| 191 | 813561 | 105 | ...OH R-Configuration | ...OH R-Configuration | 3' | | 43 | | | |

-continued

Benzisoxazolyl-, Pyridoisoxazolyl- and Benzthienyl-Phenoxy Derivatives Useful as $D_4$ Antagonists

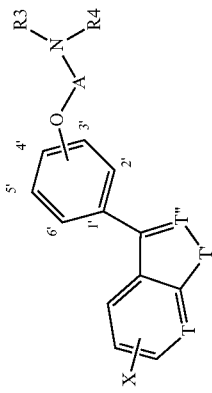

| Cmpd. No. | MDL No. | Example No. | A | N(R)$_3$(R)$_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 192 | 813567 | 102 | ⋯⋀(OH)⋯ R-Configuration | ⋯⋀(OH)⋯ R-Configuration | 3' | 0.091 | | PO | 50 | |
| 193 | 813568 | 106 | ⋯⋀(OH)⋯ R-Configuration | ⋯⋀(OH)⋯ R-Configuration | 3' | | 77 | | | |
| 194 | 813569 | 107 | ⋯⋀(OH)⋯ R-Configuration | ⋯⋀(OH)⋯ R-Configuration | 3' | | 95 | PO | 75 | |

-continued

Benzisoxazolyl-, Pyridoisoxazolyl- and Benzthienyl-Phenoxy Derivatives Useful as $D_4$ Antagonists

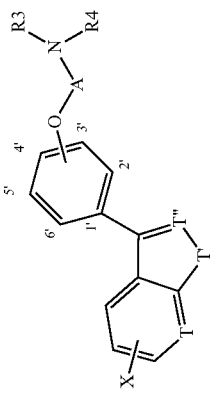

| Cmpd. No. | MDL No. | Example No. | A | $N(R)_3(R)_4$ | Number of position of oxygen substitution | $D_4$ RBA $K_i$ (μM) | $D_4$ RBA % Inhibition (@ 1 μM) | In Vivo Method | Antag. of MK 801 Stereotypy % Inhib. @ 20 mg/kg | In Vivo ED50 (mg/kg) |
|---|---|---|---|---|---|---|---|---|---|---|
| 195 | 813570 | 108 | ⠀⠀⠀OH R-Configuration | ⠀⠀⠀OH R-Configuration | 3' |  | 100 |  |  |  |
| 196 | 813571 | 109 | ⠀⠀⠀OH R-Configuration | ⠀⠀⠀OH R-Configuration | 3' |  | 100 |  |  |  |

*HCl Salt

What is claimed is:

1. A compound of Formula I:

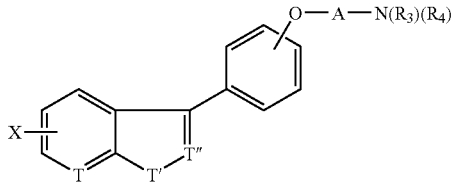

Formula I a pharmaceutically acceptable salt or stereoisomer thereof, wherein

T, T' and T" are respectively

C, O and N producing benzisoxazolyl,

C, S and C producing benzthienyl, or

N, O and N producing pyridoisoxazolyl;

X is hydrogen or halo;

A is —$CH_2CH_2$— or —$CH_2C(R_1)(R_2)CH_2$—, wherein $R_1$ is H, OH or $C_{1-6}$ alkoxy; and $R_2$ is H or $C_{1-6}$ alkyl;

$R_3$ is $(CH_2)_n$ Q, $CH_2CH(OH)Q$, $CH(CH_3)Q$, 1,2,3,4-tetrahydronaphthyl, indanyl optionally substituted with hydroxy, or adamantyl, wherein Q is thienyl, phenyl, furanyl, naphthyl, pyridyl, indolyl, indazolyl, cyclohexyl, 1,2-methylenedioxyphenyl, cyclohexenyl, 1H-pyrazolo[4.3-c]pyridyl, and Q is optionally substituted with one or two moieties independently selected from halo, $C_{1-6}$ alkyl, $C_{1-6}$ alkoxy, hydroxy, $S(O)_2NH_2$, trifluoromethyl, or cyano, and n is 0,1 or 2;

$R_4$ is H or $C_{1-6}$ alkyl; or $R_3$ and $R_4$, together with the nitrogen atom to which $R_3$ and $R_4$ are attached, form 4,5,6,7-tetrahydrothieno [3,2,c] pyridinyl,1,4-dioxa-8-azo-spiro[4.5]decanyl, piperazinyl, morpholinyl, piperidinyl, pyrrolidinyl, azepanyl, azocanyl, 1,2,3,4-tetrahydroisoquinolinyl, 1,2,3,4-tetrahydro-1H-β-yl, or 8-aza-bicyclo[3.2.1.]octanyl, each of which may be mono- or independently disubstituted with halo, $C_{1-6}$ alkyl, $C_{1-6}$ alkoxy, $C_{1-6}$ alkoxymethyl, C(O)phenyl, OH, phenyl, CN, O-phenyl or $(CH_2)_mZ$, Z is benzisoxazolyl, indazolyl, benzisothiazolyl, benzthienyl, pyrimidinyl, pyridyl, 1,2-methylenedioxyphenyl, or phenyl, and Z, CH(OH)phenyl, phenyl or O-phenyl are optionally substituted with one or two moieties independently selected from halo, $C_{1-6}$ alkyl, $C_{1-6}$alkoxy, hydroxy, trifluoromethyl, $S(O)_2NH_2$ or cyano, and m is 0 or 1.

2. A compound according to claim 1 wherein T, T', and T" are respectively C, S, and C producing benzthienyl.

3. The compound according to claim 2 which is (R)-1-(4-benzo[b]thiophen-3-yl-phenoxy)-3-benzylamino-propan-2-ol.

4. The compound according to claim 2 which is (R)-1-(4-benzo[b]thiophen-3-yl-phenoxy)-3-(2-chloro-benzylamino)-propan-2-ol.

5. The compound according to claim 2 which is (R)-1-(4-benzo[b]thiophen-3-yl-phenoxy)-3-(4-fluoro-benzylamino)-propan-2-ol.

6. The compound according to claim 2 which is (R)-1-(4-benzo[b]thiophen-3-yl-phenoxy)-3-[(thiophen-2-ylmethyl)-amino]-propan-2-ol.

7. The compound according to claim 2 which is (R)-1-(4-benzo[b]thiophen-3-yl-phenoxy)-3-[(thiophen-3-ylmethyl)-amino]-propan-2-ol.

8. The compound according to claim 2 which is (R)-1-(4-benzo[b]thiophen-3-yl-phenoxy)-3-(indan-1-ylamino)-propan-2-ol.

9. The compound according to claim 2 which is (R)-1-(4-benzo[b]thiophen-3-yl-phenoxy)-3-(3,4-dihydro-1H-isoquinolin-2-yl)-propan-2-ol.

10. The compound according to claim 2 which is (R)-1-(4-benzo[b]thiophen-3-yl-phenoxy)-3-(4-pyrimidin-2-yl-piperazin-1-yl)-propan-2-ol.

11. The compound according to claim 2 which is [3-(4-benzo[b]thiophen-3-yl-phenoxy)-propyl]-(2-chloro-benzyl)-amine.

12. The compound according to claim 2 which is 3-(4-benzo[b]thiophen-3-yl-phenoxy)-propyl]-(2-fluoro-benzyl)-amine.

13. The compound according to claim 2 which is [3-(4-benzo[b]thiophen-3-yl-phenoxy)-propyl]-(2,6-difluoro-benzyl)-amine.

14. The compound according to claim 2 which is [3-(4-benzo[b]thiophen-3-yl-phenoxy)-propyl]-thiophen-2-ylmethyl-amine.

15. The compound according to claim 2 which is 3-(4-benzo[b]thiophen-3-yl-phenoxy)-propyl]-thiophen-3-ylmethyl-amine.

16. The compound according to claim 2 which is [3-(4-benzo[b]thiophen-3-yl-phenoxy)-propyl]-indan-1-yl-amine.

17. The compound according to claim 2 which is 2-[3-(4-benzo[b]thiophen-3-yl-phenoxy)-propyl]-1,2,3,4-tetrahydro-isoquinoline.

18. The compound according to claim 2 which is 2-{4-[3-(4-benzo[b]thiophen-3-yl-phenoxy)-propyl]-piperazin-1-yl}-pyrimidine.

19. The compound according to claim 2 which is 1-[3-(4-benzo[b]thiophen-3-yl-phenoxy)-propyl]-piperidine.

20. The compound according to claim 2 which is 1-[3-(4-benzo[b]thiophen-3-yl-phenoxy)-propyl]-azepane.

21. The compound according to claim 2 which is [3-(4-benzo[b]thiophen-3-yl-phenoxy)-propyl]-benzyl-amine.

22. The compound of claim 2 which is (R)-1-(4-benzo[b]thiophen-3-yl-phenoxy)-3-(2,6-difluoro-benzylamino)-propan-2-ol.

23. A compound according to claim 1, wherein T, T', and T" are respectively N, O, and N producing pyridoisoxazolyl.

24. The compound according to claim 23 which is (R)-1-[4-(3-chloro-phenoxy)-piperidin-1-yl]-3-(3-isoxazolo[5,4-b]pyridin-3-yl-phenoxy)-propan-2-ol.

25. The compound according to claim 23 which is (R)-1-benzylamino-3-(3-isoxazolo[5,4-b]pyridin-3-yl-phenoxy)-propan-2-ol.

26. The compound according to claim 23 which is (R)-1-(3-fluoro-benzylamino)-3-(3-isoxazolo[5,4-b]pyridin-3-yl-phenoxy)-propan-2-ol.

27. The compound according to claim 23 which is (R)-1-(4-fluoro-benzylamino)-3-(3-isoxazolo[5,4-b]pyridin-3-yl-phenoxy)-propan-2-ol.

28. The compound according to claim 23 which is (R)-1-(3-isoxazolo[5,4-b]pyridin-3-yl-phenoxy)-3-(4-methyl-benzylamino)-propan-2-ol.

29. The compound according to claim 23 which is (R)-1-(3-isoxazolo[5,4-b]pyridin-3-yl-phenoxy)-3-(3-methoxy-benzylamino)-propan-2-ol.

30. The compound according to claim 23 which is (R)-1-(benzyl-methyl-amino)-3-(3-isoxazolo[5,4-b]pyridin-3-yl-phenoxy)-propan-2-ol.

31. The compound according to claim 23 which is (R)-1-(3,4-dihydro-1H-isoquinolin-2-yl)-3-(3-isoxazolo[5,4-b]pyridin-3-yl-phenoxy)-propan-2-ol.

32. The compound according to claim 23 which is (R)-1-(6,7-dihydro-4H-thieno[3,2-c]pyridin-5-yl)-3-(3-isoxazolo[5,4-b]pyridin-3-yl-phenoxy)-propan-2-ol.

33. The compound according to claim 23 which is (R)-1-(3-isoxazolo[5,4-b]pyridin-3-yl-phenoxy)-3-(4-pyrimidin-2-yl-piperazin-1-yl)-propan-2-ol.

34. The compound according to claim 23 which is (R)-2-{4-[2-hydroxy-3-(3-isoxazolo[5,4-b]pyridin-3-yl-phenoxy)-propyl]-piperazin-1-yl}-benzonitrile.

35. The compound according to claim 23 which is (R)-1-[4-(6-fluoro-benzo[d]isoxazol-3-yl)-piperidin-1-yl]-3-(3-isoxazolo[5,4-b]pyridin-3-yl-phenoxy)-propan-2-ol.

36. The compound according to claim 23 which is (R)-1-[4-(6-fluoro-1H-indazol-3-yl)-piperazin-1-yl]-3-(3-isoxazolo[5,4-b]pyridin-3-yl-phenoxy)-propan-2-ol.

37. A compound according to claim 1, wherein T, T' and T" are respectively C, O, and N producing benzisoxazolyl.

38. The compound of claim 37 which is 6-fluoro-3-[4-(2-pyrrolidin-1-yl-ethoxy)-phenyl]-benzo[d]isoxazole.

39. The compound of claim 37 which is (R)-1-[4-(6-fluoro-benzo[d]isoxazol-3-yl)-phenoxy]-3-(4-phenyl-piperazin-1-yl)-propan-2-ol.

40. The compound of claim 37 which is (R)-1-(3,4-dihydro-1H-isoquinolin-2-yl)-3-[4-(6-fluoro-benzo[d]isoxazol-3-yl)-phenoxy]-propan-2-ol.

41. The compound of claim 37 which is (R)-1-[4-(6-fluoro-benzo[d]isoxazol-3-yl)-phenoxy]-3-(4-pyridin-2-yl-piperazin-1-yl)-propan-2-ol.

42. The compound of claim 37 which is which is (R)-1-(cyclohexyl-methyl-amino)-3-[4-(6-fluoro-benzo[d]isoxazol-3-yl)-phenoxy]-propan-2-ol.

43. The compound of claim 37 which is which is (S)-1-(cyclohexyl-methyl-amino)-3-[4-(6-fluoro-benzo[d]isoxazol-3-yl)-phenoxy]-propan-2-ol.

44. The compound of claim 37 which is (R)-2-(4-{3-[4-(6-fluoro-benzo[d]isoxazol-3-yl)-phenoxy]-2-hydroxy-propyl}-piperazin-1-yl)-benzonitrile.

45. The compound of claim 37 which is (S)-1-[4-(6-fluoro-benzo[d]isoxazol-3-yl)-phenoxy]-3-(4-phenyl-piperazin-1-yl)-propan-2-ol.

46. The compound of claim 37 which is (S)-1-(3,4-dihydro-1H-isoquinolin-2-yl)-3-[4-(6-fluoro-benzo[d]isoxazol-3-yl)-phenoxy]-propan-2-ol.

47. The compound of claim 37 which is (S)-1-[4-(6-fluoro-benzo[d]isoxazol-3-yl)-phenoxy]-3-(4-pyridin-2-yl-piperazin-1-yl)-propan-2-ol.

48. The compound of claim 37 which is (R)-1-[4-(6-fluoro-benzo[d]isoxazol-3-yl)-phenoxy]-3-(4-phenyl-piperidin-1-yl)-propan-2-ol.

49. The compound of claim 37 which is (R)-1-[3-(6-fluoro-benzo[d]isoxazol-3-yl)-phenoxy]-3-(1,2,3,4-tetrahydro-naphthalen-1-ylamino)-propan-2-ol.

50. The compound of claim 37 which is (R)-1-[4-(6-fluoro-benzo[d]isoxazol-3-yl)-phenoxy]-3-(indan-1-ylamino)-propan-2-ol.

51. The compound of claim 37 which is (R)-1-(2-cyclohex-1-enyl-ethylamino)-3-[4-(6-fluoro-benzo[d]isoxazol-3-yl)-phenoxy]-propan-2-ol.

52. The compound of claim 37 which is (R)-1-{3-[4-(6-fluoro-benzo[d]isoxazol-3-yl)-phenoxy]-2-hydroxy-propylamino}-indan-2-ol.

53. The compound of claim 37 which is (R)-1-[4-(6-fluoro-benzo[d]isoxazol-3-yl)-phenoxy]-3-(indan-2-ylamino)-propan-2-ol.

54. The compound of claim 37 which is (S)-1-[4-(6-fluoro-benzo[d]isoxazol-3-yl)-phenoxy]-3-(1,2,3,4-tetrahydro-naphthalen-1-ylamino)-propan-2-ol.

55. The compound of claim 37 which is (S)-1-[4-(6-fluoro-benzo[d]isoxazol-3-yl)-phenoxy]-3-(indan-1-ylamino)-propan-2-ol.

56. The compound of claim 37 which is (S)-1-[4-(6-fluoro-benzo[d]isoxazol-3-yl)-phenoxy]-3-(indan-2-ylamino)-propan-2-ol.

57. The compound of claim 37 which is (S)-1-[4-(6-fluoro-benzo[d]isoxazol-3-yl)-phenoxy]-3-(4-pyrimidin-2-yl-piperazin-1-yl)-propan-2-ol.

58. The compound of claim 37 which is (R)-1-[4-(6-fluoro-benzo[d]isoxazol-3-yl)-phenoxy]-3-(4-pyrimidin-2-yl-piperazin-1-yl)-propan-2-ol.

59. The compound of claim 37 which is 2-{2-[4-(6-fluoro-benzo[d]isoxazol-3-yl)-phenoxy]-ethyl}-1,2,3,4-tetrahydro-isoquinoline.

60. The compound of claim 37 which is 6-fluoro-3-{4-[2-(4-phenyl-piperidin-1-yl)-ethoxy]-phenyl}-benzo[d]isoxazole.

61. The compound of claim 37 which is benzyl-{2-[4-(6-fluoro-benzo[d]isoxazol-3-yl)-phenoxy]-ethyl}-amine.

62. The compound of claim 37 which is 6-fluoro-3-[4-(2-piperidin-1-yl-ethoxy)-phenyl]-benzo[d]isoxazole.

63. The compound of claim 37 which is {3-[4-(6-fluoro-benzo[d]isoxazol-3-yl)-phenoxy]-propyl}-indan-2-yl-amine.

64. The compound of claim 37 which is 6-fluoro-3-{4-[2-(4-methyl-piperidin-1-yl)-ethoxy]-phenyl}-benzo[d]isoxazole.

65. The compound of claim 37 which is 6-fluoro-3-{4-[2-(4-propyl-piperidin-1-yl)-ethoxy]-phenyl}-benzo[d]isoxazole.

66. The compound of claim 37 which is 3-[4-(2-azepan-1-yl-ethoxy)-phenyl]-6-fluoro-benzo[d]isoxazole.

67. The compound according to claim 37 which is cyclohexylmethyl-{2-[4-(6-fluoro-benzo[d]isoxazol-3-yl)-phenoxy]-ethyl}-amine.

68. The compound according to claim 37 which is 8-{2-[4-(6-fluoro-benzo[d]isoxazol-3-yl)-phenoxy]-ethyl}-1,4-dioxa-8-aza-spiro[4.5]decane.

69. The compound according to claim 37 which is 3-[4-(3-azepan-1-yl-propoxy)-phenyl]-6-fluoro-benzo[d]isoxazole.

70. The compound according to claim 37 which is cyclohexylmethyl-{3-[4-(6-fluoro-benzo[d]isoxazol-3-yl)-phenoxy]-propyl}-amine.

71. The compound according to claim 37 which is 8-{3-[4-(6-fluoro-benzo[d]isoxazol-3-yl)-phenoxy]-propyl}-1,4-dioxa-8-aza-spiro[4.5]decane.

72. The compound according to claim 37 which is 6-fluoro-3-{4-[3-(4-phenyl-piperazin-1-ylpropoxy]-phenyl}-benzo[d]isoxazole.

73. The compound according to claim 37 which is 2-{3-[4-(6-fluoro-benzo[d]isoxazol-3-yl)-phenoxy]-propyl}-1,2,3,4-tetrahydro-isoquinoline.

74. The compound according to claim 37 which is (R)-1-[4-(6-fluoro-benzo[d]isoxazol-3-yl)-phenoxy]-3-(4-methyl-piperazin-1-yl)-propan-2-ol.

75. The compound according to claim 37 which is (R)-1-[4-(6-fluoro-benzo[d]isoxazol-3-yl)-phenoxy]-3-[4-(1H-indazol-3-yl)-piperazin-1-yl]-propan-2-ol.

76. The compound according to claim 37 which is (R)-1-[4-(6-fluoro-benzo[d]isoxazol-3-yl)-phenoxy]-3-(1,2,3,4-tetrahydro-β-carbolin-2-yl)-propan-2-ol.

77. The compound according to claim 37 which is (R)-1-[4-(6-fluoro-benzo[d]isoxazol-3-yl)-phenoxy]-3-[4-(6-fluoro-1H-indazol-3-yl)-piperazin-1-yl]-propan-2-ol.

78. The compound according to claim 37 which is (R)-1-({2-[3-(3-bromo-phenyl)-pyrazolo[4,3-c]pyridin-1-yl]-ethyl}-methyl-amino)-3-[4-(6-fluoro-benzo[d]isoxazol-3-yl)-phenoxy]-propan-2-ol.

79. The compound according to claim 37 which is (S)-1-[4-(6-fluoro-benzo[d]isoxazol-3-yl)-phenoxy]-3-[4-(1H-indazol-3-yl)-piperazin-1-yl]-propan-2-ol.

80. The compound according to claim 37 which is (S)-1-[4-(6-fluoro-benzo[d]isoxazol-3-yl)-phenoxy]-3-(1,2,3,4-tetrahydro-β-carbolin-2-yl)-propan-2-ol.

81. The compound according to claim 37 which is (S)-1-[4-(6-fluoro-benzo[d]isoxazol-3-yl)-phenoxy]-3-[4-(6-fluoro-1H-indazol-3-yl)-piperazin-1-yl]-propan-2-ol.

82. The compound according to claim 37 which is (S)-2-(4-{3-[4-(6-fluoro-benzo[d]isoxazol-3-yl)-phenoxy]-2-hydroxy-propyl}-piperazin-1-yl)-benzonitrile.

83. The compound according to claim 37 which is (R)-1-[3-(6-fluoro-benzo[d]isoxazol-3-yl)-phenoxy]-3-(indan-1-ylamino)-propan-2-ol.

84. The compound according to claim 37 which is (R)-1-[3-(6-fluoro-benzo[d]isoxazol-3-yl)-phenoxy]-3-(4-pyrimidin-2-yl-piperazin-1-yl)-propan-2-ol.

85. The compound according to claim 37 which is (S)-1-[3-(6-fluoro-benzo[d]isoxazol-3-yl)-phenoxy]-3-(4-pyrimidin-2-yl-piperazin-1-yl)-propan-2-ol.

86. The compound according to claim 37 which is (R)-1-(2-cyclohex-1-enyl-ethylamino)-3-[3-(6-fluoro-benzo[d]isoxazol-3-yl)-phenoxy]-propan-2-ol.

87. The compound according to claim 37 which is (R)-1-{3-[3-(6-fluoro-benzo[d]isoxazol-3-yl)-phenoxy]-2-hydroxy-propylamino}-indan-2-ol.

88. The compound according to claim 37 which is (S)-1-{3-[3-(6-fluoro-benzo[d]isoxazol-3-yl)-phenoxy]-2(R)-hydroxy-(S)-propylamino}-indan-2-ol.

89. The compound according to claim 37 which is (R)-1-[4-(6-fluoro-benzo[d]isoxazol-3-yl)-phenoxy]-3-(2-hydroxy-2-phenyl-ethylamino)-propan-2-ol.

90. The compound according to claim 37 which is (S)-1-[4-(6-fluoro-benzo[d]isoxazol-3-yl)-phenoxy]-3-(2-hydroxy-2-phenyl-ethylamino)-propan-2-ol.

91. The compound according to claim 37 which is (S)-1-(2-cyclohex-1-enyl-ethylamino)-3-[4-(6-fluoro-benzo[d]isoxazol-3-yl)-phenoxy]-propan-2-ol.

92. The compound according to claim 37 which is (S)-1-{3-[4-(6-fluoro-benzo[d]isoxazol-3-yl)-phenoxy]-2(R)-hydroxy-(S)-propylamino}-indan-2-ol.

93. The compound according to claim 37 which is 6-fluoro-3-(4-{2-[4-(4-fluoro-phenyl)-piperidin-1-yl]-ethoxy}-phenyl)-benzo[d]isoxazole.

94. The compound according to claim 37 which is (R)-1-(benzyl-methyl-amino)-3-[3-(6-fluoro-benzo[d]isoxazol-3-yl)-phenoxy]-propan-2-ol.

95. The compound according to claim 37 which is {2-[4-(6-fluoro-benzo[d]isoxazol-3-yl)-phenoxy]-ethyl}-(4-fluoro-benzyl)-amine.

96. The compound according to claim 37 which is (3,4-dichloro-benzyl)-{2-[4-(6-fluoro-benzo[d]isoxazol-3-yl)-phenoxy]-ethyl}-amine.

97. The compound according to claim 37 which is (R)-1-(adamantan-1-ylamino)-3-[4-6-fluoro-benzo[d]isoxazol-3-yl)-phenoxy]-propan-2-ol.

98. The compound according to claim 37 which is adamantan-1-yl-{3-[4-(6-fluoro-benzo[d]isoxazol-3-yl)-phenoxy]-propyl}-amine.

99. The compound according to claim 37 which is {3-[4-(6-fluoro-benzo[d]isoxazol-3-yl)-phenoxy]-propyl}-(3-phenyl-propyl)-amine.

100. The compound according to claim 37 which is 6-fluoro-3-[4-(2-morpholin-4-yl-ethoxy)-phenyl]-benzo[d]isoxazole.

101. The compound according to claim 37 which is 3-{4-[2-(2,6-dimethyl-piperidin-1-yl)-ethoxy]-phenyl}-6-fluoro-benzo[d]isoxazole.

102. The compound according to claim 37 which is 3-[4-(2-azocan-1-yl-ethoxy)-phenyl]-6-fluoro-benzo[d]isoxazole.

103. A compound according to claim 37 wherein
A is —CH$_2$C(R$_1$)(R$_2$)CH$_2$;
R$_1$ is H or OH;
R$_2$ is H;
R$_3$ is (CH$_2$)$_n$Q;
n is 1 or 2;
R$_4$ is H;
Q is thienyl or phenyl; or
R$_3$ and R$_4$, together with the nitrogen atom to which R$_3$ and R$_4$ are attached, form piperidinyl, azocanyl, morpholinyl, or pyrrolidinyl.

104. The compound according to claim 103 wherein Q is thienyl.

105. The compound of claim 104 which is (S)-1-[4-(6-fluoro-benzo[d]isoxazol-3-yl)-phenoxy]-3-[(thiophen-2-yl methyl)-amino]-propan-2-ol.

106. The compound according to claim 104 which is {3-[4-(6-fluoro-benzo[d]isoxazol-3-yl)-phenoxy]-propyl}-thiophen-3-ylmethyl-amine.

107. The compound according to claim 104 which is (S)-1-[3-(6-fluoro-benzo[d]isoxazol-3-yl)-phenoxy]-3-[(thiophen-2-ylmethyl)-amino]-propan-2-ol.

108. The compound of claim 104 which is (R)-1-[3-(6-fluoro-benzo[d]isoxazol-3-yl)-phenoxy]-3-[(thiophen-2-yl-methyl)-amino]-propan-2-ol.

109. The compound of claim 104 which is (R)-1-[4-(6-fluoro-benzo[d]isoxazol-3-yl)-phenoxy]-3-[(thiophen-2-yl-methyl)-amino]-propan-2-ol.

110. The compound of claim 104 which is (S)-1-[4-(6-fluoro-benzo[d]isoxazol-3-yl)-phenoxy]-3-[(thiophen-3-yl-methyl)-amino]-propan-2-ol.

111. The compound of claim 104 which is (R)-1-[3-(6-fluoro-benzo[d]isoxazol-3-yl)-phenoxy]-3-[(thiophen-3-yl-methyl)-amino]-propan-2-ol.

112. The compound of claim 104 which is (R)-1-[4-(6-fluoro-benzo[d]isoxazol-3-yl)-phenoxy]-3-[(thiophen-3-yl methyl)-amino]-propan-2-ol.

113. A compound according to claim 103 wherein Q is phenyl.

114. The compound of claim 113 which is (S)-1-benzylamino-3-[4-(6-fluoro-benzo[d]isoxazol-3-yl)-phenoxy]-propan-2-ol.

115. The compound of claim 113 which is (S)-1-[4-(6-fluoro-benzo[d]isoxazol-3-yl)-phenoxy]-3-(2-fluoro-benzylamino)-propan-2-ol.

116. The compound of claim 113 which is (S)-1-(2-chloro-benzylamino)-3-[4-(6-fluoro-benzo[d]isoxazol-3-yl)-phenoxy]-propan-2-ol.

117. The compound of claim 113 which is (S)-1-[4-(6-fluoro-benzo[d]isoxazol-3-yl)-phenoxy]-3-(2-methoxy-benzylamino)-propan-2-ol.

118. The compound of claim 113 which is (S)-1-[4-(6-fluoro-benzo[d]Isoxazol-3-yl)-phenoxy]-3-(3-fluoro-benzylamino)-propan-2-ol.

119. The compound of claim 113 which is (S)-1-[4-(6-fluoro-benzo[d]isoxazol-3-yl)-phenoxy]-3-(3-methoxy-benzylamino)-propan-2-ol.

120. The compound of claim 113 which is (S)-1-(4-chloro-benzylamino)-3-[4-(6-fluoro-benzo[d]isoxazol-3-yl)-phenoxy]-propan-2-ol.

121. The compound of claim 113 which is (S)-1-[4-(6-fluoro-benzo[d]isoxazol-3-yl)-phenoxy]-3-(4-methoxy-benzylamino)-propan-2-ol.

122. The compound of claim 113 which is (S)-1-[4-(6-fluoro-benzo[d]isoxazol-3-yl)-phenoxy]-3-(4-methyl-benzylamino)-propan-2-ol.

123. The compound according to claim 113 which is benzyl-{3-[4-(6-fluoro-benzo[d]isoxazol-3-yl)-phenoxy]-propyl}-amine.

124. The compound according to claim 113 which is {3-[4-(6-fluoro-benzo[d]isoxazol-3-yl)-phenoxy]-propyl}-phenethyl-amine.

125. The compound according to claim 113 which is (S)-1-benzylamino-3-[3-(6-fluoro-benzo[d]isoxazol-3-yl)-phenoxy]-propan-2-ol.

126. The compound according to claim 113 which is (S)-1-[4-(6-fluoro-benzo[d]isoxazol-3-yl)-phenoxy]-3-phenethylamino-propan-2-ol.

127. The compound according to claim 113 which is (S)-1-[4-(6-fluoro-benzo[d]isoxazol-3-yl)-phenoxy]-3-(4-fluoro-benzylamino)-propan-2-ol.

128. The compound according to claim 113 which is (S)-1-[3-(6-fluoro-benzo[d]isoxazol-3-yl)-phenoxy]-3-(3-fluoro-benzylamino)-propan-2-ol.

129. The compound according to claim 113 which is (S)-1-[3-(6-fluoro-benzo[d]isoxazol-3-yl)-phenoxy]-3-(4-fluoro-benzylamino)-propan-2-ol.

130. The compound according to claim 113 which is (S)-1-(4-chloro-benzylamino)-3-[3-(6-fluoro-benzo[d]isoxazol-3-yl)-phenoxy]-propan-2-ol.

131. The compound according to claim 113 which is (S)-1-[3-(6-fluoro-benzo[d]isoxazol-3-yl)-phenoxy]-3-(4-methyl-benzylamino)-propan-2-ol.

132. The compound according to claim 113 which is (S)-1-(benzyl-methyl-amino)-3-[3-(6-fluoro-benzo[d]isoxazol-3-yl)-phenoxy]-propan-2-ol.

133. The compound of claim 113 which is {3-[4-(6-fluoro-benzo[d]isoxazol-3-yl)-phenoxy]-propyl}-(2-fluoro-benzyl)-amine.

134. The compound of claim 113 which is (R)-1-[4-(6-fluoro-benzo[d]isoxazol-3-yl)-phenoxy]-3-(2-fluoro-benzylamino)-propan-2-ol.

135. The compound of claim 113 which is (R)-1-(2,6-difluoro-benzylamino)-3-[4-(6-fluoro-benzo[d]isoxazol-3-yl)-phenoxy]-propan-2-ol.

136. The compound of claim 113 which is (R)-1-[4-(6-fluoro-benzo[d]isoxazol-3-yl)-phenoxy]-3-(3-methoxy-benzylamino)-propan-2-ol.

137. The compound of claim 113 which is (2-chloro-benzyl)-{3-[4-(6-fluoro-benzo[d]isoxazol-3-yl)-phenoxy]-propyl}-amine.

138. The compound of claim 113 which is (3,4-difluoro-benzyl)-{3-[4-(6-fluoro-benzo[d]isoxazol-3-yl)-phenoxy]-propyl}-amine.

139. The compound of claim 113 which is (3,4-dichloro-benzyl)-{3-[4-(6-fluoro-benzo[d]isoxazol-3-yl)-phenoxy]-propyl}-amine.

140. The compound of claim 113 which is (R)-1-[4-(6-fluoro-benzo[d]isoxazol-3-yl)-phenoxy]-3-(methyl-phenethyl-amino)-propan-2-ol.

141. The compound of claim 113 which is (S)-1-[4-(6-fluoro-benzo[d]isoxazol-3-yl)-phenoxy]-3-(methyl-phenethyl-amino)-propan-2-ol.

142. The compound of claim 113 which is (R)-1-benzylamino-3-[3-(6-fluoro-benzo[d]isoxazol-3-yl)-phenoxy]-propan-2-ol.

143. The compound of claim 113 which is (R)-1-[3-(6-fluoro-benzo[d]isoxazol-3-yl)-phenoxy]-3-(3-fluoro-benzylamino)-propan-2-ol.

144. The compound of claim 113 which is (R)-1-[3-(6-fluoro-benzo[d]isoxazol-3-yl)-phenoxy]-3-(4-fluoro-benzylamino)-propan-2-ol.

145. The compound of claim 113 which is (R)-1-(4-chloro-benzylamino)-3-[3-(6-fluoro-benzo[d]isoxazol-3-yl)-phenoxy]-propan-2-ol.

146. The compound of claim 113 which is (R)-1-[3-(6-fluoro-benzo[d]isoxazol-3-yl)-phenoxy]-3-(4-methyl-benzylamino)-propan-2-ol.

147. The compound of claim 113 which is (R)-1-[3-(6-fluoro-benzo[d]isoxazol-3-yl)-phenoxy]-3-phenethylamino-propan-2-ol.

148. The compound of claim 113 which is (R)-1-benzylamino-3-[4-(6-fluoro-benzo[d]isoxazol-3-yl)-phenoxy]-propan-2-ol.

149. The compound of claim 113 which is (R)-1-(2-chloro-benzylamino)-3-[4-(6-fluoro-benzo[d]isoxazol-3-yl)-phenoxy]-propan-2-ol.

150. The compound of claim 113 which is (R)-1-[4-(6-fluoro-benzo[d]isoxazol-3-yl)-phenoxy]-3-(2-methoxy-benzylamino)-propan-2-ol.

151. The compound of claim 113 which is (R)-1-[4-(6-fluoro-benzo[d]isoxazol-3-yl)-phenoxy]-3-(3-fluoro-benzylamino)-propan-2-ol.

152. The compound of claim 113 which is (R)-1-[4-(6-fluoro-benzo[d]isoxazol-3-yl)-phenoxy]-3-(4-fluoro-benzylamino)-propan-2-ol.

153. The compound of claim 113 which is (R)-1-(4-chloro-benzylamino)-3-[4-(6-fluoro-benzo[d]isoxazol-3-yl)-phenoxy]-propan-2-ol.

154. The compound of claim 113 which is (R)-1-[4-(6-fluoro-benzo[d]isoxazol-3-yl)-phenoxy]-3-(4-methoxy-benzylamino)-propan-2-ol.

155. The compound of claim 113 which is (R)-1-[4-(6-fluoro-benzo[d]isoxazol-3-yl)-phenoxy]-3-(4-methyl-benzylamino)-propan-2-ol.

156. The compound of claim 113 which is (R)-1-[4-(6-fluoro-benzo[d]isoxazol-3-yl)-phenoxy]-3-phenethylamino-propan-2-ol.

157. The compound of claim 113 which is (R)-1-(3,4-dichloro-benzylamino)-3-[4-(6-fluoro-benzo[d]isoxazol-3-yl)-phenoxy]-propan-2-ol.

158. The compound of claim 113 which is (R)-1-(2,4-difluoro-benzylamino)-3-[4-(6-fluoro-benzo[d]isoxazol-3-yl)-phenoxy]-propan-2-ol.

159. The compound of claim 113 which is (R)-1-(3,4-difluoro-benzylamino)-3-[4-(6-fluoro-benzo[d]isoxazol-3-yl)-phenoxy]-propan-2-ol.

160. The compound of claim 113 which is (R)-1-[4-(6-fluoro-benzo[d]isoxazol-3-yl)-phenoxy]-3-(2-trifluoromethyl-benzylamino)-propan-2-ol.

161. The compound of claim 113 which is 1-[4-(6-fluoro-benzo[d]isoxazol-3-yl)-phenoxy]-3-(4-trifluoromethyl-benzylamino)-propan-2-ol.

162. A compound according to claim 103 wherein $R_3$ and $R_4$, together with the nitrogen atom to which $R_3$ and $R_4$ are attached, form piperidinyl.

163. The compound of claim 162 which is (R)-1-[4-(6-fluoro-benzo[d]isoxazol-3-yl)-phenoxy]-3-[4-(4-fluoro-phenyl)-piperidin-1-yl]-propan-2-ol.

164. The compound according to claim 162 which is 6-fluoro-3-[4-(3-piperidin-1-yl-propoxy)-phenyl]-benzo[d]isoxazole.

165. The compound according to claim 162 which is 6-fluoro-3-{4-[3-(4-propyl-piperidin-1-yl)-propoxy]-phenyl}-benzo[d]isoxazole.

166. The compound according to claim 162 which is (S)-1-(4-benzyl-piperidin-1-yl)-3-[4-(6-fluoro-benzo[d]isoxazol-3-yl)-phenoxy]-propan-2-ol.

167. The compound according to claim 162 which is (R)-1-(4-benzyl-piperidin-1-yl)-3-[3-(6-fluoro-benzo[d]isoxazol-3-yl)-phenoxy]-propan-2-ol.

168. The compound according to claim 162 which is (R)-1-[3-(6-fluoro-benzo[d]isoxazol-3-yl)-phenoxy]-3-(4-phenyl-piperidin-1-yl)-propan-2-ol.

169. The compound according to claim 162 which is (S)-1-[4-(3-chloro-phenoxy)-piperidin-1-yl]-3-[4-(6-fluoro-benzo[d]isoxazol-3-yl)-phenoxy]-propan-2-ol.

170. The compound according to claim 162 which is (S)-4-(4-chloro-phenyl)-1-{3-[4-(6-fluoro-benzo[d]isoxazol-3-yl)-phenoxy]-2-hydroxy-propyl}-piperidin-4-ol.

171. The compound according to claim 162 which is (S)-1-{3-[4-(6-fluoro-benzo[d]isoxazol-3-yl)-phenoxy]-2-hydroxy-propyl}4-phenyl-piperidine-4-carbonitrile.

172. The compound according to claim 162 which is 3-{4-[3-(2,6-dimethyl-piperidin-1-yl)-propoxy]-phenyl}-6-fluoro-benzo[d]isoxazole.

173. The compound according to claim 162 which is 6-fluoro-3-(4-{3-[4-(4-fluoro-phenyl)-piperidin-1-yl]-propoxy}-phenyl)-benzo[d]isoxazole.

174. The compound according to claim 162 which is (R)-1-[3-(6-fluoro-benzo[d]isoxazol-3-yl)-phenoxy]-3-(4-methyl-piperidin-1-yl)-propan-2-ol.

175. The compound of claim 162 which is 6-fluoro-3-{4-[3-(4-methyl-piperidin-1-yl)-propoxy]-phenyl}-benzo[d]isoxazole.

176. The compound of claim 162 which is (R)-1-[4-(6-fluoro-benzo[d]isoxazol-3-yl)-phenoxy]-3-piperidin-1-yl-propan-2-ol.

177. The compound of claim 162 which is (R)-1-[4-(6-fluoro-benzo[d]isoxazol-3-yl)-phenoxy]-3-[4-(6-fluoro-benzo[d]isoxazol-3-yl)-piperidin-1-yl]-propan-2-ol.

178. The compound of claim 162 which is (R)-1-(4-benzyl-piperidin-1-yl)-3-[4-(6-fluoro-benzo[d]isoxazol-3-yl)-phenoxy]-propan-2-ol.

179. The compound of claim 162 which is (R)-1-[4-(6-fluoro-benzo[d]isoxazol-3-yl)-phenoxy]-3-(4-phenyl-piperidin-1-yl)-propan-2-ol.

180. The compound of claim 162 which is (R)-1-[4-(6-fluoro-benzo[d]isoxazol-3-yl)-phenoxy]-3-[4-(4-fluoro-phenoxy)-piperidin-1-yl]-propan-2-ol.

181. The compound of claim 162 which is (R)-1-{3-[4-(6-fluoro-benzo[d]isoxazol-3-yl)-phenoxy]-2-hydroxy-propyl}4-phenyl-piperidin-4-ol.

182. The compound of claim 162 which is (S)-1-[4-(6-fluoro-benzo[d]isoxazol-3-yl)-phenoxy]-3-piperidin-1-yl-propan-2-ol.

183. The compound of claim 162 which is (S)-1-[4-(6-fluoro-benzo[d]isoxazol-3-yl)-phenoxy]-3-(4-phenyl-piperidin-1-yl)-propan-2-ol.

184. The compound of claim 162 which is (S)-1-[4-(6-fluoro-benzo[d]isoxazol-3-yl)-phenoxy]-3-[4-(4-fluoro-phenoxy)-piperidin-1-yl]-propan-2-ol.

185. The compound of claim 162 which is (S)-1-{3-[4-(6-fluoro-benzo[d]isoxazol-3-yl)-phenoxy]-2-hydroxy-propyl}-4-phenyl-piperidin-4-ol.

186. The compound of claim 162 which is (S)-1-[4-(6-fluoro-benzo[d]isoxazol-3-yl)-phenoxy]-3-[4-(4-fluoro-phenyl)-piperidin-1-yl]-propan-2-ol.

187. The compound of claim 162 which is (R)-1-[4-(3-chloro-phenoxy)-piperidin-1-yl]-3-[4-(6-fluoro-benzo[d]isoxazol-3-yl)-phenoxy]-propan-2-ol.

188. The compound of claim 162 which is (R)-4-(4-chloro-phenyl)-1-{3-[4-(6-fluoro-benzo[d]isoxazol-3-yl)-phenoxy]-2-hydroxy-propyl}-piperidin-4-ol.

189. The compound of claim 162 which is (R)-1-{3-[4-(6-fluoro-benzo[d]isoxazol-3-yl)-phenoxy]-2-hydroxy-propyl}4-phenyl-piperidin-4-carbonitrile.

190. The compound of claim 162 which is (R)-1-[4-(3-chloro-phenoxy)-piperidin-1-yl]-3-[3-(6-fluoro-benzo[d]isoxazol-3-yl)-phenoxy]-propan-2-ol.

191. The compound of claim 162 which is 4-(4-chloro-phenyl)-1-{3-[4-(6-fluoro-benzo[d]isoxazol-3-yl)-phenoxy]-propyl}-piperidin-4-ol.

192. A compound according to claim 103 wherein $R_3$ and $R_4$, together with the nitrogen atom to which $R_3$ and $R_4$ are attached, form morpholinyl.

193. The compound of claim 192 which is (R)-1-[4-(6-fluoro-benzo[d]isoxazol-3-yl)-phenoxy]-3-morpholin-4-yl-propan-2-ol.

194. The compound of claim 192 which is (S)-1-[4-(6-fluoro-benzo[d]isoxazol-3-yl)-phenoxy]-3-morpholin-4-yl-propan-2-ol.

195. A compound according to claim 103 wherein $R_3$ and $R_4$, together with the nitrogen atom to which $R_3$ and $R_4$ are attached, form pyrrolidinyl.

196. The compound of claim 195 which is (R)-(R)-1-[4-(6-fluoro-benzo[d]isoxazol-3-yl)-phenoxy]-3-(2-methoxymethyl-pyrrolidin-1-yl)-propan-2-ol.

197. The compound of claim 195 which is 6-fluoro-3-[4-(3-pyrrolidin-1-yl-propoxy)-phenyl]-benzo[d]isoxazole.

198. A compound according to claim 103 wherein $R_3$ and $R_4$, together with the nitrogen atom to which $R_3$ and $R_4$ are attached, form azocanyl.

199. The compound according to claim 198 which is 3-[4-(3-azocan-1-yl-propoxy)-phenyl]-6-fluoro-benzo[d]isoxazole.

200. A compound which is (R)-1-diethylamino-3-[4-(6-fluoro-benzo[d]isoxazol-3-yl)-phenoxy]-propan-2-ol.

201. A compound which is (R)-1-(1-benzyl-piperidin-4-ylamino)-3-[4-(6-fluoro-benzo[d]isoxazol-3-yl)-phenoxy]-propan-2-ol.

202. A compound which is (S)-1-(1-benzyl-piperidin-4-ylamino)-3-[4-(6-fluoro-benzo[d]isoxazol-3-yl)-phenoxy]-propan-2-ol.

203. A composition comprising a compound according to claim 1 in admixture with an inert carrier.

204. The composition according to claim 203 wherein said inert carrier is a pharmaceutical carrier.

205. A method of making a compound of Formula I:

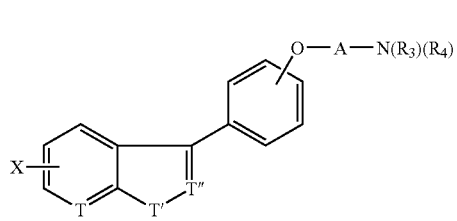

Formula I a pharmaceutically acceptable salt or stereoisomer thereof, wherein
T, T' and T" are respectively
C, O and N producing benzisoxazolyl,
C, S and C producing benzothienyl, or
N, O and N producing pyridoisoxazolyl;
X is hydrogen or halo;
A is —$CH_2C(R_1)(R_2)CH_2$—, wherein
$R_1$ is OH or $C_{1-6}$ alkoxy; and
$R_2$ is H or $C_{1-6}$ alkyl;
$R_3$ is $(CH_2)_n$ Q, $CH_2CH(OH)Q$, $CH(CH_3)Q$, 1,2,3,4-tetrahydronaphthyl, indanyl optionally substituted with hydroxy, or adamantyl, wherein
Q is thienyl, phenyl, furanyl, naphthyl, pyridyl, indolyl, indazolyl, cyclohexyl, 1,2-methylenedioxyphenyl, cyclohexenyl, 1H-pyrazolo[4.3-c]pyridyl, and
Q is optionally substituted with one or two moieties independently selected from halo, $C_{1-6}$ alkyl, $C_{1-6}$ alkoxy, hydroxy, $S(O)_2NH_2$, trifluoromethyl, or cyano, and
n is 0, 1 or 2;
$R_4$ is H or $C_{1-6}$ alkyl; or
$R_3$ and $R_4$, together with the nitrogen atom to which $R_3$ and $R_4$ are attached, form 4,5,6,7-tetrahydrothieno [3,2,c] pyridinyl,1,4-dioxa-8-azo-spiro[4.5]decanyl, piperazinyl, morpholinyl, piperidinyl, pyrrolidinyl, azocanyl, azepanyl, 1,2,3,4-tetrahydroisoquinolinyl, 1,2,3,4-tetrahydro-1H-β-carbolinyl, or 8-aza-bicyclo[3.2.1]octanyl, each of which may be mono- or independently di-substituted with halo, $C_{1-6}$ alkyl, $C_{1-6}$ alkoxy, $C_{1-6}$ alkoxymethyl, C(O)phenyl, OH, phenyl, CN, O-phenyl or $(CH_2)_mZ$,
Z is benzisoxazolyl, indazolyl, benzisothiazolyl, benzthienyl, pyrimidinyl, pyridyl, 1,2-methylenedioxyphenyl, or phenyl, and
Z, CH(OH)phenyl, phenyl or O-phenyl are optionally substituted with one or two moieties independently selected from halo, $C_{1-6}$ alkyl, $C_{1-6}$ alkoxy, hydroxy, trifluoromethyl, $S(O)_2NH_2$ or cyano, and
m is 0 or 1;
comprising the steps of:
a) coupling a compound of formula II

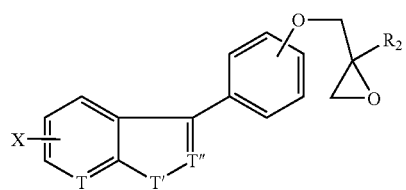

II wherein T, T', T", $R_2$ and X are as defined in formula I; with a reagent of formula III

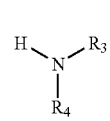

III wherein $R_3$ and $R_4$ are as defined in formula I to provide the compound of formula I wherein $R_1$ is an OH radical; and
b) optional alkylation of said OH radical to yield the compound of formula I wherein $R_1$ is a $C_1$-$C_6$alkoxy radical.

206. A method of making a compound of Formula I:

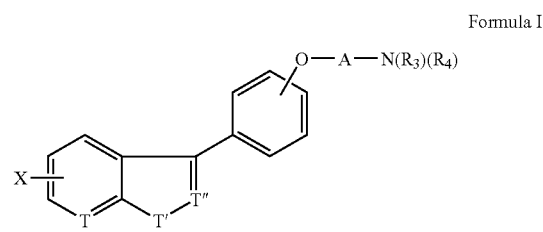

Formula I a pharmaceutically acceptable salt or stereoisomer thereof, wherein
T, T' and T" are respectively
C, O and N producing benzisoxazolyl,
C, S and C producing benzthienyl, or
N, O and N producing pyridoisoxazolyl;
X is hydrogen or halo;
A is —$CH_2CH_2$— or —$CH_2C(R_1)(R_2)CH_2$—, wherein
$R_1$ is H; and
$R_2$ is H or $C_{1-6}$ alkyl;
$R_3$ is $(CH_2)_n$ Q, $CH_2CH(OH)Q$, $CH(CH_3)Q$, 1,2,3,4-tetrahydronaphthyl, indanyl optionally substituted with hydroxy, or adamantyl, wherein
Q is thienyl, phenyl, furanyl, naphthyl, pyridyl, indolyl, indazolyl, cyclohexyl, 1,2-methylenedioxyphenyl, cyclohexenyl, 1H-pyrazolo[4.3-c]pyridyl, and
Q is optionally substituted with one or two moieties independently selected from halo, $C_{1-6}$ alkyl, $C_{1-6}$ alkoxy, hydroxy, $S(O)_2NH_2$, trifluoromethyl, or cyano, and
n is 0, 1 or 2;
$R_4$ is H or $C_{1-6}$ alkyl; or
$R_3$ and $R_4$, together with the nitrogen atom to which $R_3$ and $R_4$ are attached, form 4,5,6,7-tetrahydrothieno [3,2,c]pyridinyl,1,4-dioxa-8-azo-spiro[4.5]decanyl, piperazinyl, morpholinyl, piperidinyl, pyrrolidinyl, azepanyl, azocanyl, 1,2,3,4-tetrahydroisoquinolinyl, 1,2,3,4-tetrahydro-1H-β-carbolinyl, or 8-aza-bicyclo[3.2.1.]octanyl, each of which may be mono- or independently di-substituted with halo, $C_{1-6}$ alkyl, $C_{1-6}$ alkoxy, $C_{1-6}$ alkoxymethyl, C(O)phenyl, OH, phenyl, CN, O-phenyl or $(CH_2)_mZ$, Z is benzisoxazolyl, indazolyl, benzisothiazolyl, benzthienyl, pyrimidinyl, pyridyl, 1,2-methylenedioxyphenyl, or phenyl, and Z, CH(OH)phenyl, phenyl or O-phenyl are optionally substituted with one or two moieties independently selected from halo, $C_{1-6}$ alkyl, $C_{1-6}$ alkoxy, hydroxy, trifluoromethyl, $S(O)_2NH_2$ or cyano, and m is 0 or 1;

comprising the step of coupling a compound of formula II

<chemical structure: Formula II> wherein

T, T', T", and X are as defined in formula I r is 0 or 1;

$X_1$ is Br, Cl, I, alkyl sulfonate, aryl sulfonate, or nitrobenzoate;

$R_5$ is H or $C_{1-6}$alkyl;

with a reagent of formula III

<chemical structure: Formula III — H-N(R3)(R4)> wherein $R_3$ and $R_4$ are as defined in formula I to provide a compound of formula I.

207. A method of making a compound of Formula I:

<chemical structure: Formula I> a pharmaceutically acceptable salt or stereoisomer thereof, wherein

T, T' and T" are respectively

C, O and N producing benzisoxazolyl,

C, S and C producing benzthienyl, or

N, O and N producing pyridoisoxazolyl;

X is hydrogen or halo;

A is —$CH_2C(R_1)(R_2)CH_2$—, wherein $R_1$ is OH or $C_{1-6}$ alkoxy; and $R_2$ is H or $C_{1-6}$ alkyl;

$R_3$ is $(CH_2)_n$ Q, $CH_2CH(OH)Q$, $CH(CH_3)Q$, 1,2,3,4-tetrahydronaphthyl, indanyl optionally substituted with hydroxy, or adamantyl, wherein Q is thienyl, phenyl, furanyl, naphthyl, pyridyl, indolyl, indazolyl, cyclohexyl, 1,2-methylenedioxyphenyl, cyclohexenyl, 1H-pyrazolo[4.3-c]pyridyl, and Q is optionally substituted with one or two moieties independently selected from halo, $C_{1-6}$ alkyl, $C_{1-6}$ alkoxy, hydroxy, $S(O)_2NH_2$, trifluoromethyl, or cyano, and n is 0, 1 or 2;

$R_4$ is H or $C_{1-6}$ alkyl; or $R_3$ and $R_4$, together with the nitrogen atom to which $R_3$ and $R_4$ are attached, form 4,5,6,7-tetrahydrothieno[3,2,c]pyridinyl, 1,4-dioxa-8-azo-spiro[4.5]decanyl, piperazinyl, morpholinyl, piperidinyl, pyrrolidinyl, azepanyl, azocanyl, 1,2,3,4-tetrahydroisoquinolinyl, 1,2,3,4-tetrahydro-1H-β-carbolinyl, or 8-aza-bicyclo[3.2.1.]octanyl, each of which may be mono- or independently di-substituted with halo, $C_{1-6}$ alkyl, $C_{1-6}$ alkoxy, $C_{1-6}$ alkoxymethyl, C(O)phenyl, OH, phenyl, CN, O-phenyl or $(CH_2)_mZ$, Z is benzisoxazolyl, indazolyl, benzisothiazolyl, benzthienyl, pyrimidinyl, pyridyl, 1,2-methylenedioxyphenyl, or phenyl, and Z, CH(OH)phenyl, phenyl or O-phenyl are optionally substituted with one or two moieties independently selected from halo, $C_{1-6}$ alkyl, $C_{1-6}$ alkoxy, hydroxy, trifluoromethyl, $S(O)_2NH_2$ or cyano, and m is 0 or 1;

comprising the steps of a) coupling a compound of formula II

<chemical structure: Formula II> wherein T, T', T" and X are as defined in formula I;

with a reagent of formula III

<chemical structure: Formula III — epoxide with CH2-N(R3)(R4)> wherein $R_2$, $R_3$ and $R_4$ are as defined in formula I; to provide the compound of formula I wherein $R_1$ is a OH radical; and b) optional alkylation of said OH radical to yield the compound of formula I wherein $R_1$ is a $C_{1-6}$ alkoxy radical.

208. A method of making a compound of Formula I:

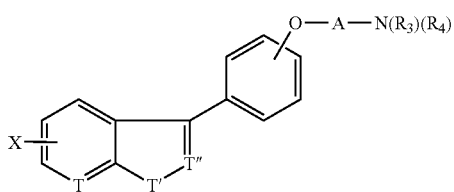

Formula I a pharmaceutically acceptable salt or stereoisomer thereof, wherein

T, T' and T" are respectively
  C, O and N producing benzisoxazolyl,
  C, S and C producing benzthienyl, or
  N, O and N producing pyridoisoxazolyl;
X is hydrogen or halo;
A is —$CH_2CH_2$— or —$CH_2C(R_1)(R_2)CH_2$—, wherein
  $R_1$ is H; and
  $R_2$ is H or $C_{1-6}$ alkyl;
$R_3$ is $(CH_2)_n$ Q, $CH_2CH(OH)Q$, $CH(CH_3)Q$, 1,2,3,4-tetrahydronaphthyl, indanyl optionally substituted with hydroxy, or adamantyl, wherein
  Q is thienyl, phenyl, furanyl, naphthyl, pyridyl, indolyl, indazolyl, cyclohexyl, 1,2-methylenedioxyphenyl, cyclohexenyl, 1H-pyrazolo[4.3-c]pyridyl, and
  Q is optionally substituted with one or two moieties independently selected from halo, $C_{1-6}$ alkyl, $C_{1-6}$ alkoxy, hydroxy, $S(O)_2NH_2$, trifluoromethyl, or cyano, and
  n is 0, 1 or 2;
$R_4$ is H or $C_{1-6}$ alkyl; or
$R_3$ and $R_4$, together with the nitrogen atom to which $R_3$ and $R_4$ are attached, form 4,5,6,7-tetrahydrothieno[3,2,c]pyridinyl,1,4-dioxa-8-azo-spiro[4.5]decanyl, piperazinyl, morpholinyl, piperidinyl, pyrrolidinyl, azepanyl, azocanyl, 1,2,3,4-tetrahydroisoquinolinyl, 1,2,3,4-tetrahydro-1H-β-carbolinyl, or 8-aza-bicyclo[3.2.1.]octanyl, each of which may be mono- or independently di-substituted with halo, $C_{1-6}$ alkyl, $C_{1-6}$ alkoxy, $C_{1-6}$alkoxymethyl, C(O)phenyl, OH, phenyl, CN, O-phenyl or $(CH_2)_mZ$,
  Z is benzisoxazolyl, indazolyl, benzisothiazolyl, benzthienyl, pyrimidinyl, pyridyl, 1,2-methylenedioxyphenyl, or phenyl, and
  Z, CH(OH)phenyl, phenyl or O-phenyl are optionally substituted with one or two moieties independently selected from halo, $C_{1-6}$ alkyl, $C_{1-6}$ alkoxy, hydroxy, trifluoromethyl, $S(O)_2NH_2$ or cyano, and
  m is 0 or 1;
comprising the step of coupling a compound of formula II

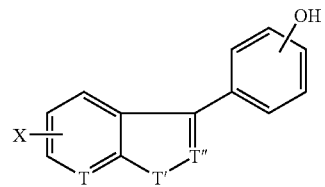

II wherein
T, T', T", and X are as defined in formula I;
with a reagent of formula III

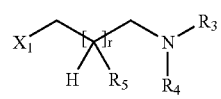

III wherein $R_3$ and $R_4$ are as defined in formula I;
  $X_1$ is Br, Cl, I, aryl sulfonate, alkyl sulfonate or nitrobenzoate;
  $R_5$ is H or $C_{1-6}$alkyl; and
  r is 0 or 1;
to provide a compound of formula I.

209. A method of making a compound of Formula I:

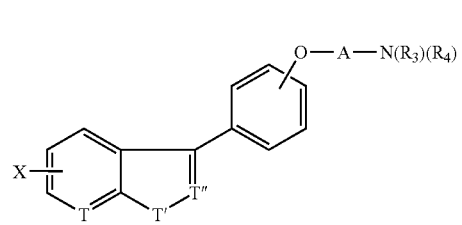

Formula I a pharmaceutically acceptable salt or stereoisomer thereof, wherein

T, T' and T" are respectively
  C, O and N producing benzisoxazolyl,
  C, S and C producing benzthienyl, or
  N, O and N producing pyridoisoxazolyl;
X is hydrogen or halo;
A is —$CH_2CH_2$— or —$CH_2C(R_1)(R_2)CH_2$—, wherein
  $R_1$ is H; and
  $R_2$ is H or $C_{1-6}$ alkyl;
$R_3$ is $(CH_2)_n$ Q, $CH_2CH(OH)Q$, $CH(CH_3)Q$, 1,2,3,4-tetrahydronaphthyl, indanyl optionally substituted with hydroxy, or adamantyl, wherein
  Q is thienyl, phenyl, furanyl, naphthyl, pyridyl, indolyl, indazolyl, cyclohexyl, 1,2-methylenedioxyphenyl, cyclohexenyl, 1H-pyrazolo[4.3-c]pyridyl, and
  Q is optionally substituted with one or two moieties independently selected from halo, $C_{1-6}$ alkyl, $C_{1-6}$ alkoxy, hydroxy, $S(O)_2NH_2$, trifluoromethyl, or cyano, and
  n is 0, 1 or 2;
$R_4$ is H or $C_{1-6}$ alkyl; or
$R_3$ and $R_4$, together with the nitrogen atom to which $R_3$ and $R_4$ are attached, form 4,5,6,7-tetrahydrothieno[3,2,c]pyridinyl,1,4-dioxa-8-azo-spiro[4.5]decanyl, piperazinyl, morpholinyl, piperidinyl, pyrrolidinyl, azepanyl, azocanyl, 1,2,3,4-tetrahydroisoquinolinyl, 1,2,3,4-tetrahydro-1H-β-carbolinyl, or 8-aza-bicyclo[3.2.1.]octanyl, each of which may be mono- or independently di-substituted with halo, $C_{1-6}$ alkyl, $C_{1-6}$ alkoxy, $C_{1-6}$alkoxymethyl, C(O)phenyl, OH, phenyl, CN, O-phenyl or $(CH_2)_m Z$, Z is benzisoxazolyl, indazolyl, benzisothiazolyl, benzthienyl, pyrimidinyl, pyridyl, 1,2-methylenedioxyphenyl, or phenyl, and Z, CH(OH)phenyl, phenyl or O-phenyl are optionally substituted with one or two moieties independently selected from halo, $C_{1-6}$ alkyl, $C_{1-6}$ alkoxy, hydroxy, trifluoromethyl, $S(O)_2NH_2$ or cyano, and m is 0 or 1;

comprising the step of coupling a compound of formula II

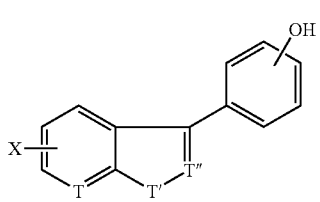

wherein
T, T', T", and X are as defined in formula I;
with a compound of formula III

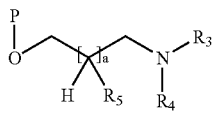

wherein
P is aryl sulfonyl, alkyl sulfonyl or a nitrobenzoyl;
$R_5$ is H or $C_{1-6}$ alkyl;
a is 0 or 1; and
$R_3$ and $R_4$ are as defined in formula I;
to provide a compound of formula I.

210. A method of of making a compound of Formula I:

Formula I

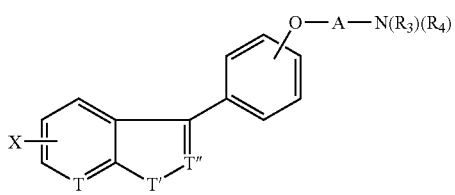

a pharmaceutically acceptable salt or stereoisomer thereof, wherein
T, T' and T" are respectively
C, O and N producing benzisoxazolyl, or
N, O and N producing pyridoisoxazolyl;
X is hydrogen or halo;
A is $-CH_2CH_2-$ or $-CH_2C(R_1)(R_2)CH_2-$, wherein
$R_1$ is H; and
$R_2$ is H or $C_{1-6}$ alkyl;

$R_3$ is $(CH_2)_n$ Q, $CH_2CH(OH)Q$, $CH(CH_3)Q$, 1,2,3,4-tetrahydronaphthyl, indanyl optionally substituted with hydroxy, or adamantyl, wherein Q is thienyl, phenyl, furanyl, naphthyl, pyridyl, indolyl, indazolyl, cyclohexyl, 1,2-methylenedioxyphenyl, cyclohexenyl, 1H-pyrazolo[4.3-c]pyridyl, and Q is optionally substituted with one or two moieties independently selected from halo, $C_{1-6}$ alkyl, $C_{1-6}$ alkoxy, hydroxy, $S(O)_2NH_2$, trifluoromethyl, or cyano, and n is 0, 1 or 2;

$R_4$ is H or $C_{1-6}$ alkyl; or $R_3$ and $R_4$, together with the nitrogen atom to which $R_3$ and $R_4$ are attached, form 4,5,6,7-tetrahydrothieno [3,2,c]pyridinyl,1,4-dioxa-8-azo-spiro[4.5]decanyl, piperazinyl, morpholinyl, piperidinyl, pyrrolidinyl, azepanyl, azocanyl, 1,2,3,4-tetrahydroisoquinolinyl, 1,2,3,4-tetrahydro-1H-β-carbolinyl, or 8-aza-bicyclo[3.2.1.]octanyl, each of which may be mono- or independently di-substituted with halo, $C_{1-6}$ alkyl, $C_{1-6}$ alkoxy, $C_{1-6}$alkoxymethyl, C(O)phenyl, OH, phenyl, CN, O-phenyl or $(CH_2)_m Z$, Z is benzisoxazolyl, indazolyl, benzisothiazolyl, benzthienyl, pyrimidinyl, pyridyl, 1,2-methylenedioxyphenyl, or phenyl, and Z, CH(OH)phenyl, phenyl or O-phenyl are optionally substituted with one or two moieties independently selected from halo, $C_{1-6}$ alkyl, $C_{1-6}$ alkoxy, hydroxy, trifluoromethyl, $S(O)_2NH_2$ or cyano, and m is 0 or 1;

comprising the step of cyclizing a compound of formula II

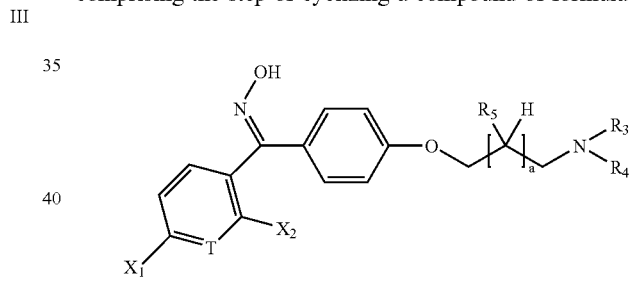

wherein
$X_1$ is hydrogen or halo;
$X_2$ is halo;
T is N or C;
$R_5$ is H or $C_{1-6}$alkyl;
a is 0 or 1; and
$R_3$ and $R_4$ are as defined in formula I;
to provide the compound of formula I.

211. A method of making a compound of Formula I:

Formula I

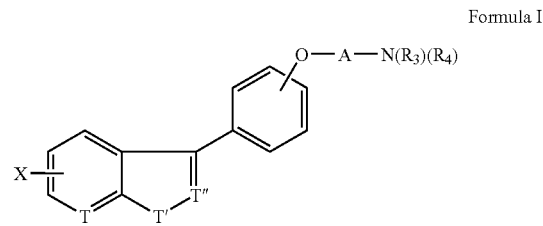

a pharmaceutically acceptable salt or stereoisomer thereof, wherein

T, T' and T" are respectively
C, O and N producing benzisoxazolyl,
C, S and C producing benzthienyl, or
N, O and N producing pyridoisoxazolyl;

X is hydrogen or halo;

A is —CH$_2$CH$_2$— or —CH$_2$C(R$_1$)(R$_2$)CH$_2$—, wherein
R$_1$ is H; and
R$_2$ is H or C$_{1-6}$ alkyl;

R$_3$ is (CH$_2$)$_n$ Q, CH$_2$CH(OH)Q, CH(CH$_3$)Q, 1,2,3,4-tetrahydronaphthyl, indanyl optionally substituted with hydroxy, or adamantyl, wherein
Q is thienyl, phenyl, furanyl, naphthyl, pyridyl, indolyl, indazolyl, cyclohexyl, 1,2-methylenedioxyphenyl, cyclohexenyl, 1H-pyrazolo[4.3-c]pyridyl, and
Q is optionally substituted with one or two moieties independently selected from halo, C$_{1-6}$ alkyl, C$_{1-6}$ alkoxy, hydroxy, S(O)$_2$NH$_2$, trifluoromethyl, or cyano, and
n is 0, 1 or 2;

R$_4$ is H or C$_{1-6}$ alkyl; or

R$_3$ and R$_4$, together with the nitrogen atom to which R$_3$ and R$_4$ are attached, form 4,5,6,7-tetrahydrothieno [3,2,c]pyridinyl, 1,4-dioxa-8-azo-spiro[4.5]decanyl, piperazinyl, morpholinyl, piperidinyl, pyrrolidinyl, azepanyl, azocanyl, 1,2,3,4-tetrahydroisoquinolinyl, 1,2,3,4-tetrahydro-1H-β-carbolinyl, or 8-aza-bicyclo[3.2.1.]octanyl, each of which may be mono- or independently di-substituted with halo, C$_{1-6}$ alkyl, C$_{1-6}$ alkoxy, C$_{1-6}$ alkoxymethyl, C(O)phenyl, OH, phenyl, CN, O-phenyl or (CH$_2$)$_m$Z, Z is benzisoxazolyl, indazolyl, benzisothiazolyl, benzthienyl, pyrimidinyl, pyridyl, 1,2-methylenedioxyphenyl, or phenyl, and Z, CH(OH)phenyl, phenyl or O-phenyl are optionally substituted with one or two moieties independently selected from halo, C$_{1-6}$ alkyl, C$_{1-6}$ alkoxy, hydroxy, trifluoromethyl, S(O)$_2$NH$_2$ or cyano, and m is 0 or 1;

comprising the step of coupling a compound of formula II

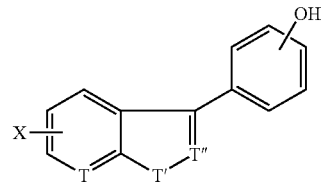

wherein
T, T', T", and X are as defined in formula I;
with a compound of formula III

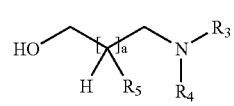

wherein
R$_5$ is H or C$_{1-6}$ alkyl;
a is 0 or 1; and
R$_3$ and R$_4$ are as defined in formula I;
in the presence of triphenylphosphene and diethylazodicarboxylate to provide a compound of formula I.

* * * * *